US011897884B2

(12) United States Patent
Rybtchinski et al.

(10) Patent No.: US 11,897,884 B2
(45) Date of Patent: Feb. 13, 2024

(54) SMALL MOLECULES BASED FREE-STANDING FILMS AND HYBRID MATERIALS

(71) Applicant: YEDA RESEARCH AND DEVELOPMENT CO. LTD., Rehovot (IL)

(72) Inventors: Boris Rybtchinski, Givaataim (IL); Haim Weissman, Rehovot (IL); Tamar Wolf, Rehovot (IL); Angelica Elkan, Rehovot (IL); Sounak Dutta, Rehovot (IL); Raja Bhaskar Kanth Siram, Rehovot (IL)

(73) Assignee: YEDA RESEARCH AND DEVELOPMENT CO. LTD., Rehovot (IL)

( * ) Notice: Subject to any disclaimer, the term of this patent is extended or adjusted under 35 U.S.C. 154(b) by 1088 days.

(21) Appl. No.: 16/621,278

(22) PCT Filed: Jun. 13, 2018

(86) PCT No.: PCT/IL2018/050649
§ 371 (c)(1),
(2) Date: Dec. 11, 2019

(87) PCT Pub. No.: WO2018/229765
PCT Pub. Date: Dec. 20, 2018

(65) Prior Publication Data
US 2020/0140439 A1    May 7, 2020

(30) Foreign Application Priority Data

Jun. 13, 2017  (IL) .......................... 252887
Oct. 23, 2017  (IL) .......................... 255218

(51) Int. Cl.
*C07D 471/22*  (2006.01)
*B01D 69/12*  (2006.01)
(Continued)

(52) U.S. Cl.
CPC ........... *C07D 471/22* (2013.01); *B01D 69/12* (2013.01); *C01B 32/174* (2017.08); *C09B 5/62* (2013.01);
(Continued)

(58) Field of Classification Search
CPC .. H10K 85/621; H10K 85/221; H10K 30/252; C07D 471/22; C01B 32/174; B01D 69/12; C09B 5/62
(Continued)

(56) References Cited

U.S. PATENT DOCUMENTS 8,968,886 B2    3/2015  Rybtchinski et al.
9,067,181 B2    6/2015  Rybtchinski et al.
(Continued)

FOREIGN PATENT DOCUMENTS

CN    101592611 A    2/2009
CN    104466134 A    3/2015
(Continued)

OTHER PUBLICATIONS

Amdursky, N. et al. (2009)—Self-assembled bioinspired quantum dots: optical properties—Applied Physics Letters, 94(26), 261907.
(Continued)

*Primary Examiner* — Thinh T Nguyen
(74) *Attorney, Agent, or Firm* — Mark S. Cohen; PEARL COHEN ZEDEK LATZER BARATZ LLP

(57) ABSTRACT

This invention is directed to an aromatic material based free-standing film, a hybrid of organic crystalline materials and inorganic carbon nanomaterials, process of preparation and uses thereof. The film, which comprises a fibrous organic nanocrystals of an aromatic material, is mechanically and thermally stable. This film is optionally reinforced by hybridization with a reinforcement material, such as carbon nanotube, carbon material, a polysaccharide, a nanoclay a metal, metal alloy, or an organic polymer. The hybrid film of organic nanocrystals and carbon nanotubes (ONC/CNT) has high conductivity and high thermal stability. The
(Continued)

films or hybrids of this invention are used as microfiltration membranes for various materials, in electrodes or perovskite solar cells.

26 Claims, 42 Drawing Sheets

(51) Int. Cl.
*H10K 30/35* (2023.01)
*C01B 32/174* (2017.01)
*C09B 5/62* (2006.01)
*H10K 85/20* (2023.01)
*H10K 85/60* (2023.01)
*B01D 61/02* (2006.01)
*B01D 61/14* (2006.01)
*B82Y 30/00* (2011.01)
*B82Y 40/00* (2011.01)

(52) U.S. Cl.
CPC ......... *H10K 30/352* (2023.02); *H10K 85/221* (2023.02); *H10K 85/621* (2023.02); *H10K 85/6572* (2023.02); *B01D 61/027* (2013.01); *B01D 61/147* (2013.01); *B01D 2325/02* (2013.01); *B01D 2325/20* (2013.01); *B82Y 30/00* (2013.01); *B82Y 40/00* (2013.01); *Y02E 10/549* (2013.01)

(58) Field of Classification Search
USPC .......................................................... 546/40
See application file for complete search history.

(56) References Cited

U.S. PATENT DOCUMENTS

| | | | |
|---|---|---|---|
| 9,623,381 | B2 | 4/2017 | Rybtchinski et al. |
| 9,701,784 | B2 | 7/2017 | Rybtchinski et al. |
| 2011/0204281 | A1 | 8/2011 | Rouse |
| 2012/0105783 | A1* | 5/2012 | Pau et al. ............... C09K 19/38 349/127 |
| 2013/0303769 | A1 | 11/2013 | Rybtchinski et al. |
| 2015/0083184 | A1 | 3/2015 | Chen et al. |
| 2015/0375180 | A1 | 12/2015 | Rybtchinski et al. |
| 2017/0191193 | A1* | 7/2017 | Joo et al. .......... H01M 10/0523 |
| 2017/0260218 | A1* | 9/2017 | Koh et al. ............... C09K 11/06 |

FOREIGN PATENT DOCUMENTS

| | | |
|---|---|---|
| CN | 105218547 | 1/2016 |
| CN | 110982114 A | 10/2020 |
| DE | 102010033025 | 8/2012 |
| JP | 2002097009 A | 2/2002 |
| JP | 2002097010 A | 2/2002 |
| WO | WO 2009/118742 | 1/2009 |
| WO | WO 2012/025928 | 1/2012 |
| WO | WO 2014/071524 A1 | 5/2014 |
| WO | WO 2015/139802 A1 | 9/2015 |
| WO | WO 2016/178671 A1 | 11/2016 |
| WO | WO 2017/006325 | 12/2017 |
| WO | WO 2017/065306 A1 | 9/2018 |
| WO | WO 2018/229765 A1 | 12/2018 |

OTHER PUBLICATIONS

Baba, K. et al. (2010)—Organic nanocrystals for nanomedicine and biophotonics—Nanocrystals, ed. Y. Masuda, Sciyo, Rijeka, 311-326.
Baba, K., et al. (2011). Functional organic nanocrystals. Nanocrystal, 397-414.
Backes, C. et al. (2009)—High Population of Individualized SWCNTs through the Adsorption of Water-Soluble Perylenes—J. Am. Chem. Soc., 131 (6), pp. 2172-2184.
Backes, C. et al. (2011)—The potential of perylene bisimide derivatives for the solubilization of carbon nanotubes and graphene—Advanced Materials, 23(22-23), 2588-2601.
Baughman, R. H. et al. (2002)—Carbon nanotubes—the route toward applications—Science, 297(5582), 787-792.
Berry, J. et al. (2015)—Hybrid organic-inorganic perovskites (HOIPs): Opportunities and challenges—Advanced Materials, 27(35), 5102-5112.
Bounioux, C. et al. (2013)—Thermoelectric composites of poly(3-hexylthiophene) and carbon nanotubes with a large power factor—Energy & Environmental Science, vol. 6, Issue 3, pp. 918-925.
Urland, D. M. et al. (1994)—Second-order nonlinearity in poled-polymer systems—Chemical Reviews, 94(1), 31-75.
Carrizales, C. et al. (2008)—Thermal and mechanical properties of electrospun PMMA, PVC, Nylon 6, and Nylon 6, 6—Polymers for Advanced Technologies, 19(2), 124-130.
Chen, K. Y. et al. (2012)—Synthesis, photophysical and electrochemical properties of 1-aminoperylene bisimides—Dyes and Pigments, 92(1), 517-523.
Chen, S. et al. (2015)—Self-assembly of perylene imide molecules into 1D nanostructures: methods, morphologies, and applications—Chemical reviews, 115(21), 11967-11998.
Coleman, JN et al. (2006)—Small but strong: A review of the mechanical properties of carbon nanotube—polymer composites—Carbon, 44(9), 1624-1652.
Compton, O. C. et al. (2012)—Tuning the mechanical properties of graphene oxide paper and its associated polymer nanocomposites by controlling cooperative intersheet hydrogen bonding. ACS nano, 6(3), 2008-2019.
Criscitiello, F. et al. (2017)—Perylene bisimide metal complexes as new MWCNTs dispersants: Role of the metal ion in stability and temperature sensing—Colloids and Surfaces A: Physicochemical and Engineering Aspects, 516, 32-38.
Dankers, P. Y. et al. (2005)—A modular and supramolecular approach to bioactive scaffolds for tissue engineering—Nature materials, 4(7), 568-574.
Dresselhaus, M. S. et al. (2004)—Unusual properties and structure of carbon nanotubes—Annu. Rev. Mater. Res., 34, 247-278.
Endo, H. et al. (2008)—Free-standing ultrathin films with universal thickness from nanometer to micrometer by polymer nanosheet assembly—Journal of Materials Chemistry, 18(12), 1302-1308.
Endo, M. et al. (2004)—Applications of carbon nanotubes in the twenty-first century—Philosophical Transactions of the Royal Society of London. Series A: Mathematical, Physical and Engineering Sciences, 362(1823), 2223-2238.
Feng, W. et al. (2005)—Perylene derivative sensitized multi-walled carbon nanotube thin film—Carbon, vol. 43, Issue 12, , pp. 2501-2507.
Fery-Forgues, S. (2013)—Fluorescent organic nanocrystals and non-doped nanoparticles for biological applications—Nanoscale, 5(18), 8428-8442.
Fornes, T. D. et al. (2004)—Nylon-6 nanocomposites from alkylammonium-modified clay: the role of alkyl tails on exfoliation—Macromolecules, 37(5), 1793-1798.
Frenot, A. et al. (2003)—Polymer nanofibers assembled by electrospinning—Current opinion in colloid & interface science, 8(1), 64-75.
Gao, F. (2004)—Clay/polymer composites: the story—Materials today, 7(11), 50-55.
Geng, H. Z. et al. (2008)—Effect of Carbon Nanotube Types in Fabricating Flexible Transparent Conducting Films—Journal of the Korean Physical Society, 53(2), 979-985.
Green, M. A. et al. (2014)—The emergence of perovskite solar cells—Nature photonics, 8(7), 506-514.
Grimme, S. (2008)—Do special noncovalent π-π stacking interactions really exist?—Angewandte Chemie International Edition, 47(18), 3430-3434.
Hasobe, T. et al. (2011)—Molecular nanoarchitectures composed of porphyrins and carbon nanomaterials for light energy conversion—Journal of Porphyrins and Phthalocyanines, 15(05n06), 301-311.
Hodes, G. et al. (2014)—Photovoltaics: perovskite cells roll forward—Nature Photonics, 8(2), 87-88.
Huang, X. et al. (2012)—Graphene-based composites—Chemical Society Reviews, 41, 666.

(56) References Cited

OTHER PUBLICATIONS

Huang, Z. et al. (2003)—A review on polymer nanofibers by electrospinning and their applications in nanocomposites—Composites Science and Technology 63(15), 2223-2253.
Hussain, F. et al. (2006)—Review article: Polymer-matrix Nanocomposites, Processing, Manufacturing, and Application: An Overview—J. Compos. Mater. , 40, 1511.
Janas, D. et al. (2017)—Free-standing films from chirality-controlled carbon nanotubes—Materials & Design, 121, 119-125.
Jee, A. Y. et al. (2010)—Comparative analysis on the nanoidentation of polymers using atomic force microscopy—Polymer Testing, 29(1), 95-99.
Kratzer, M. et al. (2016)—Thin film growth of aromatic rod-like molecules on graphene—Nanotechnology, 27(29), 292001.
Kulbak, M. et al. (2015)—How important is the organic part of lead halide perovskite photovoltaic cells? Efficient CsPbBr3 cells—The journal of physical chemistry letters, 6(13), 2452-2456.
Leijtens, T. et al. (2015)—Stability of metal halide perovskite solar cells—Advanced Energy Materials, 5(20), 1500963.
Li, L. et al. (2006)—Formation and properties of nylon-6 and nylon-6/montmorillonite composite nanofibers—Polymer, 47(17), 6208-6217.
Li, P. et al. (2017)—Nanohybrid shish-kebab supramolecular structure of single-walled carbon nanotubes/N,N?-dioctyl perylene tetracarboxylic diimide—Composites Science and Technology, vol. 148, pp. 43-48.
Light, I.et al. (2013)—Graphite Design: Prospects of Graphene-Based Nanocomposites for Solar Energy Conversion, Storage, and Sensing—Acc. Chem. Res., 46 (10), pp. 2235-2243.
Mao, B. et al. (2017)—Fluorescence-Lifetime Imaging and Super-Resolution Microscopies Shed Light on the Directed- and Self-Assembly of Functional Porphyrins onto Carbon Nanotubes and Flat Surfaces—Chemistry-A European Journal, vol. 23, Issue 41, pp. 9772-9789.
Mark, J. E. (Ed.). (2007)—Physical properties of polymers handbook (vol. 1076, p. 825)—New York: Springer.
McQuade, D. et al. (2000)—Conjugated Polymer-Based Chemical Sensors—Chemical Reviews 100, 2537-2574.
Nguyen, Q, et al. (2006)—Preparation of polymer-clay nanocomposites and their properties—Advances in Polymer Technology 25(4), 270-28.
Nisha, S. K. et al. (2014)—Random copolyesters containing perylene bisimide: flexible films and fluorescent fibers—ACS applied materials & interfaces, 6(15), 12457-12466.
Okazaki, T. et al. (2011)—Coaxially Stacked Coronene Columns inside Single-Walled Carbon Nanotubes. Angewandte Chemie—International Edition, vol. 50, Issue 21, pp. 4853-4857.
Paul, D. et al. (2008)—Polymer nanotechnology: Nanocomposites—Polymer 49(15), 3187-3204.
Peng, X. et al. (2009)—Carbon nanotube—nanocrystal heterostructures—Chemical Society Reviews, 38(4), 1076-1098.
Ploehn, H. et al. (2006)—Quantitative Analysis of Montmorillonite Platelet Size by Atomic Force Microscopy—Industrial & Engineering Chemistry Research 45(21), 7025-7034.
Potts, J. et al. (2011)—Graphene-based polymer nanocomposites—Polymer 52(1), 5-25.
Rajasingh, P. et al. (2007)—Selective Bromination of Perylene Diimides under Mild Conditions—J. Org. Chem., 72(16), 5973-5979.
Rosenne, S. et al. (2015)—Self-assembled organic nanocrystals with strong nonlinear optical response—Nano letters, 15(11), 7232-7237.
Sander, J. et al. (2014)—Sonocrystallization and sonofragmentation—Ultrasonics Sonochemistry 21, 1908-1915.
Serwer, P. (1983)—Agarose gels: Properties and use for electrophoresis—Electrophoresis 4(6), 375-382.
Shahar, C. et al. (2016)—Precrystalline Aggregates Enable Control over Organic Crystallization in Solution—Angewandte Chemie International Edition 55(1), 179-182.
Shin, W. S. et al. (2006)—Effects of functional groups at perylene diimide derivatives on organic photovoltaic device application—Journal of Materials Chemistry, 16(4), 384-390.
Sinha, R. et al. (2003)—Polymer/layered silicate nanocomposites: a review from preparation to processing—Progress in Polymer Science 28(11), 1539-1641.
Spitalsky, Z. et al. (2010)—Carbon nanotube—polymer composites: chemistry, processing, mechanical and electrical properties—Progress in polymer science, 35(3), 357-401.
Subbiah, T. et al. (2005)—Electrospinning of nanofibers. Journal of Applied Polymer Science 96, 557-569.
Tarus, B. et al. (2016)—Effect of polymer concentration on the morphology and mechanical characteristics of electrospun cellulose acetate and poly (vinyl chloride) nanofiber mats—Alexandria Engineering Journal 55(3), 2975-2984.
Tidhar, Y. et al. (2014)—Mechanism of crystalline self-assembly in aqueous medium: a combined cryo-TEM/kinetic study—Chemistry 20(33), 10332-10342.
Tsai, H. Y. et al. (2014)—1, 6-and 1, 7-Regioisomers of asymmetric and symmetric perylene bisimides: synthesis, characterization and optical properties. Molecules, 19(1), 327-341.
Tsarfati, Y. et al. (2015)—Dispersing perylene diimide/SWCNT hybrids: structural insights a the molecular level and fabricating advanced materials—Journal of the American Chemical Society, 137(23), 7429-7440.
Veleirinho, B. et al. (2008)—Solvent and concentration effects on the properties of electrospun poly(ethylene terephthalate) nanofiber mats—Journal of Polymer Science Part B: Polymer Physics 46(5), 460-471.
Wan, C. et al. (2012)—Reinforcement and interphase of polymer/graphene oxide nanocomposites—J. Mater. Chem. 22, 3637-3646.
Wang, D. et al. (2016)—Stability of perovskite solar cells—Solar Energy Materials and Solar Cells, 147, 255-275.
Wang, W. et al. (2003)—Dynamic π-π stacked molecular assemblies emit from green to red colors—Nano Letters, 3(4), 455-458.
Watson, M. et al. (2001)—Big is Beautiful—"Aromaticity" Revisited from the Viewpoint of Macromolecular and Supramolecular Benzene Chemistry—Chemical Reviews 101(5), 1267-1300.
Wu, G. et al. (2017)—Exploring High-Performance n-Type Thermoelectric Composites Using Amino-Substituted Rylene Dimides and Carbon Nanotubes—ACS NANO, vol. 11, Issue 6, , pp. 5746-5752.
Wurthner, F. (2004)—Perylene bisimide dyes as versatile building blocks for functional supramolecular architectures—Chemical Communications 0, 1564-1579.
Wurthner, F. et al. (2015)—Perylene Bisimide Dye Assemblies as Archetype Functional Supramolecular Materials—Chem. Rev. 116 (3), 962-1052.
Yan, P. et al. (2005)—Self-organized perylene diimide nanofibers—The Journal Of Physical Chemistry B, 109(2), 724-730.
Zhan, X. et al. (2011)—Rylene and related diimides for organic electronics—Advanced Materials, 23(2), 268-284.
Zhang, J. et al. (2013)—N-Alkyl substituted di(perylene bisimides) as air-stable electron transport materials for solution-processible thin-film transistors with enhanced performace—Journal of Materials Chemistry C 1, 3200-3206.
Zhang, X. et al. (2012)—Facile synthesis of 1-bromo-7-alkoxyl perylene diimide dyes: Toward unsymmetrical functionalizations at the 1, 7-positions—Tetrahedron Letters, 53(9), 1094-1097.
Zhu, Y. et al. (2010)—Graphene and Graphene Oxide: Synthesis, Properties, and Applications—Adv. Mater., 22(35), 3906-3924.
Ata et al. "New developments in non-covalent surface modification, dispersion and electrophoretic deposition of carbon nanotubes" Carbon. Apr. 1, 2018;130:584-98.

* cited by examiner

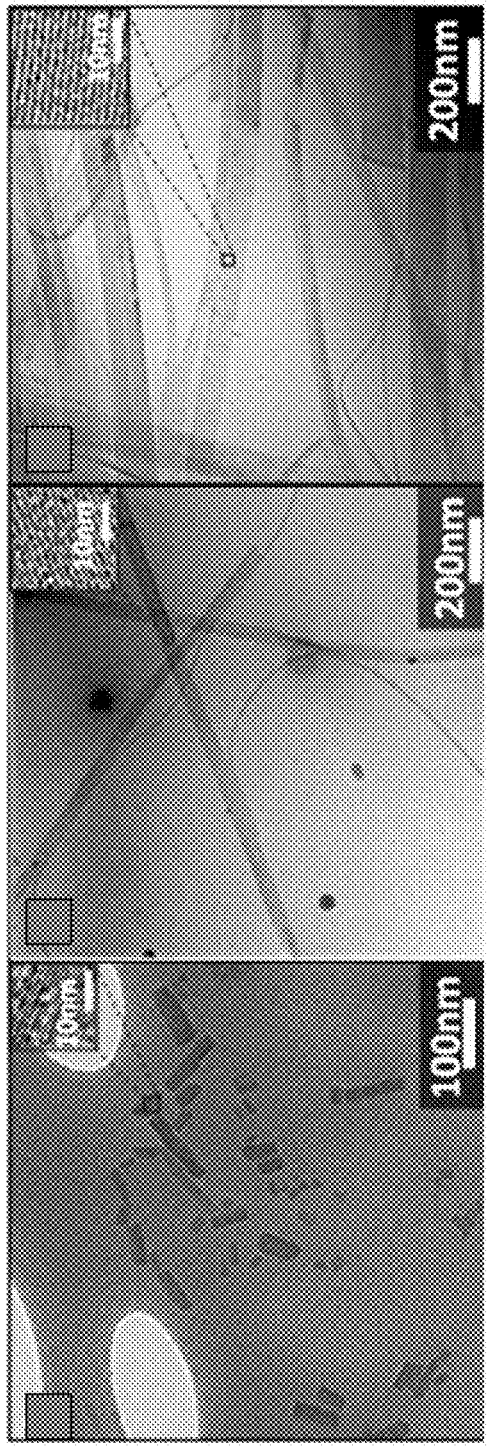
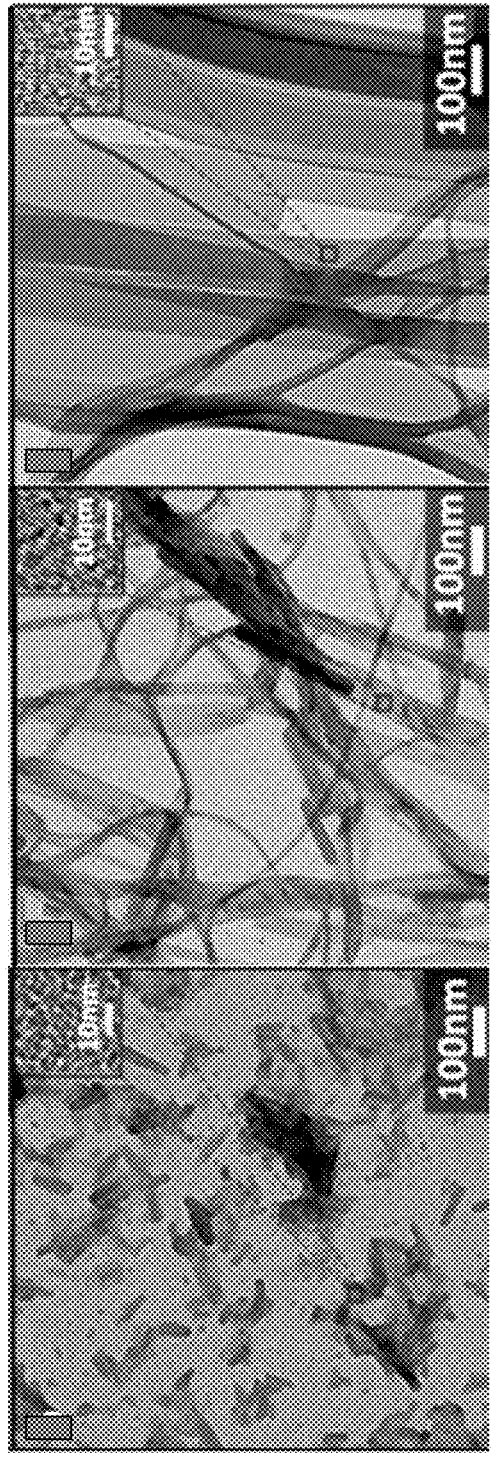
FIGURE 4A FIGURE 4B FIGURE 4C
FIGURE 4D FIGURE 4E FIGURE 4F

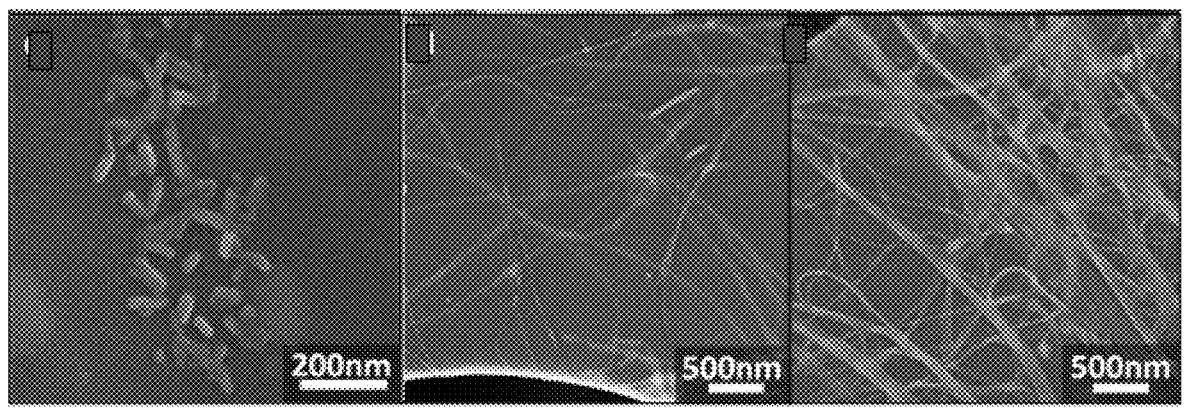
FIGURE 4G     FIGURE 4H     FIGURE 4I
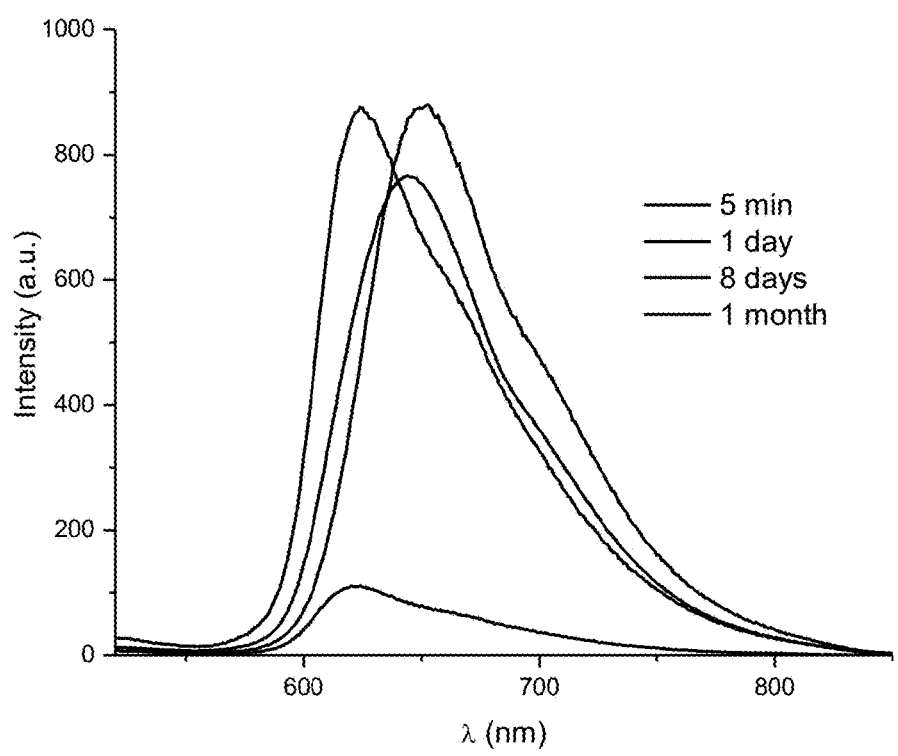
FIGURE 5

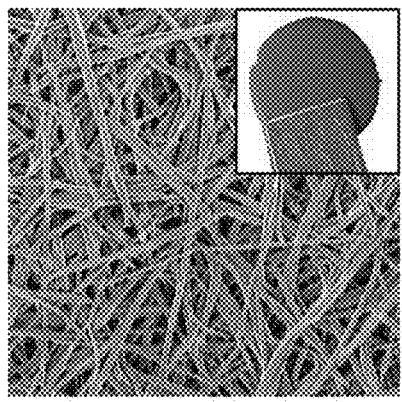 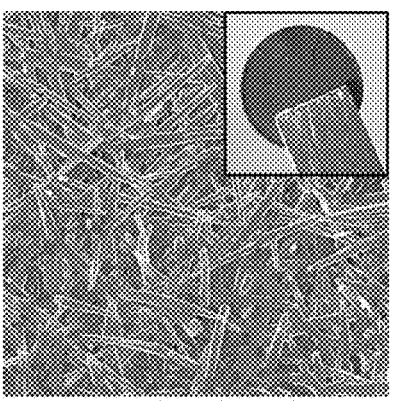 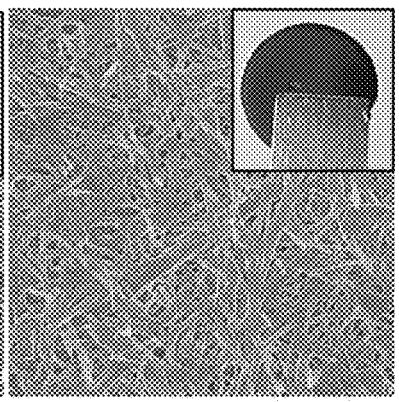
FIGURE 7        FIGURE 8        FIGURE 9
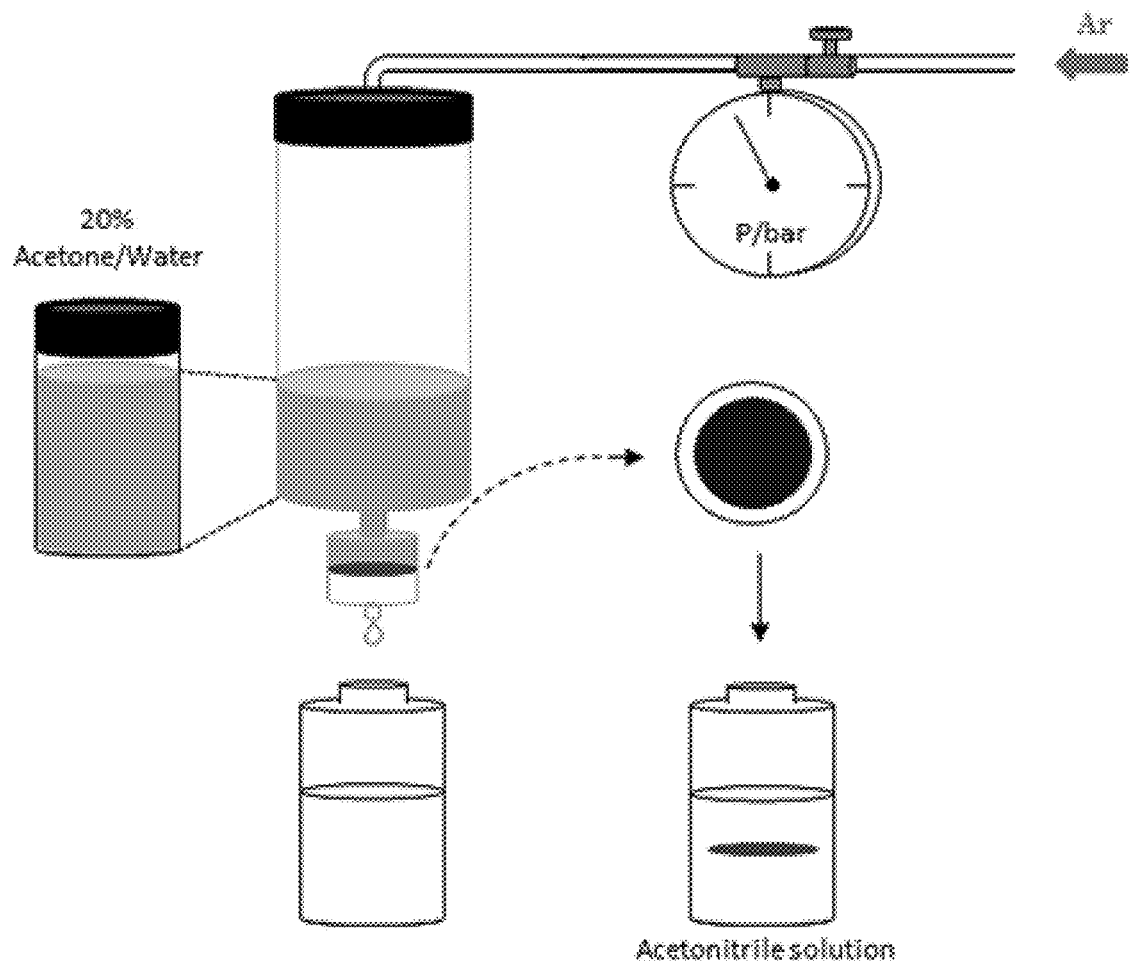
FIGURE 10

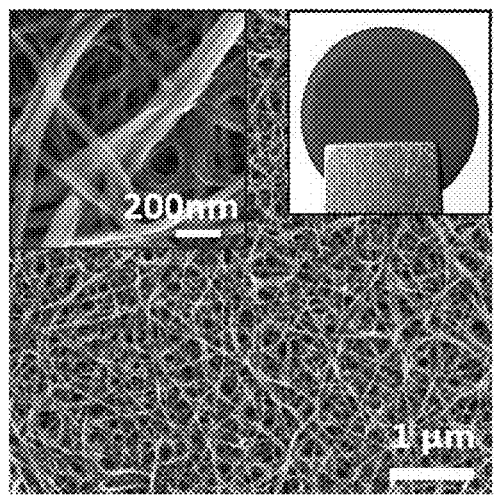
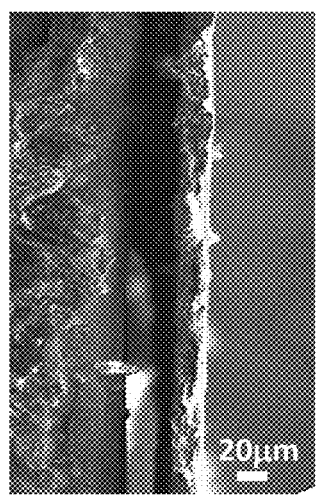
FIGURE 11A
FIGURE 11B
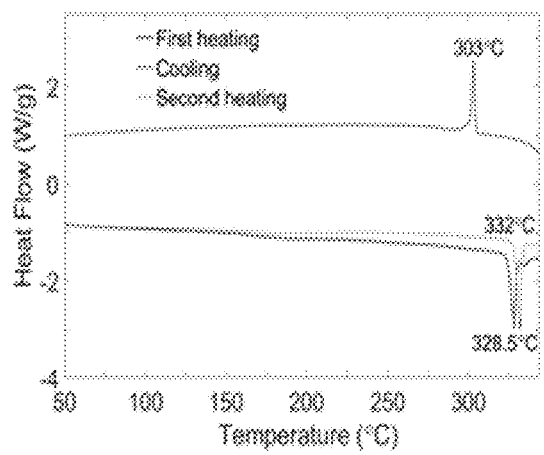
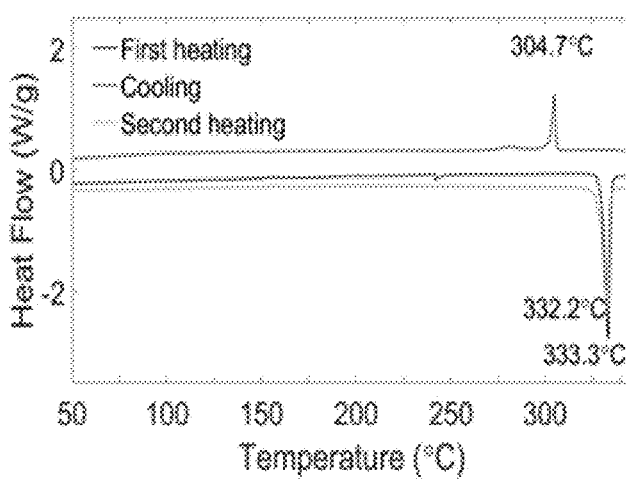
FIGURE 12A
FIGURE 12B
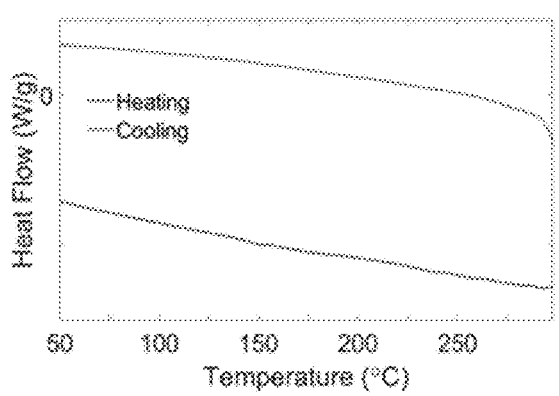
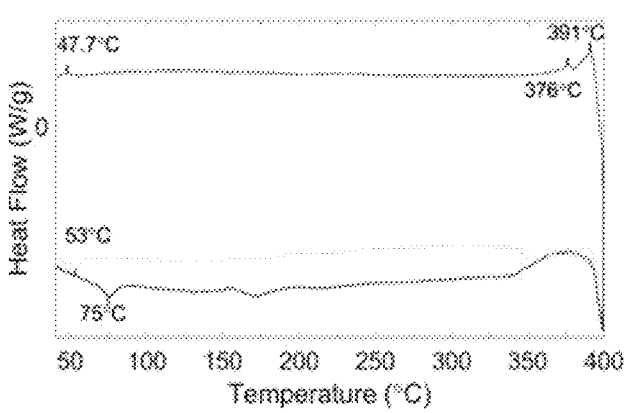
FIGURE 12C
FIGURE 12D

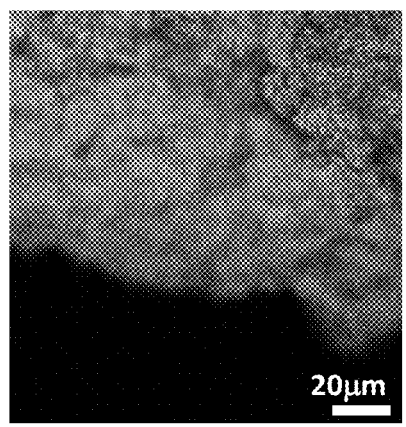
FIGURE 18
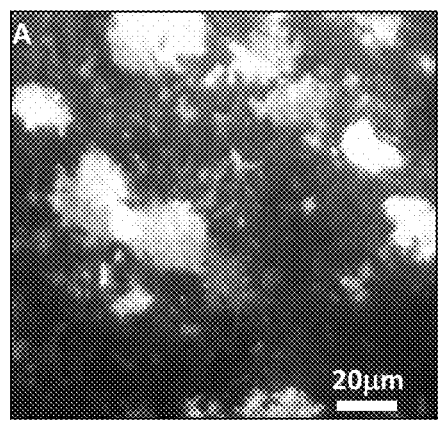 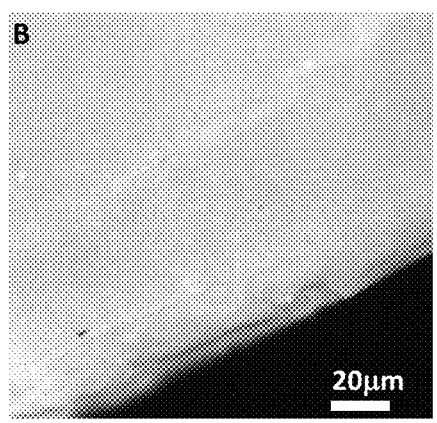
FIGURE 19A          FIGURE 19B
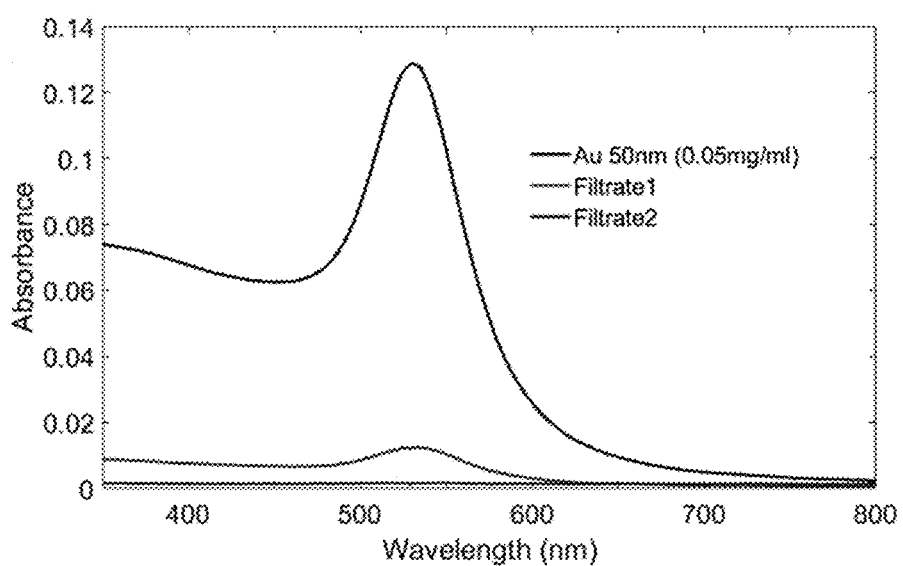
FIGURE 20

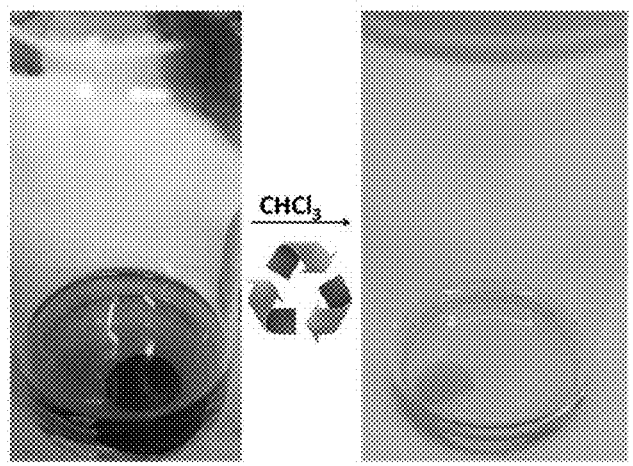
FIGURE 26
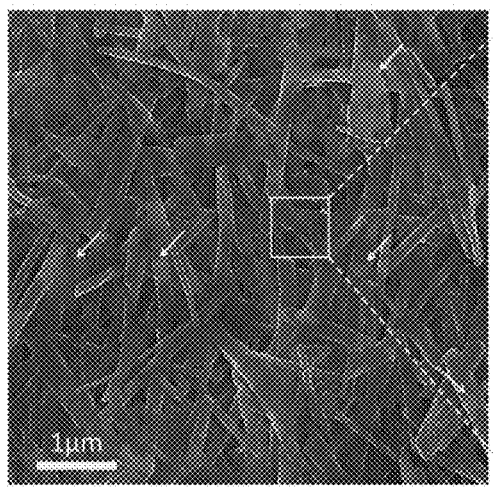 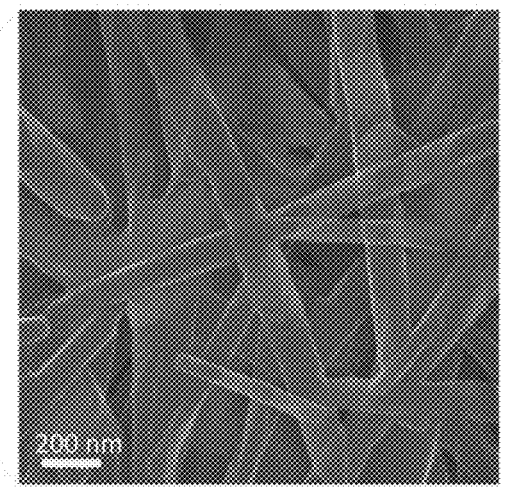
FIGURE 27A                                  FIGURE 27B

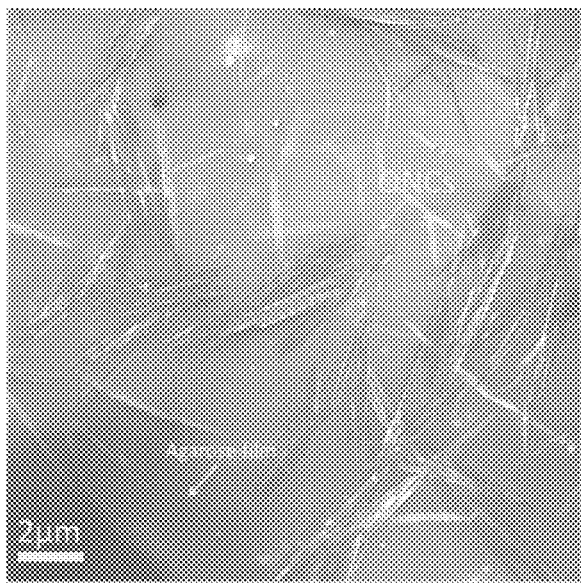
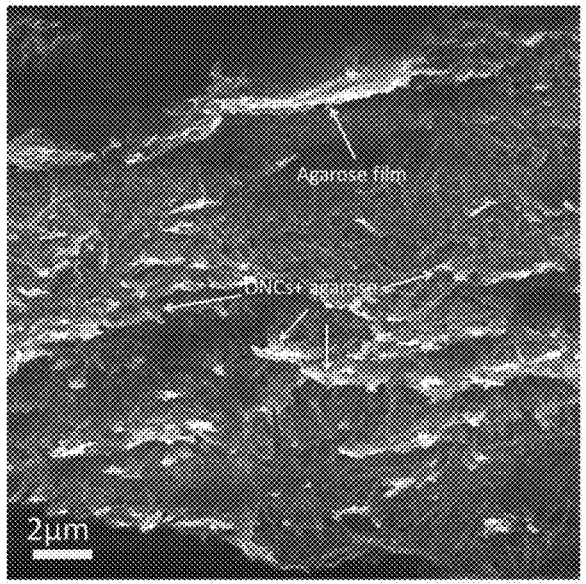
FIGURE 29A
FIGURE 29B

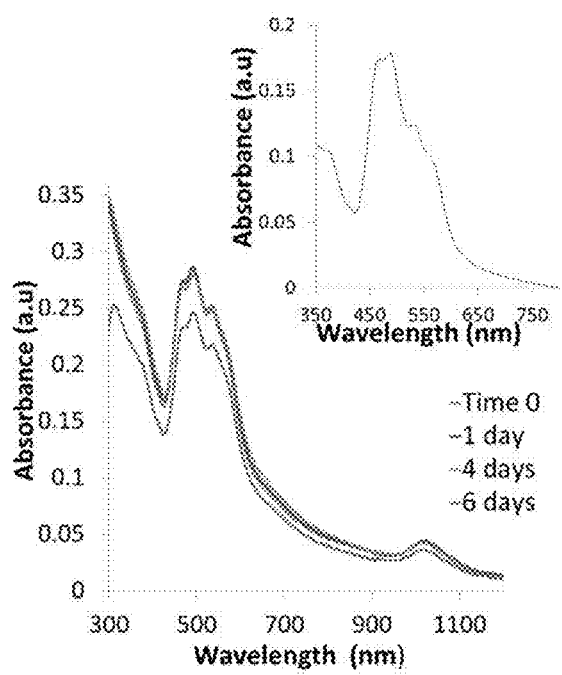
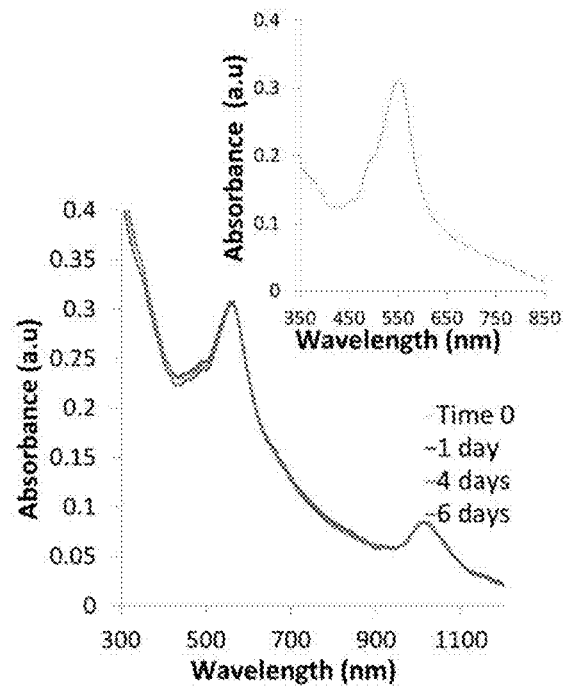
FIGURE 32A
FIGURE 32B
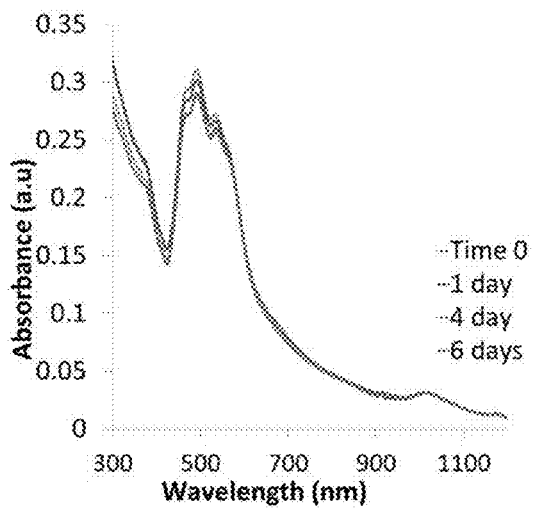
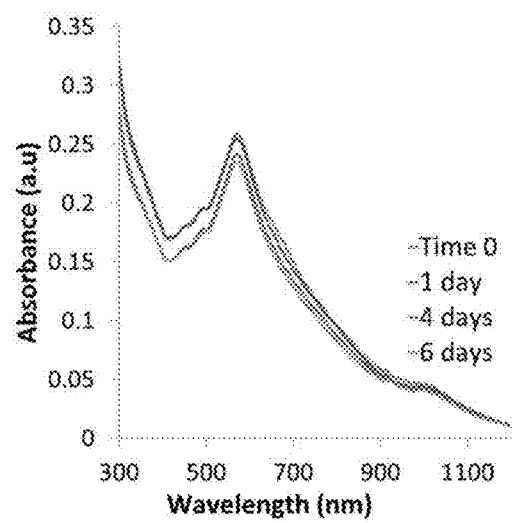
FIGURE 32C
FIGURE 32D

| | Carbon Tape | | MWCNT/P DI-NO$_2$ | | Washed d-MWCNT | | WITHOUT HTL/Au | |
|---|---|---|---|---|---|---|---|---|
| | FS | RS | FS | RS | FS | RS | FS | RS |
| $V_{oc}$ (Volts) | 1.24 | 1.24 | 1.28 | 1.28 | 1.33 | 1.33 | 1.24 | 1.23 |
| $J_{sc}$ (mA/cm$^2$) | 0.11 | 0.13 | 5.60 | 5.63 | 5.55 | 5.55 | 4.81 | 4.81 |
| Fill Factor (FF) | 0.32 | 0.29 | 0.75 | 0.76 | 0.79 | 0.80 | 0.78 | 0.79 |
| PQE (%) | 0.04 | 0.04 | 5.36 | 5.44 | 5.80 | 5.87 | 4.66 | 4.67 |

SMALL MOLECULES BASED FREE-STANDING FILMS AND HYBRID MATERIALS

CROSS-REFERENCE TO RELATED APPLICATIONS

This application is a National Phase Application of PCT International Application No. PCT/IL2018/050649, International Filing Date Jun. 13, 2018, claiming priority of IL Patent Application(s) No(s). 252887, filed Jun. 13, 2017, and 255218, filed Oct. 23, 2017, which are hereby all incorporated by reference.

FIELD OF THE INVENTION

This invention is directed to an aromatic material based free-standing film, a hybrid of organic crystalline materials and inorganic carbon nanomaterials, process of preparation and uses thereof. The film, which comprises a fibrous organic nanocrystals of an aromatic material, is mechanically and thermally stable. This film is optionally reinforced by hybridization with a reinforcement material, such as carbon nanotubes, carbon material, a polysaccharide, a nanoclay, a metal, metal alloy, or an organic polymer. The hybrid film of organic nanocrystals and carbon nanotubes (ONC/CNT) has high conductivity and high thermal stability. The films or hybrids of this invention are used as microfiltration membranes for various materials, in electrodes or perovskite solar cells.

BACKGROUND OF THE INVENTION

Macroscopic materials assembled entirely from small molecules can be very advantageous in terms of fabrication, diversity, cost, and recyclability. Yet, stability of such materials is inferior to that of polymeric materials, where size and entanglement of large molecules leads strong van der Waals interactions and 3D connectivity.

Thin films can be made from both macromolecular entities (e.g. polymers; see *Polymer Thin Film*, Tsui, O. K. C.; and Russel, T. P.; World Scientific Publishing) and small organic molecules (see for example Kratzer, m.; and Teichert, C.; *Nanotechnology*, 2016, 27, 292001)). Such thin films are fabricated as coatings on top of a substrate/support. In contrast, free-standing films may be prepared similarly but the film is separated from the substrate/support without impairing (e.g. mechanical) stability thereof, hence they are "free-standing". Since there is no any additional species "holding", or supporting, the free-standing films require additional physical properties such as mechanical strength and stability.

Macromolecular entities can therefore be chosen to comply with such requirements. Indeed, free-standing films made from macromolecular entities are known. In one study, N-Dodecylacrylamide polymer formed a well-defined monolayer on a water surface, followed by peeling such free-standing film from a sacrificial film (Endo, H.; Mitsuishi, M.; and Miyashita, T. *J. Mater. Chem.*, 2008, 18, 1302-1308). Janas et al. (Janas, D.; Rdest, M.; and Koziol, K. K. K. *Mat. Des.* 2017, 121, 119-125) showed the feasible formation of a free-standing film, based on chiral carbon nanotube.

Perylene diimide (PDI) dye derivatives provide diverse molecular constituents for self-assembled nanostructures in aqueous media. Simple monosubstituted PDIs, assemble into diverse organic nanocrystals (ONCs) in solution.

Organic nanocrystals (ONCs) have recently become an active area of research due to their useful photonic [K. Baba, H. Kasai, K. Nishida, H. Nakanishi, in *Nanocrystal*, (Ed: Y. Masuda), InTech, 2011, 397] and electronic properties. [X. Zhan, A. Facchetti, S. Barlow, T. J. Marks, M. A. Ratner, M. R. Wasielewski, S. R. Marder, *Adv. Mater.* 2011, 23, 268]. For example, ONCs have been employed as fluorescent labels in biological studies [S. Fery-Forgues, *Nanoscale* 2013, 5, 8428] and have been shown to possess advantageous nonlinear optical (NLO) properties [S. Rosenne, E. Grinvald, E. Shirman, L. Neeman, S. Dutta, O. Bar-Elli, R. Ben-Zvi, E. Oksenberg, P. Milko, V. Kalchenko, H. Weissman, D. Oron, B. Rybtchinski, *Nano Letters* 2015, 15, 7232] as well as quantum confinement, [N. Amdursky, M. Molotskii, E. Gazit, G. Rosenman, *Appl Phys Lett* 2009, 94, 261907] akin to semiconductor quantum dots. Because of their facile self-assembly, structural variability and useful photofunction, ONCs possess the essential properties to act as building blocks for hybrid nanomaterials.

This invention provides, inter alia, a facile solution-based fabrication of free-standing nanoporous films assembled from organic nanocrystals (ONCs) based on aromatic small molecules (common organic dyes—perylene diimides (PDIs)). The free-standing films feature remarkable thermal stability, and decent mechanical stability, representing the first example of molecular noncovalent free-standing materials having such high thermal and mechanical robustness. The nanoporous films display advantageous photonic properties and can be used as microfiltration membranes with a cutoff of 50 nm. Macroscopic ONC materials bridge a gap between the conventional polymers and organic crystals, enabling facile assembly/disassembly, robustness, nanoporosity, and optoelectronic functionality.

Organic crystalline materials are used as dyes/pigments, pharmaceuticals, and active components of photonic and electronic devices. There is great interest in integrating organic crystals with inorganic and carbon nanomaterials in order to create nanocomposites with enhanced properties. Such efforts are hampered by the difficulties in interfacing organic crystals with materials of dissimilar nature.

Carbon nanotubes (CNTs) possess high intrinsic conductivity and have been incorporated into various composite materials in order to improve their electrical properties [M. Endo, T. Hayashi, Y. Ahm Kim, M. Terrones, M. S. Dresselhaus, *Philos. Trans. R. Soc. London, Ser. A* 2004, 362, 2223; M. S. Dresselhaus, G. Dresselhaus, A. Jorio, *Annu. Rev. Mater. Res.* 2004, 34, 247.]. For example, CNTs enhance electrical conductivity by several orders of magnitude when blended with otherwise insulating polymer matrices. [Z. Spitalsky, D. Tasis, K. Papagelis, C. Galiotis, *Prog. Polym. Sci.* 2010, 35, 357] Interfacing CNTs with photoactive nanoparticles, such as quantum dots, leads to arrays relevant to sensing and light harvesting applications. [X. Peng, J. Chen, J. A. Misewich, S. S. Wong, *Chem. Soc. Rev.* 2009, 38, 1076].

CNT dispersions using aromatic amphiphiles have been reported, including perylene-diimide-based ones, [Y. Tsarfati, V. Strauss, S. Kuhri, E. Krieg, H. Weissman, E. Shimoni, J. Baram, D. M. Guldi, B. Rybtchinski, *J. Am. Chem. Soc.* 2015, 137, 7429; C. Bounioux, P. Diaz-Chao, M. Campoy-Quiles, M. S. Martin-Gonzalez, A. R. Goni, R. Yerushalmi-Rozen, C. Muller, *Energy Environ. Sci.* 2013, 6, 918; C. Backes, C. D. Schmidt, F. Hauke, C. Böttcher, A. Hirsch, *J. Am. Chem. Soc.* 2009, 131, 2172]. This invention is further directed to hybrids of CNT dispersions and hydrophobic molecules and/or ONCs.

SUMMARY OF THE INVENTION

In one embodiment, this invention provides a free-standing film comprising an aromatic material, wherein the aromatic material is crystalline and has a molecular weight of less than 1000 Da. In another embodiment, the aromatic material comprises a perylene-diimide, a naphthalene diimide, a phthalocyanine, derivatives thereof, or any combination thereof.

In another embodiment, the perylene diimide derivative is represented by the structure of formula IA, IB, II or III:

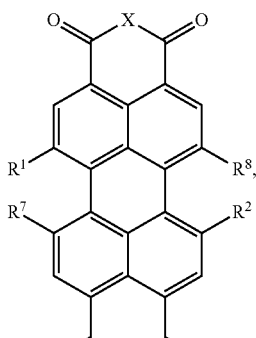

IA

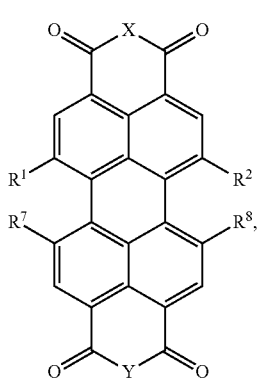

IB

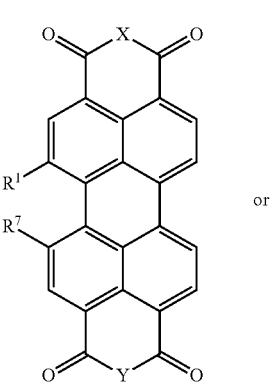

II or

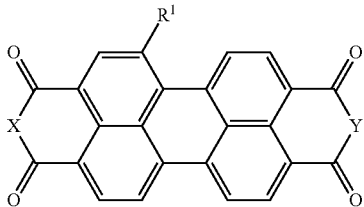

III wherein,

X is —NR$^3$;

Y is —NR$^4$;

R$^1$ is H, R$^5$, (C$_7$-C$_{10}$)alkyl, (C$_7$-C$_{10}$)haloalkyl, (C$_3$-C$_8$) cycloalkyl, aryl or heteroaryl, wherein said alkyl, haloalkyl, cycloalkyl, aryl or heteroaryl groups are optionally substituted; or R$^1$ is joined together with R$^7$ to form a substituted or unsubstituted five or six membered ring, or a substituted or unsubstituted five or six membered fused ring;

R$^2$ is H, R$^5$, (C$_7$-C$_{10}$)alkyl, (C$_7$-C$_{10}$)haloalkyl, (C$_3$-C$_8$) cycloalkyl, aryl or heteroaryl, wherein said alkyl, haloalkyl, cycloalkyl, aryl or heteroaryl groups are optionally substituted; or R$^2$ is joined together with R$^8$ to form a substituted or unsubstituted five or six membered ring, or a substituted or unsubstituted five or six membered fused ring;

R$^3$ and R$^4$ are each independently H, (C$_7$-C$_{10}$)alkyl, (C$_7$-C$_{10}$)haloalkyl, (C$_3$-C$_8$)cycloalkyl, aryl or heteroaryl, wherein said alkyl, haloalkyl, cycloalkyl, aryl or heteroaryl groups are optionally substituted;

R$^5$ is OR$^6$, OCH$_3$, CF$_3$, halide, COR$^6$, COCl, COOCOR$^6$, COOR$^6$, OCOR$^6$, OCONHR$^6$, NHCOOR$^6$, NHCONHR$^6$, OCOOR$^6$, CON(R$^6$)$_2$, SR$^6$, SO$_2$R$^6$, SO$_2$M, SOR$^6$, SO$_3$H, SO$_3$M, SO$_2$NH$_2$, SO$_2$NH(R$^6$), SO$_2$N(R$^6$)$_2$, NH$_2$, NH(R$^6$), N(R$^6$)$_2$, CONH$_2$, CONH(R$^6$), CON(R$^6$)$_2$, CO(N-heterocycle), NO$_2$, OH, CN, cyanate, isocyanate, thiocyanate, isothiocyanate, mesylate, tosylate, triflate, PO(OH)$_2$ or OPO(OH)$_2$; wherein M is a monovalent cation;

R$^6$ is H, (C$_7$-C$_{10}$)alkyl, (C$_7$-C$_{10}$)haloalkyl, (C$_3$-C$_8$)cycloalkyl, aryl or heteroaryl, wherein said alkyl, haloalkyl, cycloalkyl, aryl or heteroaryl groups are optionally substituted;

R$^7$ is H or is joined together with R$^1$ to form a substituted or unsubstituted five or six membered ring, or a substituted or unsubstituted five or six membered fused ring; and R$^8$ is H or is joined together with R$^2$ to form a substituted or unsubstituted five or six membered ring, or a substituted or unsubstituted five or six membered fused ring.

In some embodiments, this invention provides an ultrafiltration membrane, a microfiltration membrane or an electrode comprising the frees-standing films of this invention.

In one embodiment, this invention provides a nanocrystalline aromatic material and one or more of a reinforcement material, wherein said aromatic material has a molecular weight of less than 1000 Da. In another embodiment, the nanocrystalline aromatic material comprises a perylene-diimide, a naphthalene diimide, a phthalocyanine, derivatives thereof or any combination thereof. In another embodiment, the perylene diimide derivative is represented by the structure of formula IA, IB II or III as described hereinabove.

In one embodiment, this invention provides an electrode comprising the compositions as described hereinabove.

In one embodiment, this invention provides a hybrid composition comprising a carbon nanotube (CNT) and organic nanocrystals (ONC). In another embodiment, the organic nanocrystal comprises small hydrophobic organic compound. In another embodiment, the small hydrophobic organic compound comprises an aromatic core, which is substituted or unsubstituted. In another embodiment, the carbon nanotubes are single walled carbon nanotubes (SWCNTs) or a multi walled carbon nanotubes (MWCNTs). In another embodiment, the aromatic core is a perylenediimide (PDI) derivative, represented by the structure of formula IA, IB, II or III as described hereinabove. In one embodiment, this invention provides a film comprising the hybrid compositions. In another embodiment, the film is a free-standing film. In one embodiment, this invention provides a conductive colorant or a membrane for the separation of nanoparticles, biomolecules comprising the films/free-standing film which comprises the hybrid compositions. In one embodiment, this invention further provides a process for the preparation of CNT film (buckypapers) comprising:
- washing the film/free-standing as described hereinabove in a third organic solvent and thereby removing the excess of organic nanocrystal from the hybrid composition down to 0.5-10 wt % of the total mass; and obtaining porous CNT film.

In another embodiment, this invention provides a CNT film prepared according to the process described above.

In one embodiment, this invention provides an electrode comprising the hybrid compositions of this invention.

In one embodiment, this invention provides a process for the preparation of the hybrid composition of this invention, the process comprises:
- mixing a hydrophobic organic compound and a carbon nanotube (CNT) in a first organic solvent;
- optionally drying the mixture;
- adding to the mixture a second organic solvent and water to obtain an aqueous medium and mixing for a period of time to obtain the hybrid; wherein if the first organic solvent and the second organic solvent are the same, only water is added to the mixture In another embodiment, the hydrophobic organic compound is perylenediimide (PDI) derivative, represented by the structure of formula IA, IB II or III as described hereinabove.

In one embodiment, this invention provides a process for the preparation of the hybrid composition of this invention, the process comprises:
- mixing a hydrophobic organic compound and a carbon nanotube (CNT) in a first organic solvent;
- optionally drying the mixture;
- optionally, adding to the mixture a second organic solvent to obtain an organic medium and mixing for a period of time to obtain the hybrid.

In another embodiment, the hydrophobic organic compound is perylenediimide (PDI) derivative, represented by the structure of formula IA, IB II or III as described hereinabove.

In one embodiment, this invention provides a perovskite solar cell comprising the films or hybrid compositions as described hereinabove.

In one embodiment, this invention provides a process for the preparation of a dispersion of CNT, the process comprises mixing CNT and at least one perylenediimide (PDI), in a first organic solvent, wherein the PDI is represented by the structure of formula IA, IB, II or III as described hereinabove. In another embodiment, this invention provides a dispersion of CNT prepared according to the above process.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIGS. 4A-4I depict Cryo-TEM, TEM and SEM images of crystals of 1 formed in water/acetone solution (80/20, v/v) $4 \cdot 10^{-5}$M at 20-21° C. Insets: FFT-filtered magnifications of marked region showing crystalline fringes. FIG. 4A: Cryo-TEM image after 5 minutes blotless, inset: with FFT fitting of 1.61 nm spacing. FIG. 4B: Cryo-TEM image after 21.5 hours, inset: with FFT fitting of 1.96 nm spacing. FIG. 4C: Cryo-TEM image after aging of 1 month, inset: with FFT fitting of 2.02 nm spacing. FIG. 4D: TEM image at t=0, inset: FFT fitting of 1.50 nm spacing. FIG. 4E: TEM image after 1 day, inset: FFT fitting of 1.75 nm spacing. Other areas show spacing of 1.4-1.9 nm. FIG. 4F: TEM image after 3 weeks, inset: FFT fitting of 1.61 nm spacing. FIG. 4G: SEM image at t=0. FIG. 4H: SEM image after 1 day. FIG. 4I: SEM image after 3 weeks.

FIG. 5 depicts fluorescence spectra of compound 1 in water/acetone (80/20, v/v) solution at a concentration of $4 \times 10^{-5}$M during crystal evolution at 20° C., excitation at 490 nm.

FIG. 6A: general scheme; FIG. 6B: scheme depicting the short fabrication process of films from nonuniform crystalline fibers; FIG. 6C: SEM image of nanocrystals of 2 formed in THF/water (30/70, v/v) $1 \cdot 10^{-4}$M at RT after sonication for 10 minutes; upon sonication the crystalline fibers are broken to shorter crystals which serve as seeds for crystal growth when molecular solution is added FIG. 6D: SEM image of nanocrystals of 2 formed after addition of molecular solution of 2 and deposition as film.

FIG. 7 depicts SEM image of film 1b from compound 1, prepared via rapid method of sonication, followed by addition of molecular solution of 1 in THF. Inset (right) shows self-standing film 1b with a diameter of 10 mm collected with forceps FIG. 8 depicts SEM image of film 2 from compound 2, prepared via rapid method of sonication, followed by addition of molecular solution of 2 in THF. Inset (right) shows self-standing film 2 with a diameter of 10 mm collected with forceps FIG. 9 depicts SEM image of film 3 from compound 3, prepared via rapid method of sonication without addition of molecular solution. Inset (right) shows self-standing film 3 with a diameter of 10 mm collected with forceps FIG. 10 depicts a controlled pressure setup for fabrication of films.

FIGS. 11A-11B depict SEM images of a representative dry film 1a prepared from acetone/water solution (1:4, v/v) 4×10$^{-5}$M after aging. FIG. 11A: entangled, porous, fibrous network. Inset (right) shows self-standing film 1a with a diameter of 10 mm collected with forceps, and FIG. 11B: a cross section of film 1a with a thickness of 14 mm±2 mm.

FIGS. 12A-12D depict DSC heat-cool-heat thermograms of the dry films of film 1a (FIG. 12A): film 1b (FIG. 12B), film 2 (FIG. 12C); and film 3 (FIG. 12D).

FIG. 13A: SEM image of film 1a; FIG. 13B: SEM image of film 1b; FIG. 13C: SEM image of film 2.

FIG. 14A: SEM image of film 1a from compound 1; FIG. 14B: SEM image of film 1b from compound 1;

FIG. 14C: SEM image of film 2 from compound 2; and FIG. 14D: SEM image of film 3 from compound 3. Inset (right) shows the free-standing films after heating up to 250° C. and cooling; Except for film 3, the SEM images show that, the microstructure is maintained up to 300° C. FIG. 14E: Powder X-ray diffraction (PXRD) of films 1a-1b and 2-3 at various temperatures. Films 1a-1b and 2: bottom- room temperature, middle- 250° C and top- 300° C. Film 3: top- room temperature, middle- 250° C and middle- 300° C.

FIG. 15A: film 1a; FIG. 15B: film 2; and FIG. 15C: film 3.

FIG. 16A: film 1a; FIG. 16B: film 1b; FIG. 16C: film 2; and FIG. 16D: film 3.

FIGS. 17A and 17B depict SEM images of the fracture surface of film 2 following a tensile test. The crystals appear layered and there are some voids in between the layers. FIG. 17C depict bending of film 2.

FIG. 18 depicts SHG microscopy image of film 2, excitation at 800 nm,

FIGS. 19A-19B depict fluorescence microscopy images of films 1-2. FIG. 19A: film 1a and FIG. 19B: film 2.

FIG. 20 depicts UV/Vis spectra of the Au solution before filtration and filtrates.

FIG. 21A: with GO content of 5 wt. % at 1 kV electron beam tension; FIG. 21B: zoom in image of FIG. 21A;

FIG. 21C: with GO content of 5 wt % at 20 kV electron beam tension; and FIG. 21D: zoomed-in image, the arrows mark the "wrinkles" of the GO sheets.

FIG. 26 depicts the recycling process of 2/bentonite film.

FIGS. 27A-27B depict SEM images of 2/organoclay composite films (FIG. 27A) and zoom in image of FIG. 27A (FIG. 27B); the arrows mark the organoclay platelets.

FIG. 28A: EDS mapping image and FIG. 28B: EDS spectrum.

FIGS. 29A-29B depict SEM images of 2/agarose composite films. FIG. 29A: film image and FIG. 29B: film cross-section.

FIG. 30A: Cryo-TEM images of 2/MWCNT 50 wt % (the arrows point to ONCs). Inset shows MWCNTs coiled around the ONC of 2. FIG. 30B: Magnification of the ONCs in FIG. 30A marked by the yellow box, showing crystalline fringes. Inset: Fast Fourier transform (FFT) of the ONCs, indicating crystallinity. FIG. 30C: SEM image of 2/SWCNT 20 wt %. FIG. 30D: SEM image of 4/SWCNT 40 wt %. FIG. 30E: SEM image of PDI-OH/SWCNT. FIG. 30F: SEM image of PDI-NH$_2$/SWCNT.

FIG. 31A presents XRD spectra of 2 (green), 2/SWCNT with $C_{SWCNT}$ 8 wt % (red), and 2/MWCNT with $C_{MWCNTs}$ 5 wt % (blue). FIG. 31B presents XRD spectra of ONCs of 4 (green), 2/SWCNT with $C_{SWCNT}$ 5 wt % (red), and 2/MWCNT with $C_{MWCNT}$ 5 wt % (blue). FIG. 31C presents XRD spectra ONCs of 3 (green) and 3/MWCNT with $C_{MWCNTs}$ 5 wt % (blue).

FIGS. 32A-32D present UV-vis-NIR spectra of ONC/CNT hybrids. FIG. 32A presents UV-vis-NIR spectra of 2/SWCNT, $C_{SWCNTs}$ 40 wt % (Inset: the spectrum of ONCs of 1). FIG. 32B presents UV-vis-NIR spectra of 4/SWCNT, $C_{SWCNTs}$ 40 wt % (Inset: the spectrum of ONCs of 4). FIG. 32C presents UV-vis-NIR spectra of (c) 2/SWCNT, $C_{SWCNT}$ 8 wt %, and FIG. 32D presents UV-vis-NIR spectra of 4/SWCNT, $C_{SWCNT}$ 5 wt %.

FIG. 33A shows cryo-TEM image of 2/SWCNT, inset shows SWCNTs interacting with the ONC of 2.

FIG. 33C shows cryo-TEM image of 4/MWCNT, inset shows well-dispersed MWCNTs.

FIG. 33E shows cryo-TEM image of 4/SWCNT, inset shows exfoliated SWCNTs (indicated by arrows). FIGS. 33B, 33D and 33F respectively, show crystalline order; Insets: Fast Fourier Transform (FFT) of the marked areas of the ONCs, indicating crystallinity.

FIGS. 34A and 34B show two different views of the DFT-optimized structure.

FIG. 34C presents NCI plot, the noncovalent interactions are depicted as a green surface.

FIG. 34D presents electron density difference plot, plotted at ±0.0012 a.u., where electron density moves from yellow (positive) to blue (negative) regions.

FIG. 35A: SEM images of 2/SWCNT, $C_{CNT}$ 8 wt %. FIG. 35B: SEM images of 2/SWCNT, $C_{CNT}$ 40 wt %.

FIG. 35C: SEM images of 2/MWCNT, $C_{CNT}$ 5 wt %. FIG. 35D: SEM images of 2/MWCNT, $C_{CNT}$ 67 wt %. FIG. 35E: SEM images of 4/MWCNT, $C_{CNT}$ 5 wt %. FIG. 35F: SEM images of 4/MWCNT, $C_{CNT}$ 65 wt %. FIG. 35G: SEM images of 4/SWCNT, $C_{CNT}$ 5 wt %. FIG. 35H: SEM images of 4/SWCNT, $C_{CNT}$ 40 wt %. FIG. 35I: SEM images of 3/MWCNT, $C_{CNT}$ 5 wt %. FIG. 35J: SEM images of 3/MWCNT, $C_{CNT}$ 60 wt %. Insets: higher magnification images and FIGS. 35A-35D—left side, photographs of the free-standing films.

FIG. 36A: DSC of 2/SWCNTs. FIG. 36B: DSC of 2/MWCNTs.

FIG. 36C: DSC analysis of 4/MWCNTs. FIG. 36D: DSC of 3/MWCNTs. The DSC analyses were under nitrogen done with a heat/cool/heat cycle.

FIG. 37A: 2/SWCNT and FIG. 37B: 1/MWCNT.

FIG. 38A shows electrical conductivity (o) of 2/SWCNT (blue) and 2/MWCNT (red) versus the CNT concentration. The SWCNT hybrids were measured under an inert atmosphere, while those of MWCNT were measured under ambient conditions. FIG. 38B shows electrical conductivity versus CNT content of 2/SWCNT (blue) and 2/MWCNT (red). FIG. 38C shows electrical conductivity versus CNT content of 3/MWCNT. FIG. 38D shows representative IV curve of 2/MWCNT films with $C_{MWCNT}$ 5 wt % (blue) and $C_{MWCNT}$ 67 wt % (red).

FIG. 40A presents pristine ONCs of 2 vs 2/SWCNT. FIG. 40B presents pristine ONCs of 2 vs 2/MWCNT. FIG. 40C presents pristine ONCs of 4 vs 4/SWCNT. FIG. 40D presents pristine ONCs of 4 vs 4/MWCNT.

FIG. 41A presents florescence micrograph of 2/SWCNT, $C_{CNT}$ 40 wt % (left) versus ONCs of 2 (right), and FIG. 41A presents florescence micrograph of 2/SWCNT, $C_{CNT}$ 8 wt % (left) versus ONCs of 2 (right).

FIG. 45A presents DPV voltammogram of pristine 2. FIG. 45B presents DPV voltammogram of buckypaper prepared from 2/SWCNTs. FIG. 45C presents DPV voltammogram of buckypaper prepared from 2/MWCNTs. FIG. 45D presents DPV voltammogram of pristine 4. FIG. 45E presents DPV voltammogram of buckypaper prepared from 4/SWCNTs. FIG. 45F presents DPV voltammogram of buckypaper prepared from 4/MWCNTs. FIG. 45G presents DPV voltammogram of pristine 3. FIG. 45H presents DPV voltammogram of buckypaper prepared from 3/MWCNTs.

FIG. 46A presents Micro-Raman spectra of the radial breathing modes (RBM) and the G-bands of pristine SWCNTs (green), buckypaper prepared from 2/SWCNT (red), and buckypaper prepared from 4/SWCNT (blue).

FIG. 46B presents Micro-Raman spectra of the D- and G-bands of pristine MWCNTs (green), buckypaper prepared from 2/MWCNT (red), and buckypaper prepared from 4/MWCNT (blue). Inset: the G-band. All of the spectra were recorded with excitation at 785 nm and are baseline-corrected and normalized with respect to the G-band.

FIG. 50A: film image and FIG. 50B: film cross-section.

Figure 1:
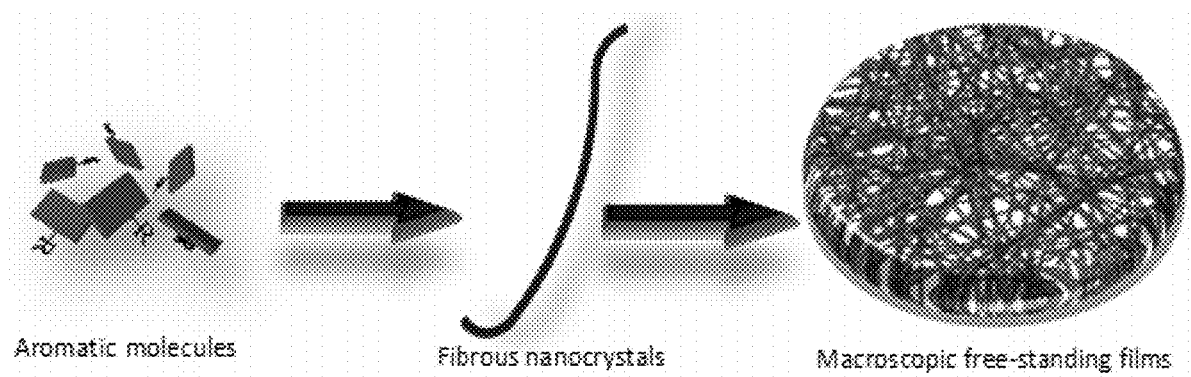
FIG. 1 depicts a general scheme for the fabrication of a free-standing film of the current invention.
Figure 2:
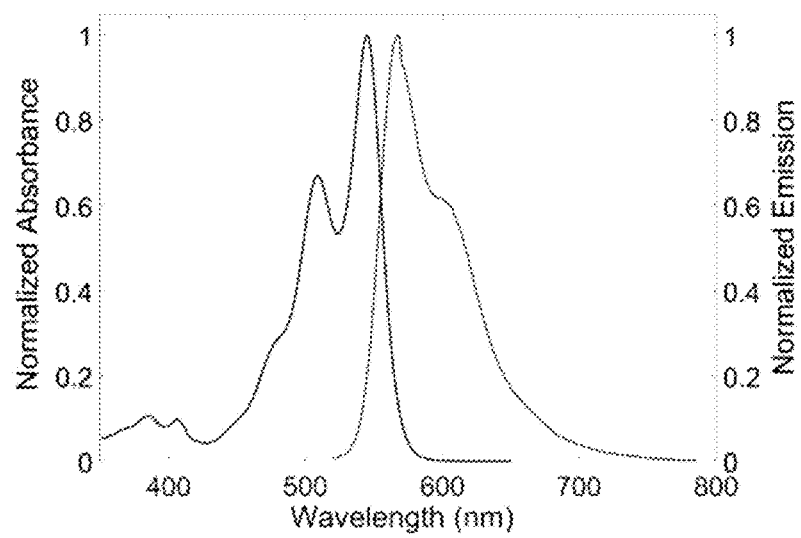
FIG. 2 depicts normalized absorbance (black trace) and normalized emission of a $1 \times 10^{-5}$M solution of 1 in THF.

It will be appreciated that for simplicity and clarity of illustration, elements shown in the Figures have not necessarily been drawn to scale. For example, the dimensions of some of the elements may be exaggerated relative to other elements for clarity. Further, where considered appropriate, reference numerals may be repeated among the Figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Free-Standing Films

In one embodiment, this invention provides a free-standing film comprising an aromatic material. In another embodiment, the aromatic material is nanocrystalline. In another embodiment, the aromatic material is small aromatic molecules (typically below 1000 Da). In another embodiment, the aromatic material is a dimer or trimer of the small aromatic molecule. In another embodiment, the free-standing film is a hybrid film, which comprises an aromatic material and a reinforcement material. In another embodiment, the invention further provides a composition which is a hybrid composition comprising an organic nanocrystals of an aromatic material and a reinforcement material. In another embodiment, the composition comprises a nanocrystalline aromatic material and two different reinforcement materials. In another embodiment, the composition comprises a nanocrystalline aromatic material and three different reinforcement materials.

In some embodiments, the invention provides a free-standing film comprising organic nanocrystals (ONC) of an aromatic material. In another embodiment, the invention provides a free-standing film comprising a reinforcement material and organic nanocrystals (ONC) of an aromatic material. In another embodiment, the invention provides a free-standing film comprising an aromatic material and a reinforcement material, wherein the free-standing film is found in any known morphology as known in the art. In one embodiment, the current invention provides a microfiltration or an ultrafiltration membrane comprising the free-standing film of the current invention.

The term "free-standing film" or "self-standing film" are used interchangeably to describe a film which is mechanically stable without support of a substrate. In some embodiments, the free-standing film of the current invention comprises an aromatic material. In another embodiment, the free-standing film is a hybrid film which comprises an aromatic material and a reinforcement material.

In some embodiments, the aromatic material is an aromatic small molecule having a molecular weight of less than 1000 Da. In other embodiments, the aromatic material is a dimer or a trimer of the aromatic small molecule, which optionally comprises at least one linker, which links between two adjacent aromatic small molecules. In other embodiments the aromatic material is a dimer of perylene diimide derivatives connected via an ethynyl or a bipyridyl linker. In other embodiments the aromatic material is a trimer of perylene diimide derivatives connected via two ethynyl or bipyridyl linkers. In other embodiments, the aromatic material is a mixture of different aromatic small molecules.

In other embodiments, the aromatic material has a molecular weight of less than 1000 Da. In other embodiments, the aromatic material has a molecular weight of less than 800 Da. In other embodiments, the aromatic material has a molecular weight of less than 700 Da. In other embodiments, the aromatic material has a molecular weight of less than 600 Da. In other embodiments, the aromatic material has a molecular weight of less than 500 Da. In other embodiments, the aromatic material has a molecular weight of less than 400 Da. In other embodiments, the aromatic material has a molecular weight of between 100-1000 Da. In other embodiments the aromatic material has a molecular weight of between 200-800 Da. In other embodiments, the aromatic material has a molecular weight of between 300-600 Da. In other embodiments, the aromatic material has a molecular weight of between 100-600 Da. In other embodiments, the aromatic material has a molecular weight of between 500-1000 Da. In other embodiments, the aromatic material has a molecular weight of between 600-800 Da. In other embodiments, the aromatic material may have a molecular weight larger than 1000 Da, when the aromatic material is a dimer or trimer of an aromatic small molecule.

In various embodiments, the aromatic material is in crystalline form. In other embodiment, the aromatic material is nanocrystalline. In other embodiments, the aromatic material forms nanocrystalline fibers. In other embodiments, the aromatic material comprises perylene diimide, naphthalene diimide, a phthalocyanine, derivatives thereof, dimers thereof, trimers thereof, or any mixture thereof.

In other embodiments, a derivative of perylene diimide, naphthalene diimide or phthalocyanine refers to perylene diimide, naphthalene diimide or phthalocyanine substituted with one or more substituents selected from $(C_7-C_{10})$alkyl, $(C_7-C_{10})$haloalkyl, $(C_3-C_8)$cycloalkyl, aryl or heteroaryl (wherein said alkyl, haloalkyl, cycloalkyl, aryl or heteroaryl groups are optionally substituted), OH, $OR^4$, $OCH_3$, $CF_3$, halide, F, $COR^4$, COCl, $COOCOR^4$, COOH, $COOR^4$, $OCOR^4$, $OCONHR^4$, $NHCOOR^4$, $NHCONHR^4$, $OCOOR^4$, CN, $CON(R^4)_2$, $SR^4$, $SO_2R^4$, $SO_2M$, $SOR^4$ $SO_3H$, $SO_3M$ $SO_2NH_2$, $SO_2NH(R^4)$, $SO_2N(R^4)_2$, $NH_2$, $NH(R^4)$, $N(R^4)_2$, $CONH_2$, $CONH(R^4)$, $CON(R^4)_2$, CO(N-heterocycle), C(O) $(C_7-C_{10})$alkyl, $NO_2$, CN, cyanate, isocyanate, thiocyanate, isothiocyanate, mesylate, tosylate, triflate, $PO(OH)_2$ or $OPO(OH)_2$, wherein $R^4$ is H, $(C_7-C_{10})$alkyl, $(C_7-C_{10})$haloalkyl, $(C_3-C_8)$cycloalkyl, aryl or heteroaryl, (wherein said alkyl, haloalkyl, cycloalkyl, aryl or heteroaryl groups are optionally substituted).

In some embodiments, the perylene diimide derivative is represented by the structure of formula IA or IB:

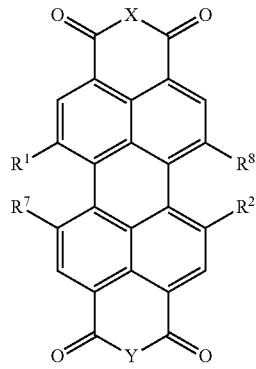

IA

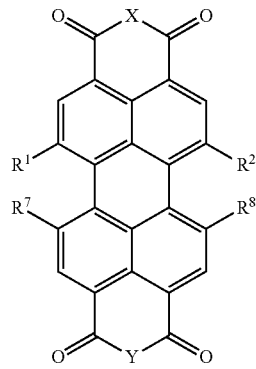

IB wherein,

X is $—NR^3$;

Y is $—NR^4$;

$R^1$ is H, $R^5$, $(C_1-C_{10})$alkyl, $(C_1-C_{10})$haloalkyl, $(C_3-C_8)$ cycloalkyl, aryl or heteroaryl, wherein said alkyl, haloalkyl, cycloalkyl, aryl or heteroaryl groups are optionally substituted; or $R^1$ is joined together with $R^7$ to form a substituted or unsubstituted five or six membered ring, or a substituted or unsubstituted five or six membered fused ring;

$R^2$ is H, $R^5$, $(C_7-C_{10})$alkyl, $(C_7-C_{10})$haloalkyl, $(C_3-C_8)$ cycloalkyl, aryl or heteroaryl, wherein said alkyl, haloalkyl, cycloalkyl, aryl or heteroaryl groups are optionally substituted; or $R^2$ is joined together with $R^8$ to form a substituted or unsubstituted five or six membered ring, or a substituted or unsubstituted five or six membered fused ring;

$R^3$ and $R^4$ are each independently H, $(C_7-C_{10})$alkyl, $(C_7-C_{10})$haloalkyl, $(C_3-C_8)$cycloalkyl, aryl or heteroaryl, wherein said alkyl, haloalkyl, cycloalkyl, aryl or heteroaryl groups are optionally substituted;

$R^5$ is $OR^6$, $OCH_3$, $CF_3$, halide, $COR^6$, COCl, $COOCOR^6$, $COOR^6$, $OCOR^6$, $OCONHR^6$, $NHCOOR^6$, $NHCONHR^6$, $OCOOR^6$, $CON(R^6)_2$, $SR^6$, $SO_2R^6$, $SO_2M$, $SOR^6$, $SO_3H$, $SO_3M$, $SO_2NH_2$, $SO_2NH(R^6)$, $SO_2N(R^6)_2$, $NH_2$, $NH(R^6)$, $N(R^6)_2$, $CONH_2$, $CONH(R^6)$, $CON(R^6)_2$, CO(N-heterocycle), $NO_2$, OH, CN, cyanate, isocyanate, thiocyanate, isothiocyanate, mesylate, tosylate, triflate, $PO(OH)_2$ or $OPO(OH)_2$; wherein M is a monovalent cation;

R[6] is H, (C$_7$-C$_{10}$)alkyl, (C$_7$-C$_{10}$)haloalkyl, (C$_3$-C$_8$)cycloalkyl, aryl or heteroaryl, wherein said alkyl, haloalkyl, cycloalkyl, aryl or heteroaryl groups are optionally substituted;

R[7] is H or is joined together with R[1] to form a substituted or unsubstituted five or six membered ring, or a substituted or unsubstituted five or six membered fused ring; and R[8] is H or is joined together with R[2] to form a substituted or unsubstituted five or six membered ring, or a substituted or unsubstituted five or six membered fused ring.

In some embodiments, the perylene diimide derivative is represented by the structure of formula II:

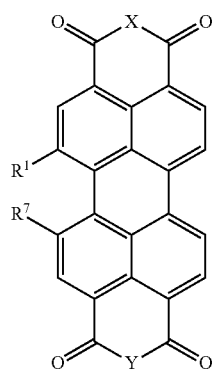

II wherein,

X is —NR[3];

Y is —NR[4];

R[1] is H, R[5], (C$_1$-C$_{10}$)alkyl, (C$_1$-C$_{10}$)haloalkyl, (C$_3$-C$_8$) cycloalkyl, aryl or heteroaryl, wherein said alkyl, haloalkyl, cycloalkyl, aryl or heteroaryl groups are optionally substituted; or R[1] is joined together with R[7] to form a substituted or unsubstituted five or six membered ring, or a substituted or unsubstituted five or six membered fused ring;

R[3] and R[4] are each independently H, (C$_7$-C$_{10}$)alkyl, (C$_7$-C$_{10}$)haloalkyl, (C$_3$-C$_8$)cycloalkyl, aryl or heteroaryl, wherein said alkyl, haloalkyl, cycloalkyl, aryl or heteroaryl groups are optionally substituted;

R[5] is OR[6], OCH$_3$, CF$_3$, halide, COR[6], COCl, COOCOR[6], COOR[6], OCOR[6], OCONHR[6], NHCOOR[6], NHCONHR[6], OCOOR[6], CON(R[6])$_2$, SR[6], SO$_2$R[6], SO$_2$M, SOR[6] SO$_3$H, SO$_3$M, SO$_2$NH$_2$, SO$_2$NH(R[6]), SO$_2$N(R[6])$_2$, NH$_2$, NH(R[6]), N(R[6])$_2$, CONH$_2$, CONH(R[6]), CON(R[6])$_2$, CO(N-heterocycle), NO$_2$, OH, CN, cyanate, isocyanate, thiocyanate, isothiocyanate, mesylate, tosylate, triflate, PO(OH)$_2$ or OPO(OH)$_2$; wherein M is a monovalent cation;

R[6] is H, (C$_1$-C$_{10}$)alkyl, (C$_7$-C$_{10}$)haloalkyl, (C$_3$-C$_8$)cycloalkyl, aryl or heteroaryl, wherein said alkyl, haloalkyl, cycloalkyl, aryl or heteroaryl groups are optionally substituted; and R[7] is H or joined together with R[1] to form a substituted or unsubstituted five or six membered ring, or a substituted or unsubstituted five or six membered fused ring.

In some embodiments, the perylene diimide derivative is represented by the structure of formula III:

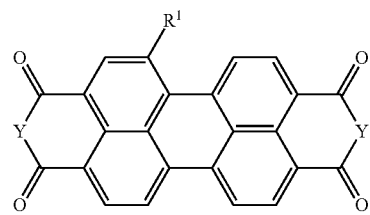

III wherein,

X is —NR[3];

Y is —NR[4];

R[1] is H, (C$_7$-C$_{10}$)alkyl, (C$_7$-C$_{10}$)haloalkyl, (C$_3$-C$_8$)cycloalkyl, aryl or heteroaryl, wherein said alkyl, haloalkyl, cycloalkyl, aryl or heteroaryl groups are optionally substituted or R[5];

R[3] and R[4] are each independently H, (C$_7$-C$_{10}$)alkyl, (C$_7$-C$_{10}$)haloalkyl, (C$_3$-C$_8$)cycloalkyl, aryl or heteroaryl, wherein said alkyl, haloalkyl, cycloalkyl, aryl or heteroaryl groups are optionally substituted;

R[5] is OR[6], OCH$_3$, CF$_3$, halide, COR[6], COCl, COOCOR[6], COOR[6], OCOR[6], OCONHR[6], NHCOOR[6], NHCONHR[6], OCOOR[6], CN, CON(R[6])$_2$, SR[6], SO$_2$R[6], SO$_2$M, SOR[6] SO$_3$H, SO$_3$M SO$_2$NH$_2$, SO$_2$NH(R[6]), SO$_2$N(R[6])$_2$, NH$_2$, NH(R[6]), N(R[6])$_2$, CONH$_2$, CONH(R[6]), CON(R[6])$_2$, CO(N-heterocycle), C(O)(C$_1$-C$_{10}$)alkyl, NO$_2$, CN, cyanate, isocyanate, thiocyanate, isothiocyanate, mesylate, tosylate, triflate, PO(OH)$_2$ or OPO(OH)$_2$;

R[6] is H, (C$_1$-C$_{10}$)alkyl, (C$_7$-C$_{10}$)haloalkyl, (C$_3$-C$_8$)cycloalkyl, aryl or heteroaryl, wherein said alkyl, haloalkyl, cycloalkyl, aryl or heteroaryl groups are optionally substituted; and M is a monovalent cation.

In other embodiments, the perylene diimide derivative is represented by the structure of 1', 2a', 2b', 3' or 4':

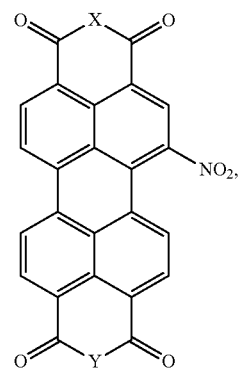

1'

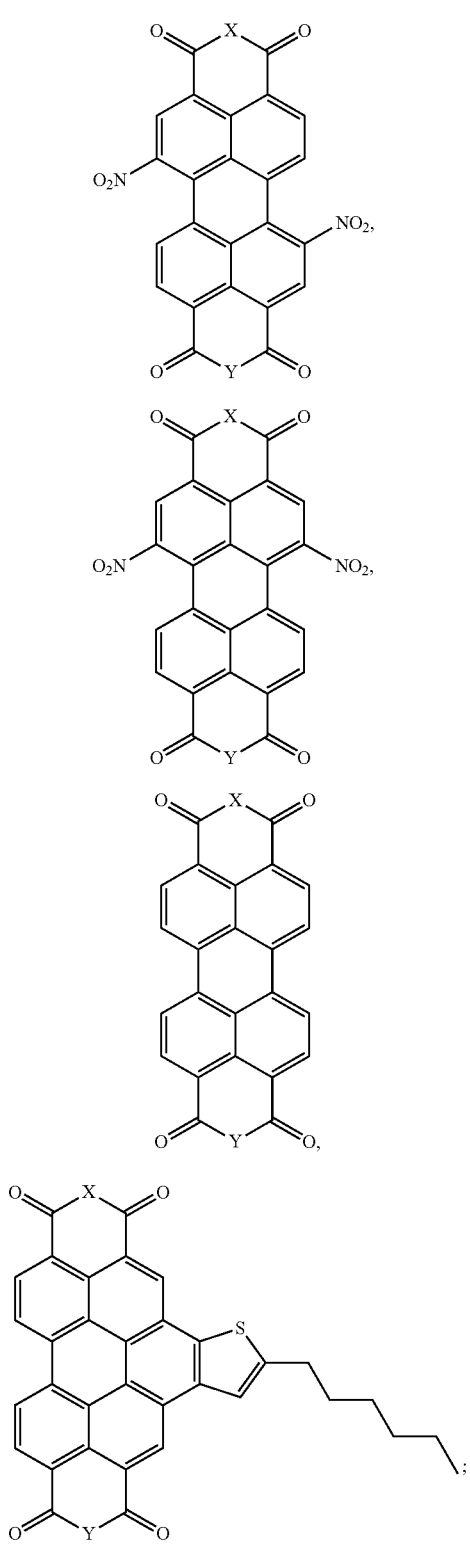

wherein;
X is —NR³;
Y is —NR⁴; and
R³ and R⁴ are each independently H, $(C_7-C_{10})$alkyl, $(C_7-C_{10})$haloalkyl, $(C_3-C_8)$cycloalkyl, aryl or heteroaryl, wherein said alkyl, haloalkyl, cycloalkyl, aryl or heteroaryl groups are optionally substituted.

In some embodiments, the free-standing film of this invention comprises one or more different perylene diimide derivatives. In other embodiments the free-standing film comprises 2, 3, 4, 5 different perylene diimide derivatives. Each represents a separate embodiment of this invention.

In some embodiments, $R^1$ is H, $(C_7-C_{10})$alkyl, $(C_7-C_{10})$haloalkyl, $(C_3-C_8)$cycloalkyl, aryl or heteroaryl, $OR^6$, $OCH_3$, $CF_3$, halide, F, $COR^6$, COCl, $COOCOR^6$, $COOR^6$, $OCOR^6$, $OCONHR^6$, $NHCOOR^6$, $NHCONHR^6$, $OCOOR^6$, CN, $CON(R^6)_2$, $SR^6$, $SO_2R^6$, $SO_2M$, $SOR^6$, $SO_3H$, $SO_3M$, $SO_2NH_2$, $SO_2NH(R^6)$, $SO_2N(R^6)_2$, $NH_2$, $NH(R^6)$, $N(R^6)_2$, $CONH_2$, $CONH(R^6)$, $CON(R^6)_2$, CO(N-heterocycle), $C(O)(C_1-C_{10})$alkyl, $NO_2$, CN, cyanate, isocyanate, thiocyanate, isothiocyanate, mesylate, tosylate, triflate, $PO(OH)_2$, $OPO(OH)_2$ or $R^1$ is joined together with $R^7$ to form a substituted or unsubstituted five or six membered ring, or a substituted or unsubstituted five or six membered fused ring; wherein said alkyl, haloalkyl, cycloalkyl, aryl or heteroaryl groups are optionally substituted; and each represents a separate embodiment of this invention. In other embodiments $R^1$ is H. In other embodiments $R^1$ is $NO_2$. In other embodiments $R^1$ is OMe.

In some embodiments, $R^2$ is H, $(C_1-C_{10})$alkyl, $(C_1-C_{10})$haloalkyl, $(C_3-C_8)$cycloalkyl, aryl or heteroaryl, $OR^6$, $OCH_3$, $CF_3$, halide, F, $COR^6$, COCl, $COOCOR^6$, $COOR^6$, $OCOR^6$, $OCONHR^6$, $NHCOOR^6$, $NHCONHR^6$, $OCOOR^6$, CN, $CON(R^6)_2$, $SR^6$, $SO_2R^6$, $SO_2M$, $SOR^6$, $SO_3H$, $SO_3M$, $SO_2NH_2$, $SO_2NH(R^6)$, $SO_2N(R^6)_2$, $NH_2$, $NH(R^6)$, $N(R^6)_2$, $CONH_2$, $CONH(R^6)$, $CON(R^6)_2$, CO(N-heterocycle), $C(O)(C_7-C_{10})$alkyl, $NO_2$, CN, cyanate, isocyanate, thiocyanate, isothiocyanate, mesylate, tosylate, triflate, $PO(OH)_2$, $OPO(OH)_2$ or $R^2$ is joined together with $R^8$ to form a substituted or unsubstituted five or six membered ring, or a substituted or unsubstituted five or six membered fused ring; wherein said alkyl, haloalkyl, cycloalkyl, aryl or heteroaryl groups are optionally substituted; and each represents a separate embodiment of this invention. In other embodiments $R^2$ is H. In other embodiments $R^2$ is $NO_2$. In other embodiments $R^2$ is OMe.

In some embodiments $R^3$ and $R^4$ are each independently H, $(C_7-C_{10})$alkyl, $(C_1-C_{10})$haloalkyl, $(C_3-C_8)$cycloalkyl, aryl or heteroaryl, wherein said alkyl, haloalkyl, cycloalkyl, aryl or heteroaryl groups are optionally substituted. Each represents a separate embodiment of this invention.

In some embodiments, $R^1$, $R^2$, $R^3$, $R^4$ and $R^6$ are each independently $(C_1-C_{10})$alkyl, $(C_7-C_{10})$haloalkyl, $(C_3-C_8)$cycloalkyl, aryl or heteroaryl. In other embodiments, $R^1$, $R^2$, $R^3$, $R^4$ and $R^6$ are each independently $(C_7-C_{10})$alkyl. In other embodiments, the $(C_1-C_{10})$alkyl is methyl, ethyl, propyl, isopropyl, butyl, t-butyl, pentyl, neopentyl, 3-pentyl, sec-pentyl, tert-pentyl, iso-pentyl, hexyl, or heptyl, each represents a separate embodiment of this invention. In other embodiments, $R^1$, $R^2$, $R^3$, $R^4$ and $R^6$ are each independently is $(C_1-C_{10})$haloalkyl. In another embodiment, the $(C_7-C_{10})$haloalkyl is $CF_3$, $CF_2CF_3$, iodomethyl, bromomethyl, bromoethyl, bromopropyl, each represents a separate embodiment of the invention. In other embodiments, $R^1$, $R^2$, $R^3$, $R^4$ and $R^6$ are each independently is $(C_3-C_8)$cycloalkyl. In other embodiments, $(C_3-C_8)$cycloalkyl is cyclopropyl, cyclobutyl, cyclopentyl, cyclohexyl, cycloheptyl; each represents a separate embodiment of this invention. In various embodiments, the alkyl, haloalkyl, cycloalkyl, aryl or heteroaryl of $R^1$, $R^2$, $R^3$, $R^4$ and $R^6$ are further substituted by one or more groups selected from: halide, CN, $CO_2H$, OH, SH, $NH_2$, $NO_2$, $CO_2$—($C_1$-$C_6$ alkyl) or O—($C_1$-$C_6$ alkyl); each represents a separate embodiment of this invention.

In some embodiments, $R^1$, $R^2$ and/or $R^5$ is $OR^6$, $OCH_3$, $CF_3$, halide, F, $COR^6$, COCl, $COOCOR^6$, $COOR^6$, $OCOR^6$, $OCONHR^6$, $NHCOOR^6$, $NHCONHR^6$, $OCOOR^6$, CN, $CON(R^6)_2$, $SR^6$, $SO_2R^6$, $SO_2M$, $SOR^6$ $SO_3H$, $SO_3M$ $SO_2NH_2$, $SO_2NH(R^6)$, $SO_2N(R^6)_2$, $NH_2$, $NH(R^6)$, $N(R^6)_2$, $CONH_2$, $CONH(R^6)$, $CON(R^6)_2$, CO(N-heterocycle), C(O) ($C_1$-$C_{10}$)alkyl, $NO_2$, CN, cyanate, isocyanate, thiocyanate, isothiocyanate, mesylate, tosylate, triflate, $PO(OH)_2$ or $OPO(OH)_2$; wherein M is a monovalent cation; each represents a separate embodiment of this invention.

In other embodiments, $R^1$, $R^2$ and/or $R^5$ is $OR^6$. In other embodiments, $OR^6$ is methoxy, ethoxy, propoxy, isopropoxy, butoxy, t-butoxy, each represents a separate embodiment of this invention. In other embodiments, $R^1$, $R^2$ and/or $R^5$ is $OCH_3$. In other embodiments, $R^1$, $R^2$ and/or $R^5$ is $CF_3$. In other embodiments $R^1$, $R^2$ and/or $R^5$ is halide. In other embodiments, $R^1$, $R^2$ and/or $R^5$ is F.

In other embodiments, $R^1$, $R^2$ and/or $R^5$ is $COR^6$. In other embodiments, $COR^6$ is $CO(($C_1$-$C_{10}$)alkyl)$. In other embodiments, $CO(($C_1$-$C_{10}$)alkyl)$ is $COCH_3$, $COCH_2CH_3$, $COCH_2CH_2CH_3$, $COCH(CH_3)_2$, $COCH_2CH_2CH_2CH_3$, $COC(CH_3)_3$, $COCH_2CH_2CH_2CH_2CH_3$, $COCH_2C(CH_3)_3$, $COCH(CH_2CH_3)_2$, $COCH(CH_3)(CH_2CH_2CH_3)$, $COCH(CH_3)_2(CH_2CH_3)$, $COCH_2CH_2CH(CH_3)_2$, $COCH_2CH_2CH_2CH_2CH_2CH_3$ or $COCH_2CH_2CH_2CH_2CH_2CH_2CH_3$, each represents a separate embodiment of this invention. In other embodiments, $COR^6$ is $CO(($C_1$-$C_{10}$)haloalkyl)$. In other embodiments, $CO(($C_1$-$C_{10}$)haloalkyl)$ is $COCF_3$, $COCF_2CF_3$, $COCH_2I$, $COCH_2Br$, $COCH_2CH_2Br$, $COCHBrCH_3$, $COCH_2CH_2CH_2Br$, $COCH_2CHBrCH_3$ or $COCHBrCH_2CH_3$, each represents a separate embodiment of the invention. In other embodiments, $COR^6$ is a $CO(($C_3$-$C_8$)cycloalkyl)$. In other embodiments, $CO(($C_3$-$C_8$)cycloalkyl)$ is CO(cyclobutyl), CO(cyclopentyl) or CO(cyclohexyl), each represents a separate embodiment of the invention. In other embodiments, $COR^4$ is a CO(aryl). In other embodiments, CO(aryl) is CO(phenyl), CO(naphtyl) or CO(perylenyl), each represents a separate embodiment of the invention. In other embodiments, $COR^6$ is a CO(heteroaryl). In other embodiments, CO(heteroaryl) is CO(pyranyl), CO(pyrrolyl), CO(pyrazinyl), CO(pyrimidinyl), CO(pyrazolyl), CO(pyridinyl), CO(furanyl), CO(thiophenyl), CO(thiazolyl), CO(indolyl), CO(imidazolyl), CO(isoxazolyl), each represents a separate embodiment of the invention. In other embodiments, $R^1$, $R^2$ and/or $R^5$ is COCl. In other embodiments, $R^1$, $R^2$ and/or $R^5$ is $COOCOR^4$. In other embodiments, $COOCOR^6$ is $COOCO(($C_1$-$C_{10}$)alkyl)$. In other embodiments, $COOCO(($C_1$-$C_{10}$)alkyl)$ is $COOCOCH_3$, $COOCOCH_2CH_3$, $COOCOCH_2CH_2CH_3$, $COOCOCH(CH_3)_2$, $COOCOCH_2CH_2CH_2CH_3$, $COOCOC(CH_3)_3$, $COOCOCH_2CH_2CH_2CH_2CH_3$, $COOCOCH_2C(CH_3)_3$, $COOCOCH(CH_2CH_3)_2$, $COOCOCH(CH_3)(CH_2CH_3)$, $COOCOCH(CH_3)_2(CH_2CH_3)$, $COOCOCH_2CH_2CH(CH_3)_2$, $COOCOCH_2CH_2CH_2CH_2CH_2CH_3$ or $COOCOCH_2CH_2CH_2CH_2CH_2CH_2CH_3$, each represents a separate embodiment of this invention. In other embodiments, $COOCOR^6$ is $COOCO(($C_1$-$C_{10}$)haloalkyl)$. In other embodiments, $COOCO(($C_1$-$C_{10}$)haloalkyl)$ is $COOCOCF_3$, $COOCOCF_2CF_3$, $COOCOCH_2I$, $COOCOCH_2Br$, $COOCOCH_2CH_2Br$, $COOCOCHBrCH_3$, $COOCOCH_2CH_2CH_2Br$, $COOCOCH_2CHBrCH_3$ or $COOCOCHBrCH_2CH_3$, each represents a separate embodiment of the invention. In other embodiments, $COOCOR^6$ is a $COOCO(($C_3$-$C_8$)cycloalkyl)$. In another embodiment, $COOCO(($C_3$-$C_8$)cycloalkyl)$ is COOCO(cyclobutyl), COOCO(cyclopentyl) or COOCO(cyclohexyl), each represents a separate embodiment of the invention. In other embodiments, $COOCOR^6$ is a COOCO(aryl). In another embodiment, COOCO(aryl) is COOCO(phenyl), COOCO(naphtyl) or COOCO(perylenyl), each represents a separate embodiment of the invention. In other embodiments, $COOCOR^6$ is a COOCO(heteroaryl). In other embodiments, COOCO(heteroaryl) is COOCO(pyranyl), COOCO(pyrrolyl), COOCO(pyrazinyl), COOCO(pyrimidinyl), COOCO(pyrazolyl), COOCO(pyridinyl), COOCO(furanyl), COOCO(thiophenyl), COOCO(thiazolyl), COOCO(indolyl), COOCO(imidazolyl), COOCO(isoxazolyl), each represents a separate embodiment of the invention.

In another embodiment, $R^1$, $R^2$ and/or $R^5$ is $COOR^6$. In other embodiments, $COOR^6$ is $COO(C_1$-$C_{10}$)alkyl. In other embodiments, $COO(C_1$-$C_{10}$)alkyl is $COOCH_3$, $COOCH_2CH_3$, $COOCH_2CH_2CH_3$, $COOCH(CH_3)_2$, $COOCH_2CH_2CH_2CH_3$, $COOC(CH_3)_3$, $COOCH_2CH_2CH_2CH_2CH_3$, $COOCH_2C(CH_3)_3$ $COOCH(CH_2CH_3)_2$, $COOCH(CH_3)(CH_2CH_2CH_3)$ $COOCH(CH_3)_2(CH_2CH_3)$, $COOCH_2CH_2CH(CH_3)_2$, $COOCH_2CH_2CH_2CH_2CH_2CH_3$ or $COOCH_2CH_2CH_2CH_2CH_2CH_2CH_3$, each represents a separate embodiment of this invention. In other embodiments, $COOR^6$ is $COO(C_7$-$C_{10}$)haloalkyl. In other embodiments, $COO(C_1$-$C_{10}$)haloalkyl is $COOCF_3$, $COOCF_2CF_3$, $COOCH_2I$, $COOCH_2Br$, $COOCH_2CH_2Br$, $COOCHBrCH_3$, $COOCH_2CH_2CH_2Br$, $COOCH_2CHBrCH_3$ or $COOCHBrCH_2CH_3$, each represents a separate embodiment of the invention. In other embodiments, $COOR^4$ is a $COO(C_3$-$C_8$)cycloalkyl. In other embodiments, $COO(C_3$-$C_8$)cycloalkyl is COO(cyclobutyl), COO(cyclopentyl) or COO(cyclohexyl), each represents a separate embodiment of the invention. In other embodiments, $COOR^6$ is a OCO(aryl). In other embodiments, COO(aryl) is COO(phenyl), COO(naphtyl) or COO(perylenyl), each represents a separate embodiment of the invention. In another embodiment, $COOR^6$ is a COO(heteroaryl). In other embodiments, COO(heteroaryl) is COO(pyranyl), COO(pyrrolyl), COO(pyrazinyl), COO(pyrimidinyl), COO(pyrazolyl), COO(pyridinyl), COO(furanyl), COO(thiophenyl), COO(thiazolyl), COO(indolyl), COO(imidazolyl), COO(isoxazolyl), each represents a separate embodiment of the invention.

In another embodiment, $R^1$, $R^2$ and/or $R^5$ is $OCOR^6$. In other embodiments, $OCOR^6$ is $OCO(($C_7$-$C_{10}$)alkyl)$. In other embodiments, $OCO(($C_7$-$C_{10}$)alkyl)$ is $OCOCH_3$, $OCOCH_2CH_3$, $OCOCH_2CH_2CH_3$, $OCOCH(CH_3)_2$, $OCOCH_2CH_2CH_2CH_3$, $OCOC(CH_3)_3$, $OCOCH_2CH_2CH_2CH_2CH_3$, $OCOCH_2C(CH_3)_3$, $OCOCH(CH_2CH_3)_2$, $OCOCH(CH_3)(CH_2CH_2CH_3)$, $OCOCH(CH_3)_2(CH_2CH_3)$, $OCOCH_2CH_2CH(CH_3)_2$, $OCOCH_2CH_2CH_2CH_2CH_2CH_3$ or $OCOCH_2CH_2CH_2CH_2CH_2CH_2CH_3$, each represents a separate embodiment of this invention. In other embodiments, $OCOR^6$ is $OCO(($C_1$-$C_{10}$)haloalkyl)$. In other embodiments, $OCO(($C_1$-$C_{10}$)haloalkyl)$ is $OCOCF_3$, $OCOCF_2CF_3$, $OCOCH_2I$, $OCOCH_2Br$, $OCOCH_2CH_2Br$, $OCOCHBrCH_3$, $OCOCH_2CH_2CH_2Br$, $OCOCH_2CHBrCH_3$ or $OCOCHBrCH_2CH_3$, each represents a separate embodiment of the invention. In other embodiments, $OCOR^6$ is a $OCO(($C_3$-$C_8$)cycloalkyl)$. In other embodiments, $OCO(($C_3$-$C_8$)cycloalkyl)$ is OCO(cyclobutyl), OCO(cyclopentyl) or OCO(cyclohexyl), each represents a separate embodiment of the invention. In other embodiments, $OCOR^6$ is a OCO(aryl). In other embodiments, OCO(aryl) is OCO(phenyl), OCO(naphtyl) or OCO(perylenyl), each represents a separate embodiment of the invention. In another embodiment, OCOR$^6$ is a OCO(heteroaryl). In another embodiment, OCO (heteroaryl) is OCO(pyranyl), OCO(pyrrolyl), OCO(pyrazinyl), OCO(pyrimidinyl), OCO(pyrazolyl), OCO(pyridinyl), OCO(furanyl), OCO(thiophenyl), OCO(thiazolyl), OCO(indolyl), OCO(imidazolyl), OCO(isoxazolyl), each represents a separate embodiment of the invention.

In other embodiments, R$^1$, R$^2$ and/or R$^5$ is OCONHR$^6$. In other embodiments, OCONHR$^6$ is OCONH((C$_1$-C$_{10}$)alkyl). In other embodiments, OCONH((C$_1$-C$_{10}$)alkyl) is OCONHCH$_3$, OCONHCH$_2$CH$_3$, OCONHCH$_2$CH$_2$CH$_3$, OCONHCH(CH$_3$)$_2$, OCONHCH$_2$CH$_2$CH$_2$CH$_3$, OCONHC(CH$_3$)$_3$, OCONHCH$_2$CH$_2$CH$_2$CH$_2$CH$_3$, OCONHCH$_2$C(CH$_3$)$_3$, OCONHCH(CH$_2$CH$_3$)$_2$, OCONHCH(CH$_3$)(CH$_2$CH$_2$CH$_3$), OCONHCH(CH$_3$)$_2$(CH$_2$CH$_3$), OCONHCH$_2$CH$_2$CH(CH$_3$)$_2$, OCONHCH$_2$CH$_2$CH$_2$CH$_2$CH$_2$CH$_3$ or OCONHCH$_2$CH$_2$CH$_2$CH$_2$CH$_2$CH$_2$CH$_3$, each represents a separate embodiment of this invention. In other embodiments, OCONHR$^6$ is OCONH((C$_1$-C$_{10}$)haloalkyl). In other embodiments, OCONH((C$_1$-C$_{10}$)haloalkyl) is OCONHCF$_3$, OCONHCF$_2$CF$_3$, OCONHCH$_2$I, OCONHCH$_2$Br, OCONHCH$_2$CH$_2$Br, OCONHCHBrCH$_3$, OCONHCH$_2$CH$_2$CH$_2$Br, OCONHCH$_2$CHBrCH$_3$ or OCONHCHBrCH$_2$CH$_3$, each represents a separate embodiment of the invention. In other embodiments, OCONHR$^6$ is a OCONH((C$_3$-C$_8$)cycloalkyl). In other embodiments, OCONH((C$_3$-C$_8$)cycloalkyl) is OCONH(cyclobutyl), OCONH(cyclopentyl) or OCONH (cyclohexyl), each represents a separate embodiment of the invention. In other embodiment, OCONHR$^6$ is a OCONH(aryl). In other embodiments, OCONH(aryl) is OCONH(phenyl), OCONH(naphtyl) or OCONH(perylenyl), each represents a separate embodiment of the invention. In other embodiments, OCONHR$^6$ is a OCONH (heteroaryl). In other embodiments, OCONH(heteroaryl) is OCONH(pyranyl), OCONH(pyrrolyl), OCONH(pyrazinyl), OCONH(pyrimidinyl), OCONH(pyrazolyl), OCONH(pyridinyl), OCONH(furanyl), OCONH(thiophenyl), OCONH(thiazolyl), OCONH(indolyl), OCONH(imidazolyl), OCONH(isoxazolyl), each represents a separate embodiment of the invention.

In other embodiment, R$^1$, R$^2$ and/or R$^5$ is NHCOOR$^6$. In other embodiments, NHCOOR$^6$ is NHCOO((C$_7$-C$_{10}$)alkyl). In other embodiments, NHCOO((C$_7$-C$_{10}$)alkyl) is NHCOOCH$_3$, NHCOOCH$_2$CH$_3$, NHCOOCH$_2$CH$_2$CH$_3$, NHCOOCH(CH$_3$)$_2$, NHCOOCH$_2$CH$_2$CH$_2$CH$_3$, NHCOOC(CH$_3$)$_3$, NHCOOCH$_2$CH$_2$CH$_2$CH$_2$CH$_3$, NHCOOCH$_2$C(CH$_3$)$_3$, NHCOOCH(CH$_2$CH$_3$)$_2$, NHCOOCH(CH$_3$)(CH$_2$CH$_2$CH$_3$), NHCOOCH(CH$_3$)$_2$(CH$_2$CH$_3$), NHCOOCH$_2$CH$_2$CH(CH$_3$)$_2$, NHCOOCH$_2$CH$_2$CH$_2$CH$_2$CH$_2$CH$_3$ or NHCOOCH$_2$CH$_2$CH$_2$CH$_2$CH$_2$CH$_2$CH$_3$, each represents a separate embodiment of this invention. In other embodiments, NHCOOR$^6$ is NHCOO((C$_7$-C$_{10}$)haloalkyl). In other embodiments, NHCOO((C$_1$-C$_{10}$)haloalkyl) is NHCOOCF$_3$, NHCOOCF$_2$CF$_3$, NHCOOCH$_2$I, NHCOOCH$_2$Br, NHCOOCH$_2$CH$_2$Br, NHCOOCHBrCH$_3$, NHCOOCH$_2$CH$_2$CH$_2$Br, NHCOOCH$_2$CHBrCH$_3$ or NHCOOCHBrCH$_2$CH$_3$, each represents a separate embodiment of the invention. In other embodiments, NHCOOR$^6$ is a NHCOO((C$_3$-C$_8$)cycloalkyl). In another embodiment, NHCOO((C$_3$-C$_8$)cycloalkyl) is NHCOO(cyclobutyl), NHCOO(cyclopentyl) or NHCOO(cyclohexyl), each represents a separate embodiment of the invention. In other embodiments, NHCOOR$^6$ is a NHCOO(aryl). In other embodiments, NHCOO(aryl) is NHCOO(phenyl), NHCOO(naphtyl) or NHCOO(perylenyl), each represents a separate embodiment of the invention. In other embodiments, NHCOOR$^6$ is a NHCOO(heteroaryl). In other embodiments, NHCOO(heteroaryl) is NHCOO(pyranyl), NHCOO(pyrrolyl), NHCOO(pyrazinyl), NHCOO(pyrimidinyl), NHCOO(pyrazolyl), NHCOO(pyridinyl), NHCOO (furanyl), NHCOO(thiophenyl), NHCOO(thiazolyl), NHCOO(indolyl), NHCOO(imidazolyl), NHCOO(isoxazolyl), each represents a separate embodiment of the invention.

In another embodiment, R$^1$, R$^2$ and/or R$^5$ is NHCONHR$^6$. In other embodiments, NHCONHR$^6$ is NHCONH((C$_7$-C$_{10}$) alkyl). In other embodiments, NHCONH((C$_7$-C$_{10}$)alkyl) is NHCONHCH$_3$, NHCONHCH$_2$CH$_3$, NHCONHCH$_2$CH$_2$CH$_3$, NHCONHCH(CH$_3$)$_2$, NHCONHCH$_2$CH$_2$CH$_2$CH$_3$, NHCONHC(CH$_3$)$_3$, NHCONHCH$_2$CH$_2$CH$_2$CH$_2$CH$_3$, NHCONHCH$_2$C(CH$_3$)$_3$, NHCONHCH(CH$_2$CH$_3$)$_2$, NHCONHCH(CH$_3$)(CH$_2$CH$_2$CH$_3$) NHCONHCH(CH$_3$)$_2$(CH$_2$CH$_3$), NHCONHCH$_2$CH$_2$CH(CH$_3$)$_2$, NHCONHCH$_2$CH$_2$CH$_2$CH$_2$CH$_2$CH$_3$ or NHCONHCH$_2$CH$_2$CH$_2$CH$_2$CH$_2$CH$_2$CH$_3$, each represents a separate embodiment of this invention. In other embodiments, NHCONHR$^6$ is NHCONH((C$_1$-C$_{10}$)haloalkyl). In other embodiments, NHCONH((C$_1$-C$_{10}$)haloalkyl) is NHCONHCF$_3$, NHCONHCF$_2$CF$_3$, NHCONHCH$_2$I, NHCONHCH$_2$Br, NHCONHCH$_2$CH$_2$Br, NHCONHCHBrCH$_3$, NHCONHCH$_2$CH$_2$CH$_2$Br, NHCONHCH$_2$CHBrCH$_3$ or NHCONHCHBrCH$_2$CH$_3$, each represents a separate embodiment of the invention. In other embodiments, NHCONHR$^6$ is a NHCONH((C$_3$-C$_8$)cycloalkyl). In other embodiments, NHCONH((C$_3$-C$_8$)cycloalkyl) is NHCONH(cyclobutyl), NHCONH(cyclopentyl) or NHCONH (cyclohexyl), each represents a separate embodiment of the invention. In other embodiments, NHCONHR$^4$ is a NHCONH(aryl). In other embodiments, NHCONH(aryl) is NHCONH(phenyl), NHCONH(naphtyl) or NHCONH (perylenyl), each represents a separate embodiment of the invention. In other embodiments, NHCONHR$^6$ is a NHCONH (heteroaryl). In other embodiments, NHCONH(heteroaryl) is NHCONH(pyranyl), NHCONH(pyrrolyl), NHCONH(pyrazinyl), NHCONH(pyrimidinyl), NHCONH(pyrazolyl), NHCONH(pyridinyl), NHCONH (furanyl), NHCONH(thiophenyl), NHCONH(thiazolyl), NHCONH(indolyl), NHCONH(imidazolyl), NHCONH (isoxazolyl), each represents a separate embodiment of the invention.

In another embodiment, R$^1$, R$^2$ and/or R$^5$ is OCOOR$^6$. In other embodiments, OCOOR$^6$ is OCOO((C$_7$-C$_{10}$)alkyl). In other embodiments, OCOO((C$_1$-C$_{10}$)alkyl) is OCOOCH$_3$, OCOOCH$_2$CH$_3$, OCOOCH$_2$CH$_2$CH$_3$, OCOOCH(CH$_3$)$_2$, OCOOCH$_2$CH$_2$CH$_2$CH$_3$, OCOOC(CH$_3$)$_3$, OCOOCH$_2$CH$_2$CH$_2$CH$_2$CH$_3$, OCOOCH$_2$C(CH$_3$)$_3$, OCOOCH(CH$_2$CH$_3$)$_2$, OCOOCH(CH$_3$)(CH$_2$CH$_2$CH$_3$) OCOOCH(CH$_3$)$_2$(CH$_2$CH$_3$), OCOOCH$_2$CH$_2$CH(CH$_3$)$_2$, OCOOCH$_2$CH$_2$CH$_2$CH$_2$CH$_2$CH$_3$ or OCOOCH$_2$CH$_2$CH$_2$CH$_2$CH$_2$CH$_2$CH$_3$, each represents a separate embodiment of this invention. In other embodiments, OCOOR$^6$ is OCOO((C$_1$-C$_{10}$)haloalkyl). In other embodiments, OCOO((C$_1$-C$_{10}$)haloalkyl) is OCOOCF$_3$, OCOOCF$_2$CF$_3$, OCOOCH$_2$I, OCOOCH$_2$Br, OCOOCH$_2$CH$_2$Br, OCOOCHBrCH$_3$, OCOOCH$_2$CH$_2$CH$_2$Br, OCOOCH$_2$CHBrCH$_3$ or OCOOCHBrCH$_2$CH$_3$, each represents a separate embodiment of the invention. In other embodiments, OCOOR$^6$ is a OCOO((C$_3$-C$_8$)cycloalkyl). In other embodiments, OCOO((C$_3$-C$_8$)cycloalkyl) is OCOO(cyclobutyl), OCOO(cyclopentyl) or OCOO(cyclohexyl), each represents a separate embodiment of the invention. In another embodiment, OCOOR$^6$ is a OCOO(aryl). In other embodiments, OCOO (aryl) is OCOO(phenyl), OCOO(naphtyl) or OCOO(perylenyl), each represents a separate embodiment of the invention. In other embodiments, OCOOR$^6$ is a OCOO (heteroaryl). In another embodiment, OCOO(heteroaryl) is OCOO(pyranyl), OCOO(pyrrolyl), OCOO(pyrazinyl), OCOO(pyrimidinyl), OCOO(pyrazolyl), OCOO(pyridinyl), OCOO(furanyl), OCOO(thiophenyl), OCOO(thiazolyl), OCOO(indolyl), OCOO(imidazolyl), OCOO(isoxazolyl), each represents a separate embodiment of the invention.

In other embodiments, R$^1$, R$^2$ and/or R$^5$ is CN.

In other embodiments, R$^1$, R$^2$ and/or R$^5$ is CON(R$^6$)$_2$. In other embodiment, CON(R$^6$)$_2$ is CON((C$_1$-C$_{10}$)alkyl)$_2$. In other embodiments, CON((C$_1$-C$_{10}$)alkyl)$_2$ is CON(CH$_3$)$_2$, CON(CH$_2$CH$_3$)$_2$, CON(CH$_2$CH$_2$CH$_3$)$_2$, CON(CH(CH$_3$)$_2$)$_2$, CON(CH$_2$CH$_2$CH$_2$CH$_3$)$_2$, CON(C(CH$_3$)$_3$)$_2$, CON (CH$_2$CH$_2$CH$_2$CH$_2$CH$_3$)$_2$, CON(CH$_2$C(CH$_3$)$_3$)$_2$, CON(CH (CH$_2$CH$_3$)$_2$)$_2$, CON(CH(CH$_3$)(CH$_2$CH$_3$))$_2$, CON(CH (CH$_3$)$_2$(CH$_2$CH$_3$)$_2$, CON(CH$_2$CH$_2$CH(CH$_3$)$_2$)$_2$, CON (CH$_2$CH$_2$CH$_2$CH$_2$CH$_2$CH$_3$)$_2$ or CON (CH$_2$CH$_2$CH$_2$CH$_2$CH$_2$CH$_2$CH$_3$)$_2$, each represents a separate embodiment of this invention.

In other embodiments, CON(R$^6$)$_2$ is CON((C$_1$-C$_{10}$)haloalkyl)$_2$. In other embodiment, CON((C$_1$-C$_{10}$)haloalkyl)$_2$ is CON(CF$_3$)$_2$, CON(CF$_2$CF$_3$)$_2$, CON(CH$_2$I)$_2$, CON(CH$_2$Br)$_2$, CON(CH$_2$CH$_2$Br)$_2$, CON(CHBrCH$_3$)$_2$, CON (CH$_2$CH$_2$CH$_2$Br)$_2$, CON(CH$_2$CHBrCH$_3$)$_2$ or CON (CHBrCH$_2$CH$_3$)$_2$, each represents a separate embodiment of the invention. In other embodiments, CON(R$^6$)$_2$ is a CON ((C$_3$-C$_8$)cycloalkyl)$_2$. In other embodiments, CON((C$_3$-C$_8$) cycloalkyl)$_2$ is CON(cyclobutyl)$_2$, CON(cyclopentyl)$_2$ or CON(cyclohexyl)$_2$, each represents a separate embodiment of the invention. In other embodiments, CON(R$^6$)$_2$ is a CON(aryl)$_2$. In other embodiments, CON(aryl)$_2$ is CON (phenyl)$_2$, CON(naphtyl)$_2$ or CON(perylenyl)$_2$, each represents a separate embodiment of the invention. In another embodiment, CON(R$^6$)$_2$ is a CON(heteroaryl)$_2$. In another embodiment, CON(heteroaryl)$_2$ is CON(pyranyl)$_2$, CON (pyrrolyl)$_2$, CON(pyrazinyl)$_2$, CON(pyrimidinyl)$_2$, CON (pyrazolyl)$_2$, CON(pyridinyl)$_2$, CON(furanyl)$_2$, CON(thiophenyl)$_2$, CON(thiazolyl)$_2$, CON(indolyl)$_2$, CON (imidazolyl)$_2$, CON(isoxazolyl)$_2$, each represents a separate embodiment of the invention.

In another embodiment, R$^1$, R$^2$ and/or R$^5$ is SR$^6$. In another embodiment, SR$^6$ is S((C$_7$-C$_{10}$)alkyl). In another embodiment, S((C$_7$-C$_{10}$)alkyl) is SCH$_3$, SCH$_2$CH$_3$, SCH$_2$CH$_2$CH$_3$, SCH(CH$_3$)$_2$, SCH$_2$CH$_2$CH$_2$CH$_3$, SC(CH$_3$)$_3$, SCH$_2$CH$_2$CH$_2$CH$_2$CH$_3$, SCH$_2$C(CH$_3$)$_3$, SCH(CH$_2$CH$_3$)$_2$, SCH(CH$_3$)(CH$_2$CH$_3$), SCH(CH$_3$)$_2$(CH$_2$CH$_3$), SCH$_2$CH$_2$CH(CH$_3$)$_2$, SCH$_2$CH$_2$CH$_2$CH$_2$CH$_2$CH$_3$ or SCH$_2$CH$_2$CH$_2$CH$_2$CH$_2$CH$_2$CH$_3$, each represents a separate embodiment of this invention. In other embodiments, SR$^6$ is S((C$_1$-C$_{10}$)haloalkyl). In another embodiment, S((C$_1$-C$_{10}$) haloalkyl) is SCF$_3$, SCF$_2$CF$_3$, SCH$_2$I, SCH$_2$Br, SCH$_2$CH$_2$Br, SCHBrCH$_3$, SCH$_2$CH$_2$CH$_2$Br, SCH$_2$CHBrCH$_3$ or SCHBrCH$_2$CH$_3$, each represents a separate embodiment of the invention. In another embodiment, SR$^6$ is a S((C$_3$-C$_8$)cycloalkyl). In another embodiment, S((C$_3$-C$_8$)cycloalkyl) is S(cyclobutyl), S(cyclopentyl) or S(cyclohexyl), each represents a separate embodiment of the invention. In another embodiment, SR$^6$ is S(aryl). In another embodiment, S(aryl) is S(phenyl), S(naphtyl) or S(perylenyl), each represents a separate embodiment of the invention. In other embodiments, SR$^6$ is a S(heteroaryl). In another embodiment, S(heteroaryl) is S(pyranyl), S(pyrrolyl), S(pyrazinyl), S(pyrimidinyl), S(pyrazolyl), S(pyridinyl), S(furanyl), S(thiophenyl), S(thiazolyl), S(indolyl), S(imidazolyl), S(isoxazolyl), each represents a separate embodiment of the invention.

In another embodiment, R$^1$, R$^2$ and/or R$^5$ is SO$_2$R$^6$. In another embodiment, SO$_2$R$^6$ is SO$_2$((C$_1$-C$_{10}$)alkyl). In another embodiment, SO$_2$((C$_1$-C$_{10}$)alkyl) is SO$_2$CH$_3$, SO$_2$CH$_2$CH$_3$, SO$_2$CH$_2$CH$_2$CH$_3$, SO$_2$CH(CH$_3$)$_2$, SO$_2$CH$_2$CH$_2$CH$_2$CH$_3$, SO$_2$C(CH$_3$)$_3$, SO$_2$CH$_2$CH$_2$CH$_2$CH$_2$CH$_3$, SO$_2$CH$_2$C(CH$_3$)$_3$, SO$_2$CH (CH$_2$CH$_3$)$_2$, SO$_2$CH(CH$_3$)(CH$_2$CH$_2$CH$_3$), SO$_2$CH(CH$_3$)$_2$ (CH$_2$CH$_3$), SO$_2$CH$_2$CH$_2$CH(CH$_3$)$_2$, SO$_2$CH$_2$CH$_2$CH$_2$CH$_2$CH$_2$CH$_3$ or SO$_2$CH$_2$CH$_2$CH$_2$CH$_2$CH$_2$CH$_2$CH$_3$, each represents a separate embodiment of this invention. In other embodiments, SO$_2$R$^6$ is SO$_2$((C$_1$-C$_{10}$)haloalkyl). In another embodiment, SO$_2$((C$_1$-C$_{10}$)haloalkyl) is SO$_2$CF$_3$, SO$_2$CF$_2$CF$_3$, SO$_2$CH$_2$I, SO$_2$CH$_2$Br, SO$_2$CH$_2$CH$_2$Br, SO$_2$CHBrCH$_3$, SO$_2$CH$_2$CH$_2$CH$_2$Br, SO$_2$CH$_2$CHBrCH$_3$ or SO$_2$CHBrCH$_2$CH$_3$, each represents a separate embodiment of the invention. In another embodiment, SO$_2$R$^6$ is a SO$_2$ ((C$_3$-C$_8$)cycloalkyl). In another embodiment, SO$_2$((C$_3$-C$_8$) cycloalkyl) is SO$_2$(cyclobutyl), SO$_2$(cyclopentyl) or SO$_2$ (cyclohexyl), each represents a separate embodiment of the invention. In another embodiment, SO$_2$R$^6$ is SO$_2$(aryl). In another embodiment, SO$_2$(aryl) is SO$_2$(phenyl), SO$_2$(naphtyl) or SO$_2$(perylenyl), each represents a separate embodiment of the invention. In another embodiment, SO$_2$R$^6$ is a SO$_2$(heteroaryl). In another embodiment, SO$_2$(heteroaryl) is SO$_2$(pyranyl), SO$_2$(pyrrolyl), SO$_2$(pyrazinyl), SO$_2$(pyrimidinyl), SO$_2$(pyrazolyl), SO$_2$(pyridinyl), SO$_2$(furanyl), SO$_2$ (thiophenyl), SO$_2$(thiazolyl), SO$_2$(indolyl), SO$_2$(imidazolyl), SO$_2$(isoxazolyl), each represents a separate embodiment of the invention.

In another embodiment, R$^1$, R$^2$ and/or R$^5$ is SO$_2$M. In some embodiments, SO$_2$M is a SO$_2$(monovalent cation). In another embodiment, SO$_2$(monovalent cation) includes SO$_2$ (alkali metal cation), SO$_2$(NH$_4$+), SO$_2$ (quaternary ammonium cation), and SO$_2$ (quaternary phoshphonium cation). In another embodiment, SO$_2$M is SO$_2$Li. In another embodiment, SO$_2$M is SO$_2$Na. In another embodiment, SO$_2$M is SO$_2$K. In another embodiment, SO$_2$M is SO$_2$Rb. In another embodiment, SO$_2$M is SO$_2$Cs. In another embodiment, non-limiting examples of the SO$_2$ (quarternary ammonium cation), include SO$_2$(tetrametylammonium), SO$_2$(tetraethylammonium), SO$_2$(tetrabutylammonium), SO$_2$(tetraoctylammonium), SO$_2$(trimethyloctylammonium) and SO$_2$(cetyltrimethylammonium), each represents a separate embodiment of the invention. In another embodiment, non-limiting examples of the SO$_2$ (quarternary phosphonium cation), include SO$_2$(tetraphenylphosphonium), SO$_2$(dimethyldiphenylphosphonium), SO$_2$(tetrabutylphosphonium), SO$_2$(methyltriphenoxyphosphonium) and SO$_2$(tetramethylphosphonium), each represents a separate embodiment of the invention.

In another embodiment, R$^1$, R$^2$ and/or R$^5$ is SOR$^6$. In another embodiment, SOR$^6$ is SO((C$_7$-C$_{10}$)alkyl). In another embodiment, SO((C$_7$-C$_{10}$)alkyl) is SOCH$_3$, SOCH$_2$CH$_3$, SOCH$_2$CH$_2$CH$_3$, SOCH(CH$_3$)$_2$, SOCH$_2$CH$_2$CH$_2$CH$_3$, SOC (CH$_3$)$_3$, SOCH$_2$CH$_2$CH$_2$CH$_2$CH$_3$, SOCH$_2$C(CH$_3$)$_3$, SOCH (CH$_2$CH$_3$)$_2$, SOCH(CH$_3$)(CH$_2$CH$_3$), SOCH(CH$_3$)$_2$ (CH$_2$CH$_3$) SOCH$_2$CH$_2$CH(CH$_3$)$_2$, SOCH$_2$CH$_2$CH$_2$CH$_2$CH$_2$CH$_3$ or SOCH$_2$CH$_2$CH$_2$CH$_2$CH$_2$CH$_2$CH$_3$, each represents a separate embodiment of this invention. In other embodiments, SOR$^6$ is SO((C$_1$-C$_{10}$)haloalkyl). In another embodiment, SO((C$_1$-C$_{10}$)haloalkyl) is SOCF$_3$, SOCF$_2$CF$_3$, SOCH$_2$I, SOCH$_2$Br, SOCH$_2$CH$_2$Br, SOCHBrCH$_3$, SOCH$_2$CH$_2$CH$_2$Br, SOCH$_2$CHBrCH$_3$ or SOCHBrCH$_2$CH$_3$, each represents a separate embodiment of the invention. In another embodiment, SOR$^6$ is a SO((C$_3$-C$_8$)cycloalkyl). In another embodiment, SO((C$_3$-C$_8$)cycloalkyl) is SO(cyclobutyl), SO(cyclopentyl) or SO(cyclohexyl), each represents a separate embodiment of the invention. In another embodiment, SOR$^6$ is SO(aryl). In another embodiment, SO(aryl) is SO(phenyl), SO(naphtyl) or SO(perylenyl), each represents a separate embodiment of the invention. In another embodiment, SOR$^6$ is a SO(heteroaryl). In another embodiment, SO(heteroaryl) is SO(pyranyl), SO(pyrrolyl), SO(pyrazinyl), SO(pyrimidinyl), SO(pyrazolyl), SO(pyridinyl), SO(furanyl), SO(thiophenyl), SO(thiazolyl), SO(indolyl), SO(imidazolyl), SO(isoxazolyl), each represents a separate embodiment of the invention.

In another embodiment, R$^1$, R$^2$ and/or R$^5$ is SO$_3$H.

In another embodiment, R$^1$, R$^2$ and/or R$^5$ is SO$_3$M. In some embodiments, SO$_3$M is a SO$_3$(monovalent cation). In another embodiment, SO$_3$(monovalent cation) includes SO$_3$(alkali metal cation), SO$_3$(NH$_4$+), SO$_3$ (quaternary ammonium cation), and SO$_3$ (quaternary phoshphonium cation). In another embodiment, SO$_3$M is SO$_3$Li. In another embodiment, SO$_3$M is SO$_3$Na. In another embodiment, SO$_3$M is SO$_3$K. In another embodiment, SO$_3$M is SO$_3$Rb. In another embodiment, SO$_3$M is SO$_3$Cs. In another embodiment, non-limiting examples of the SO$_3$ (quarternary ammonium cation), include SO$_3$(tetrametylammonium), SO$_3$(tetraethylammonium), SO$_3$(tetrabutylammonium), SO$_3$(tetraoctylammonium), SO$_3$(trimethyloctylammonium) and SO$_3$(cetyltrimethylammonium), each represents a separate embodiment of the invention. In another embodiment, non-limiting examples of the SO$_3$ (quarternary phosphonium cation), include SO$_3$(tetraphenylphosphonium), SO$_3$(dimethyldiphenylphosphonium), SO$_3$(tetrabutylphosphonium), SO$_3$(methyltriphenoxyphosphonium) and SO$_3$(tetramethylphosphonium), each represents a separate embodiment of the invention.

In another embodiment, R$^1$, R$^2$ and/or R$^5$ is SO$_2$NH$_2$. In another embodiment, R$^1$ and/or R$^5$ is SO$_2$NH(R$^6$). In another embodiment, SO$_2$NHR$^6$ is SO$_2$NH((C$_7$-C$_{10}$)alkyl). In another embodiment, SO$_2$NH((C$_7$-C$_{10}$)alkyl) is SO$_2$NHCH$_3$, SO$_2$NHCH$_2$CH$_3$, SO$_2$NHCH$_2$CH$_2$CH$_3$, SO$_2$NHCH(CH$_3$)$_2$, SO$_2$NHCH$_2$CH$_2$CH$_2$CH$_3$, SO$_2$NHC(CH$_3$)$_3$, SO$_2$NHCH$_2$CH$_2$CH$_2$CH$_2$CH$_3$, SO$_2$NHCH$_2$C(CH$_3$)$_3$, SO$_2$NHCH(CH$_2$CH$_3$)$_2$, SO$_2$NHCH(CH$_3$)(CH$_2$CH$_3$), SO$_2$NH CH(CH$_3$)$_2$(CH$_2$CH$_3$) SO$_2$NHCH$_2$CH$_2$CH(CH$_3$)$_2$, SO$_2$NHCH$_2$CH$_2$CH$_2$CH$_2$CH$_2$CH$_3$ or SO$_2$NH CH$_2$CH$_2$CH$_2$CH$_2$CH$_2$CH$_2$CH$_3$, each represents a separate embodiment of this invention. In other embodiments, SO$_2$NHR$^6$ is SO$_2$NH((C$_1$-C$_{10}$)haloalkyl). In another embodiment, SO$_2$NH((C$_7$-C$_{10}$)haloalkyl) is SO$_2$NHCF$_3$, SO$_2$NHCF$_2$CF$_3$, SO$_2$NHCH$_2$I, SO$_2$NHCH$_2$Br, SO$_2$NHCH$_2$CH$_2$Br, SO$_2$NHCHBrCH$_3$, SO$_2$NHCH$_2$CH$_2$CH$_2$Br, SO$_2$NHCH$_2$CHBrCH$_3$ or SO$_2$NHCHBrCH$_2$CH$_3$, each represents a separate embodiment of the invention. In another embodiment, SO$_2$NHR$^6$ is a SO$_2$NH((C$_3$-C$_8$)cycloalkyl). In another embodiment, SO$_2$NH((C$_3$-C$_8$)cycloalkyl) is SO$_2$NH(cyclobutyl), SO$_2$NH(cyclopentyl) or SO$_2$NH(cyclohexyl), each represents a separate embodiment of the invention. In another embodiment, SO$_2$NHR$^6$ is a SO$_2$NH(aryl). In another embodiment, SO$_2$NH(aryl) is SO$_2$NH(phenyl), SO$_2$NH(naphtyl) or SO$_2$NH(perylenyl), each represents a separate embodiment of the invention. In another embodiment, SO$_2$NHR$^6$ is a SO$_2$NH(heteroaryl). In another embodiment, SO$_2$NH(heteroaryl) is SO$_2$NH(pyranyl), SO$_2$NH(pyrrolyl), SO$_2$NH(pyrazinyl), SO$_2$NH(pyrimidinyl), SO$_2$NH(pyrazolyl), SO$_2$NH(pyridinyl), SO$_2$NH(furanyl), SO$_2$NH(thiophenyl), SO$_2$NH (thiazolyl), SO$_2$NH(indolyl), SO$_2$NH(imidazolyl), SO$_2$NH(isoxazolyl), each represents a separate embodiment of the invention.

In another embodiment, R$^1$, R$^2$ and/or R$^5$ is SO$_2$N(R$^6$)$_2$. In another embodiment, SO$_2$N(R$^6$)$_2$ is SO$_2$N((C$_1$-C$_{10}$)alkyl)$_2$. In another embodiment, SO$_2$N((C$_1$-C$_{10}$)alkyl)$_2$ is SO$_2$N(CH$_3$)$_2$, SO$_2$N(CH$_2$CH$_3$)$_2$, SO$_2$N(CH$_2$CH$_2$CH$_3$)$_2$, SO$_2$N(CH(CH$_3$)$_2$)$_2$, SO$_2$N(CH$_2$CH$_2$CH$_2$CH$_3$)$_2$, SO$_2$N(C (CH$_3$)$_3$)$_2$, SO$_2$N(CH$_2$CH$_2$CH$_2$CH$_2$CH$_3$)$_2$, SO$_2$N(CH$_2$C (CH$_3$)$_3$)$_2$, SO$_2$N(CH(CH$_2$CH$_3$)$_2$)$_2$, SO$_2$N(CH(CH$_3$) (CH$_2$CH$_3$))$_2$, SO$_2$N(CH(CH$_3$)$_2$(CH$_2$CH$_3$))$_2$, SO$_2$N (CH$_2$CH$_2$CH(CH$_3$)$_2$)$_2$, SO$_2$N(CH$_2$CH$_2$CH$_2$CH$_2$CH$_2$CH$_3$)$_2$ or SO$_2$N(CH$_2$CH$_2$CH$_2$CH$_2$CH$_2$CH$_2$CH$_3$)$_2$, each represents a separate embodiment of this invention. In other embodiments, SO$_2$N(R$^6$)$_2$ is SO$_2$N((C$_1$-C$_{10}$)haloalkyl)$_2$. In another embodiment, SO$_2$N((C$_1$-C$_{10}$)haloalkyl)$_2$ is SO$_2$N(CF$_3$)$_2$, SO$_2$N(CF$_2$CF$_3$)$_2$, SO$_2$N(CH$_2$I)$_2$, SO$_2$N(CH$_2$Br)$_2$, SO$_2$N (CH$_2$CH$_2$Br)$_2$, SO$_2$N(CHBrCH$_3$)$_2$, SO$_2$N(CH$_2$CH$_2$CH$_2$Br)$_2$, SO$_2$N(CH$_2$CHBrCH$_3$)$_2$ or SO$_2$N(CHBrCH$_2$CH$_3$)$_2$, each represents a separate embodiment of the invention. In another embodiment, SO$_2$N(R$^6$)$_2$ is a SO$_2$N((C$_3$-C$_8$) cycloalkyl)$_2$. In another embodiment, SO$_2$N((C$_3$-C$_8$)cycloalkyl)$_2$ is SO$_2$N(cyclobutyl)$_2$, SO$_2$N(cyclopentyl)$_2$ or SO$_2$N(cyclohexyl)$_2$, each represents a separate embodiment of the invention. In another embodiment, SO$_2$N(R$^6$)$_2$ is a SO$_2$N(aryl)$_2$. In another embodiment, SO$_2$N(aryl)$_2$ is SO$_2$N (phenyl)$_2$, SO$_2$N(naphtyl)$_2$ or SO$_2$N(perylenyl)$_2$, each represents a separate embodiment of the invention. In another embodiment, SO$_2$N(R$^6$)$_2$ is a SO$_2$N(heteroaryl)$_2$. In another embodiment, SO$_2$N(heteroaryl)$_2$ is SO$_2$N(pyranyl)$_2$, SO$_2$N (pyrrolyl)$_2$, SO$_2$N(pyrazinyl)$_2$, SO$_2$N(pyrimidinyl)$_2$, SO$_2$N (pyrazolyl)$_2$, SO$_2$N(pyridinyl)$_2$, SO$_2$N(furanyl)$_2$, SO$_2$N (thiophenyl)$_2$, SO$_2$N(thiazolyl)$_2$, SO$_2$N(indolyl)$_2$, SO$_2$N (imidazolyl)$_2$, SO$_2$N(isoxazolyl)$_2$, each represents a separate embodiment of the invention.

In another embodiment, R$^1$, R$^2$ and/or R$^5$ is NH$_2$.

In another embodiment, R$^1$, R$^2$ and/or R$^5$ is NH(R$^6$). In another embodiment, NHR$^6$ is NH((C$_7$-C$_{10}$)alkyl). In another embodiment, NH((C$_7$-C$_{10}$)alkyl) is NHCH$_3$, NHCH$_2$CH$_3$, NHCH$_2$CH$_2$CH$_3$, NHCH(CH$_3$)$_2$, NHCH$_2$CH$_2$CH$_2$CH$_3$, NHC(CH$_3$)$_3$, NHCH$_2$CH$_2$CH$_2$CH$_2$CH$_3$, NHCH$_2$C(CH$_3$)$_3$, NHCH (CH$_2$CH$_3$)$_2$, NHCH(CH$_3$)(CH$_2$CH$_3$), NHCH(CH$_3$)$_2$ (CH$_2$CH$_3$), NHCH$_2$CH$_2$CH(CH$_3$)$_2$, NHCH$_2$CH$_2$CH$_2$CH$_2$CH$_2$CH$_3$ or NHCH$_2$CH$_2$CH$_2$CH$_2$CH$_2$CH$_2$CH$_3$, each represents a separate embodiment of this invention. In other embodiments, NHR$^6$ is NH((C$_1$-C$_{10}$)haloalkyl). In another embodiment, NH((C$_1$-C$_{10}$)haloalkyl) is NHCF$_3$, NHCF$_2$CF$_3$, NHCH$_2$I, NHCH$_2$Br, NHCH$_2$CH$_2$Br, NHCHBrCH$_3$, NHCH$_2$CH$_2$CH$_2$Br, NHCH$_2$CHBrCH$_3$ or NHCHBrCH$_2$CH$_3$, each represents a separate embodiment of the invention. In another embodiment, NHR$^6$ is a NH((C$_3$-C$_8$)cycloalkyl). In another embodiment, NH((C$_3$-

$C_8$)cycloalkyl) is NH(cyclobutyl), NH(cyclopentyl) or NH(cyclohexyl), each represents a separate embodiment of the invention. In another embodiment, $NHR^6$ is a NH(aryl). In another embodiment, NH(aryl) is NH(phenyl), NH(naphtyl) or NH(perylenyl), each represents a separate embodiment of the invention. In another embodiment, $NHR^6$ is a NH(heteroaryl). In another embodiment, NH(heteroaryl) is NH(pyranyl), NH(pyrrolyl), NH(pyrazinyl), NH(pyrimidinyl), NH(pyrazolyl), NH(pyridinyl), NH(furanyl), NH(thiophenyl), NH(thiazolyl), NH(indolyl), NH(imidazolyl), NH(isoxazolyl), each represents a separate embodiment of the invention.

In another embodiment, $R^1$, $R^2$ and/or $R^5$ is $N(R^6)_2$. In another embodiment, $N(R^6)_2$ is $N((C_1-C_{10})alkyl)_2$. In another embodiment, $N((C_1-C_{10})alkyl)_2$ is $N(CH_3)_2$, $N(CH_2CH_3)_2$, $N(CH_2CH_2CH_3)_2$, $N(CH(CH_3)_2)_2$, $N(CH_2CH_2CH_2CH_3)_2$, $N(C(CH_3)_3)_2$, $N(CH_2CH_2CH_2CH_2CH_3)_2$, $N(CH_2C(CH_3)_3)_2$, $N(CH(CH_2CH_3)_2)_2$, $N(CH(CH_3)(CH_2CH_3))_2$ $N(CH(CH_3)_2(CH_2CH_3))_2$, $N(CH_2CH_2CH(CH_3)_2)_2$ $N(CH_2CH_2CH_2CH_2CH_3)_2$ or $N(CH_2CH_2CH_2CH_2CH_2CH_2CH_3)_2$, each represents a separate embodiment of this invention. In other embodiments, $N(R^6)_2$ is $N((C_1-C_{10})haloalkyl)_2$. In another embodiment, $N((C_1-C_{10})haloalkyl)_2$ is $N(CF_3)_2$, $N(CF_2CF_3)_2$, $N(CH_2I)_2$, $N(CH_2Br)_2$, $N(CH_2CH_2Br)_2$, $N(CHBrCH_3)_2$, $N(CH_2CH_2CH_2Br)_2$, $N(CH_2CHBrCH_3)_2$ or $N(CHBrCH_2CH_3)_2$, each represents a separate embodiment of the invention. In another embodiment, $N(R^6)_2$ is a $N((C_3-C_8)cycloalkyl)_2$. In another embodiment, $N((C_3-C_8)cycloalkyl)_2$ is $N(cyclobutyl)_2$, $N(cyclopentyl)_2$ or $N(cyclohexyl)_2$, each represents a separate embodiment of the invention. In another embodiment, $N(R^6)_2$ is a $N(aryl)_2$. In another embodiment, $N(aryl)_2$ is $N(phenyl)_2$, $N(naphtyl)_2$ or $N(perylenyl)_2$, each represents a separate embodiment of the invention. In another embodiment, $N(R^6)_2$ is a $CON(heteroaryl)_2$. In another embodiment, $N(heteroaryl)_2$ is $N(pyranyl)_2$, $N(pyrrolyl)_2$, $N(pyrazinyl)_2$, $N(pyrimidinyl)_2$, $N(pyrazolyl)_2$, $N(pyridinyl)_2$, $N(furanyl)_2$, $N(thiophenyl)_2$, $N(thiazolyl)_2$, $N(indolyl)_2$, $N(imidazolyl)_2$, $N(isoxazolyl)_2$, each represents a separate embodiment of the invention.

In another embodiment, $R^1$, $R^2$ and/or $R^5$ is $CONH_2$.

In another embodiment, $R^1$, $R^2$ and/or $R^5$ is $CONH(R^6)$. In another embodiment, $CONHR^6$ is CONH $((C_7-C_{10})alkyl)$. In another embodiment, CONH $((C_7-C_{10})alkyl)$ is $CONHCH_3$, $CONHCH_2CH_3$, $CONHCH_2CH_2CH_3$, $CONHCH(CH_3)_2$, $CONHCH_2CH_2CH_2CH_3$, $CONHC(CH_3)_3$, $CONHCH_2CH_2CH_2CH_2CH_3$, $CONHCH_2C(CH_3)_3$, $CONHCH(CH_2CH_3)_2$, $CONHCH(CH_3)(CH_2CH_3)$, $CONHCH(CH_3)_2(CH_2CH_3)$, $CONHCH_2CH_2CH(CH_3)_2$, $CONHCH_2CH_2CH_2CH_2CH_3$ or $CONHCH_2CH_2CH_2CH_2CH_2CH_2CH_3$, each represents a separate embodiment of this invention. In other embodiments, $CONHR^6$ is CONH $((C_1-C_{10})haloalkyl)$. In another embodiment, $CONH((C_7-C_{10})haloalkyl)$ is $CONHCF_3$, $CONHCF_2CF_3$, $CONHCH_2I$, $CONHCH_2Br$, $CONHCH_2CH_2Br$, $CONHCHBrCH_3$, $CONHCH_2CH_2CH_2Br$, $CONHCH_2CHBrCH_3$ or $CONHCHBrCH_2CH_3$, each represents a separate embodiment of the invention. In another embodiment, $CONHR^6$ is a $CONH((C_3-C_8)cycloalkyl)$. In another embodiment, $CONH((C_3-C_8)cycloalkyl)$ is CONH(cyclobutyl), CONH(cyclopentyl) or CONH (cyclohexyl), each represents a separate embodiment of the invention. In another embodiment, $CONHR^6$ is a CONH(aryl). In another embodiment, CONH(aryl) is CONH(phenyl), CONH(naphtyl) or CONH (perylenyl), each represents a separate embodiment of the invention. In another embodiment, $CONHR^6$ is a CONH (heteroaryl). In another embodiment, CONH(heteroaryl) is CONH(pyranyl), CONH(pyrrolyl), CONH(pyrazinyl), CONH(pyrimidinyl), CONH(pyrazolyl), CONH(pyridinyl), CONH(furanyl), CONH(thiophenyl), CONH(thiazolyl), CONH(indolyl), CONH(imidazolyl), CONH(isoxazolyl), each represents a separate embodiment of the invention.

In another embodiment, $R^1$, $R^2$ and/or $R^5$ is CO(N-heterocycle). In another embodiment, CO(N-heterocycle) is CO(pyridine), CO(piperidine), CO(morpholine), CO(piperazine), CO(pyrrolidine), CO(pyrrole), CO(imidazole), CO(pyrazole), CO(pyrazolidine), CO(triazole), CO(tetrazole), CO(piperazine), CO(diazine), or CO(triazine), each represents a separate embodiment of the invention.

In another embodiment, $R^1$, $R^2$ and/or $R^5$ is $NO_2$. In another embodiment, $R^1$, $R^2$ and/or $R^5$ is CN. In another embodiment, $R^1$, $R^2$ and/or $R^5$ is cyanate. In another embodiment, $R^1$, $R^2$ and/or $R^5$ is isocyanate. In another embodiment, $R^1$, $R^2$ and/or $R^5$ is thiocyanate. In another embodiment, $R^1$, $R^2$ and/or $R^5$ is isothiocyanate. In another embodiment, $R^1$, $R^2$ and/or $R^5$ is mesylate. In another embodiment, $R^1$, $R^2$ and/or $R^5$ is triflate. In another embodiment, $R^1$, $R^2$ and/or $R^5$ is tosylate. In another embodiment, $R^1$, $R^2$ and/or $R^5$ is $PO(OH)_2$. In another embodiment, $R^1$, $R^2$ and/or $R^5$ is $OPO(OH)_2$.

The term "alkyl" group refers to a saturated aliphatic hydrocarbon, including straight-chain or branched-chain. In one embodiment, alkyl group is linear or branched. In another embodiment, alkyl is optionally substituted linear or branched. In one embodiment, the alkyl group has between 1-20 carbons. In one embodiment, the alkyl group has between 1-10 carbons. In one embodiment, the alkyl group has between 2-10 carbons. In one embodiment, the alkyl group has between 1-6 carbons. In one embodiment, the alkyl group has between 2-8 carbons. In another embodiment, non-limiting examples of alkyl groups include methyl, ethyl, propyl, isopropyl, isobutyl, butyl, pentyl, 3-pentyl, hexyl heptyl, octyl and hexadecyl. In another embodiment, the alkyl group is optionally substituted by one or more halogens, hydroxides, alkoxides, carboxylic acids, phosphates, phosphonates, sulfates, sulfonates amidates, cyanates, and a nitro group. Each possibility represents a separate embodiment of the invention.

The term "cycloalkyl" group refers to a ring structure comprising carbon atoms as ring atoms, which are saturated, substituted or unsubstituted. In another embodiment the cycloalkyl is a 5-6 membered ring. In another embodiment, the cycloalkyl group may be unsubstituted or substituted by a halogen, an alkyl group, haloalkyl group, an hydroxide, an alkoxide, an amide, a nitro group, a cyano groups, or a carboxylate. Each possibility represents a separate embodiment of the invention.

The term "haloalkyl" refers to an alkyl as defined above which is substituted with one or more halides. Non limiting examples of haloalkyls include: $CF_3$, $CF_2CF_3$, $CH_2I$, CH₂Br, CH₂CH₂Br, CHBrCH₃, CH₂CH₂CH₂Br, CH₂CHBrCH₃ or CHBrCH₂CH₃, each represents a separate embodiment of the invention.

The term "aryl" refers to an aromatic group having at least one carbocyclic aromatic ring, which may be unsubstituted or substituted by one or more groups selected from halogen, cyano, aryl, heteroaryl, haloalkyl, hydroxy, alkoxy carbonyl, amido, alkylamido, dialkylamido, nitro, amino, alkylamino, dialkylamino, carboxy or thio or thioalkyl. Non limiting examples of aryl rings are phenyl, naphthyl, perylene and the like. In one embodiment, the aryl group is a 5-12 membered ring. In another embodiment, the aryl group is a 5-8 membered ring. In one embodiment, the aryl group is a five membered ring. In one embodiment, the aryl group is a six membered ring. In another embodiment, the aryl group comprises of 1-4 fused rings.

The term "heteroaryl" refers to an aromatic group having at least one heterocyclic aromatic ring. In one embodiment, the heteroaryl comprises at least one heteroatom such as sulfur, oxygen, nitrogen, silicon, phosphorous or any combination thereof, as part of the ring. In another embodiment, the heteroaryl may be unsubstituted or substituted by one or more groups selected from halogen, aryl, heteroaryl, cyano, haloalkyl, hydroxy, alkoxy carbonyl, amido, alkylamido, dialkylamido, nitro, amino, alkylamino, dialkylamino, carboxy or thio or thioalkyl. Nonlimiting examples of heteroaryl rings are pyranyl, pyrrolyl, pyrazinyl, pyrimidinyl, pyrazolyl, pyridinyl, furanyl, thiophenyl, thiazolyl, indolyl, imidazolyl, isoxazolyl, and the like. In one embodiment, the heteroaryl group is a 5-12 membered ring. In one embodiment, the heteroaryl group is a five membered ring. In one embodiment, the heteroaryl group is a six membered ring. In another embodiment, the heteroaryl group is a 5-8 membered ring. In another embodiment, the heteroaryl group comprises of 1-4 fused rings. In one embodiment, the heteroaryl group is 1,2,3-triazole. In one embodiment the heteroaryl is a pyridyl. In one embodiment the heteroaryl is a bipyridyl. In one embodiment the heteroaryl is a terpyridyl.

In some embodiments, M is a monovalent cation. In another embodiment, M includes alkali metal cations, $NH_4^+$, quaternary ammonium cation, and quaternary phoshphonium cation. In another embodiment, M is $Li^+$. In another embodiment, M is $Na^+$. In another embodiment, M is $K^+$. In another embodiment, M is $Rb^+$. In another embodiment, M is $Cs^+$. In another embodiment, non-limiting examples of the quarternary ammonium cation, include tetrametylammonium, tetraethylammonium, tetrabutylammonium, tetraoctylammonium, trimethyloctylammonium and cetyltrimethylammonium. In another embodiment, non-limiting examples of the quarternary phosphonium cation, include tetraphenylphosphonium, dimethyldiphenylphosphonium, tetrabutylphosphonium, methyltriphenoxyphosphonium and tetramethylphosphonium.

In some embodiments, the term "halide" used herein refers to any substituent of the halogen group (group 17). In another embodiment, halide is fluoride, chloride, bromide or iodide. In another embodiment, halide is fluoride. In another embodiment, halide is chloride. In another embodiment, halide is bromide. In another embodiment, halide is iodide.

In other embodiments, the perylene diimide derivative is represented by the structure of 1, 2, 3, 4a, 4b or 5:

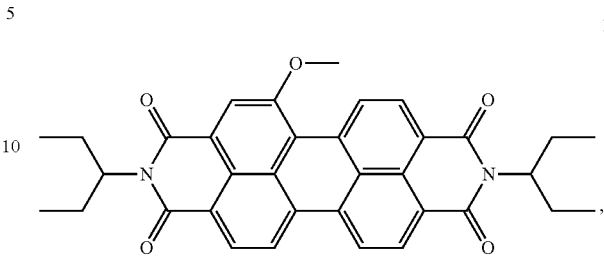

1

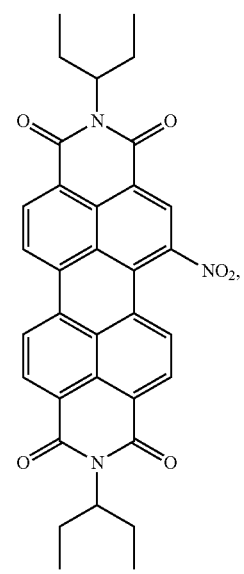

2

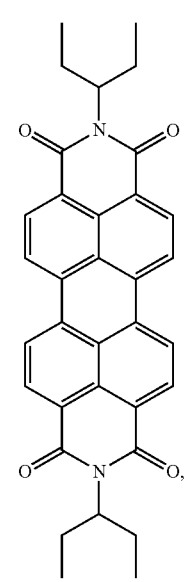

3

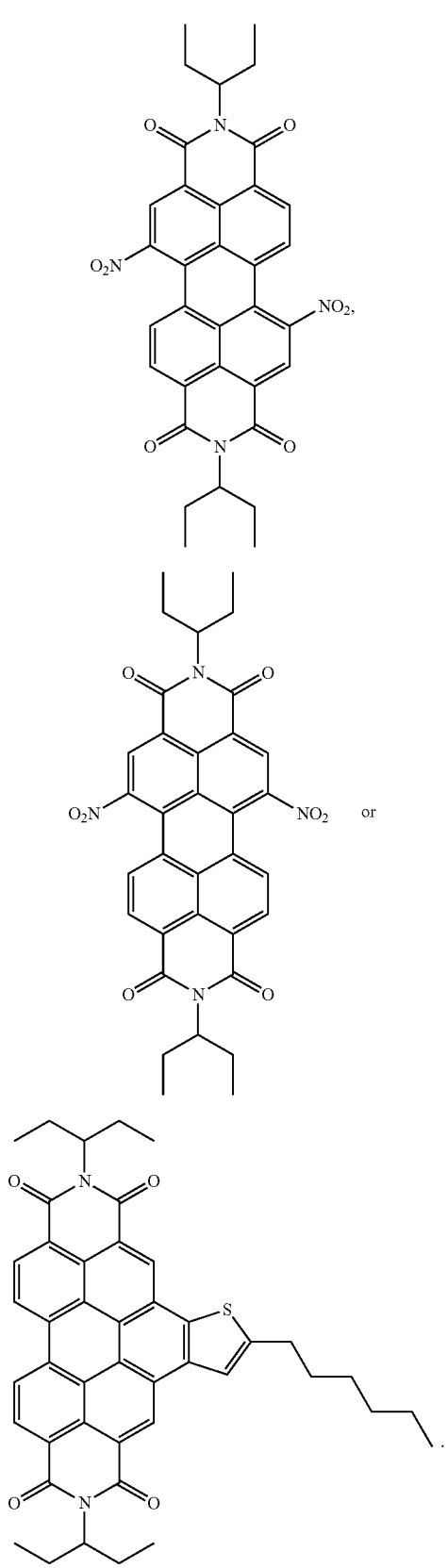

Surprisingly, in some embodiments, the free-standing film of the current invention provides a mechanical and thermal strength and durability, despite the fact that it comprises small organic molecules (less than 1000 Da or its dimers or its trimers). Further, significant enhancement in the mechanical properties is found upon adding a small amount (typically, less than 10% by weight) of a reinforcement material, without any negative effect on other properties of the film.

In various embodiments, the free-standing film of this invention is soluble in organic solvents. In other embodiments, the free-standing film of this invention is soluble is polar organic solvents. In other embodiments, the freestanding film is not soluble in water.

In some embodiments, this invention provides a free-standing film comprising an aromatic material. In other embodiments, this invention provides a microfiltration or an ultrafiltration membrane comprising the free-standing film of the invention. In other embodiments, this invention provides a composition comprising a nanocrystalline aromatic material. In some embodiments, the free-standing film, the microfiltration membrane, the ultrafiltration membrane and the composition of this invention further comprise a reinforcement material. In some embodiments, the reinforcement material comprises a carbon material, a polysaccharide, a nanoclay, a metal, a metal alloy, an organic polymer or any combination thereof, each represents a separate embodiment of the invention. In other embodiments, the free-standing film, the microfiltration/ultrafiltration membrane and/or the composition comprise one or more different reinforcement materials. In another embodiment, the free-standing film, the microfiltration/ultrafiltration membrane and/or the composition comprise one reinforcement material. In another embodiment, the free-standing film, the microfiltration/ultrafiltration membrane and/or the composition comprise two different reinforcement materials. In another embodiment, the free-standing film, the microfiltration/ultrafiltration membrane and/or the composition comprise three different reinforcement materials. In another embodiment, the free-standing film, the microfiltration/ultrafiltration membrane and/or the composition comprise between 1-5 different reinforcement materials. In other embodiments, the reinforcement material is soluble in aqueous media.

In one embodiment, the carbon material of the reinforcement material within the embodiments of the current invention comprises graphene, graphene oxide, graphite, carbon fibers or any combination thereof. In another embodiment, the carbon material is graphene. In another embodiment, the carbon material is graphene oxide. In another embodiment, the carbon material is graphite. In another embodiment, the carbon material is carbon fibers. In another embodiment, the carbon material is any combination of the foregoing.

In another embodiment, the carbon materials are provided as a powder, a dispersion or any other known form in the art. In another embodiment, graphene oxide is dispersed in a solvent. In another embodiment, graphene oxide is a powder. In another embodiment, the solvent is water. In another embodiment, the solvent is toluene.

In some embodiments, the polysaccharide of the reinforcement material within the embodiments of the current invention comprises agarose, cellulose, microfiber cellulose, hydroxyethyl cellulose, amylose, amylopectin, starch, glycogen, hemicellulose, arabinoxylan, chitin, pectin or any combination thereof. In another embodiment, the polysaccharide is agarose. In another embodiment, the polysaccharide is cellulose. In another embodiment, the polysaccharide is microfiber cellulose. In another embodiment, the polysaccharide is hydroxyethyl cellulose. In another embodiment, the polysaccharide is amylose. In another embodiment, the polysaccharide is amylopectin. In another embodiment, the polysaccharide is starch. In another embodiment, the polysaccharide is glycogen. In another embodiment, the polysaccharide is hemicellulose. In another embodiment, the polysaccharide is arabinoxylan. In another embodiment, the polysaccharide is chitin. In another embodiment, the polysaccharide is pectin. In another embodiment, the polysaccharide is any combination of the foregoing. In another embodiment, the polysaccharide is provided as a gel, dispersion, solution, powder or any other known form in the art.

In some embodiments, the term "nanoclay" of the reinforcement material within the embodiments of the current invention refers to a layered aluminosilicate ($SiO_2/Al_2O_3$) mineral that forms 2D platelets upon exfoliation. In another embodiment the nanoclay forms 2D platelets upon exfoliation like montmorillonite which consists of ~1 nm thick aluminosilicate layers surface-substituted with transition metal cations, alkaline metal cations, alkali earth metal cations or any other cations known in the art. In another embodiment the layers are stacked in ~10 μm-sized multilayer particles. Organo-clays are surface modified nanoclays in which the metal cations are exchanged by quaternary alkylamines. Non limiting examples of nanoclay include hydrophilic bentonite, organoclay-surface modified trimethylstearylammonium montmorillonite, organoclay-surface modified dimethyldialkylamine montmorillonite, organoclay-surface modified aminopropyltrietoxysilane\octadecylamine montmorillonite, organoclay-surface modified methyl dihydroxyethyl hydrogenated tallow ammonium montmorillonite, organoclay-surface modified quaternary ammonium montmorillonite and any combination thereof. Each represents a separate embodiment of this invention. In another embodiment, non limiting examples of quaternary ammonium include methyl dihydroxyethyl hydrogenated tallow ammonium, trioctylmethylammonium, tetrabutylammonium, hexadecyltrimethylammonium, tetrahexylammonium, tetramethylammonium, alkylbenzyldimethylammonium or any combination thereof. Each represents a separate embodiment of this invention. In another embodiment, the nanoclay is hydrophilic bentonite. In another embodiment, the nanoclay is organoclay-surface modified methyl dihydroxyethyl hydrogenated tallow ammonium montmorillonite.

In some embodiments, the organic polymer of the reinforcement material within the embodiments of the current invention comprises a water soluble polymer or a non water soluble polymer. Non limiting examples of organic polymers as reinforcement materials include polyvinyl alcohol, polyethylene glycol (PEG), polyethylene, polypropylene, polystyrene, polyacrylonitrile, polyamide, polyimide, polyester or any combination thereof.

In one embodiment, the free-standing film of the current invention is fabricated in various dimensions and shapes.

In some embodiments, a free-standing film of the current invention has a thickness of between 100 nm to 500 microns. In another embodiment, the film has a thickness of between 100 nm to 10 μm. In another embodiment, the film has a thickness of between 5-50 μm. In another embodiment, the film has a thickness of between 10-30 μm. In another embodiment, the film has a thickness of between 20-100 μm. In another embodiment, the film has a thickness of about 15-50 μm.

Figure 6A:
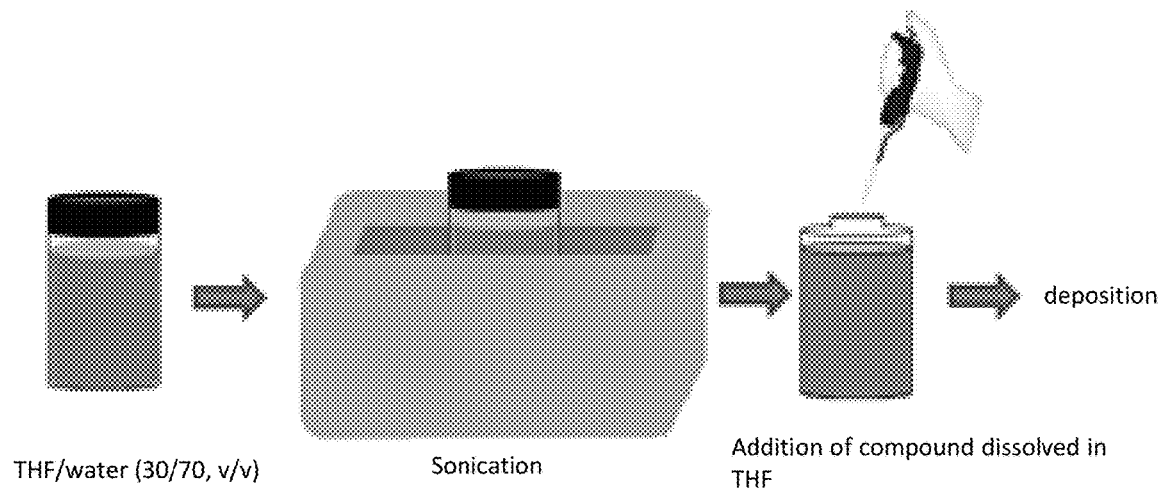
FIGS. 6A-6D depict a short fabrication process of free-standing films from compounds 1-3.
Figure 6B:
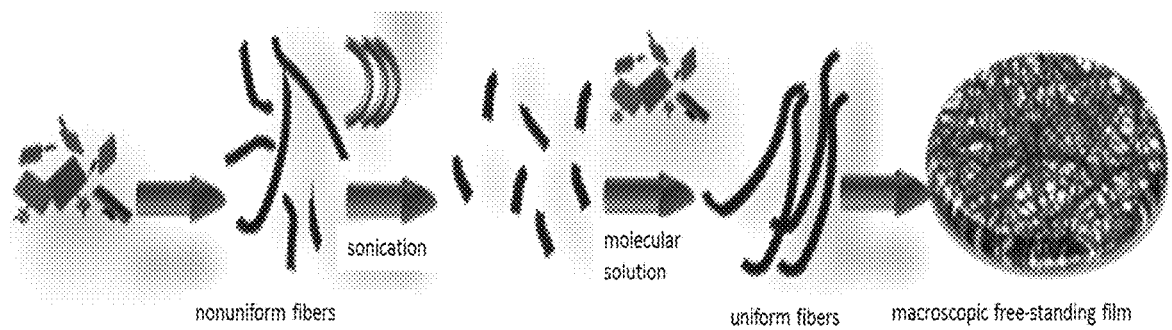

In various embodiments, the aromatic material self assemble in solution, into organic nanocrystals fibers due to strong 7-interactions of the aromatic building blocks. As a result, nanocrystalline fibrous structure comprising the aromatic material is formed, both in i) free-standing films comprising an aromatic material and ii) free-standing films comprising an aromatic material and a reinforcement material (hybrid films). A free-standing film of the current invention comprises such nanocrystalline fibrous structure. In one embodiment, a general scheme depicting fabrication of the free-standing film is presented in FIG. 1. In another embodiment, alternative fabrication process is used as presented in schemes in FIGS. 6A-B. In another embodiment, the alternative fabrication process comprises a seeded growth process of the organic nanocrystals of the current invention.

Fibers within the nanocrystalline fibrous structure are tailor made to accommodate various dimensions and characteristics.

In some embodiments, fibers of the nanocrystalline fibrous structure have high aspect ratios. In another embodiment, fibers have average aspect ratio of between 5-50.

In some embodiments, fibers of the nanocrystalline fibrous structure of the film have an average length of between 0.5-30 μm. In another embodiment, the average length is of between 1-20 μm. In another embodiment, the average length is of between 1-15 μm. In another embodiment, the average length is between 1-10 μm. In another embodiment, the average length is between 1-5 μm. In one embodiment, fibers of the nanocrystalline fibrous structure of the film have an average width of between 2-200 nm. In one embodiment, the average width is of between 10-150 nm. In one embodiment, the average width is of between 15-140 nm. In one embodiment, the average width is of between 20-130 nm.

In some embodiments, fibers of the nanocrystalline fibrous structure of the film are uniform in size. In another embodiment, fibers of the nanocrystalline fibrous structure of the film are non-uniform in size.

In some embodiments, fibers of the nanocrystalline fibrous structure of the film, and hybrid compositions of the current invention are photo active. In some embodiments, fibers of the nanocrystalline fibrous structure of the film, and hybrid compositions of the current invention emit at wavelengths of between 610-640 nm. In another embodiment, the fibers emit at between 610-615 nm. In another embodiment, the fibers emit at between 615-625 nm. In another embodiment, fibers emit at between 620-630 nm. In another embodiment, fibers emit at 624 nm.

In some embodiments, fibers of the nanocrystalline fibrous structure, films and hybrid compositions of the current invention have a quantum yield for emission of between 70-100%. In another embodiment, the quantum yield is between 70-75%. In another embodiment, the quantum yield is between 75-80%. In another embodiment, the quantum yield is between 80-85%. In another embodiment, the quantum yield is between 85-90%. In another embodiment, the quantum yield is between 90-95%. In another embodiment, the quantum yield is between 95-100%. In another embodiment, the quantum yield is 80%.

In some embodiments, the morphology of the nanocrystalline fibrous structure enables fibers entanglement and large surface area of interaction, leading to structural robustness. This can be seen, inter alia, in the young modulus of the films of the current invention. In some embodiments, hybrid films of the current invention (i.e., films which comprise aromatic material and reinforcement material) have better mechanical properties compared to films without reinforcements. In another embodiment, without being bound by any particular theory and mechanism of action, the reinforcement materials give rise to improved mechanical properties of the hybrid films due to resulting supercoiled structure, resulting interpenetrating network structure or to any combination thereof.

In some embodiments, a free-standing film of the current invention is mechanically stable. In some embodiments, a free-standing film of the current invention has a young modulus of between 30-1000 MPa. In another embodiment, a free-standing film of the current invention has a young modulus of between 70-950 MPa. In another embodiment, a free-standing film of the current invention has a young modulus of between 150-900 MPa. In another embodiment, a free-standing film of the current invention has a young modulus of between 200-800 MPa. In another embodiment, a free-standing film of the current invention has a young modulus of between 300-700 MPa. In another embodiment, a free-standing film of the current invention has a young modulus of between 400-650 MPa. In another embodiment, a free-standing film of the current invention has a young modulus of between 500-700 MPa. In another embodiment, a free-standing film of the current invention has a young modulus of between 80-220 MPa. In another embodiment, a free-standing film of the current invention has a young modulus of between 110-210 MPa. In another embodiment, a free-standing film of the current invention has a young modulus of between 170-230 MPa. In another embodiment, a free-standing film of the current invention has a young modulus of 600±100 MPa. In another embodiment, a free-standing film of the current invention has a young modulus of 160±50 MPa In another embodiment, a free-standing film of the current invention has a young modulus of 200±30 MPa In another embodiment, a free-standing film of the current invention has a young modulus of 150±70 MPa. In another embodiment, a free-standing film of the current invention has a young modulus of between 50-110 MPa. In another embodiment, a free-standing film of the current invention has a young modulus of between 70-110 MPa. In another embodiment, a free-standing film of the current invention has a young modulus of between 90-190 MPa. In another embodiment, a free-standing film of the current invention has a young modulus of between 210-390 MPa. In another embodiment, a free-standing film of the current invention has a young modulus of 90±20 MPa. In another embodiment, a free-standing film of the current invention has a young modulus of 140±50 MPa.

In some embodiments, a free-standing film of the current invention has a tensile strength of between 0.1-30 MPa. In another embodiment, a free-standing film of the current invention has a tensile strength of between 0.1-1 MPa. In another embodiment, a free-standing film of the current invention has a tensile strength of between 1-5 MPa In another embodiment, a free-standing film of the current invention has a tensile strength of between 1-10 MPa. In another embodiment, a free-standing film of the current invention has a tensile strength of between 1-15 MPa In another embodiment, a free-standing film of the current invention has a tensile strength of between 10-20 MPa. In another embodiment, a free-standing film of the current invention has a tensile strength of between 10-30 MPa. In another embodiment, a free-standing film of the current invention has a tensile strength of between 25-30 MPa.

In some embodiments, the free-standing film of the current invention elongates to between 0.1-5%. In another embodiment, the free-standing film of the current invention elongates to between 0.1-0.5%. In another embodiment, the free-standing film of the current invention elongates to between 0.5-1%. In another embodiment, the free-standing film of the current invention elongates to between 0.5-3%. In another embodiment, a free-standing film of the current invention elongates to between 1-5%. In another embodiment, a free-standing film of the current invention elongates to between 1-3%.

In some embodiments, the free-standing film of the current invention has toughness of between 0.1-30 MPa. In another embodiment, the free-standing film of the current invention has toughness of between 0.1-1 MPa. In another embodiment, the free-standing film of the current invention has toughness of between 0.5-1 MPa. In another embodiment, the free-standing film of the current invention has toughness of between 0.5-5 MPa. In another embodiment, the free-standing film of the current invention has toughness of between 2-3 MPa. In another embodiment, the free-standing film of the current invention has toughness of between 1-10 MPa. In another embodiment, the free-standing film of the current invention has toughness of between 5-15 MPa. In another embodiment, the free-standing film of the current invention has toughness of between 1-15 MPa. In another embodiment, the free-standing film of the current invention has toughness of between 5-20 MPa. In another embodiment, the free-standing film of the current invention has toughness of between 5-30 MPa. In another embodiment, the free-standing film of the current invention has toughness of between 10-30 MPa. In another embodiment, the free-standing film of the current invention has toughness of between 15-30 MPa.

Additional advantageous property of the films of the current invention is their thermal stability.

In some embodiments, the films of the current invention are stable up to a temperature of 500° C. In another embodiment, the films are stable up to a temperature of between 100-150° C. In another embodiment, the films are stable up to a temperature of between 150-200° C. In another embodiment, the films are stable up to a temperature of between 200-250° C. In another embodiment, the films are stable up to a temperature of between 250-300° C. In another embodiment, the films are stable up to a temperature of between 300-450° C. In another embodiment, the films are stable up to a temperature of between 300-400° C. In another embodiment, the films are stable up to a temperature of between 300-350° C.

Due to the nanocrystalline structure of the films they demonstrate advantageous properties. In one embodiment, the films of the current invention are emissive and have non linear optical (NLO) effects due to the aromatic material. Macroscopic organic non linear optical (NLO) materials are normally based on NLO active molecules embedded into polymers and poled, resulting in poor long-term thermal stability; on the other hand, the free-standing films of the current invention show NLO response, and such response is surprisingly unchanged over time and after heating.

In some embodiments, the free-standing films and hybrid compositions of the current invention have non linear optical (NLO) properties. In another embodiment, the NLO effect is of the second harmonic generation (SHG) type. In another embodiment, the films of the materials of the current invention show unchanged NLO response over several months at room temperature and up to few hours after heating to 300° C.

In one embodiment, the free-standing films and hybrid compositions of the current invention are used as sensors to quenching fluorescence.

In one embodiment, the free-standing film and hybrid composition of the current invention is porous. In other embodiments, the porous size is between 0.5-100 nm. In other embodiments, the porous size is between 0.5 to 5 nm. In other embodiments, the porous size is between 1-10 nm. In other embodiments, the porous size is between 5-15 nm. In other embodiments, the porous size is between 10-25 nm. In other embodiments, the porous size is between 10-50 nm. In other embodiments, the porous size is between 25-75 nm. In other embodiments, the porous size is between 40-100 nm.

In some embodiments, the weight ratio of the aromatic material to the reinforcement material is between 50:50 to 99.9:0.1. In another embodiment, the weight ratio is between 50:50 to 90:10. In another embodiment, the weight ratio is between 60:40 to 99.9:0.1. In another embodiment, the weight ratio is between 70:30 to 99.9:0.1. In another embodiment, the weight ratio is between 80:20 to 99.9:0.1. In another embodiment, the weight ratio is equal or above 90:10. In another embodiment the weight ratio of the aromatic material to the reinforcement material is between 90:10 to 99.9:0.1. In another embodiment, the weight ratio is between 90:10-99.99:0.01. In another embodiment, the weight ratio is between 95:5-99.99-0.01. In another embodiment, the weight ratio is between 99:1-99.99-0.01. In another embodiment, the weight ratio is 90:10. In another embodiment, the weight ratio is 95:5. In another embodiment, the weight ratio is 99.8:0.2.

Nanoporous structure of the free-standing films of the current invention enables their utilization as microfiltration or ultrafiltration membranes. These films can be disassembled and recycled as a way to manage membrane fouling.

In one embodiment, the free-standing films of the current invention are used as microfiltration or ultrafiltration membranes. In other embodiments, the membranes are recyclable. In other embodiments, the membranes have a filtration cutoff of between 0.5-100 nm. In other embodiments, the cutoff is between 40-60 nm. In other embodiments, the cutoff is 50 nm. In other embodiments, the cutoff is between 10-40 nm. In other embodiments, the cutoff is between 1-10 nm. In other embodiments, the cutoff is 1 nm. In other embodiments, the cutoff is between 0.5 to 5 nm. In other embodiments, the cutoff is between 1-10 nm. In other embodiments, the cutoff is between 5-15 nm. In other embodiments, the cutoff is between 10-25 nm. In other embodiments, the cutoff is between 10-50 nm. In other embodiments, the cutoff is between 25-75 nm. In other embodiments, the cutoff is between 40-100 nm.

A "microfiltration membrane" refers herein to a membrane having a pore size of approximately 0.03 to 10 microns.

An "ultrafiltration membrane" refers herein a membrane having a pore size of approximately 0.002 to 0.1 microns.

In some embodiments, the microfiltration/ultrafiltration membrane of the current invention is used in filtration. In another embodiment, it is used in filtration of particles. In another embodiment, it is used in filtration of nanoparticles. In another embodiment, it is used in filtration of biomolecules. In another embodiment, the biomolecules comprise proteins, nucleic acids and any combination thereof.

In various embodiments, the free-standing film of this invention is used as a mold or a template for generation of porous materials. In other embodiments, the porous material is a porous polymeric film, a porous metal film, a porous nanoclay film, a porous inorganic fullerene film or a porous carbon material film.

In various embodiments, a porous polymeric film, a porous metal film, a porous nanoclay film, a porous inorganic fullerene film or a porous carbon material film is prepared by forming a polymeric layer, a metal layer, a nanoclay layer, an inorganic fullerene layer or a carbon material layer on or around the free-standing film of this invention followed by removal of the free-standing film by dissolving it in an organic solvent and thereby obtaining a porous polymeric film, a porous metal film, a porous nanoclay film, a porous inorganic fullerene film or a porous carbon material film. In other embodiments the metal layer is formed on the free-standing film by metal vapor deposition, by reducing a metal salt, by heating of metal nanoparticles, or by any other technique known in the art. In other embodiments the polymeric layer is formed by melting a thermoplastic polymer on the free-standing film, or by in situ polymerization of monomers in the presence of the free-standing film. In other embodiment the polymer is coated on the surface of the free-standing film by any technique known in the art. In other embodiment, the nanoclay layer is formed by deposition of a solution or suspension of nanoclay on the free-standing film of this invention, or by any other technique known in the art. In other embodiment, the carbon material layer is formed by deposition of a solution or suspension of carbon material on the free-standing film of this invention, or by any other technique known in the art. In other embodiment, the inorganic fullerene layer is formed by deposition of a solution or suspension of inorganic fullerene material on the free-standing film of this invention, or by any other technique known in the art.

Electrodes Comprising a Free-Standing Film or a Composition

In one embodiment, the current invention provides an electrode comprising a free-standing film or a composition according to this invention. In another embodiment, the electrode is a cathode or an anode. In another embodiment, the electrode further comprises a binder, an additive, a current collector or any combination thereof. In another embodiment, the free-standing film or composition according to this invention is used as a binder, an additive, a current collector or any combination thereof.

Process of Preparation of the Free-Standing Film

In one embodiment, the current invention provides a process for preparing free-standing films according to this invention.

In one embodiment, this invention provides a process for the preparation of free-standing films, comprising the following steps:
  a) dissolving an aromatic material in a solvent or a mixture of solvents;
  b) optionally, mixing a reinforcement material dissolved in a solvent or a mixture of solvents, with the aromatic material solution of step (a);
  c) aging the solution of step (a) or (b);
  d) filtering the aged solution of step (c) over a support and forming a film on top of the surface; and
  e) separating the resulting film of step (d), giving rise to delamination thereof.

In one embodiment, this invention provides a process for the preparation of free-standing films comprising an aromatic material and a reinforcement material, comprising the following steps:
  a) dissolving an aromatic material in a solvent or a mixture of solvents;
  b) mixing a reinforcement material dissolved in a solvent or a mixture of solvents, with the aromatic material solution of step (a);
  c) aging the solution of step (b);
  d) filtering the aged solution of step (c) over a support and forming a film on top of the surface; and
  e) separating the resulting film of step (d), giving rise to delamination thereof.

In one embodiment, this invention provides a process for the preparation of free-standing films, comprising:
a) dissolving an aromatic material in a solvent or a mixture of solvents;
b) optionally, mixing dissolving a reinforcement material dissolved in a solvent or a mixture of solvents, with the aromatic material solution of step (a);
wherein seeds of said aromatic material are added to the solution of step (a) or (b);
c) aging the solution of step (a) or (b);
d) filtering the aged solution of step (c) over a support and forming a film on top of the surface; and
e) separating the resulting film of step (d), giving rise to delamination thereof.

In one embodiment, this invention provides a process for the preparation of free-standing films, comprising an aromatic material and a reinforcement material comprising the following steps:
a) dissolving an aromatic material in a solvent or a mixture of solvents;
b) mixing a reinforcement material dissolved in a solvent or a mixture of solvents with the aromatic material solution of step (a);
wherein seeds of said aromatic material are added to the solution of step (a) or (b);
c) aging the solution of step (a) or (b);
d) filtering the aged solution of step (c) over a support and forming a film on top of the surface; and
e) separating the resulting film of step (d), giving rise to delamination thereof.

In one embodiment, seeds of aromatic material are prepared by dissolving the aromatic material in organic solvent and adding water to it.

In one embodiment, a solvent is used for the dissolution of step (a) and (b). In another embodiment, the solvent is organic. In another embodiment, the solvent is aqueous. In another embodiment, a mixture of solvents is used. In another embodiment, the mixture is a mixture of organic solvents. In another embodiment, the mixture is a mixture of water and at least one organic solvent. In another embodiment, non limiting examples of organic solvents include THF, acetone, DMF or acetonitrile. In another embodiment, THF/water mixture is used in various ratios. In another embodiment, THF/water is used in 1:4 volumetric ratio. In another embodiment the THF/water volume ratio is between 10:90 to 50:50.

In one embodiment, the resulting film of step (d) is separated in step (e). In another embodiment, the film is separated manually. In another embodiment, the film is separated by dipping in solvent or mixture of solvents. In another embodiment, the film is separated by drying.

In one embodiment, the separation of the film from the support is carried out by dipping the film in a solvent. In another embodiment, the dipping solvent is organic. In another embodiment, the dipping solvent is water. In another embodiment, a mixture of solvents is used. In another embodiment, the mixture is a mixture of organic solvents. In another embodiment, the mixture is a mixture of water and organic solvent or solvents. In another embodiment, non limiting examples of organic solvents include THF, acetone, acetonitrile and DMF. In another embodiment, acetonitrile is used.

In one embodiment, aging of step (c) is of between 1-50 days. In another embodiment, the aging is of between 5-40 days. In another embodiment, the aging is of between 5-35 days. In another embodiment, the aging is of between 1-30 days. In another embodiment, the aging is of between 15-40 days. In another embodiment, the aging is of between 5-30 days.

In one embodiment, the support of step (d) is selected from polyethersulphone (PES), Polyvinylidene fluoride (PVDF), Teflon, or any other polymer that is not dissolved in water.

In one embodiment, the dissolution of step (b) of a reinforcement material with the aromatic material of step (a) is done simultaneously with the dissolution of the aromatic compound. In another embodiment, the reinforcement material dissolution is done prior to the dissolution of the aromatic compound. In another embodiment, the reinforcement material dissolution is done following the dissolution of the aromatic compound. In another embodiment, the dissolution of the aromatic compound and the reinforcement material, together or separately is done with sonication or without sonication.

Hybrid Compositions

In various embodiments, this invention provides a hybrid composition comprising a carbon nanotube (CNT) and organic nanocrystals (ONC).

In another embodiment, the hybrid composition further comprises an organic polymer. In another embodiment, the organic polymer is selected from the group consisting of: polyvinyl alcohol, polyethylene glycol (PEG), polyethylene, polypropylene, polystyrene, polyacrylonitrile, polyamide, polyimide, polyester and any combination thereof. Each possibility represents a separate embodiment of this invention.

In other embodiments the organic nanocrystals are not soluble in water.

In other embodiment, the small hydrophobic organic compound is below 2 kD. In other embodiment, the small hydrophobic organic compound is below 1 kD. In other embodiments, the hydrophobic organic compound comprises an aromatic core, which is substituted or unsubstituted. In other embodiments, the aromatic core is substituted by electron deficient groups. In other embodiments, the aromatic core is substituted by $(C_7-C_{10})$alkyl, $(C_1-C_{10})$haloalkyl, $(C_3-C_8)$cycloalkyl, aryl or heteroaryl (wherein said alkyl, haloalkyl, cycloalkyl, aryl or heteroaryl groups are optionally substituted), $CF_3$, halide, $OR^6$, $OCH_3$, $COR^6$, $COCl$, $COOCOR^6$, $COOR^6$, $OCOR^6$, $OCONHR^6$, $NHCOOR^6$, $NHCONHR^6$, $OCOOR^6$, $CON(R^6)_2$, $SR^6$, $SO_2R^6$, $SOR^6$ $SO_2NH_2$, $SO_2NH(R^6)$, $SO_2N(R^6)_2$, $NH_2$, $NH(R^6)$, $N(R^6)_2$, $CONH_2$, $CONH(R^6)$, $CON(R^6)_2$, CO(N-heterocycle), $NO_2$, OH, CN, cyanate, isocyanate, thiocyanate, isothiocyanate, mesylate, tosylate or triflate; wherein $R^6$ is H, $(C_7-C_{10})$alkyl, $(C_7-C_{10})$haloalkyl, $(C_3-C_8)$cycloalkyl, aryl or heteroaryl, wherein the alkyl, haloalkyl, cycloalkyl, aryl or heteroaryl groups are optionally substituted; and all substituents are described hereinabove. Each represents a separate embodiment of this invention.

In other embodiments, the carbon nanotube is a single walled carbon nanotube (SWCNT). In other embodiments, the carbon nanotube is a (6,5)-single walled carbon nanotube. In other embodiments, the carbon nanotube is a multi-walled carbon nanotube.

"Carbon nanotubes," refers herein to sheets of graphene that form tubes.

"Single-walled nanotube," as defined herein, refers to a nanotube that does not contain another nanotube.

"Multi-walled carbon nanotube," refers herein to more than one nanotube within nanotubes (including for example double walled nanotube).

"Nanotube," refers herein to any tube with nanoscale dimensions.

In various embodiments, the hybrid composition of this invention comprises between 3 wt % to 85 wt % of carbon nanotube (CNT). In other embodiments, the hybrid composition comprises between 3 wt % to 80 wt % of carbon nanotube (CNT). In other embodiments, the hybrid composition comprises between 3 wt % to 75 wt % of carbon nanotube (CNT). In other embodiments, the hybrid composition comprises between 3 wt % to 70 wt % of carbon nanotube (CNT). In other embodiments, the hybrid composition comprises between 3 wt % to 40 wt % of carbon nanotube (CNT). In other embodiments, the hybrid composition comprises between 5 wt % to 10 wt % of carbon nanotube (CNT). In other embodiments, the hybrid composition comprises between 5 wt % to 15 wt % of carbon nanotube (CNT). In other embodiments, the hybrid composition comprises between 10 wt % to 30 wt % of carbon nanotube (CNT). In other embodiments, the hybrid composition comprises between 5 wt % to 20 wt % of carbon nanotube (CNT). In other embodiments, the hybrid composition comprises between 15 wt % to 60 wt % of carbon nanotube (CNT). In other embodiments, the hybrid composition comprises between 20 wt % to 70 wt % of carbon nanotube (CNT). In other embodiments, the hybrid composition comprises between 35 wt % to 75 wt % of carbon nanotube (CNT). In other embodiments, the hybrid composition comprises between 65 wt % to 70 wt % of carbon nanotube (CNT). In other embodiments, the hybrid composition comprises between 3 wt % to 70 wt % of multi-walled carbon nanotube (CNT). In other embodiments, the hybrid composition comprises between 3 wt % to 40 wt % of single-walled carbon nanotube (CNT).

Hybrid materials based on ONCs have not been investigated, because the methodologies to control ONC formation in solution are limited.

In other embodiments, the hybrid composition of this invention comprises an organic crystalline hydrophobic material and carbon nanotubes. In another embodiment, the hybrid composition comprises organic nanocrystalline hydrophobic material and carbon nanotubes. In another embodiment, the hybrid composition comprises nanocrystalline aromatic material and carbon nanotubes. In another embodiment, the organic nanocrystalline hydrophobic material is rylenediimide derivatives, dimers thereof, trimers thereof or any mixtures thereof. In other embodiments the rylenediimide derivatives include-nephthalene diimide derivatives, perylene diimide derivatives, terrylene diimide derivatives or combination thereof. Each represents a separate embodiment of this invention.

In other embodiments, a derivative of perylene diimide, naphthalene diimide or terrylene diimide refers to perylene diimide, naphthalene diimide or terrylene diimide substituted with one or more substituents selected from $(C_7-C_{10})$ alkyl, $(C_7-C_{10})$haloalkyl, $(C_3-C_8)$cycloalkyl, aryl or heteroaryl (wherein said alkyl, haloalkyl, cycloalkyl, aryl or heteroaryl groups are optionally substituted), OH, OR$^6$, OCH$_3$, CF$_3$, halide, F, COR$^6$, COCl, COOCOR$^6$, COOH, COOR$^6$, OCOR$^6$, OCONHR$^6$, NHCOOR$^6$, NHCONHR$^6$, OCOOR$^6$, CN, CON(R$^6$)$_2$, SR$^6$, SO$_2$R$^6$, SOR$^6$, SO$_3$H, SO$_2$M, SO$_3$M, SO$_2$NH$_2$, SO$_2$NH(R$^6$), SO$_2$N(R$^6$)$_2$, NH$_2$, NH(R$^6$), N(R$^6$)$_2$, CONH$_2$, CONH(R$^6$), CON(R$^6$)$_2$, CO(N-heterocycle), C(O)(C$_7$-C$_{10}$)alkyl, NO$_2$, CN, cyanate, isocyanate, thiocyanate, isothiocyanate, mesylate, tosylate, triflate, PO(OH)$_2$ or OPO(OH)$_2$, wherein R$^6$ is H, (C$_7$-C$_{10}$)alkyl, (C$_7$-C$_{10}$)haloalkyl, (C$_3$-C$_8$)cycloalkyl, aryl or heteroaryl, (wherein said alkyl, haloalkyl, cycloalkyl, aryl or heteroaryl groups are optionally substituted); wherein M is a monovalent cation; and all substituents are described hereinabove.

In various embodiments, the nanocrystalline hydrophobic material is a perylene diimide derivative represented by the structure of IA, IB, II, III, 1', 2a', 2b', 3', 4', 1, 2, 3, 4a, 4b or 5, as described hereinabove.

In other embodiments, the hybrid composition of this invention comprises one or more different perylene diimide derivatives. In other embodiments the hybrid composition comprises 2, 3, 4, 5 different perylene diimide derivatives. Each represents a separate embodiment of this invention.

In other embodiments, the hybrid composition comprises a mixture of perylene diimide 4a and 4b. In other embodiments, the mixture of 4a and 4b is in a ratio of between 1:9 to 9:1, respectively. In another embodiment, the mixture of 4a and 4b is in a ratio of 3:7, respectively.

Process of Preparation of the Hybrid Composition

In various embodiments, this invention provides a process for the preparation of the ONC/CNT hybrid composition of this invention, the process comprises:
  mixing a hydrophobic organic compound and a carbon nanotube (CNT) in a first organic solvent;
  optionally drying the mixture;
  adding to the mixture a second organic solvent and water to obtain an aqueous medium and mixing for a period of time to obtain the hybrid; wherein if the first organic solvent and the second organic solvent are the same, only water is added to the mixture.

In various embodiments, this invention provides a process for the preparation of the ONC/CNT hybrid composition of this invention, the process comprises:
  mixing a hydrophobic organic compound and a carbon nanotube (CNT) in a first organic solvent;
  optionally drying the mixture;
  optionally, adding to the mixture a second organic solvent to obtain an organic medium and mixing for a period of time to obtain the hybrid.

In various embodiments, this invention provides a process for the preparation of the ONC/CNT hybrid composition of this invention, the process comprises:
  mixing a hydrophobic organic compound and a carbon nanotube (CNT) in a first organic solvent;
  optionally drying the mixture;
  optionally adding to the mixture a second organic solvent, water or any combination thereof to obtain an organic or aqueous medium and mixing for a period of time to obtain the hybrid In various embodiments, the process for the preparation of the hybrid composition of this invention further comprises purification of the hybrid by centrifugation, or precipitation to yield homogeneous ONC/CNT hybrid composition.

In various embodiments, the process for the preparation of the hybrid composition of this invention comprises mixing a hydrophobic organic compound and a CNT in a first organic solvent. In various embodiment, the process for the preparation of a CNT dispersion comprising mixing CNT with PDI of formula IA or IB in a first organic solvent. In other embodiments, the first organic solvent is chloroform, methylene chloride, carbon tetrachloride dichloroethane, glyme, diglyme, triglyme, triethylene glycol, trichloroethane, tertbutyl methyl ether, tetrachloro ethane, acetone, THF, DMSO, toluene, benzene, alcohol, chlorobenzene, acetonitrile, dioxane, ether, NMP, DME, DMF, ethyl-acetate or combination thereof. Each represents a separate embodiment of this invention.

In various embodiments, the process for the preparation of the hybrid composition of this invention comprises adding to the dried mixture an aqueous medium and mixing it for a period of time to obtain a hybrid of this invention. In other embodiments, the process for the preparation the hybrid composition of this invention comprises adding an aqueous medium to the mixture with the first organic solvent (without the drying step), and mixing it for a period of time to obtain a hybrid composition of this invention.

In various embodiments, the process for the preparation of the hybrid composition of this invention comprises adding to the dried mixture or to the mixture with the first organic solvent a second organic solvent and water to obtain an aqueous medium. In various embodiments, the process for the preparation of a CNT dispersion of this invention comprises adding to the dried mixture or to the mixture with the first organic solvent a second organic solvent and water to obtain an aqueous medium In other embodiments, the second organic solvent is any solvent which is solubilized in water. In other embodiments, the second organic solvent is, acetone, THF, DMSO, NMP, DME, alcohol, DMF, acetonitrile, dioxane or combination thereof. Each represents a separate embodiment of this invention.

In other embodiments, the aqueous medium comprises a mixture of a second organic solvent and water. In other embodiments, the aqueous medium comprises a mixture of a first organic solvent, a second organic solvent and water. In other embodiments, the aqueous medium comprises a mixture of a first organic solvent and water (when the first and second organic solvent are the same). In other embodiments the first organic solvent includes more than one organic solvent. In other embodiments the second organic solvent includes more than one organic solvent.

In other embodiment, the process for the preparation of hybrid composition comprising mixing the hydrophobic organic compound and the carbon nanotube in chloroform, followed by drying the mixture and adding an aqueous medium for a period of time to obtain the hybrid composition.

In various embodiments, the aqueous medium used in the process includes THF and water. In other embodiments the aqueous medium used in the process includes acetone and water. In other embodiments the aqueous medium used in the process includes acetone, THF and water. In other embodiments the aqueous medium used in the process includes acetone, chloroform and water. In other embodiments the aqueous medium used in the process includes acetone, THF, chloroform and water. In other embodiments the aqueous medium used in the process includes alcohol and water. In other embodiments the aqueous medium used in the process includes DMF and water. In other embodiments the aqueous medium used in the process includes DMSO and water. In other embodiment, the aqueous medium mixture is mixed at room temperature. In other embodiment, the aqueous medium mixture is heated. In other embodiment, the aqueous medium mixture is mixed under sonication. In other embodiment, the aqueous medium mixture is mixed for a period of time to obtain an homogeneous mixture. In other embodiment, the aqueous medium mixture is mixed under sonication for between 30 min to 1 hr.

Properties of the Hybrid Composition and uses Thereof

In various embodiments, the hybrid composition of this invention is stable for a period of at least seven days. In other embodiment, ONC/SWCNT with 40 wt % SWCNT are stable for at least seven days. In other embodiment, ONC/MWCNT with 60-67 wt % MWCNT are stable for up to three days. In other embodiment, ONC/SWCNT with 3-8 wt % SWCNT are stable for at least a month. In other embodiment, ONC/MWCNT with 3-8 wt % SWCNT are stable for at least a month.

In various embodiments, the conductivity of the hybrid composition of this invention is higher than the conductivity of a polymer/CNT for the same percentage of CNT.

In various embodiments, the hybrid composition of this invention is thermally stable up to a temperature of 250° C. deg. In other embodiment, the hybrid composition of this invention is thermally stable up to a temperature of between 250° C. deg. to 500° C. deg. In other embodiment, the hybrid composition of this invention is thermally stable up to a temperature of between 250° C. deg. to 400° C. deg In some embodiments, this invention provides a film comprising the hybrid composition of this invention. In other embodiments, the film is a free-standing film. In other embodiment, the film or the free-standing film is further coated by an additional organic nanocrystal hydrophobic material. In other embodiment, the film or the free-standing film is further coated by a dye material. In other embodiment, the film or the free-standing film further comprises an organic polymer. In other embodiment, the film or the free-standing film further comprises nanoclays.

The ONC/CNT hybrid of this invention is self-assembled in aqueous medium as a dispersion and is subsequently used to prepare ONC/CNT films. These films have high conductivity due to the formation of uninterrupted 3D CNT networks, and high thermal stability due to the robustness of ONCs. The ONC/CNT hybrid materials assembled from common perylene diimide dyes advantageously combine the optical and electrical properties of the two constituent components. In other embodiments, the ONC/CNT films are free-standing films.

In various embodiments, the ONC/CNT hybrid film is prepared by filtration of the ONC/CNT dispersion on a solid support to obtain the film deposited on the solid support. Non-limiting examples of solid support include polyvinylidene fluoride (PVDF), polyethersulphone (PES), Teflon, glass membrane or nylon. Each represents a separate embodiment of this invention.

In other embodiment, the free-standing film is obtained by releasing the deposited film from the support manually, by washing/dipping in solvent or mixture of solvents. In another embodiment, the film is separated by drying. Non limiting examples of solvent or mixture of solvents used to separate the film from the solid support include THF, acetone, acetonitrile, DMF or combination thereof. Each represents a separate embodiment of this invention.

In one embodiment, the film/free-standing film of the current invention is fabricated in various dimensions and shapes.

In some embodiments, a film/free-standing film of the current invention has a thickness of between 100 nm to 500 microns. In another embodiment, the film/free-standing film has a thickness of between 100 nm to 10 μm. In another embodiment, the film/free-standing film has a thickness of between 5-50 μm. In another embodiment, the film/free-standing film has a thickness of between 10-30 μm. In another embodiment, the film has a thickness of between 20-100 μm. In another embodiment, the film/free-standing film has a thickness of about 15-50 μm.

In some embodiments, the hybrid composition and/or film comprising thereof demonstrate advantageous properties. In one embodiment, the hybrid composition and/or film comprising thereof of the current invention are emissive and have non linear optical (NLO) effects due to the aromatic material. Macroscopic organic non linear optical (NLO) materials are normally based on NLO active molecules embedded into polymers and poled, resulting in poor long-term thermal stability; on the other hand, the hybrid composition and/or film comprising thereof of the current invention show NLO response, and such response is surprisingly unchanged over time and after heating. In another embodiment, the film is a free-standing film.

In some embodiments, the hybrid composition and/or film comprising thereof of the current invention have non linear optical (NLO) properties. In another embodiment, the NLO effect is of the second harmonic generation (SHG) type. In another embodiment, the films of the materials of the current invention show unchanged NLO response over several months at room temperature and up to few hours after heating to 250° C. In another embodiment, the film is a free-standing film.

In one embodiment, the hybrid composition and/or film comprising thereof compositions of the current invention are used as sensors to quenching fluorescence. In another embodiment, the film is a free-standing film.

In one embodiment, the hybrid composition and/or film comprising thereof of the current invention is porous. In other embodiments, the porous size is between 0.5-100 nm. In other embodiments, the porous size is between 0.5 to 5 nm. In other embodiments, the porous size is between 1-10 nm. In other embodiments, the porous size is between 5-15 nm. In other embodiments, the porous size is between 10-25 nm. In other embodiments, the porous size is between 10-50 nm. In other embodiments, the porous size is between 25-75 nm. In other embodiments, the porous size is between 40-100 nm. In another embodiment, the film is a free-standing film.

Nanoporous structure of the hybrid composition and/or film comprising thereof the current invention enables their utilization as microfiltration or ultrafiltration membranes. These films can be disassembled and recycled as a way to manage membrane fouling. In another embodiment, the film is a free-standing film.

In other embodiments, this invention provides a microfiltration or an ultrafiltration membrane comprising the free-standing film of the invention. In another embodiment, the film is a free-standing film.

In one embodiment, the film/free-standing films of the current invention are used as microfiltration or ultrafiltration membranes. In other embodiments, the membranes are recyclable. In other embodiments, the membranes have a filtration cutoff of between 0.5-100 nm. In other embodiments, the cutoff is between 40-60 nm. In other embodiments, the cutoff is 50 nm. In other embodiments, the cutoff is between 10-40 nm. In other embodiments, the cutoff is between 1-10 nm. In other embodiments, the cutoff is 1 nm. In other embodiments, the cutoff is between 0.5 to 5 nm. In other embodiments, the cutoff is between 1-10 nm. In other embodiments, the cutoff is between 5-15 nm. In other embodiments, the cutoff is between 10-25 nm. In other embodiments, the cutoff is between 10-50 nm. In other embodiments, the cutoff is between 25-75 nm. In other embodiments, the cutoff is between 40-100 nm.

A "microfiltration membrane" refers herein to a membrane having a pore size of approximately 0.03 to 10 microns.

An "ultrafiltration membrane" refers herein a membrane having a pore size of approximately 0.002 to 0.1 microns.

In some embodiments, the microfiltration/ultrafiltration membrane of the current invention is used in filtration. In another embodiment, it is used in filtration of particles. In another embodiment, it is used in filtration of nanoparticles. In another embodiment, it is used in filtration of biomolecules. In another embodiment, the biomolecules comprise proteins, nucleic acids and any combination thereof.

In some embodiments, this invention provides a membrane for the separation of nanoparticles, biomolecules, comprising the free-standing film of this invention.

In various embodiments, the film/free-standing film of this invention is used as a mold or a template for generation of porous materials. In other embodiments, the porous material is a porous polymeric film, a porous metal film, a porous nanoclay film, a porous inorganic fullerene film or a porous carbon material film.

In various embodiments, a porous polymeric film, a porous metal film, a porous nanoclay film, a porous inorganic fullerene film or a porous carbon material film is prepared by forming a polymeric layer, a metal layer, a nanoclay layer, an inorganic fullerene layer or a carbon material layer on or around the free-standing film of this invention followed by removal of the free-standing film by dissolving it in an organic solvent and thereby obtaining a porous polymeric film, a porous metal film, a porous nanoclay film, a porous inorganic fullerene film or a porous carbon material film. In other embodiments the metal layer is formed on the free-standing film by metal vapor deposition, by reducing a metal salt, by heating of metal nanoparticles, or by any other technique known in the art. In other embodiments the polymeric layer is formed by melting a thermoplastic polymer on the free-standing film, or by in situ polymerization of monomers in the presence of the free-standing film. In other embodiment the polymer is coated on the surface of the free-standing film by any technique known in the art. In other embodiment, the nanoclay layer is formed by deposition of a solution or suspension of nanoclay on the free-standing film of this invention, or by any other technique known in the art. In other embodiment, the carbon material layer is formed by deposition of a solution or suspension of carbon material on the free-standing film of this invention, or by any other technique known in the art. In other embodiment, the inorganic fullerene layer is formed by deposition of a solution or suspension of inorganic fullerene material on the free-standing film of this invention, or by any other technique known in the art.

In other embodiments, this invention provides a conductive colorant comprising the free-standing film of this invention.

CNT Dispersion and CNT Film (Buckypapers)

In one embodiment, this invention provides a CNT dispersion comprising a CNT and a PDI of formula IA, IB or combination thereof. The unique properties of CNT are advantageous for emerging applications. Yet, the CNT insolubility hampers their potential. This invention provides stable dispersions of CNTs.

In some embodiments, this invention provides a process for the preparation of a CNT dispersion, the process comprises mixing CNT in a first organic solvent, with perylenediimide (PDI) represented by the structure of formula IA or 1B or combination thereof to obtain a CNT dispersion. In other embodiment, the CNT dispersion comprises a PDI/CNT hybrid.

In some embodiments, this invention provides a process for the preparation of a CNT dispersion, the process comprises: (i) mixing CNT in a first organic solvent, with perylenediimide (PDI) represented by the structure of formula IA or 1B or combination thereof; (ii) optionally drying the mixture; and (iii) adding to the mixture a second organic solvent and water to obtain an aqueous medium and mixing for a period of time to obtain a CNT dispersion; wherein if the first organic solvent and the second organic solvent are the same, only water is added to the mixture. In other embodiment, the CNT dispersion comprises an ONC/CNT hybrid of this invention.

In some embodiments, this invention provides a process for the preparation of a CNT dispersion, the process comprises: (i) mixing CNT in a first organic solvent, with perylenediimide (PDI) represented by the structure of formula IA or 1B or combination thereof; (ii) optionally drying the mixture; and (iii) adding to the mixture a different first organic solvent and mixing for a period of time to obtain a CNT dispersion. In other embodiment, the CNT dispersion comprises a PDI/CNT hybrid.

The efficient dispersion and exfoliation using the mixture of CNT and PDI or the mixture of CNT and ONC is attributed to a charge shift (electron transfer) from CNT to the PDI/ONC (such as to the perylene diimide (PDI)) layer absorbed on the CNT walls).

On other embodiments CNT dispersion with various PDI derivatives are presented in FIGS. 1A to 1F. The charge shift is supported by computational (DFT), electrochemical studies, and Raman spectroscopy studies (Example 2, FIG. 17A, 17B). The charge shift results in repulsion between CNTs and promotes solvation, eliminating the need for hydrophilic groups.

In some embodiments a CNT dispersion is applied on solid surfaces such as non limiting examples of glass, silicon oxide, PP, PVC, PET and paper by drop casting to form conductive ONC/CNT hybrid films or PDI/CNT hybrid films (depending on the process for the preparation of the CNT dispersion). In other embodiment, the CNT dispersion comprises a ONC/CNT hybrid. In other embodiment, the CNT dispersion comprises a PDI/CNT hybrid.

In some embodiment, a CNT dispersion is applied on solid surfaces as presented in Example 22 to form a conductive film.

In various embodiments, this invention provides an ONC/CNT hybrid film. In other embodiments, this invention provides a PDI/CNT hybrid film.

In various embodiments, the ONC/CNT and/or PDI/CNT films prepared by the process of this invention are used for the preparation of electrodes. In other embodiments, the ONC/CNT and/or PDI/CNT films prepared by the process of this invention are used for the preparation of porous electrodes. In other embodiments, the ONC/CNT and/or PDI/CNT films prepared by the process of this invention are used for the preparation of transparent electrodes.

In various embodiments, this invention provides an electrode comprising the ONC/CNT and/or PDI/CNT films prepared by the process of this invention. In other embodiments, this invention provides a porous electrode comprising the ONC/CNT and/or PDI/CNT films prepared by the process of this invention. In other embodiments, this invention provides a transparent electrode comprising the ONC/CNT and/or PDI/CNT films prepared by the process of this invention.

In some embodiments, this invention provides a process for the preparation of CNT film (buckypapers), the process comprises washing the ONC/CNT hybrid film or a PDI/CNT film of this invention with a third organic solvent and thereby removing the organic nanocrystals (ONC) from the ONC/CNT hybrid or removing the PDI from the PDI/CNT hybrid composition down to a range of between 0.1-10 wt % of the total mass of the hybrid; and obtaining porous CNT film.

In other embodiments, the CNT films are prepared according to Example 20.

In other embodiments, the organic nanocrystals and/or PDI are removed from the ONC/CNT or PDI/CNT hybrid compositions down to a range of between 0.1-10 wt % of the total mass of the hybrid. In other embodiments, the organic nanocrystals and/or PDI are removed from the ONC/CNT or PDI/CNT hybrid compositions down to about 1 wt % of the total mass of the hybrid. In other embodiments, the organic nanocrystals and/or PDI are removed from the ONC/CNT or PDI/CNT hybrid compositions down to a range of between 0.5-10 wt % of the total mass of the hybrid. In other embodiments, the organic nanocrystals and/or PDI are removed from the ONC/CNT or PDI/CNT hybrid compositions down to a range of between 0.5-5 wt % of the total mass of the hybrid. In other embodiments, the organic nanocrystals and/or PDI are removed from the ONC/CNT or PDI/CNT hybrid compositions down to a range of between 1-5 wt % of the total mass of the hybrid. In other embodiments, the organic nanocrystals and/or PDI are removed from the ONC/CNT or PDI/CNT hybrid compositions down to a range of between 1-3 wt % of the total mass of the hybrid.

In other embodiments, the third organic solvent used for removing the organic nanocrystals from the hybrid composition includes chloroform, methylene chloride, DMF, DMSO, THF, acetone, toluene, tertbutyl methyl ether, tetrachloro ethane, carbon tetrachloride, trichloroethane or combination thereof. Each represents a separate embodiment of this invention.

In various embodiments, the CNT films prepared by the process of this invention are used for the preparation of electrodes. In other embodiments, the CNT films prepared by the process of this invention are used for the preparation of porous electrodes. In other embodiments, the CNT films prepared by the process of this invention are used for the preparation of transparent electrodes.

In various embodiments, this invention provides an electrode comprising the CNT films prepared by the process of this invention. In other embodiments, this invention provides a porous electrode comprising the CNT films prepared by the process of this invention. In other embodiments, this invention provides a transparent electrode comprising the CNT films prepared by the process of this invention.

Perovskite Solar Cells

In various embodiments, this invention provides a perovskite solar cell comprising an ONC/CNT hybrid composition of this invention. In other embodiments, this invention provides a perovskite solar cell comprising a PDI/CNT hybrid composition of this invention. In other embodiments, this invention provides a perovskite solar cell comprising a CNT hybrid composition of this invention.

Although extremely efficient (~20%) and easy to fabricate, [Hodes, G.; Cahen, D. *Nat. Photonics* 2014, 8, 87-88.] hybrid organic/inorganic perovskite (such as methyl ammonium lead iodide, $MAPbI_3$) solar cells suffer from intrinsic instability. [Leijtens, T.; Eperon, G. E.; Noel, N. K.; Habisreutinger, S. N.; Petrozza, A.; Snaith, H. J. *Adv. Energy Mater.* 2015, 5; Wang, D.; Wright, M.; Elumalai, N. K.; Uddin, A. *Sol. Energ. Mat. Sol. C* 2016, 147, 255-275; Berry, J. et al. *Adv. Mater.* 2015, 27, 5102-5112.] Furthermore, rather complex organic hole transporting materials (HTMs) that also lack stability are needed to yield high efficiencies. [Green, M. A.; Ho-Baillie, A.; Snaith, H. J. *Nat. Photonics* 2014, 8, 506-514.]

The commonly employed HTMs are organic materials with appropriately tuned HOMO energy levels. These are complex organic molecules or polymers, whose involved synthesis and low stability at harsh device operating conditions is a drawback for creating cheap and stable solar cell. Furthermore, in most systems, in order to improve charge transport properties of poorly conducting organics, the latter are heavily doped with inorganic salts and oxygen, further complicating reproducible device fabrication and making the devices sensitive to humidity. Doping of HTMs was also observed to be damaging to the underlying perovskite layers. Finally, gold electrodes that are normally employed are expensive and give unstable interfaces with perovskite layers.

Overall, hybrid perovskite devices are prone to changes in structure and chemical composition that leads to hysteresis and efficiency losses, representing a key obstacle to their industrialization. It was recently reported that solar cells based on inorganic CsPbBr$_3$ perovskite can reach 5.6% efficiencies. [Kulbak, M.; Cahen, D.; Hodes, G. *J. Phys. Chem. Lett.* 2015, 6, 2452-2456.]

Unlike hybrid systems, these fully inorganic perovskites are stable up to at least 500° C. [Kulbak, M.; Cahen, D.; Hodes, G. *J. Phys. Chem. Lett.* 2015, 6, 2452-2456.] The efficiency of this system is limited by its bandgap (~2.3 eV) and voltage losses at interfaces as well as the presence of gold electrodes.

In various embodiments, this invention provides a perovskite solar cell comprising the ONC/CNT or PDI/CNT film or the CNT film of this invention which addresses the above stability/electrode-related challenges. In other embodiments, the perovskite solar cell of this invention are highly conductive, even in the presence of small amounts of CNTs (~1%), and are easily transferrable on to the perovskite cells.

In other embodiments, the perovskite solar cell of this invention demonstrated an efficiency of about 6%.

In other embodiments, the perovskite solar cell of this invention is stable for a period of at least two months. In another embodiment it prevents the chemical deterioration of the perovskite.

In one embodiment, the perovskite solar cell refers to lead halide and tin halide perovskites.

Electrodes Comprising a Hybrid Composition

In one embodiment, the current invention provides an electrode comprising a hybrid composition according to this invention. In another embodiment, the electrode is a cathode or an anode. In another embodiment, the electrode further comprises a binder, an additive, a current collector or any combination thereof. In another embodiment, the hybrid composition according to this invention is used as a binder, an additive, a current collector or any combination thereof.

In one embodiment, the terms "a" or "an" as used herein, refer to at least one, or multiples of the indicated element, which may be present in any desired order of magnitude, to suit a particular application, as will be appreciated by the skilled artisan.

In one embodiment, the term "about", refers to a deviance of between 0.0001-5% from the indicated number or range of numbers. In one embodiment, the term "about", refers to a deviance of between 1-10% from the indicated number or range of numbers.

In one embodiment, the term "room temperature" refers to the temperature of the environment where the relevant experiment has taken place. In another embodiment, "room temperature" is the temperature of 25±10° C. In another embodiment, "room temperature" is 25° C. In another embodiment, "room temperature" is 30° C. In another embodiment, "room temperature" is 35° C. In another embodiment, "room temperature" is 20° C. In another embodiment, "room temperature" is 15° C.

The following examples are presented in order to more fully illustrate the preferred embodiments of the invention. They should in no way, however, be construed as limiting the broad scope of the invention.

EXAMPLES

Example 1

Synthesis of Compound 1

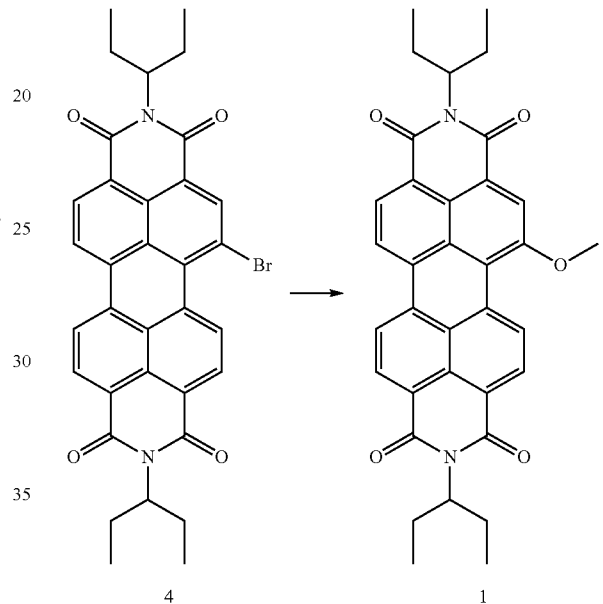

EP-PDI-OMe (1):

EP-PDI-Br (300 mg, 0.49 mmol, (4) (synthesized according to Rajasingh, P.; Cohen, R.; Shirman, E.; Shimon, L. J. W.; Rybtchinski, B. *The Journal of Organic Chemistry* 2007, 72, 5973) was dissolved in 10 mL THF. 1.4 mL of 0.5M KOH in MeOH was added. Upon addition of base, the solution changed color immediately to dark purple. The reaction was left stirring in ambient conditions over night. The reaction mixture was washed with 1M HCL and water, extracted to CHCl$_3$, Dried over MgSO$_4$ and concentrated under reduced pressure. The material was purified by silica gel column chromatography using chloroform as an eluent with gradual increase in polarity from 5% hexane to 2% methanol. Compound 1 (187 mg, 68%) was extracted and dried as a purple solid.

$^1$H NMR (toluene-d8, 300 MHz): δ=9.3 (d, 1H, J$_{HH}$=8.4 Hz, perylene-H), 8.71 (d, 1H, J$_{HH}$=8.4 Hz, perylene-H), 8.62 (d, 1H, J$_{HH}$=8.2 Hz, perylene-H), 8.51 (d, 1H, J$_{HH}$=8.4 Hz, perylene-H), 8.25 (s, 1H, perylene-H), 7.83 (dd, 2H, J$_{HH}$=8.2, 10 Hz, perylene-H), 5.33 (m, 2H, N(CH(CH$_2$CH$_3$)$_2$)), 3.41 (s, 3H, OMe-H), 2.54 (m, 4H, N(CH(CH$_2$CH$_3$)$_2$)), 1.93 (m, 4H, N(CH(CH$_2$CH$_3$)$_2$)), 1.01 (m 12H, N(CH(CH$_2$CH$_3$)$_2$)). $^{13}$C NMR (CDCl$_3$): 158.51, 134.72, 134.54, 134.17, 128.76, 128.62, 124.69, 123.66, 122.11, 57.97, 57.71, 57.0, 25.19, 11.50 MS-ESI (m/z): calculated for [M-H]$^-$ C$_{35}$H$_{32}$N$_2$O$_5$ 560.23; found: 560.25.

UV/Vis (THF): $\lambda_{max}$/nm=477, 509, 545. Fluorescence (THF): $\lambda_{max}$=568 nm; fluorescence quantum yield $\Phi_f$=0.94.

Example 2

Synthesis of Compound 2

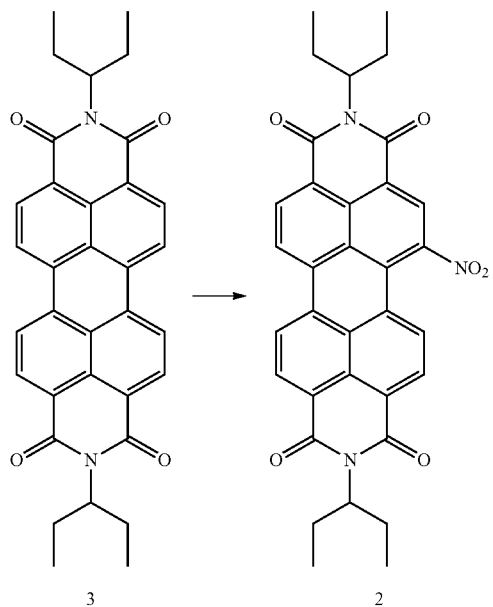 [SMILES: CCC(CC)N1C(=O)c2ccc3c4ccc5c6c(ccc(c7ccc(c2c37)C1=O)c64)C(=O)N(C(CC)CC)C5=O ; CCC(CC)N1C(=O)c2ccc3c4ccc5c6c(cc([N+](=O)[O-])c(c7ccc(c2c37)C1=O)c64)C(=O)N(C(CC)CC)C5=O]

3    2

EP-PDI-NO$_2$ (2):

(modification of: Chen, K.-Y.; Fang, T.-C.; Chang, M.-J. *Dyes and Pigments* 2012, 92, 517). Cerium Ammonium Nitrate (CAN, 100 mg, 0.18 mmol) was added to a solution of EP-PDI (3, 100 mg, 0.16 mmol) in dichloromethane (40 mL) under inert atmosphere. The reaction mixture was taken outside the glovebox and stirred under nitrogen for 15 minutes. Concentrated HNO$_3$ (58 µL) was added under nitrogen and the mixture stirred for 45 minutes. The solution changed color from orange to red. The reaction mixture was neutralized using KOH. The organic layer was washed thrice with water, dried over MgSO$_4$ and concentrated under reduced pressure. Silica gel column chromatography (dichloromethane as an eluent) of the residue gave 2 (92% yield).

$^1$H NMR (CDCl$_3$): δ=9.75 (m, 4H, overlapped perylene-H), 8.61 (d, 1H, $^3J_{HH}$=8.1 Hz, perylene-H), 8.26 (d, 1H, $^3J_{HH}$=8.1 Hz, perylene-H), 5.03 (m, 2H, N(CH(CH$_2$CH$_3$)$_2$)), 2.24 (m, 4H, N(CH(CH$_2$CH$_3$)$_2$)), 1.93 (m, 4H, N(CH(CH$_2$CH$_3$)$_2$)), 0.91 (t, 12H, $^3J_{HH}$=7.5, N(CH(CH$_2$CH$_3$)$_2$)). $^{13}$C NMR (75 MHz, CDCl$_3$): δ 147.66, 135.46, 132.91, 129.48, 129.35, 129.10, 127.92, 127.49, 126.66, 126.47, 124.43, 124.01, 58.91, 57.90, 24.94, 24.86, 11.28, 11.25. ESI-MS (m/z) [M]$^+$ calcd. for C$_{45}$H$_{41}$N$_3$O$_8$, 575.20; found, 575.21.

Example 3

Figure 3:
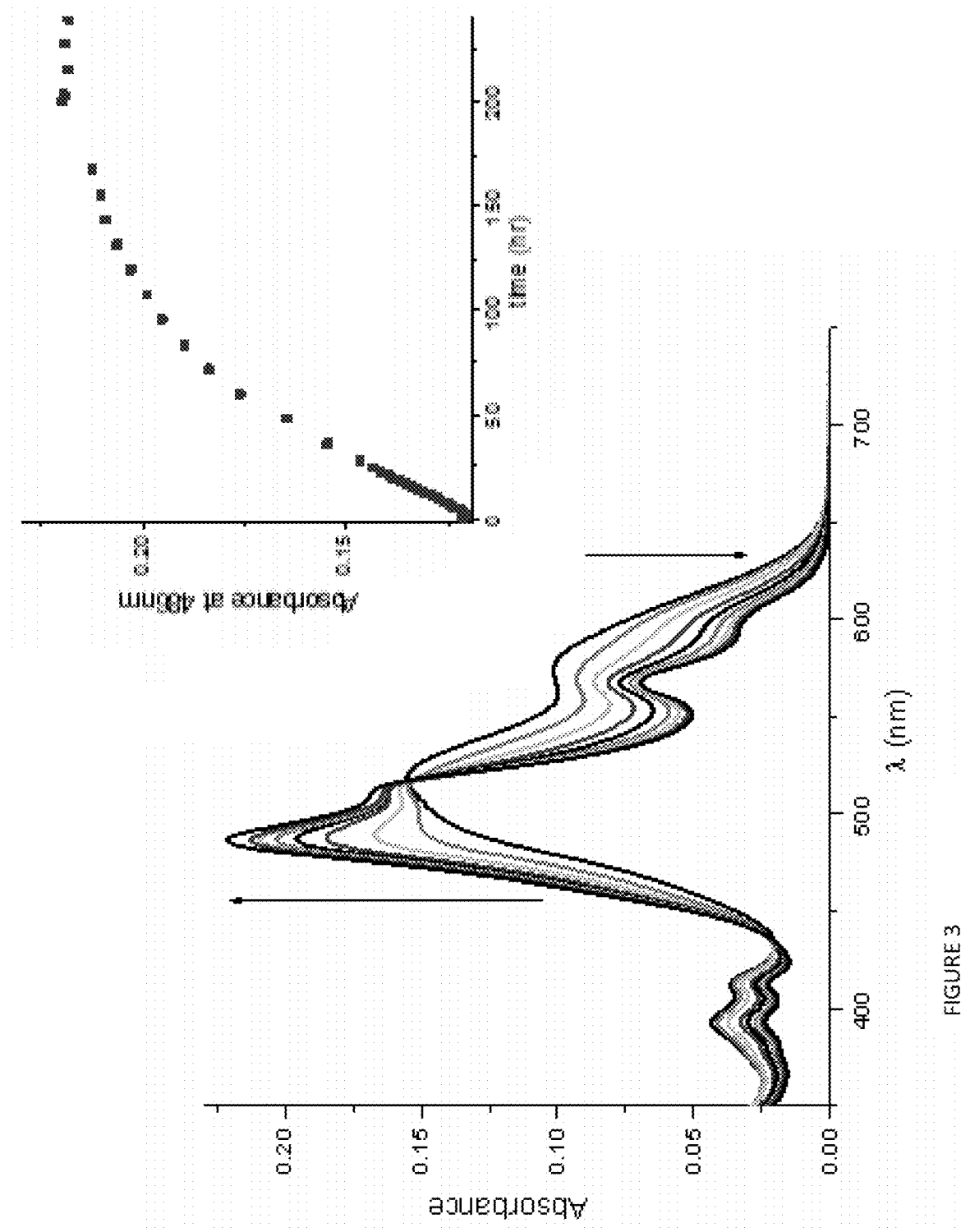
FIG. 3 depicts UV/VIS spectra of compound 1 in water/acetone (80/20, v/v) solution at a concentration of $4 \times 10^{-5}$M during crystal evolution (aging) at 20° C. Inset shows kinetic trace of absorbance signal at 486 nm.

Self-Assembly of Nanocrystalline Fibrous Structure Comprising Aromatic Material—Method A Compound 1 was dissolved in acetone, sonicated and was injected to double distilled water (4×10$^{-5}$M in acetone/water solution of 1:4, v/v). The resulting solution was aged (8-10 days) in a sealed vial or cuvette and the aging process was probed by UV-Vis spectroscopy (FIG. 3). Interestingly, the interaction mode between the aromatic cores of 1 changes substantially during the crystal transformation as evidenced by UV/Vis absorption changes. Initially, there was a broadening and 0-0/0-1 vibronic band inversion typical to cofacial π-π stacking of PDI (Wurthner, F. *Chemical Communications* 2004, 1564; Yan, P.; Chowdhury, A; Holman, M. W.; Adams, D. M. *The Journal of Physical Chemistry B* 2005, 109, 724; Wang, W.; Han, J. J.; Wang, L.-Q.; Li, L.-S.; Shaw, W. J.; Li, A. D. Q. *Nano Letters* 2003, 3, 455). Following that, a hypsochromic shift occurred and an intriguing increase in relative intensity of higher vibronic bands, located by order at 486 nm, 512 nm, 568 nm and 600 nm.

Following the aging, SEM and cryo-TEM images revealed the formation of high-aspect ratio flexible nanocrystalline fibers in solution, which were between 20-130 nm in width and several micrometers in length (FIGS. 4A and 4B). The nanofibers were stable in solution, without significant precipitation after a month of aging. The fibers exhibited emission peaking at 624 nm, with a quantum yield of 80% after aging for one month (FIG. 5).

Example 4

Figures 6C, 6D:
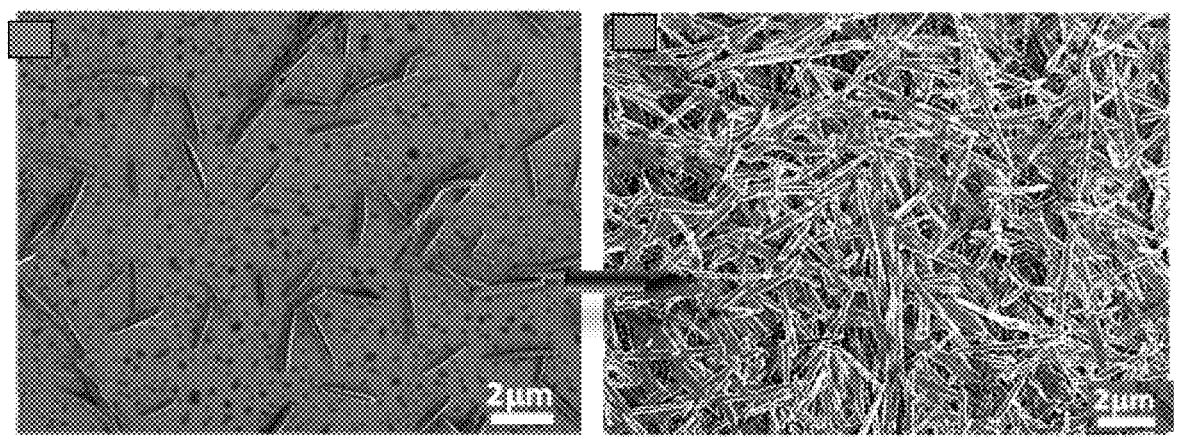

Self Assembly of Nanocrystalline Fibrous Structure Comprising Aromatic Material—Method B For precursor solution of compound 1 a solution of water\THF was mixed in a ratio of 70:30 v\v and a final concentration of 5·10$^{-5}$M—the solid compound was first dissolved in THF, and then double-distilled water was rapidly added to the THF solution. This solution was sonicated for 10 minutes, and then 3 eq. of compound 1 dissolved in 500 µl of THF were injected rapidly (for a 20 ml solution). For precursor solution of compound 2 (synthesized according to Rosenne, S. et al. (Self-Assembled Organic Nanocrystals with Strong Nonlinear Optical Response. *Nano Letters* 15, 7232-7237 2015)) a solution of water\THF was mixed in a ratio of 70:30 v\v and a final concentration of 1·10$^{-4}$M of the solid compound was obtained. First, the compound dissolved in THF, and then double-distilled water was rapidly added to THF solution. The current solution was sonicated for 10 minutes, and then 3 eq. of compound 1 dissolved in 500 µl of THF were injected rapidly (for a 20 ml solution). SEM images of resulting crystals of 2 can be seen in FIGS. 6C-D (S9C-D): FIG. 6C shows nanocrystals of 2 after sonication and FIG. 6D shows the same after addition of 3 eq. of compound 1 and deposition as film. Elongation of the NCs was evident. For precursor solution of compound 3, a solution of water\THF was mixed in a ratio of 70:30 v\v and a final concentration of 1·10$^{-4}$M—the solid compound was first dissolved in THF, and then double-distilled water was rapidly added to THF solution. This solution was sonicated for 8 minutes.

Example 5

Films Fabrication Comprising Aromatic Material

A controlled pressure setup (FIG. 10) was used for filtration of aqueous solutions of compounds 1-3. Preparation of film 1a: 40 mL of an aged aqueous (precursor) solution of compound 1 from Example 4 (4×10$^{-5}$M, 0.9 mg) was deposited over PES support (Merck Millipore, HPWP01300|Millipore Express PLUS Membrane Filter, polyethersulfone, Hydrophilic, 0.45 μm, 13 mm, effective filtration area 0.95 cm$^2$) enclosed in a 13 mm in-line stainless steel swinney filter holder (Pall life sciences). During filtration, the transmembrane pressure increased up to 2.5 bar.

Film 1b: 20 ml of an aqueous (precursor) solution of compound 1 from Example 4 (2 mg) was deposited over PVDF support (GE Healthcare Life Sciences, RPN1416F, Amersham Hybond-P PVDF Membrane optimized for protein transfer, hydrophobic PVDF, 0.45 μm) enclosed in a 13 mm in-line stainless steel Swinney filter holder.

Film 2: 10 ml of an aqueous (precursor) solution of compound 2 from Example 4 (2 mg) was deposited over PVDF support enclosed in a 13 mm in-line stainless steel Swinney filter holder. Film 3: 40 ml of an aqueous (precursor) solution of compound 3 from Example 4 (2 mg) was deposited over PVDF support enclosed in a 13 mm in-line stainless steel Swinney filter holder.

Free-standing macroscopic film 1a was obtained with a diameter of 10 mm (FIG. 11A) and thicknesses of ~15 m (FIG. 11B). The microstructure of this film, was investigated using scanning electron microscopy (SEM) which revealed entangled nanocrystalline fibers, creating a porous network (FIG. 11A). This network formed by facile solution processing resembles electrospun polymer nanofiber films.

Film 1b includes larger faceted NCs of 1 compared to film 1a, whereas film 2 is formed from belt-like NCs, and film 3 assembled from long nanostripes (FIGS. 7-9). Their crystallinity was confirmed by XRD. By the method of fabrication, stable, crystalline macroscopic free-standing films were constructed. The construction is unexpected, since the free-standing films were fabricated entirely from small molecular building blocks (~1×2 nm).

The microstructure of the dry film, obtained in Example 4, was investigated using scanning electron microscopy (SEM) which revealed entangled nanocrystalline fibers, creating a porous network (FIG. 11A). This network formed by facile solution processing resembles electrospun polymer nanofiber films.

In a control experiment, where a film was prepared from shorter crystals (without aging, FIG. 3*b*), delamination of the film failed and only small fragments were released. Similarly, deposition from an aged crystallization solution of THF/water (1:9, v/v) with nanocrystals of non-uniform dimensions impaired formation of free-standing films (FIG. 11). Remarkably, very small amounts of compound 1 (>0.4 mg) were necessary for successful film delamination following deposition of aged solutions (long ONCs). XRD indicates crystallinity of the film (FIG. 12).

Example 6

Thermal Properties of Films of the Current Invention

The thermal behavior of the films was analyzed by differential scanning calorimetry (DSC), revealing exceptionally high thermal robustness of the films.

The DSC thermograms of films 1-3 (FIGS. 12A-D) showed (heating rate of 10° C./min and cooling rate of 5° C./min, under N$_2$ flow) the following:
in film 1a (FIG. 12A), the melting peak appeared between 330-336° C. upon heating, and the crystallization occurred at 303° C. upon cooling;
in film 1b (FIG. 12B), the melting peak appeared at 332-333° C. upon heating and the crystallization occurred at 305° C. upon cooling with a shoulder at 280° C.;
film 2 (FIG. 12C) decomposed at ~320° C. without melting; and
film 3 (FIG. 12D) exhibited a phase transition below 100° C. (at 75° C. in the first heating), whereas the onset of melting was near 400° C., and the recrystallization occurred at 391° C. upon cooling with a shoulder at 376° C.

Figure 13A:
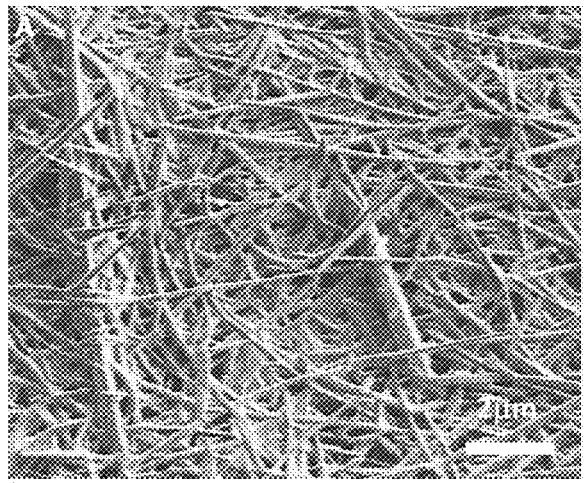
FIGS. 13A-13C depict SEM images of films 1-3 heated up to 300° C. under inert conditions and cooled.
Figure 13B:
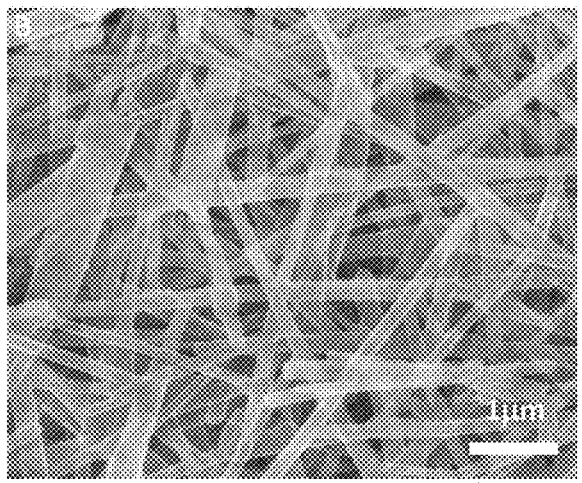
Figure 13C:
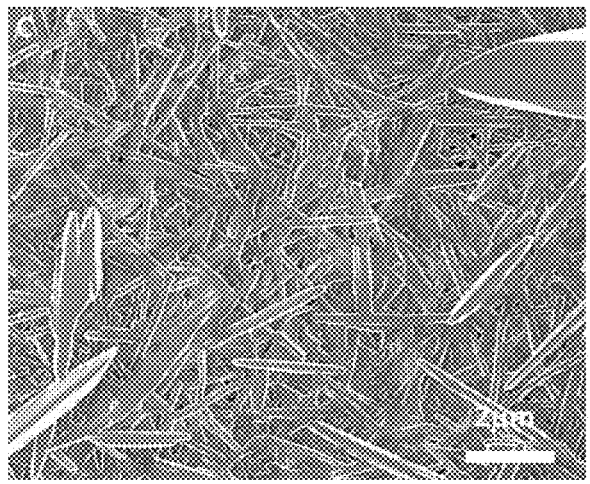
Figure 13D:
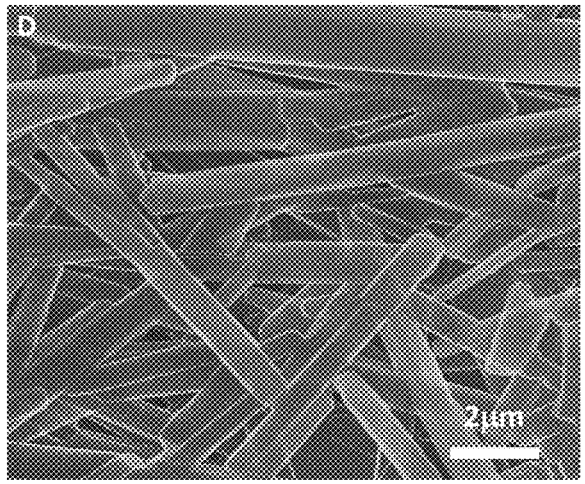
FIG. 13D: SEM image of film 3.
Figure 14A:
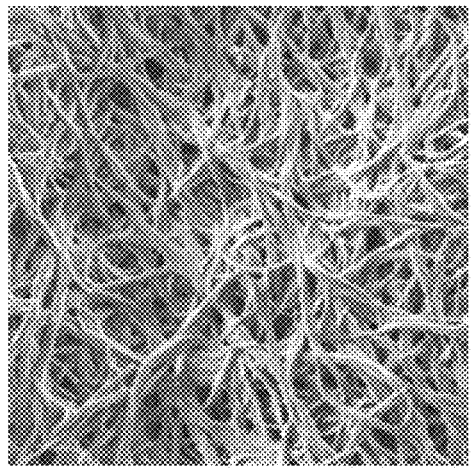
FIGS. 14A-14E depict thermal stability of films from compounds 1-3. SEM images of the films heated up to 250° C. under inert conditions and cooled.
Figure 14B:
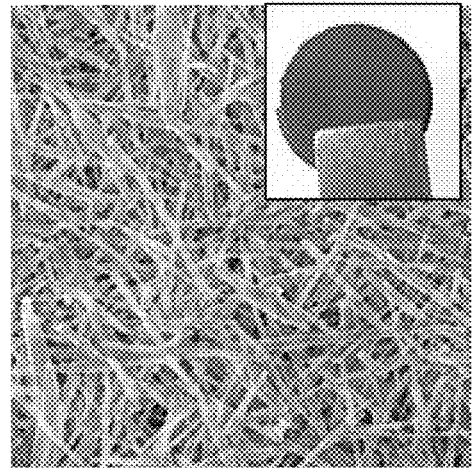
Figure 14C:
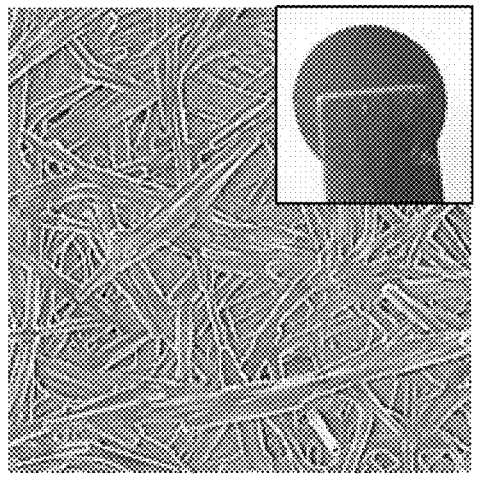
Figure 14D:
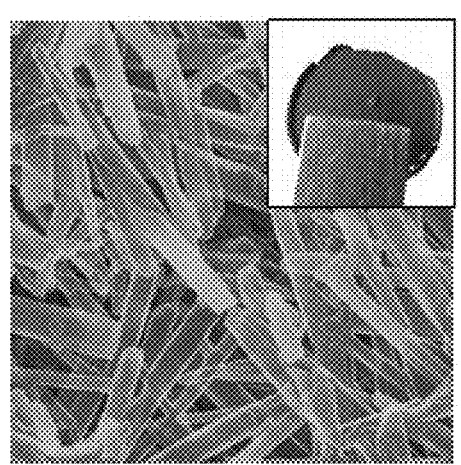

Surprisingly, it was observed that even upon heating up to 250-300° C. films 1a, 1*b* and 2 retained their microstructures and macroscopic shapes whereas film 3 did not retain them, as can be seen in the SEM images of films 1-3 (heated up to 250° C.-300° C. under inert conditions and cooled):
in film 1a (FIGS. 13A, 14A), the fibrous network was maintained yet there appears some fusion and the crystals seemed more faceted;
film 1b (FIGS. 13B, 14B) maintained its microstructure;
film 2 (FIGS. 13C, 14C) appeared very similar in its microstructure, some larger crystals appear (perhaps due to fusion); and
film 3 (FIGS. 13D, 14D) was morphologically different compared to RT.

Figure 14E:
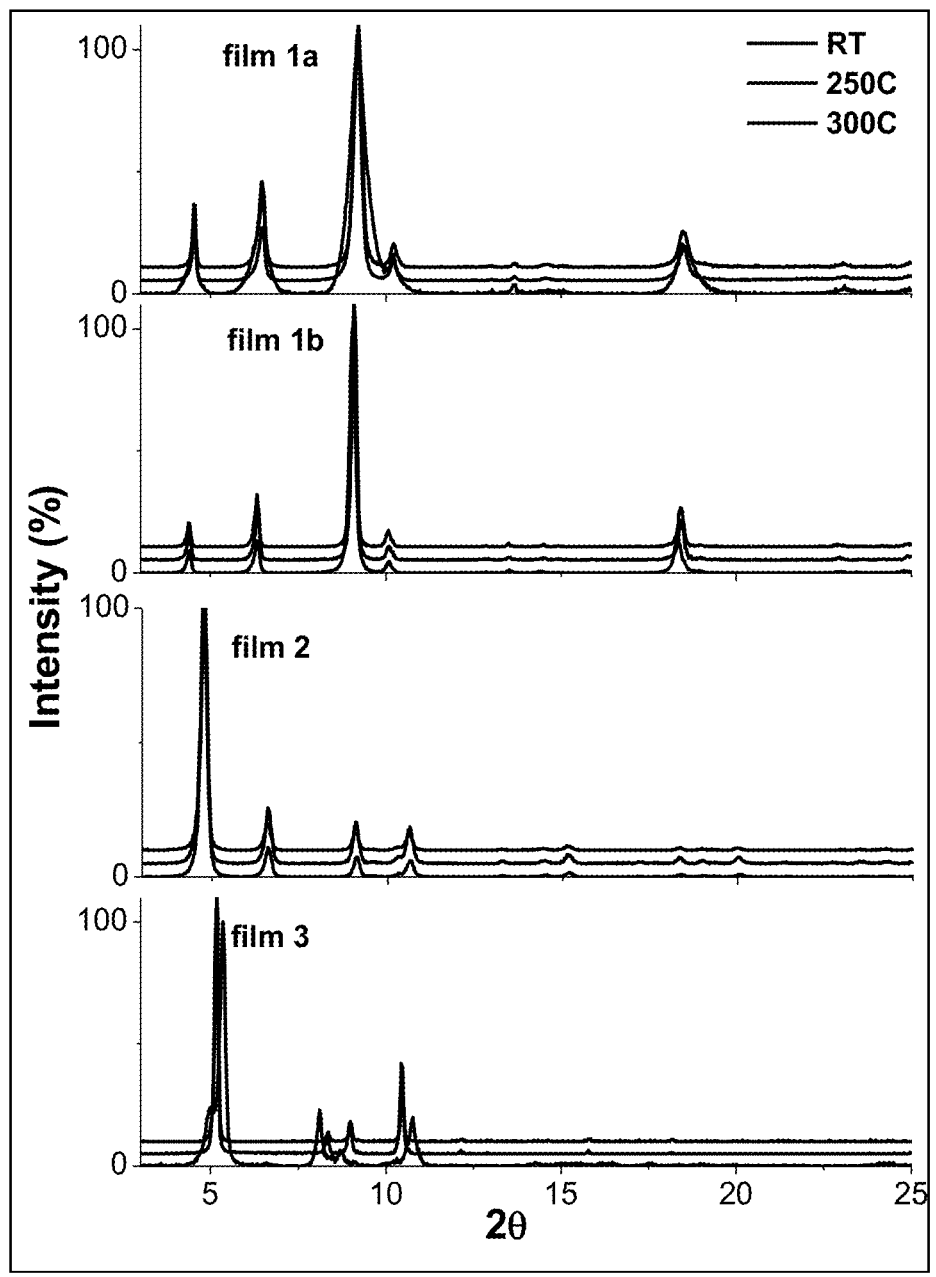
Figure 15A:
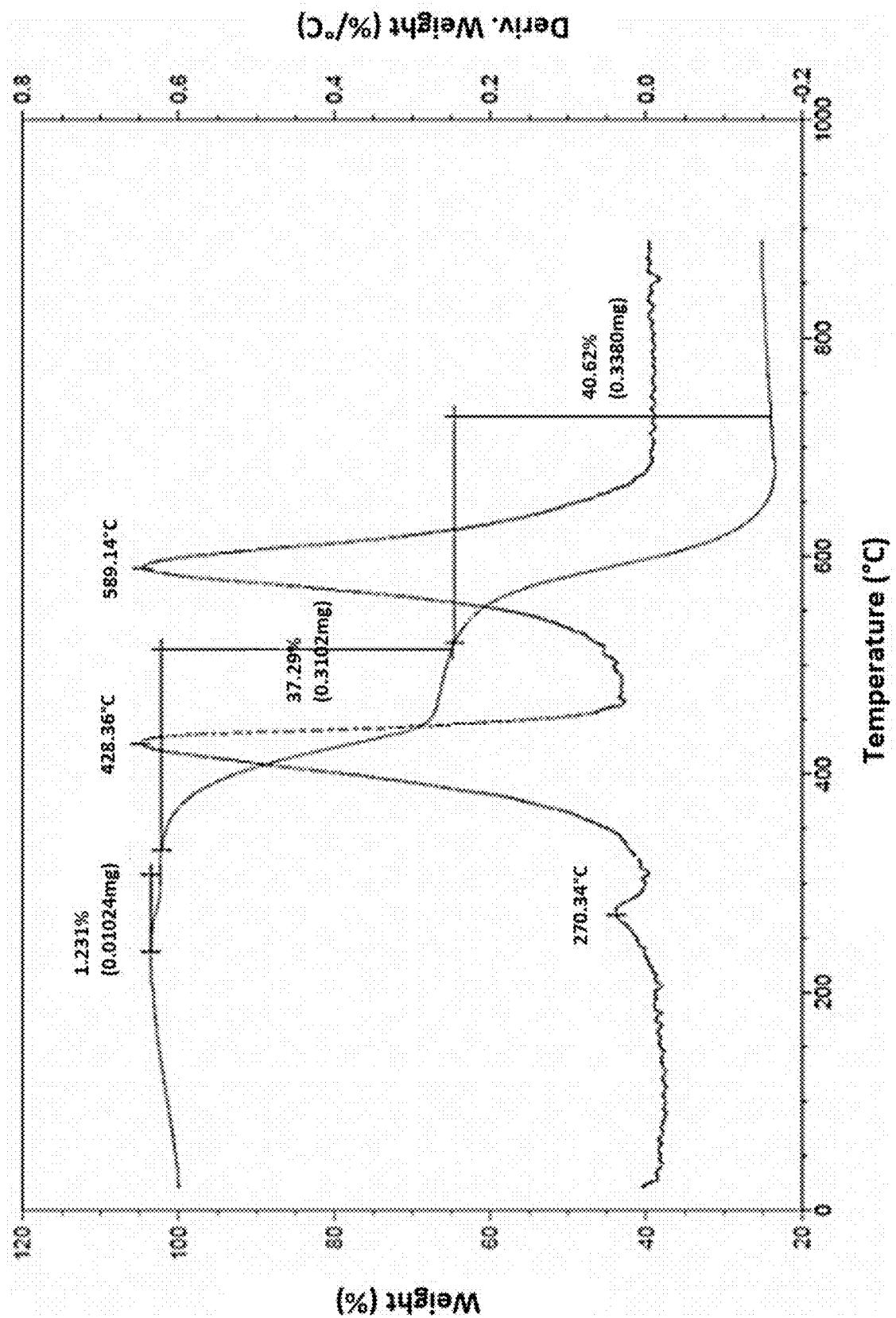
FIGS. 15A-15C depict TGA of films 1-3 at a heating rate of 20° C./min under air flow.
Figure 15B:
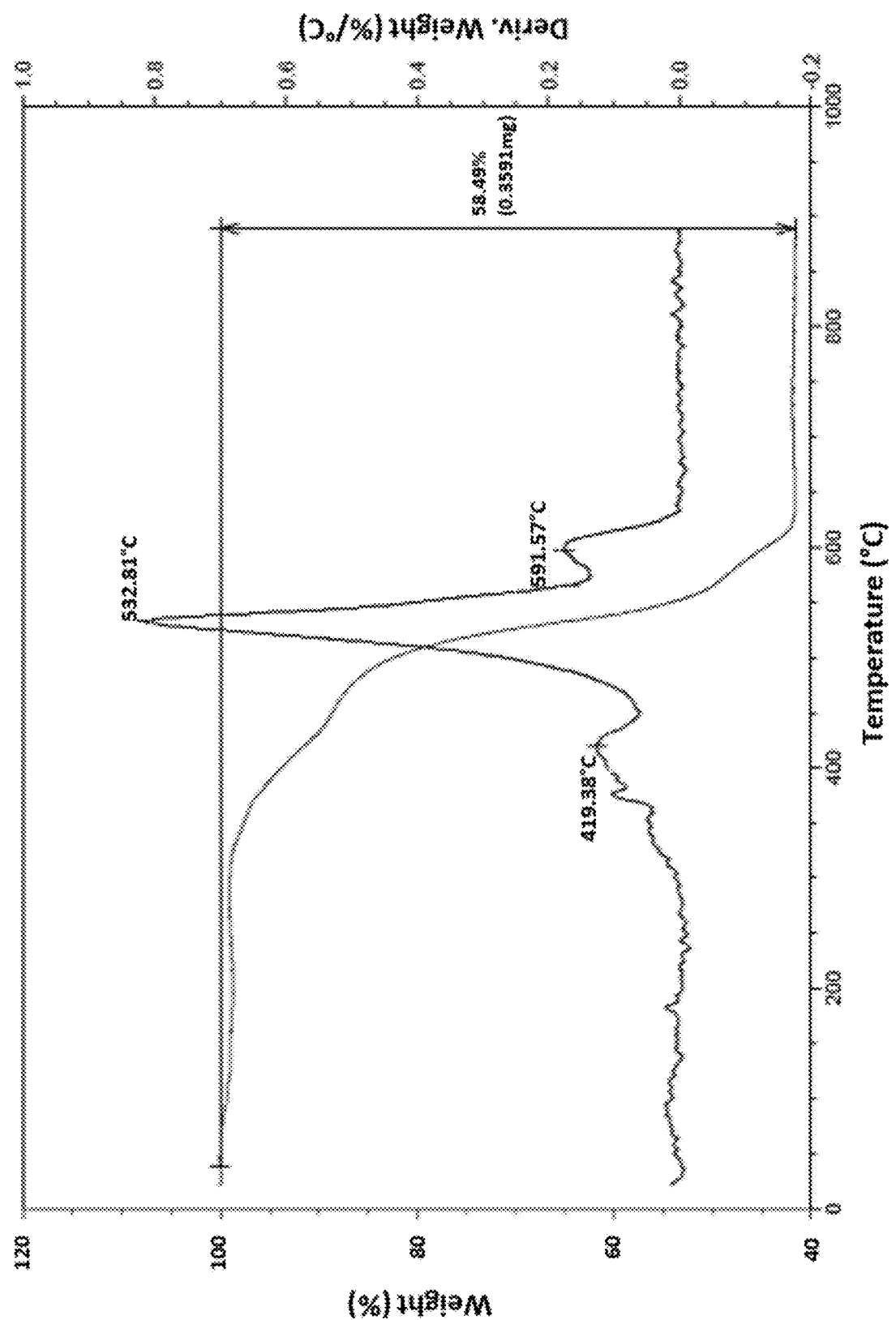
Figure 15C:
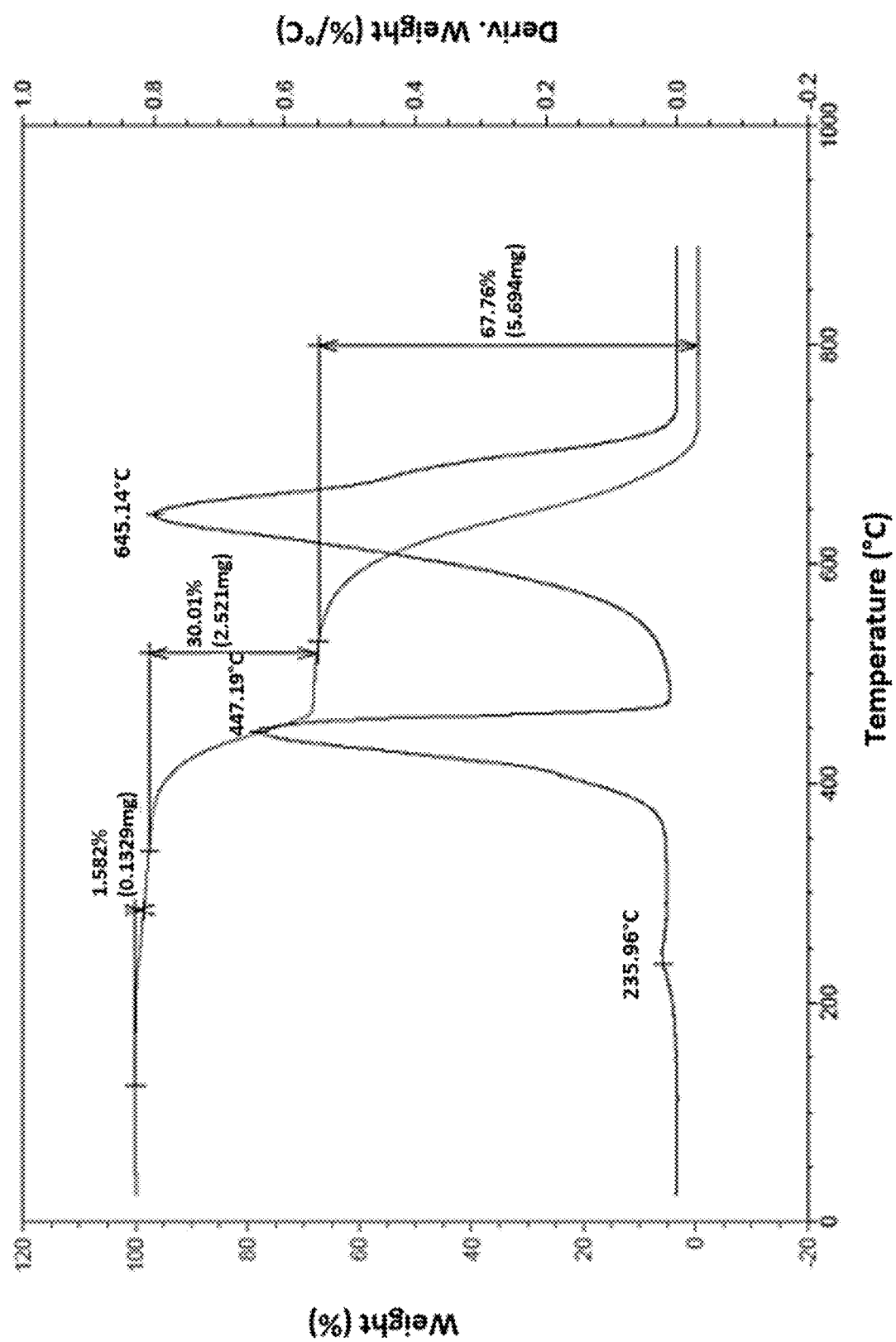
Figure 16A:
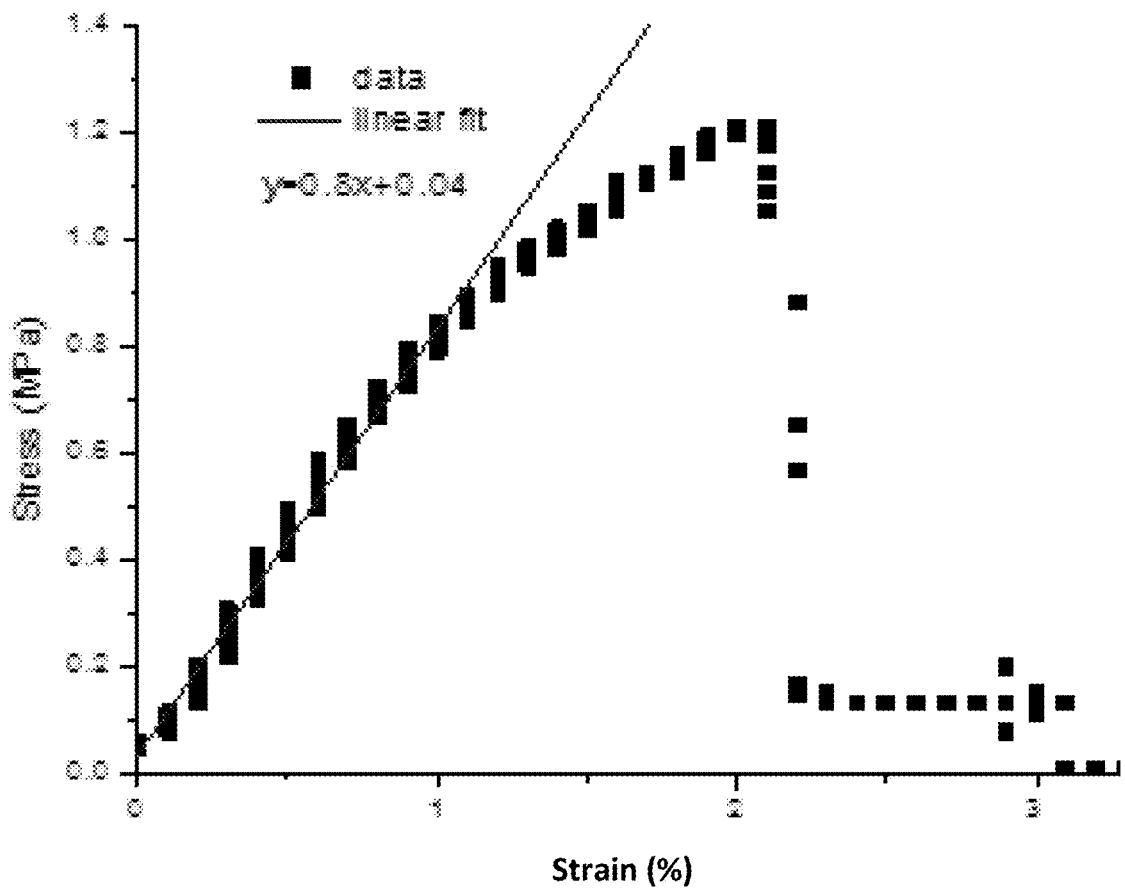
FIGS. 16A-16D depict representative stress-strain curves of films 1-3. The data is displayed with the linear fit (straight line) for the linear part of the stress-strain curve.
Figure 16B:
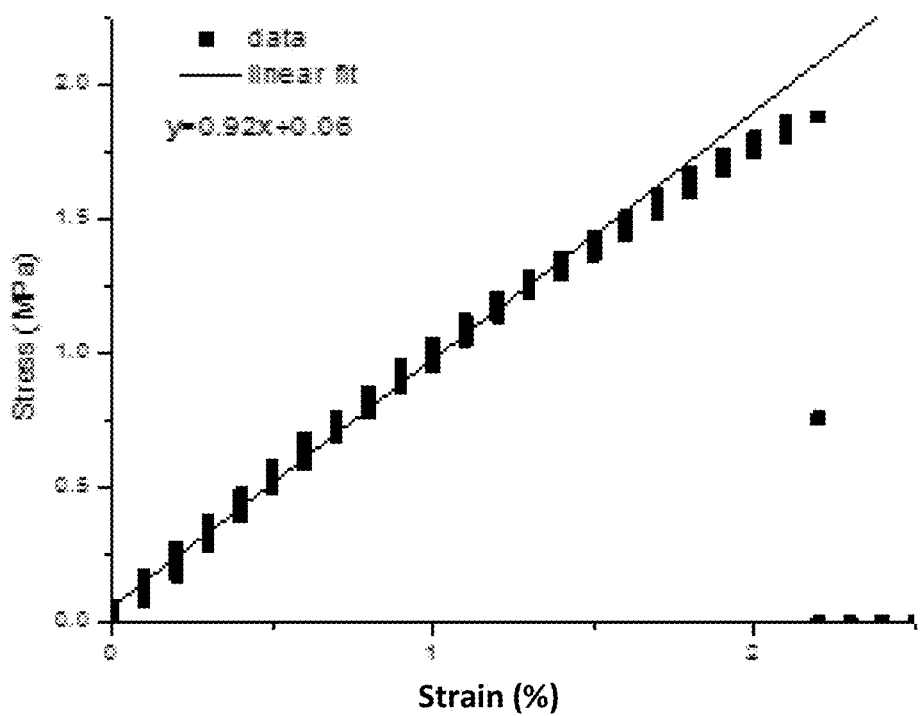
Figure 16C:
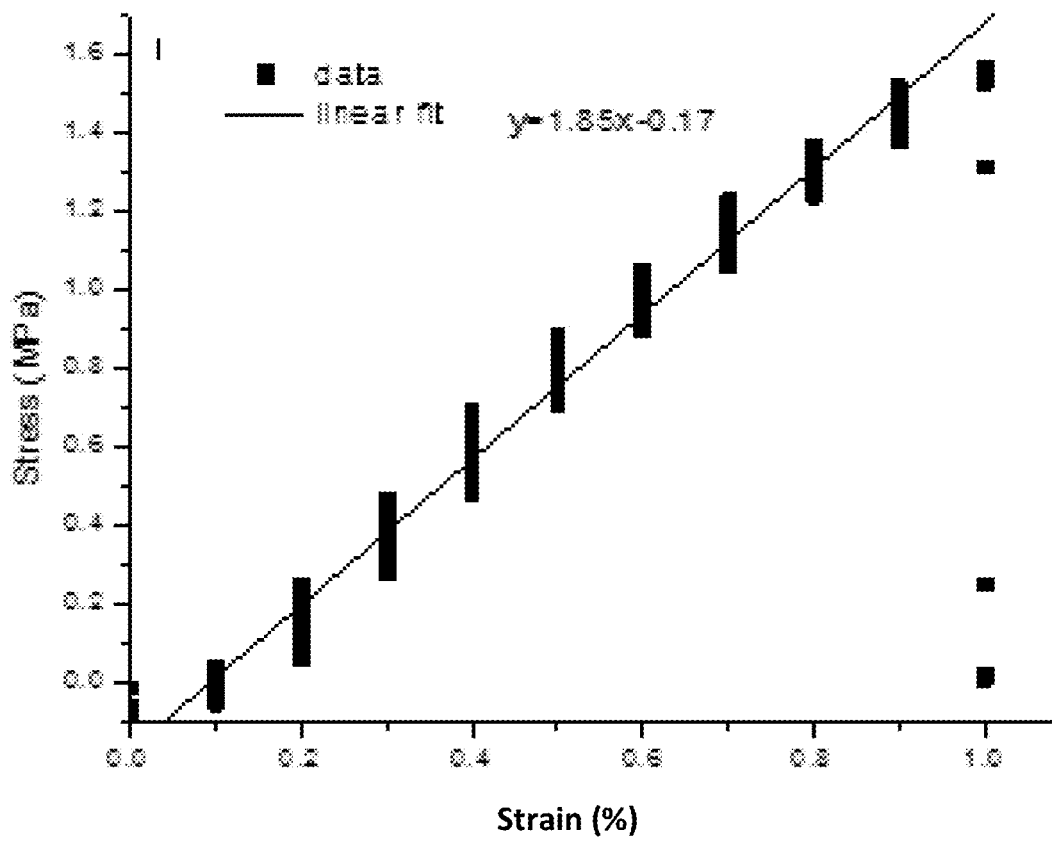
Figure 16D:
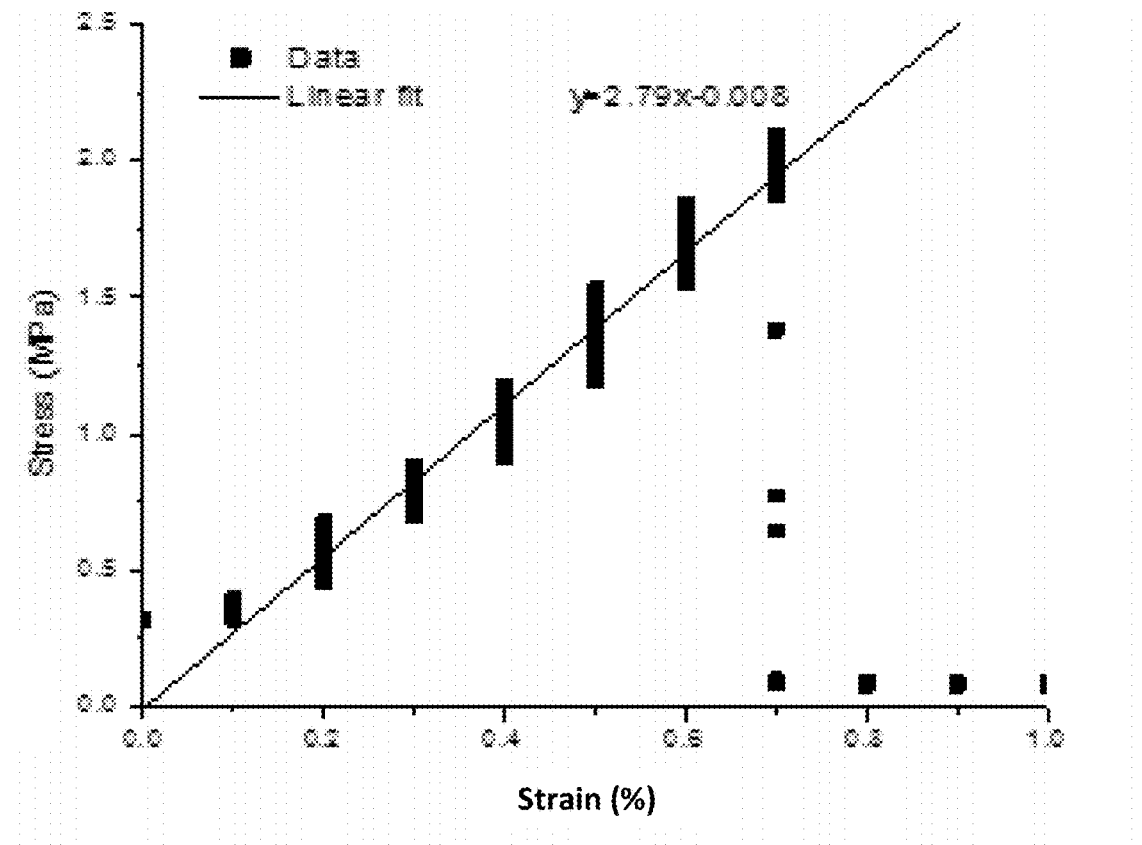

The structural integrity of the films following heating was also validated by powder X-ray diffraction (XRD) (FIG. 14E). Film 3 was the least stable, featuring morphological and structural changes upon heating (FIGS. 13D, 14D, 14E, 12D). Complimentary thermal gravimetric analysis (TGA) data (done with heating rate of 20° C./min under air flow) revealed that the stability of compounds 1 and 3 was high up to 400° C., while compound 2 was stable up to 350° C. (FIG. 15B), as can be seen in the following:
Film 1a (FIG. 15A), was thermally stable up to 400° C.: 393° C. corresponds to the 5% weight loss. There was first a minor weight loss of 1.23% around 270° C. After that, there were two main steps of weight loss—the first is 37.29% in the range of 400–500° C. (peak of the derivative is located at 428° C.) and the second was 40.62% in the range of 500–650° C. (peak of derivative at 589° C.). The first step loss point could be explained by decomposition of the alkyl groups at the imide nitrogens (Shin, W. S.; Jeong, H.-H.; Kim, M.-K.; Jin, S.-H.; Kim, M.-R.; Lee, J.-K.; Lee, J. W.; Gal, Y.-S. Journal of Materials Chemistry 2006, 16, 384), yet it doesn't match the expected mass percentages: the ethylpropyl (EP) group at the diimide nitrogen constitutes 25.4% of compound 1 ((71.14[g\mole]·2)/560.65 [g/mol])·100%=25.4%). It seems that some other species is formed in the presence of O$_2$ which changes the expected mass ratio.
Film 2 (FIG. 15B) was thermally stable up to 300° C.; and
Film 3 (FIG. 15C) was thermally stable up to 400° C.: 398° C. corresponds to the 5% weight loss.
Such stability is remarkable for both organic supramolecular polymers and covalent polymers.

Example 7

Physical Properties of the Films of this Invention

Mechanical Properties

Figures 17A, 17B, 17C:
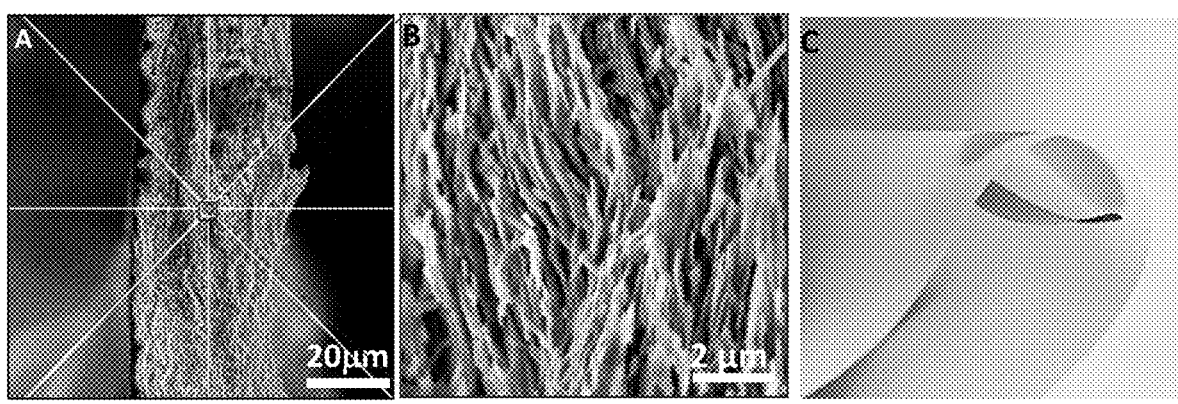
FIGS. 17A-17C depict fracture surface of film 2.

The mechanical properties of the films 1-3 were evaluated by tensile test, featuring Young's moduli of 300-80 MPa (Tables 1-2, FIGS. 16A-D). Notably, the Young's moduli and tensile strength of the films were comparable to values measured for elecrospun nonwoven polymer fiber films (Li, L., Bellan, L. M., Craighead, H. G. & Frey, M. W. Formation and properties of nylon-6 and nylon-6/montmorillonite composite nanofibers. *Polymer* 47, 6208-6217 (2006). Jee, A.-Y. & Lee, M. Comparative analysis on the nanoindentation of polymers using atomic force microscopy. *Polymer Testing* 29, 95-99 (2010) and even to moduli of bulk polymer films such as LDPE and PVA (Mark, J. E. Physical Properties of Polymers Handbook, Edn. 2nd. (Springer, 2007).). Film 3 featured the highest modulus—(300 MPa) and lowest elongation (0.6%) while films 1a, 1b and film 2 exhibited moduli of between 140-80 MPa. Films 1a and 1b showed similar mechanical results despite the difference in their fiber diameter (FIGS. 11, 6), meaning that this wasn't the determining factor. Differences could be due to different intrinsic fiber moduli, as well as different porosity or voids and surface area of contact (FIGS. 17A-B). Additionally, the films could be bent to a certain extent (FIG. 17C).

TABLE 1

Summary of the tensile test results.

| | Young's Modulus (MPa) | Tensile Strength (MPa) | Elongation (%) | Toughness (MPa) |
|---|---|---|---|---|
| Film 1a | 600 ± 100 | — | — | — |
| Film 1b | 160 ± 50 | 2.7 ± 0.7 | 1.4 ± 0.3 | 1.6 ± 0.8 |
| Film 2 | 200 ± 30 | 2.3 ± 0.5 | 1.3 ± 0.2 | 1.5 ± 0.6 |
| Film 3 | 150 ± 70 | 1.6 ± 0.4 | 1.2 ± 0.3 | 0.9 ± 0.6 |

TABLE 2

Summary of the tensile test results of films 1-3 with a 10N load cell. The modulus is the slope of the linear part of the stress-strain curve, and the toughness is simply taken as the area under the stress-strain curve. The tensile strength is the stress at breaking point.

| Film | Sample | Young's Modulus (MPa) | Tensile Strength (MPa) | Elongation (%) | Toughness (MPa) |
|---|---|---|---|---|---|
| Film 1a | 1 | 128 | 1.61 | 1.4 | 1.19 |
| | 2 | 51 | 1.07 | 2.6 | 1.51 |
| | 3 | 60 | 1.08 | 2.6 | 1.75 |
| | 4 | 63 | 1.17 | 2.5 | 1.87 |
| | 5 | 80 | 1.21 | 2.1 | 1.59 |
| | Average | 80 ± 30 | 1.2 ± 0.2 | 2.2 ± 0.5 | 1.6 ± 0.3 |
| Film 1b | 1 | 134 | 3.9 | 3.07 | 6.74 |
| | 2 | 87 | 1.65 | 1.9 | 1.86 |
| | 3 | 90 | 1.46 | 1.7 | 1.41 |
| | 4 | 69 | 2.16 | 2.7 | 3.43 |
| | 5 | 92 | 1.88 | 2.2 | 2.3 |
| | Average | 90 ± 20 | 2.0 ± 1.0 | 2.3 ± 0.6 | 3.0 ± 2.0 |
| Film 2 | 1 | 185 | 1.57 | 0.9 | 0.76 |
| | 2 | 184 | 0.98 | 0.7 | 0.26 |
| | 3 | 115 | 1.12 | 0.9 | 0.6 |
| | 4 | 130 | 1.9 | 1 | 1.3 |
| | 5 | 64 | 0.72 | 1 | 0.49 |
| | Average | 140 ± 50 | 1.3 ± 0.5 | 0.9 ± 0.1 | 0.7 ± 0.4 |
| Film 3 | 1 | 279 | 2.1 | 0.6 | 0.66 |
| | 2 | 414 | 2.17 | 0.6 | 0.65 |
| | 3 | 324 | 1.94 | 0.6 | 0.56 |
| | 4 | 198 | 1.18 | 0.6 | 0.31 |
| | Average | 300 ± 90 | 1.8 ± 0.5 | 0.6 ± 0.05 | 0.5 ± 0.2 |
| Film 4 | 1 | 119 | 1.3 | 1.5 | 1.33 |
| | 2 | 154 | 0.99 | 1 | 0.68 |
| | 3 | 133 | 1.1 | 1.1 | 0.99 |
| | 4 | 107 | 1.12 | 1.2 | 0.69 |
| | 5 | 126 | 1.1 | 1.1 | 0.68 |
| | Average | 128 ± 18 | 1.14 ± 0.1 | 1.18 ± 0.19 | 0.87 ± 0.3 |

Non Linear Optical Properties

Film 2 shows nonlinear optical (NLO) properties with strong second harmonic generation (SHG) (FIG. 18) effect. Films of 2 are thermally stable and showed unchanged NLO response over time and after heating. This is surprising since usually NLO active materials contain an NLO active compound embedded within polymer and poled; however, the current invention does not provide such embedding/poling.

Optical Properties

Films 1-3 are emissive as can be seen in FIG. 19.

Example 8

Microfiltration Membranes Using Films of the Current Invention

The filtration capabilities were demonstrated on film 2, where a cutoff of 50 nm was demonstrated on Au 50 nm nanoparticles (NPs) (FIG. 20) and 50 and 100 nm Si NPs. In both Au and Si NPs the filtrates following the filtration of the NPs solutions had very low concentration of the NPs. While commercial filters of this size are available, these films can be disassembled and recycled as a way to manage membrane fouling. The filtration capabilities demonstrates also cutoffs of between 10-40 nm.

Example 9

Hybrid Graphene Oxide (GO)/2 Composition

Preparation and Film Fabrication 100-400 μl of aqueous graphene oxide (GO) dispersion (2 mg/ml) was dispersed in 14 ml of DDW. The dispersion was bath-sonicated for 30 minutes. Following sonication, the GO dispersion was quickly added to 6 ml THF solution of 2 (0.11 mg/ml), the resulting dispersion was sonicated for 10 minutes in order to fragment the ONCs prior to their precipitation, and then 3 eq. of compound 2 dissolved in 1 ml of THF were injected rapidly (for a 20 ml solution). The final dispersion was divided into four fractions, each fraction was deposited on PVDF membrane in a controlled pressure setup (FIG. 10), the transmembrane pressure during filtration was set to 4 bars. The film was then dried and manually detached from the PVDF support.

Morphology

Figure 21A:
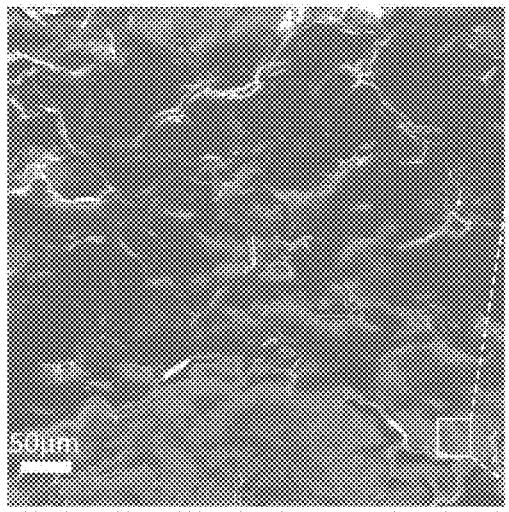
FIGS. 21A-21D depict SEM images of 2/GO films.
Figure 21B:
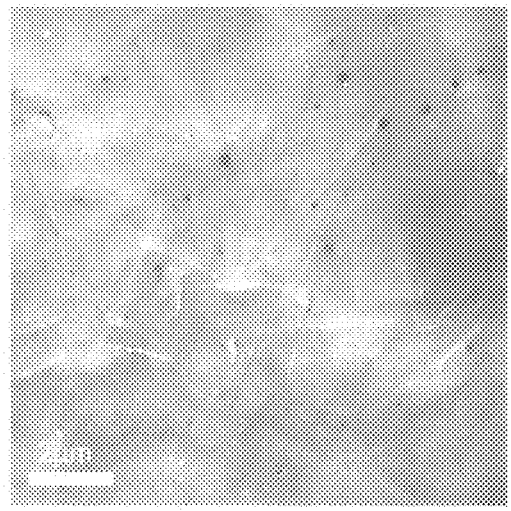
Figure 21C:
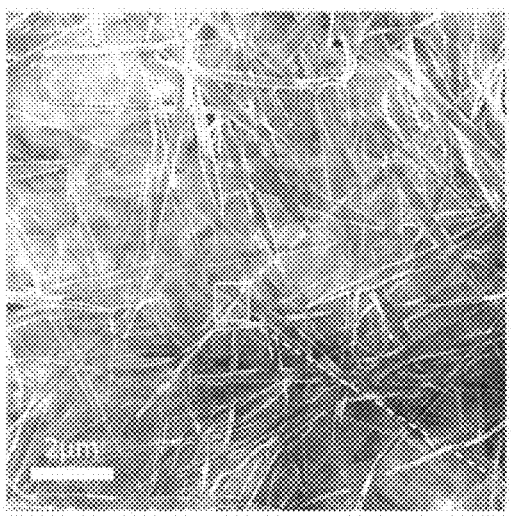
Figure 21D:
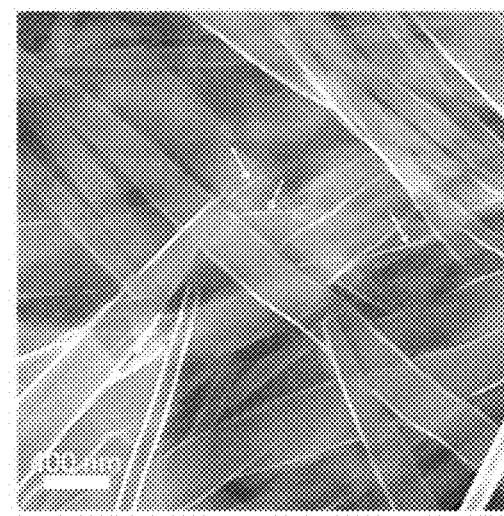

The morphology of the film was investigated by scanning electron microscopy (SEM). Images (taken at 1 kV) showed that the ONCs were covered by a layer of what appears to be GO sheets (FIGS. 21A-B). Upon increasing the voltage to 20 kV the electron beam penetrated the GO layer and the ONCs were clearly visible, while the nano-belts appeared to have "wrinkled" structures attached to them, presumably the GO sheets (FIG. 21C).

Figure 22:
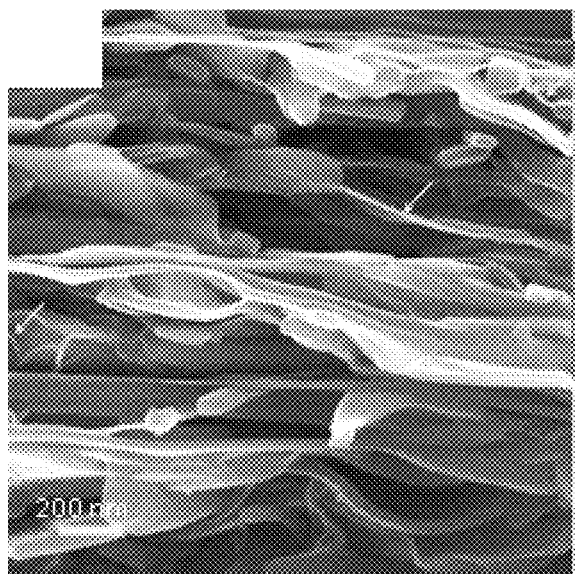
FIG. 22 depicts SEM cross-section image of 2/GO films, with GO content of 5 wt %, the arrows mark the GO sheets.
Figure 23:
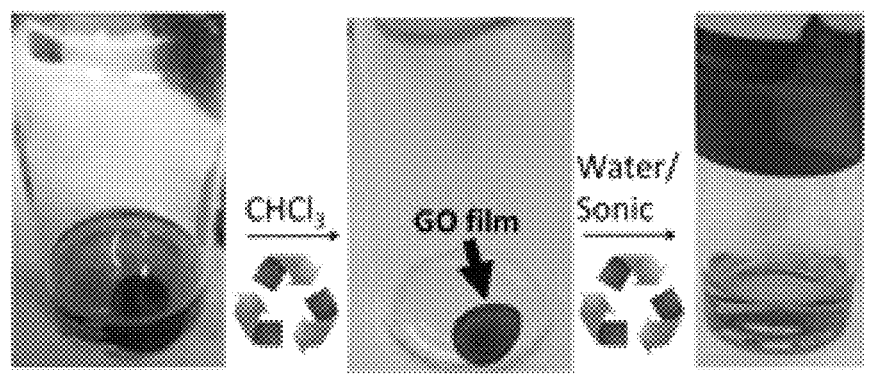
FIG. 23 depicts the recycling process of 2/GO film.

The film cross-section is shown in FIG. 22. The composite was recyclable, as 2 was highly soluble in chloroform: upon immersing the film in chloroform, the ONCs of 2 dissolved, leaving a GO film ("buckypaper"), which was dispersed in water by mild sonication (FIG. 23).

Mechanical Properties

Figure 24:
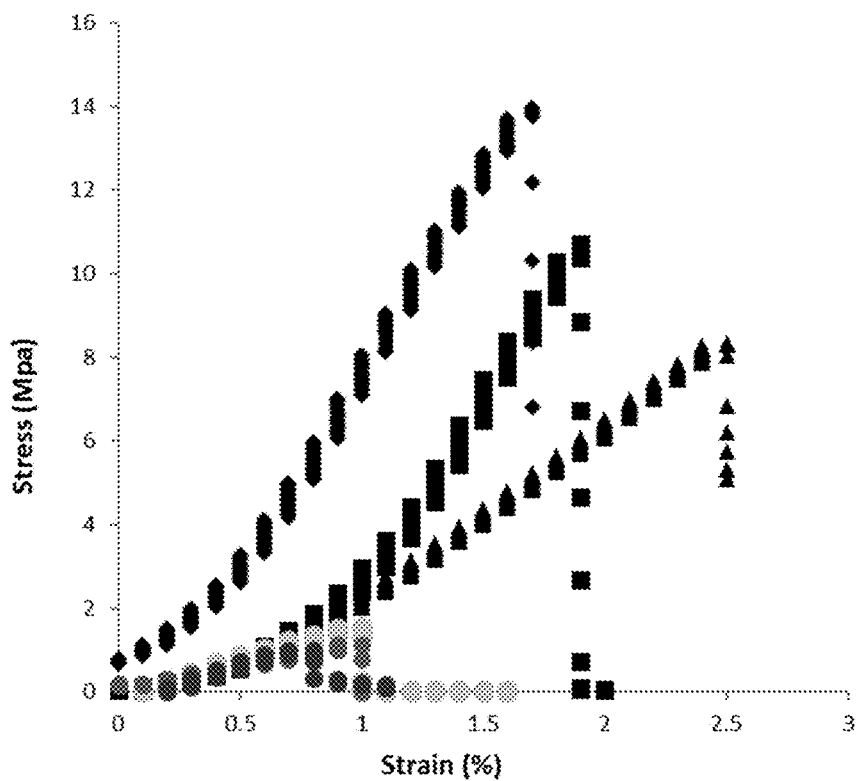
FIG. 24 depicts stress vs strain curves of three independently prepared composites 2/GO films (triangles, rhomboids, squares; higher maximal stress values) and three independently prepared films of pristine ONCs of 2 (circles; lower maximal stress values).

The mechanical properties of the composite were examined by a tensile test. FIG. 24 depicts the stress vs strain curves of composite 2/GO films, with GO content of 5 wt % and the film made of pristine 2. The tensile test results are summarized in Table 3, revealing substantially enhanced mechanical robustness of the composites.

TABLE 3

Tensile data of pristine 2 ONCs films vs 2/GO hybrids (GO content 5 wt %)

| Film | Sample | Young's Modulus (MPa) | Tensile Strength (MPa) | Elongation (%) | Toughness (MPa) |
|---|---|---|---|---|---|
| Film 2 | 1 | 184 | 0.98 | 0.7 | 0.26 |
|  | 2 | 115 | 1.12 | 0.9 | 0.6 |
|  | 3 | 130 | 1.9 | 1.0 | 1.3 |
| Film 2/ GO | 1 | 877 | 14 | 1.7 | 11.0 |
|  | 2 | 888 | 11 | 1.9 | 6.7 |
|  | 3 | 402.1 | 8 | 2.5 | 8.7 |

Example 10

Hybrid Nanoclay Bentonite/2 Composition

Preparation and Film Fabrication 2 mg of Bentonite were dispersed in 15 ml of DDW by tip-sonication, the resulting dispersion was centrifuged and 14 ml of the clear aliquot were quickly added to 6 ml THF solution of 1 (0.16 mg/ml). The resulting dispersion was sonicated for 10 minutes and then 3 eq. of compound 2 dissolved in 1 ml of THF were injected rapidly. The final dispersion was divided into four fractions, each fraction was deposited on PVDF membrane by controlled pressure setup (FIG. 10), the transmembrane pressure during filtration was set 4 bars.

Example 11

Hybrid Nanoclay Bentonite/2 Composition: Au NPs Filtration

Figure 25A:
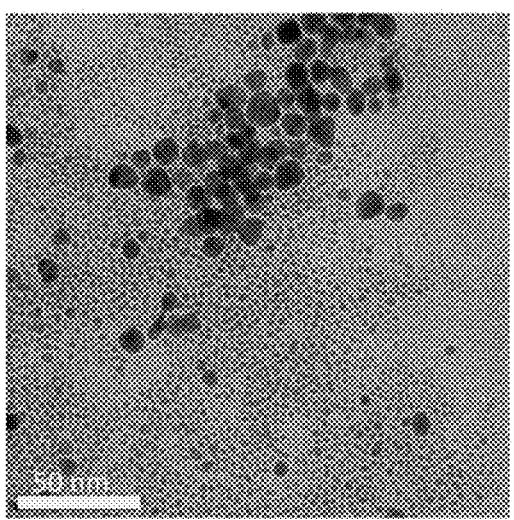
FIGS. 25A-25B depict TEM images of Au particles 1-10 nm stock solution (FIG. 25A) and filtrate (FIG. 25B), filtrated through 2/Bentonite on a PVDF support.
Figure 25B:
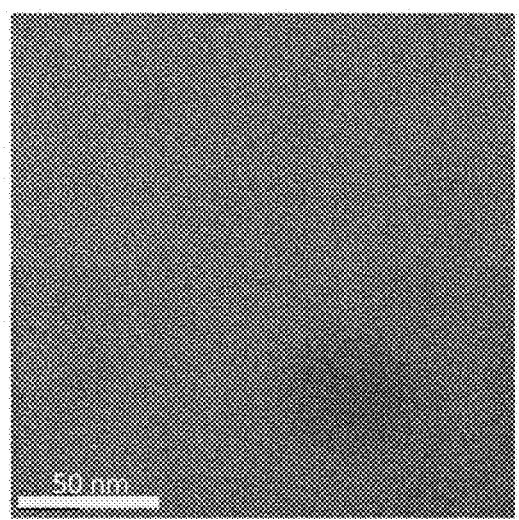

A dispersion of Au particles (1-10 nm) was filtrated through 2/Bentonite on a PVDF support at 2 bars pressure, the filtrate was divided into three fractions and the Au content of the filtrate was examined by TEM.
TEM images did not reveal any particles of 1-10 nm size on the grids. FIG. 25A-B show TEM images of Au dispersion before and after filtration (FIGS. 25A-B, respectively). The composite was recyclable: upon immersing the film in chloroform, the ONCs of 2 dissolved, leaving a NC palate, which is dispersed in water by sonication (FIG. 26).

Example 12

Hybrid Organoclay/2 Composition

Preparation and Film Fabrication 2 mg of surface modified clay were dispersed in 2 ml of THF by bath sonication, the resulting dispersion was centrifuged to get rid of the non-dispersed clay to form dispersion A.
14 ml of DDW were quickly added to 6 ml THF solution of 2 (0.1 mg/ml), the resulting dispersion was sonicated for 10 minutes to form dispersion B. 3 eq. of compound 2 were dissolved in 1 ml of dispersion A, the resulting solution was rapidly injected to dispersion B to produce a composite dispersion. The final dispersion was divided into two fraction, each fraction was deposited on PVDF membrane by controlled pressure setup, the transmembrane pressure during filtration was set 4 bars. The film was then dried and manually detached from the PVDF support.

Morphology

Figure 28A:
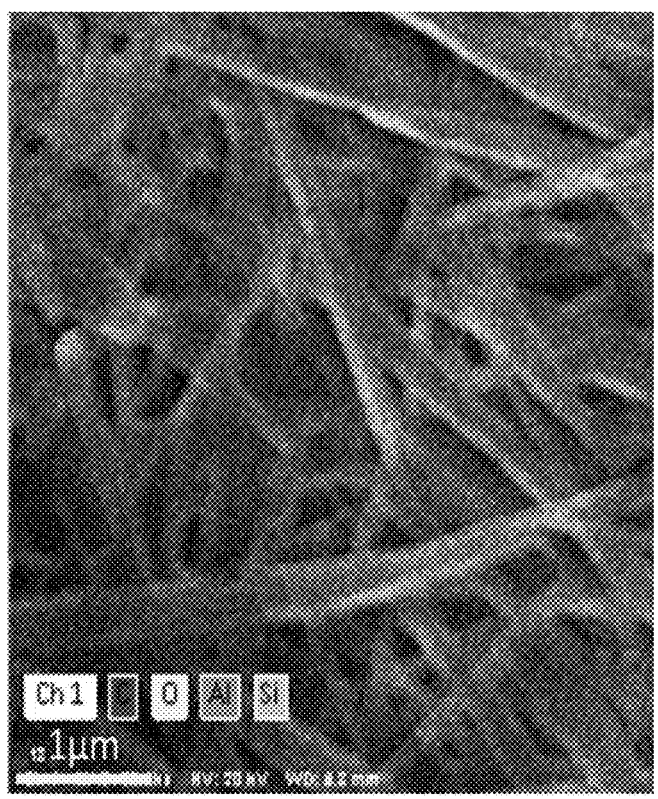
FIGS. 28A-28B depict EDS analysis of the 2/organoclay composite film.
Figure 28B:
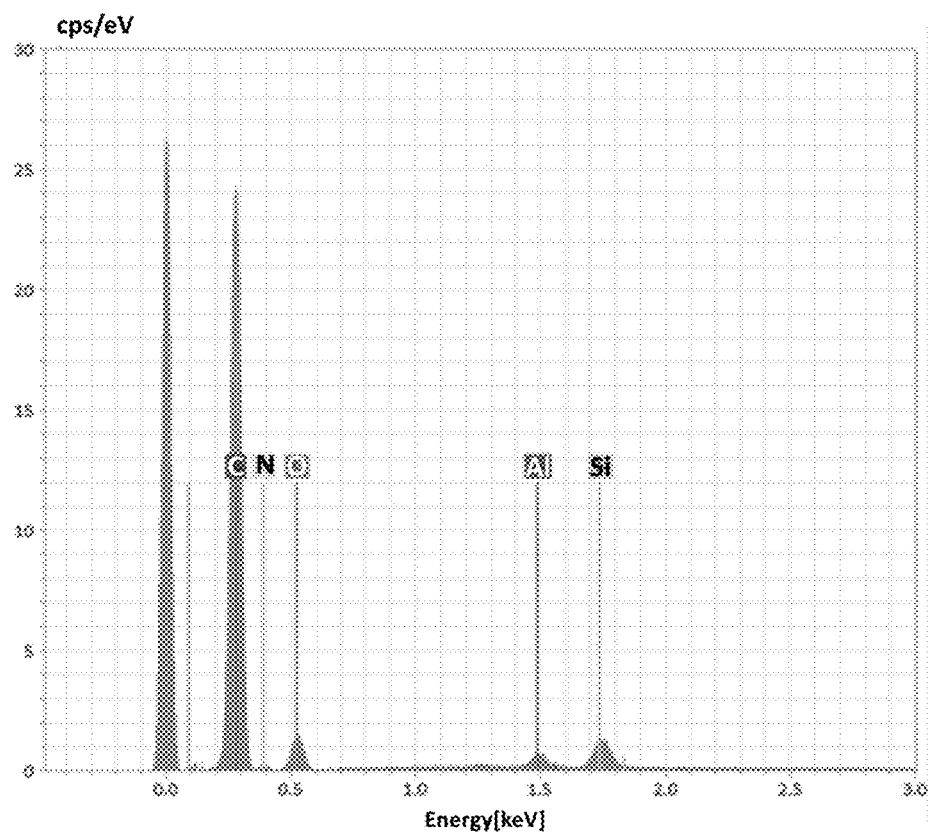

The morphology of the 2/organoclay composite film was investigated by scanning electron microscopy (SEM) and Energy-dispersive X-ray spectroscopy (EDS). SEM clearly showed the homogeneous distribution of the NCs platelets in the ONCs matrix (FIG. 27) and these platelets were indeed of NC, as confirmed by EDS (FIG. 28).

Example 13

Hybrid Agarose/2 Composition

Preparation and Film Fabrication 14 ml of DDW were quickly added to 6 ml THF solution of 2 (0.16 mg/ml), the resulting dispersion was sonicated for 10 minutes to form dispersion A. Then 3 eq. of compound 2 in 1 ml of THF was added and the resulting solution was rapidly injected into the aqueous dispersion A. The final dispersion was divided into two fractions, each fraction was deposited on PVDF membrane by controlled pressure setup (FIG. 10), the transmembrane pressure during filtration was set 2 bars.

Low gelling temperature Agarose (100 mg) was dissolved in 50 ml of boiling DDW, and was left to cool to 50° C., and then 200 µL of solution were deposited on the ONCs film by low pressure filtration at 1 bar. The resulting film was allowed to dry in air, and the film was manually detached from the PVDF support.

Morphology

The morphology of the film was studied by SEM, which showed that the ONCs are covered with homogeneous film (FIG. 29A), and the cross-section showed that the agarose indeed penetrated into the bulk of the film (FIG. 29B). Based on the images, it seems that the agarose matrix functioned as an adhesive that filled the pores of the ONCs matrix and binded the matrix together.

Example 14

Preparation and Characterization of ONC/CNT Hybrids of this Invention

Materials:

Compounds 2-4 have been previously reported. Compound 3 [X. Zhang, S. Pang, Z. Zhang, X. Ding, S. Zhang, S. He, C. Zhan, *Tetrahedron Lett.* 2012, 53, 1094] is a precursor for the synthesis of 1 [K.-Y. Chen, T.-C. Fang, M.-J. Chang, *Dyes and Pigments* 2012, 92, 517] and 2. [H.-Y. Tsai, C.-W. Chang, K.-Y. Chen, *Molecules* 2014, 19, 327] PDI-OH and PDI-NH$_2$ (PDI-OH or PDI-NH$_2$ refer to a similar compound of 2 only having a OH or NH$_2$ groups instead of the NO$_2$ of 1) were prepared according to a literature procedure [S. Rosenne, E. Grinvald, E. Shirman, L. Neeman, S. Dutta, O. Bar-Elli, R. Ben-Zvi, E. Oksenberg, P. Milko, V. Kalchenko, H. Weissman, D. Oron, B. Rybtchinski, *Nano Lett.* 2015, 15, 7232].

All reagents and CNTs were purchased from Sigma-Aldrich and used as received. SWCNTs: purified CoMo-CAT-single-walled carbon nanotubes SG-65, carbon>90% (≥77% carbon as SWCNT), 0.7-0.9 nm diameter, and chirality distribution>50% (6,5). MWCNTs: purified CCVD thin multiwall carbon nanotubes, <5% metal oxides (by thermogravimetric analysis, TGA), 9.5 nm diameter, 1.5 µm length (by TEM). Some MWCNT were purchased from CheapTubes.com (outer diameter: 1-20 nm; inside diameter 3-5 nm; length 10-30 µm purity>95 wt %, Ash<1.5 wt %, Specific surface area 233 m²/g, electrical conductivity>100 S/cm, bulk density 0.22 g/cm³)

ONC/CNT Hybrid Preparation and Dispersion Preparation:

Compounds 2-4 were bath-sonicated with various amounts of either (6,5)-SWCNTs (single wall CNTs, hereinafter SWCNTs) or MWCNTs (multiwall CNTs) in chloroform for 30 min, after which the mixture was dried and dissolved in THF, followed by the addition of water and bath sonication for 30 min. The resulting mixture was centrifuged to yield dispersions with varying ONC/CNT hybrid ratios.

2 mg of PDI derivatives 2-4 were sonicated with various amounts of either SWCNTs or MWCNTs in chloroform for 30 minutes, and afterwards the mixture was dried under vacuum. Then 6 mL of THF was added to the dry mixture followed by the quick addition of 14 mL of water. The dispersion (comprising ONC/CNT hybrid) was sonicated in a bath sonicator for 30 minutes, and finally the dispersion was centrifuged (3 kg, 7 minutes).

Detailed compositions: SWCNT average concentration of 40 wt % was achieved by mixing 2.3 mg of SWCNTs with 2 mg 2, and 2 mg of SWCNTs with 2 mg of 4.

SWCNT average concentration of 3 wt % was achieved by mixing 0.15 mg of SWCNTs with 2 mg of 2, and 0.1 mg of SWCNTs with 2 mg of 4.

MWCNT average concentration of 67 wt % was achieved by mixing 2 mg MWCNTs with 2 mg of 2, while mixing 2 mg MWCNTs with 2 mg of 4 yields 65 wt % CNT concentration.

Concentration of 60 wt % was achieved by mixing 2 mg MWCNTs with 2 mg of 3. Concentration of 3 wt % was achieved by mixing 0.025 mg MWCNTs with 2 mg of 2, 0.08 mg MWCNTs with 2 mg of 4 and 0.05 mg MWCNTs with 2 mg of 3.

PDI-OH/1/MWCNTs hybrid: 1 mg of 2 was hybridized with 1 mg of MWCNTs. 2 mg of PDI-OH solution in 1 ml of THF was added to the above mixture after centrifugation.

CNT Concentration.

The CNT and PDI concentrations were determined as follows: the hybrid films were weighed on an analytical balance, then the films were thoroughly washed with chloroform to dissolve the ONCs. After washing and drying, the CNTs films were weighed again to determine the weight fraction of CNTs in the film. The optical density (O.D.) of the chloroform solutions containing PDI was measured by UV-vis-NIR spectroscopy, and the amount of PDI in the films was determined using a calibration curve for each PDI derivative.

Surface coverage of (6,5) SWCNTs.

The surface coverage of SWCNTs by molecules of 1 was calculated by using XPS measurements and surface analysis with Materials Studio v6.1.200, 2012.

Results.

Homogenous dispersions were observed with the electron deficient nitro-PDI derivatives 2 and 4, which result in the most stable CNT/ONC dispersions (vide infra). MWCNTs were efficiently dispersed by 2, 4, and the weaker acceptor 3, apparently due to the lower surface energy of MWCNTs.

MWCNTs concentrations of ~3-67 wt % and SWCNT concentrations of ~3-40 wt % in the dispersion can be achieved. In all dispersions, formation of PDI nanocrystals was observed (FIGS. 30A-30F). Mild bath sonication is sufficient to give stable dispersions of CNTs stabilized by 2-4.

Figure 30A:
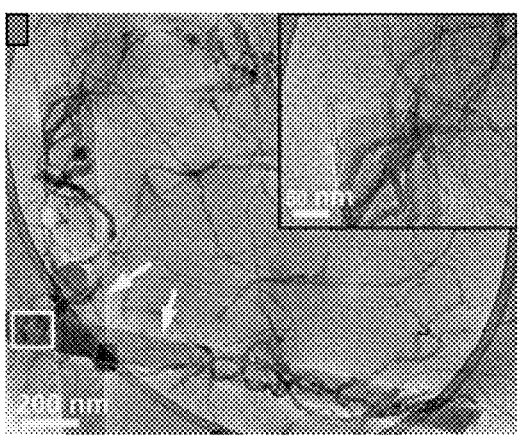
FIGS. 30A-30F present images of ONC/CNT hybrids.
Figure 30B:
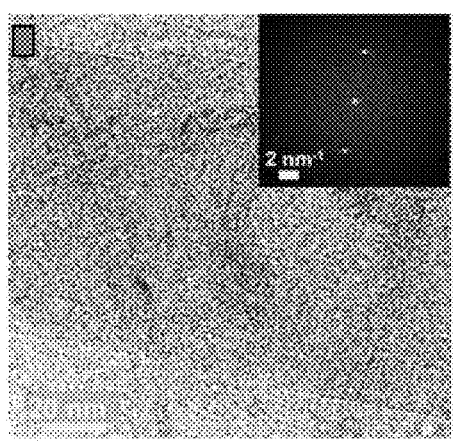
Figure 30C:
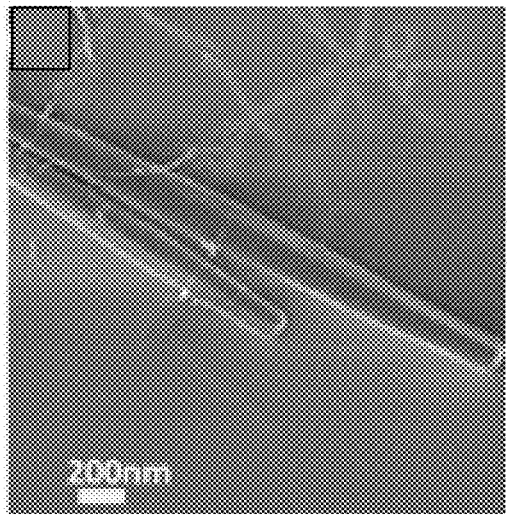
Figure 30D:
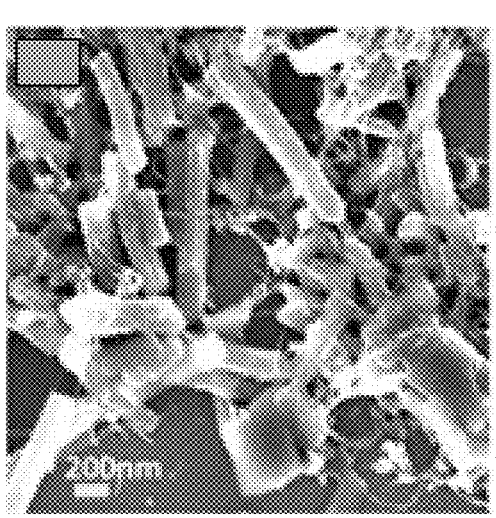
Figure 30E:
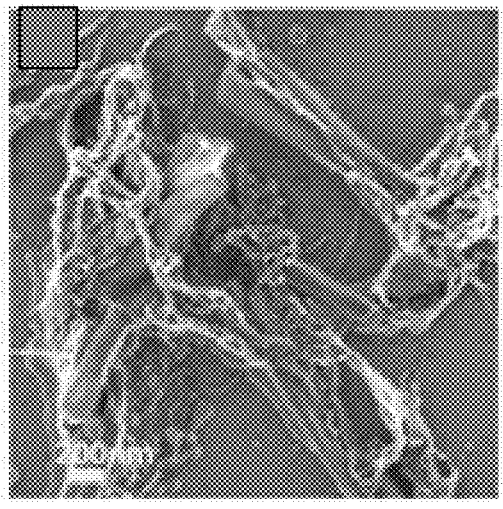
Figure 30F:
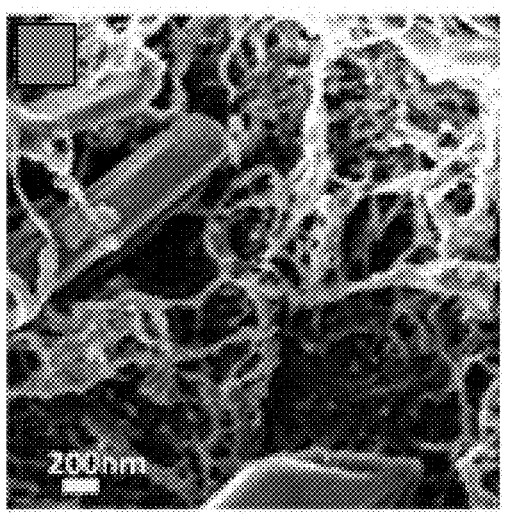

Attempts to form dispersions with PDIs substituted with electron donating groups (OH and NH₂) attached to the aromatic core were unsuccessful: the CNTs remained heavily bundled and fast precipitation was observed (FIGS. 30E, 30F).

The efficient dispersion and exfoliation is attributed to a charge shift (electron transfer) from CNTs to the PDI layer absorbed on CNT walls and crystallization of the dispersant (FIGS. 30A-30F, 31).

Figure 31A:
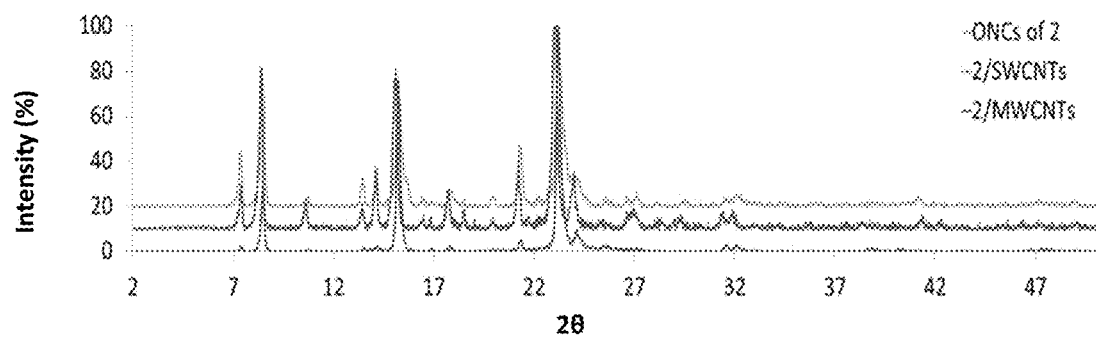
FIGS. 31A-31C present XRD spectra of ONC/CNT hybrids.
Figure 31B:
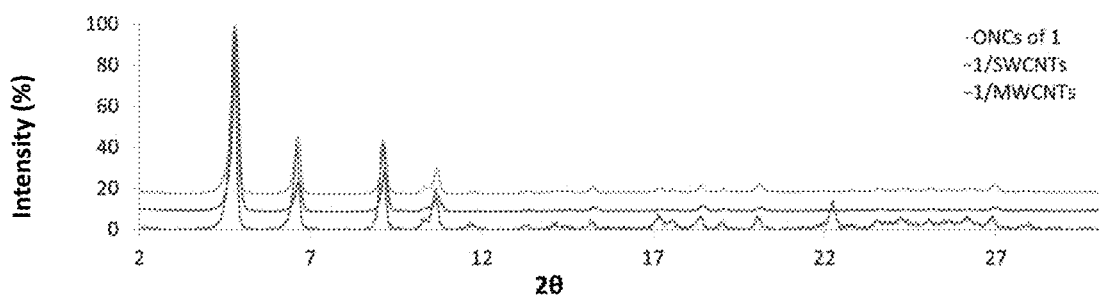
Figure 31C:
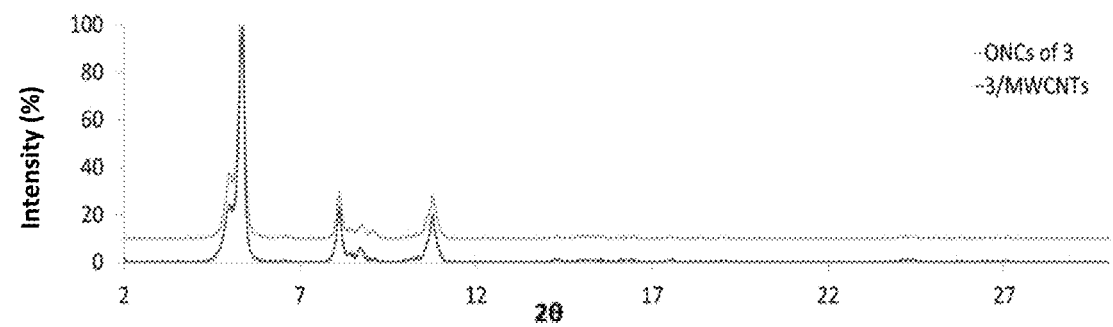
Figure 33A:
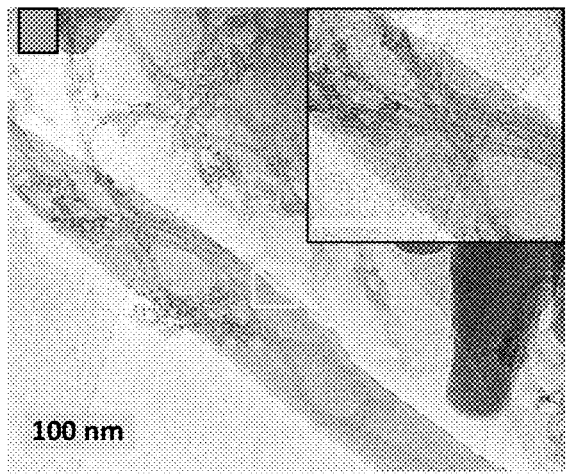
FIGS. 33A-33F present cryo-TEM images of ONC/CNT hybrids.
Figure 33B:
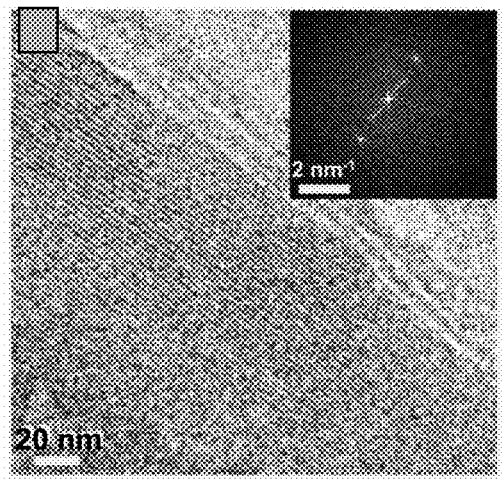
Figure 33C:
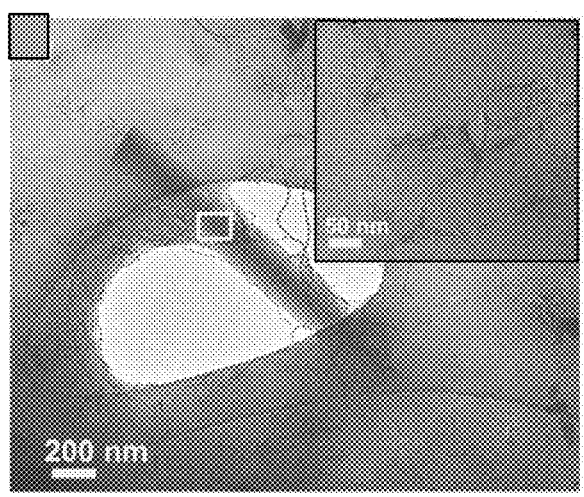
Figure 33D:
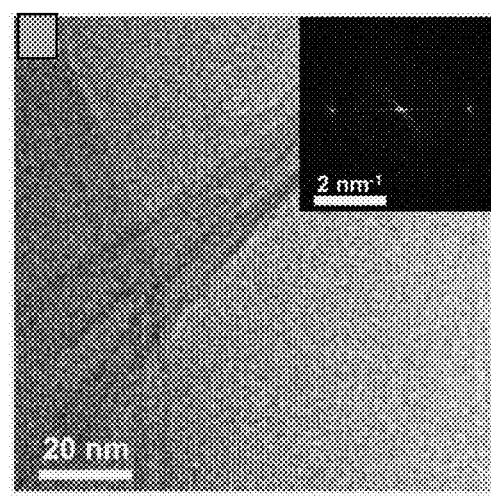
Figure 33E:
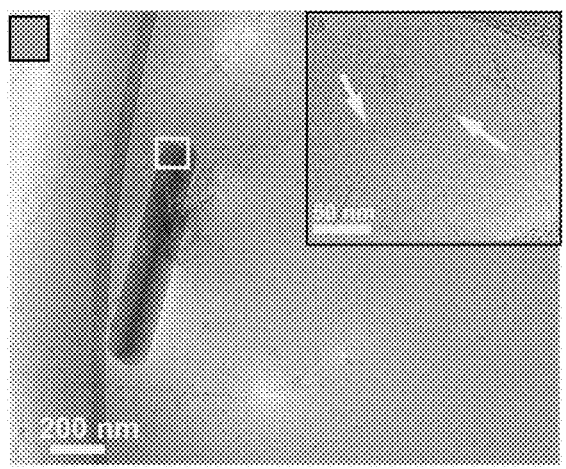
Figure 33F:
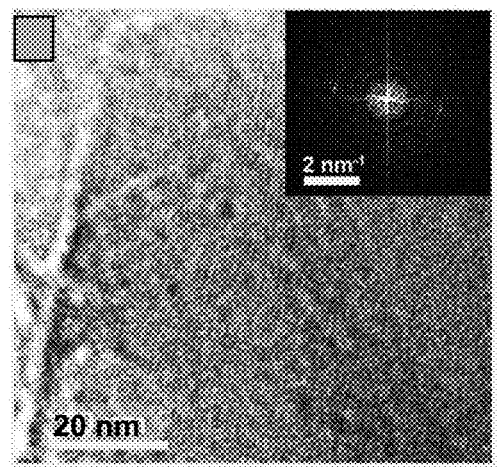
Figure 34A:
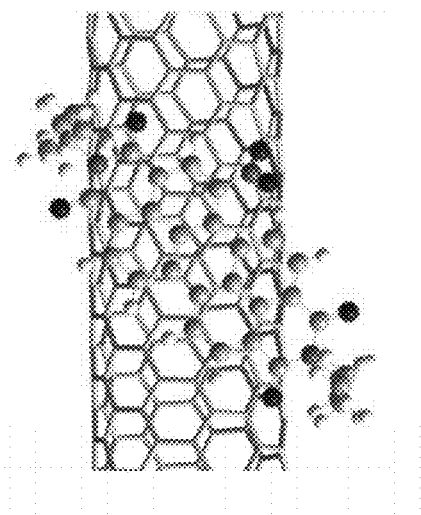
FIGS. 34A-34D present computational structures of 2/SWCNT hybrids and interactions.
Figure 34B:
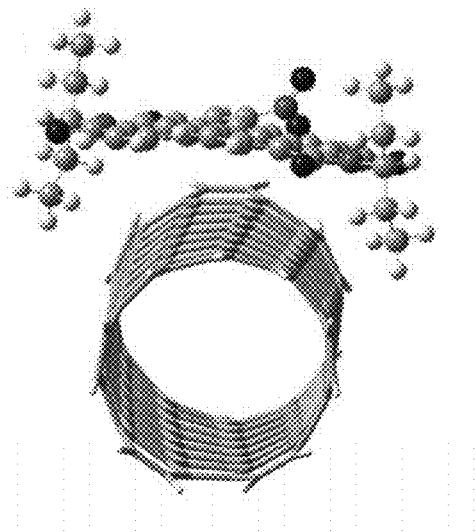
Figure 34C:
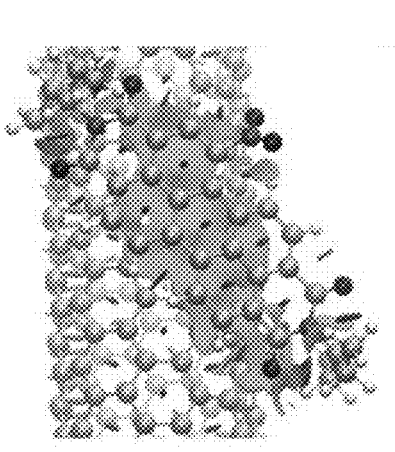
Figure 34D:
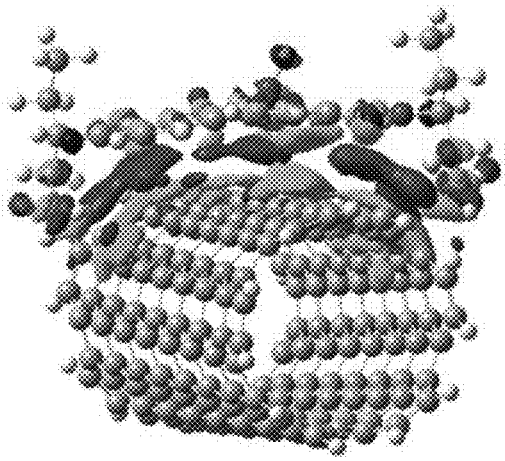

The XRD spectra in FIG. 31 show that all the PDI derivatives that were hybridized with CNTs self-assemble into crystals. Spectra of the hybrid films 2/CNT, 4/CNT and 3/CNT were recorded with low CNT content ($C_{CNTs}$ 5-8 wt %), so that the features of the CNTs did not mask the peak of the ONCs. The spectra of pure ONCs of 2-4 are also shown.

The stability of the CNT dispersions was followed by UV-vis-NIR spectroscopy in the case of SWCNTs and by visual observation of precipitation in the case of both SWCNTs and MWCNTs. The UV-vis-NIR absorption spectra of 2/SWCNT and 4/SWCNT dispersions (FIG. 32A-32D) demonstrated the SWCNTs van Hove peak (1020 nm) and the typical absorption bands of crystalline 2 or 4. The 2/SWCNT and 4/SWCNT dispersions (40 wt % CNT) were stable for at least seven days without any significant precipitation. Dispersions of 2-4 with a high concentration of MWCNTs (60-67 wt % CNT) were stable for up to three days, while dispersions containing low concentration of CNTs (3-8 wt % of SWCNTs and MWCNTs) showed remarkable stability for at least a month.

In order to characterize the solution-phase structure of the hybrids, the ONC/CNT dispersions were studied by cryogenic transmission electron microscopy (cryo-TEM). Cryo-TEM images revealed well-exfoliated CNTs that directly interact with ONCs, with the CNTs either coiled around the ONCs or freely dispersed (FIGS. 30A, 30B and FIG. 33A-33F). Apparently, crystallization of the dispersant into well-defined nanocrystals created a separate phase, preventing the dispersant from depositing onto the partially charged CNT surface, which would interfere with exfoliation and solvation.

Example 15

Charge Shift from CNTs to the Perylene Diimide Compounds

The hybrids of this invention demonstrate a charge shift (electron transfer) from CNTs to the PDI layer absorbed on CNT walls.

Figure 46A:
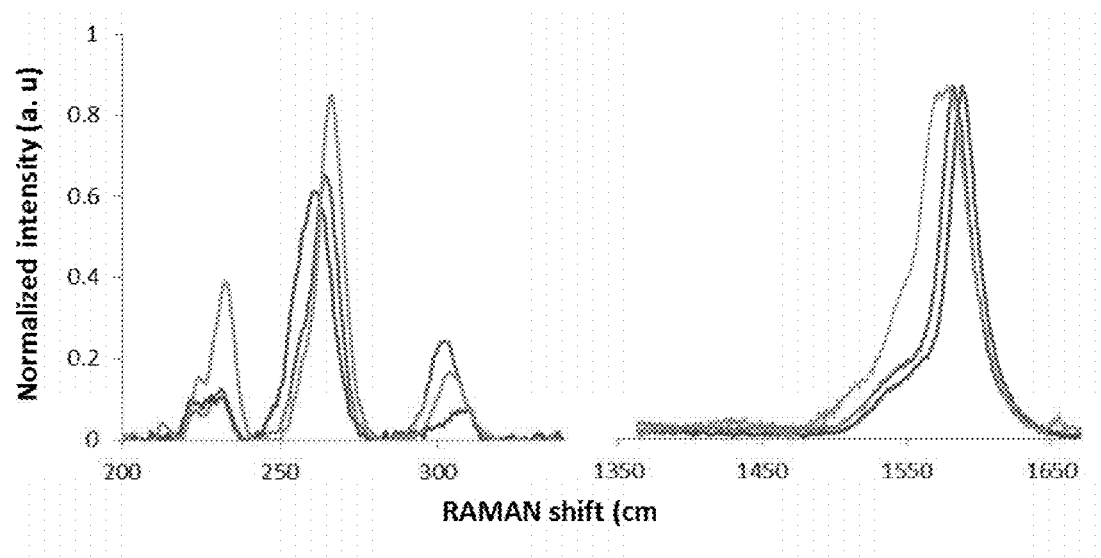
FIGS. 46A-46B present Micro-Raman spectra.
Figure 46B:
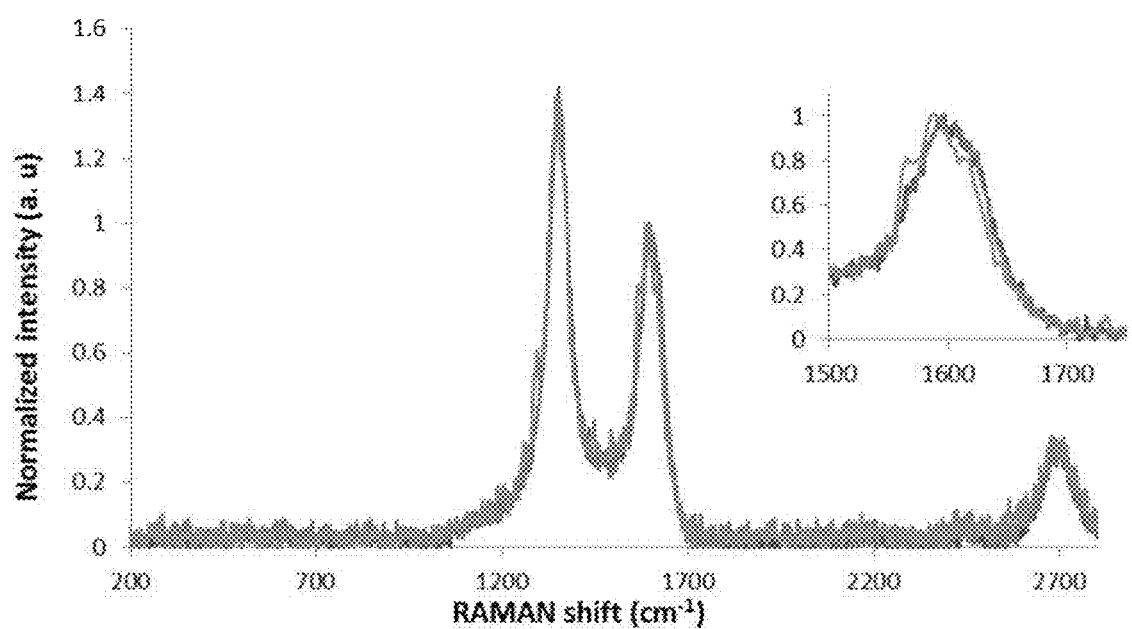

The charge shift is supported by computational (DFT), electrochemical studies, and Raman spectroscopy studies. (FIGS. 46A, 46B)

The structure of 2 complexed to an ~18.5 Å long SWCNT segment (total 204 atoms, including hydrogen atoms capping the two ends of the CNT, FIGS. 32A and 32B) was optimized using DFT. The PDI frame is slightly twisted, allowing it to follow the contours of the CNT; this is facilitated by the nonaromatic central ring. In aqueous solution (modeled with a polarized continuum model), this complexation involves an interaction energy of $\Delta G_{298,sol}=-22.6$ kcal/mol. The noncovalent interaction (NCI) plot (FIG. 32C) shows an extensive interaction surface, while the electron density difference plot (FIG. 32D) shows that upon complexation electron density is transferred from the SWCNT to 2 (or more accurately, to the bonding region between the two). As a result of this electron density transfer, which according to the CHelpG charge scheme amounts to −0.34 e−, the SWCNT dipole moment (directed outward from the center of the SWCNT) increases from 0.69 to 5.04 debye.

Thus, DFT calculations reveal an electron density transfer of −0.34 e− from the SWCNT to 2, resulting in an increase of the SWCNT dipole moment (directed outward from the center of the SWCNT) from 0.69 to 5.04 debye. This charge shift results in repulsion between CNTs and promotes solvation by water, eliminating the need for hydrophilic groups.

Example 16

Films of ONC/CNT Hybrids of this Invention

Hybrid Film Casting:

20 mL of aqueous dispersion was deposited onto a polyvinylidene fluoride (PVDF) membrane (Amersham™ Hybond® P Western blotting membranes, PVDF pore size 0.45 μm) using a controlled-pressure filtration setup. The film was separated from the PVDF support either mechanically or by immersing the deposited support in cold ACN, to yield a free-standing hybrid film.

Figure 35A:
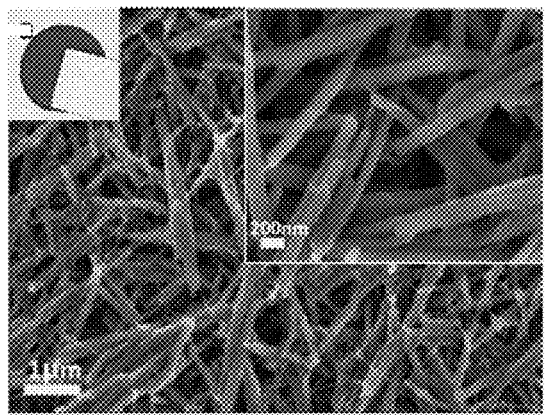
FIG. 35A-35J present SEM images of the 2/CNT hybrid films.
Figure 35B:
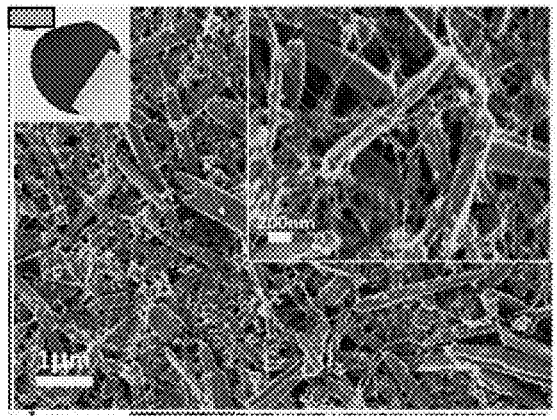
Figure 35C:
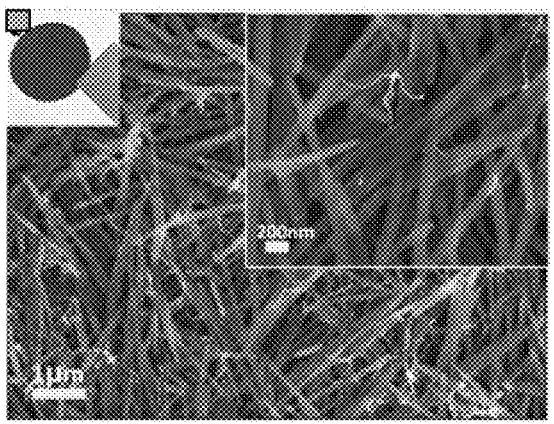
Figure 35D:
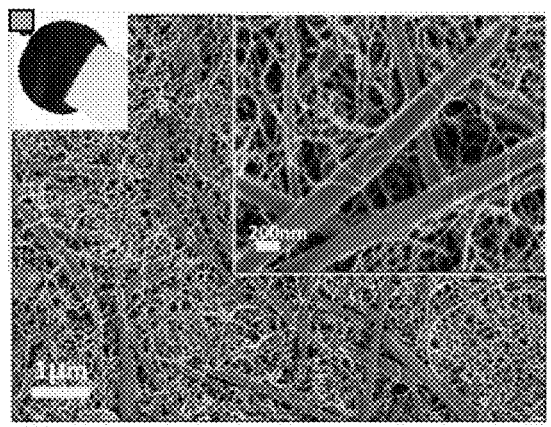
Figure 35E:
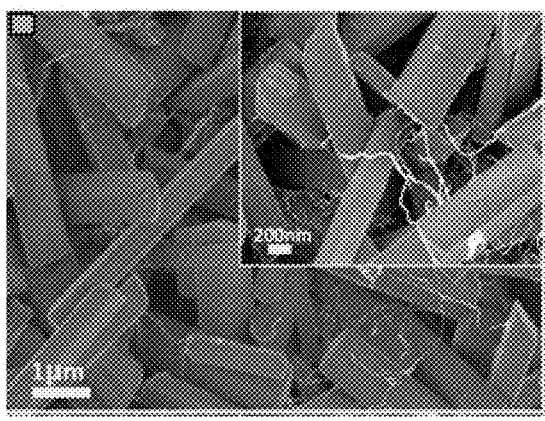
Figure 35F:
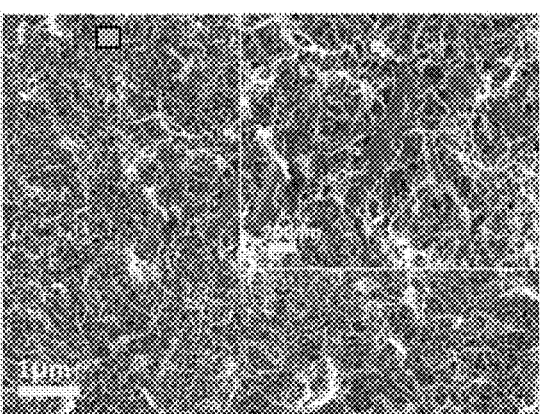
Figure 35G:
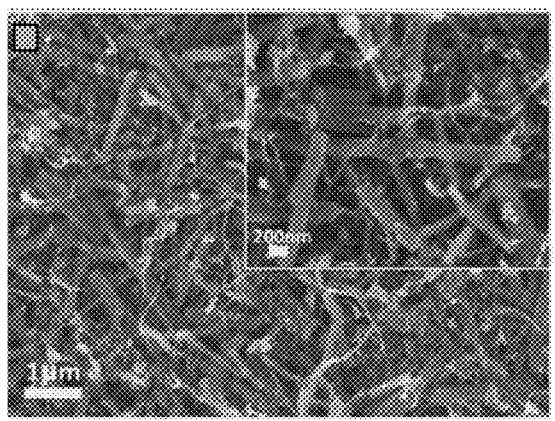
Figure 35H:
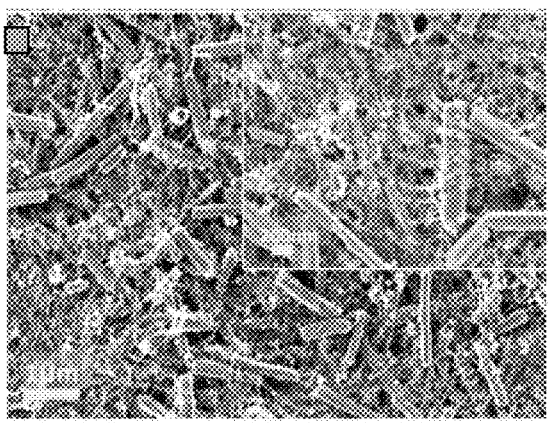
Figure 35I:
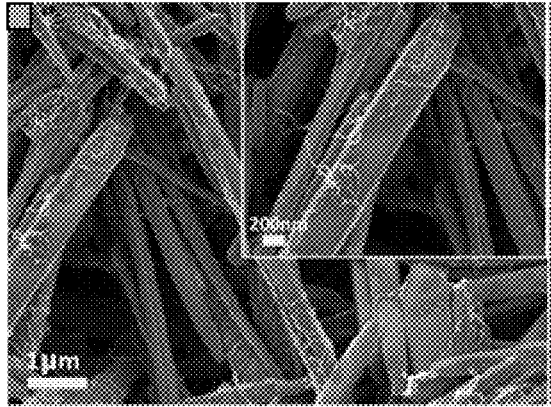
Figure 35J:
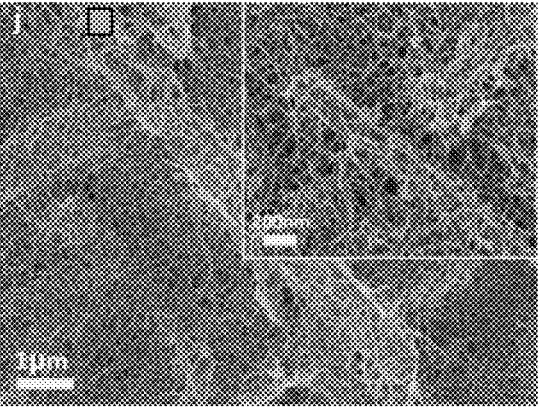

Stable ONC/CNT dispersions enable solution-processed fabrication of free-standing hybrid films with varying CNT concentration (FIG. 35A-35J). Solid films were formed by depositing the aqueous ONC/CNT dispersions by filtration onto a polyvinylidene fluoride (PVDF) support (standard syringe filter membrane). The deposit was detached from the support to yield a free-standing film (FIGS. 35A-35D, insets). Scanning electron microscopy (SEM) images of 2/SWCNT and 2/MWCNT hybrid films with different concentrations of CNTs are presented in FIGS. 35A-6D. The image in FIG. 35A shows a 2/SWCNT hybrid with a low SWCNT concentration of 8 wt % where the ONCs constitute the dominant component of the hybrid. With a higher (40 wt %) average concentration of SWCNTs (FIG. 35B), a homogenous distribution of ONCs and an interconnected network of SWCNTs were obtained. In the 2/MWCNT hybrid with a low MWCNT concentration (5 wt %), the MWCNTs were evenly distributed throughout the matrix (FIG. 35C). With a much higher MWCNT concentration (67 wt %, FIG. 35D), the MWCNTs were the dominant component. The SEM images of 3-4/CNTs are shown in FIGS. 35E-35J. All SEM images reveal uniform mixing of ONCs with well exfoliated CNTs as well as interconnected ONC/CNT networks.

Example 17

Thermal Stability of ONC/CNT Hybrid Films of this Invention

Figure 36A:
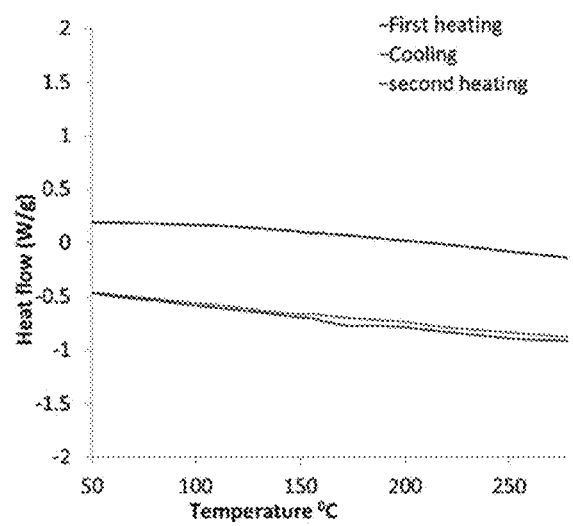
FIGS. 36A-36D present differential scanning calorimetry (DSC) analysis of ONC/CNT hybrids.
Figure 36B:
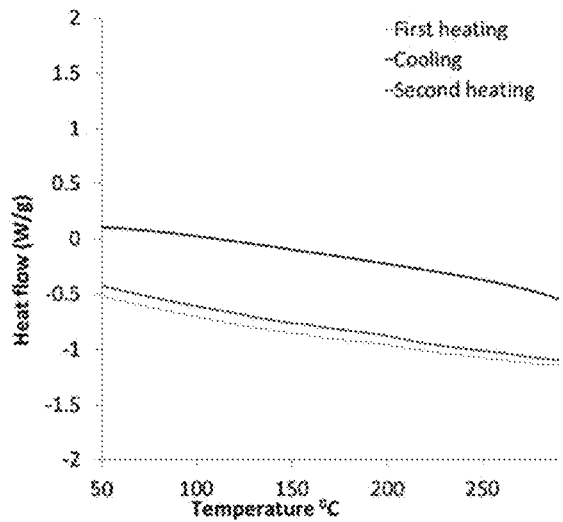
Figure 36C:
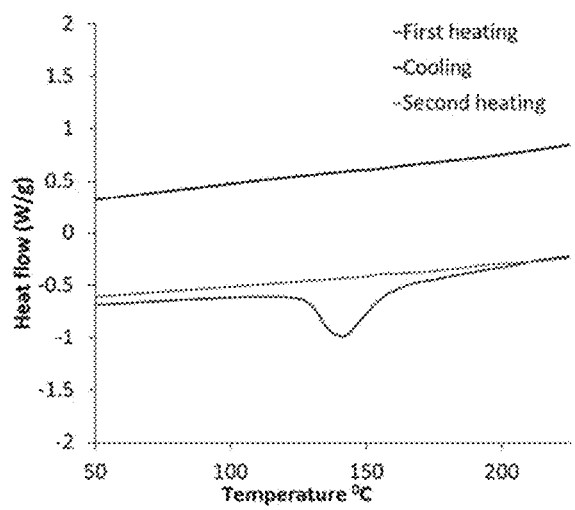

The thermal properties of the hybrid films were studied by differential scanning calorimetry (DSC, see FIG. 36A-36D). Hybrids based on 2 showed high thermal stability with no morphological changes observed upon heating up to 300° C. (FIG. 36A-36B). This exceeds the thermal limits of common polymer/CNT hybrids.

Figure 36D:
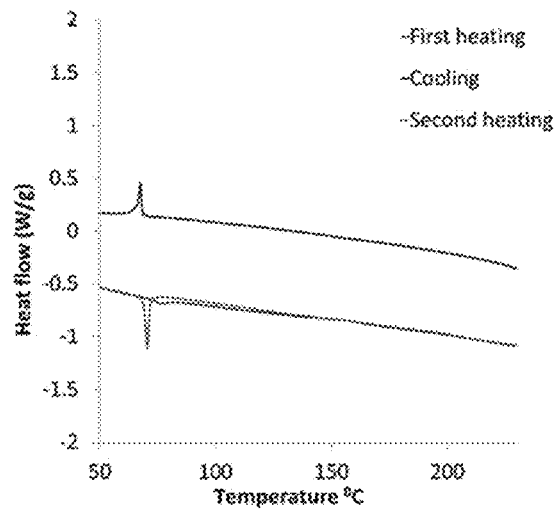
Figure 37A:
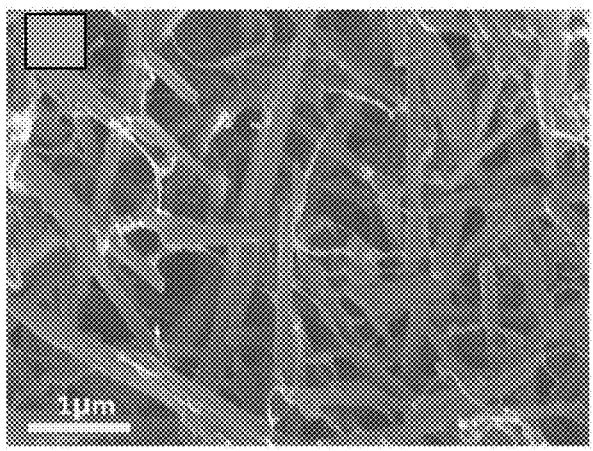
FIGS. 37A-37B present SEM images of the hybrid films after heating to 300° C. in DSC.
Figure 37B:
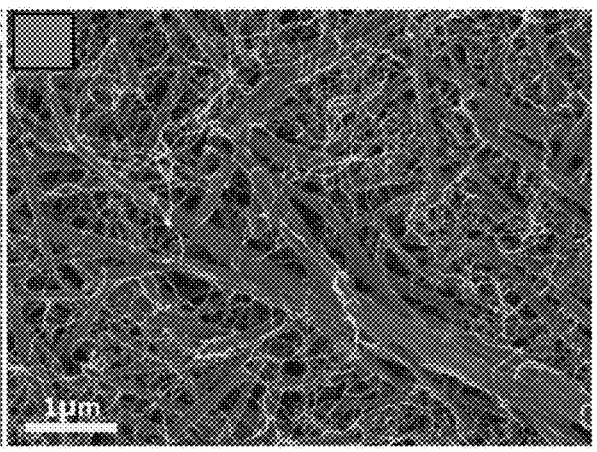
Figure 38A:
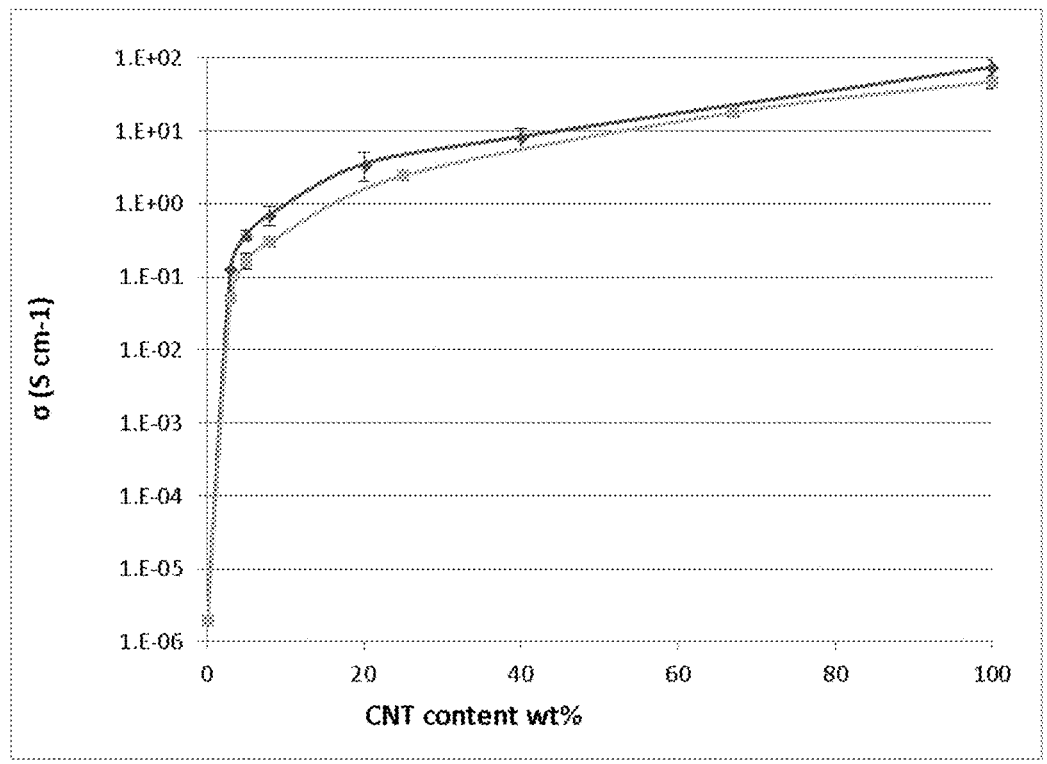
FIGS. 38A-38D present electrical conductivity of ONC/CNT hybrids.
Figure 38B:
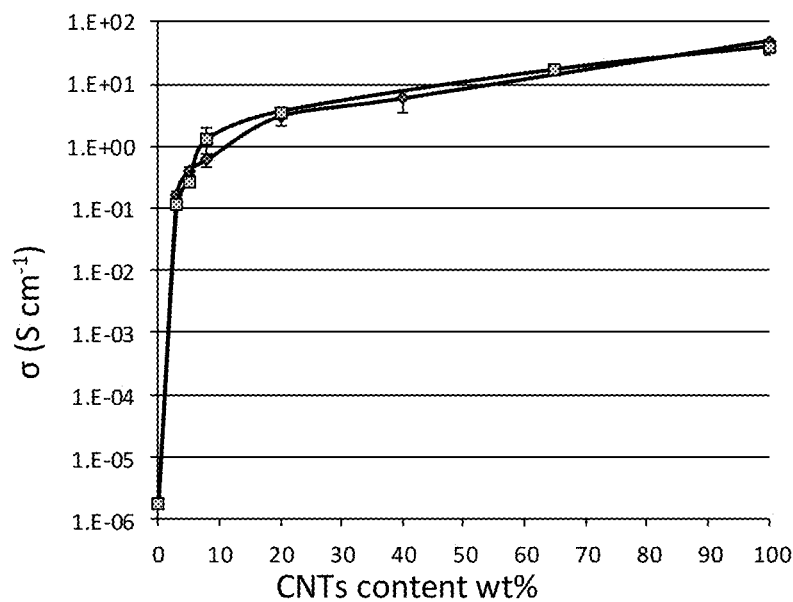
Figure 38C:
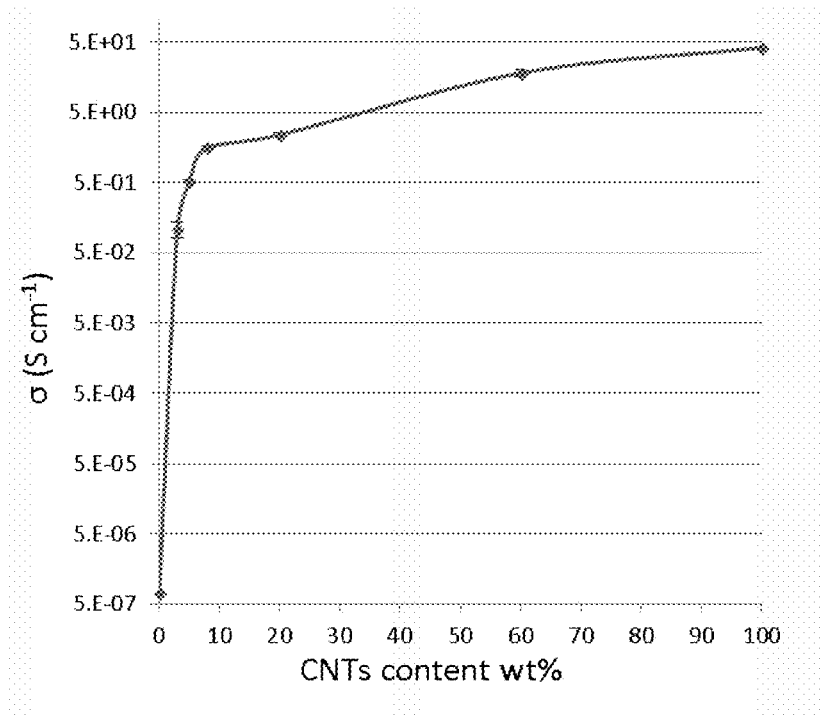
Figure 38D:
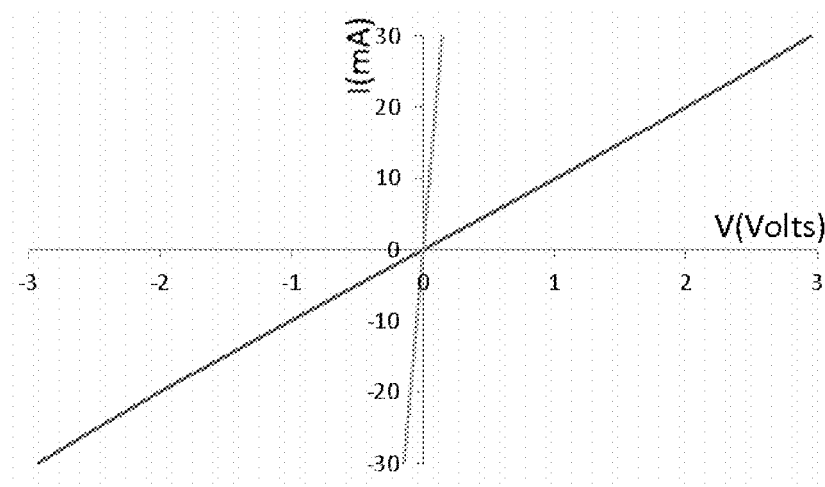

The hybrids were tested at low CNT content, as high CNT content hinders the thermal transitions of the ONCs in the thermogram. The morphology of the films after heating was analyzed by SEM imaging FIG. 37). In the case of 2/CNTs, no phase transitions occur upon heating to 300° C. Hybrid 4/MWCNT undergoes a phase transition at 145° C. (FIG. 36C), and 3/MWCNTs at 75° C. (FIG. 36D).

Example 18

Conductivity Studies of ONC/CNT Hybrid Films of this Invention

The bulk conductivity of the hybrids was studied using a standard four-point probe methodology. The ONC/CNT hybrids showed Ohmic behavior and had good electrical conductivities (FIGS. 38A-38D), while ONCs had much lower conductivity (e.g., σ(ONC 2)=2.0×10−6 S·cm−1, and FIGS. 39A-39B). Hybrids of SWCNTs were measured under an inert atmosphere while hybrids of MWCNTs were measured under ambient conditions.

Pristine ONC Conductivity.

Figure 39A:
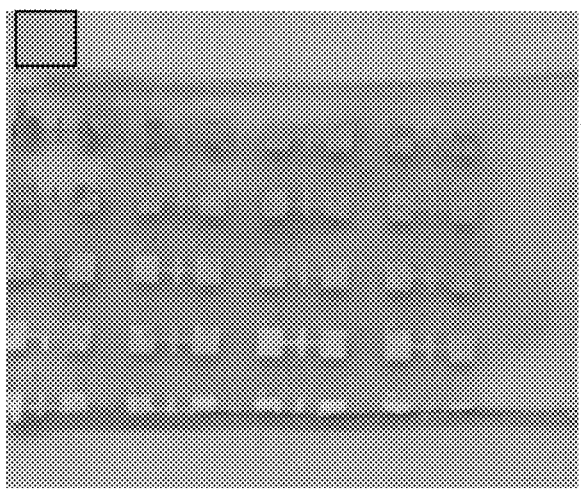
FIGS. 39A-39B present photograph of Au electrodes deposited onto a glass slide modified with ONCs of 2 (FIG. 39A) and light microscope image of 2 between two electrodes (FIG. 39B).
Figure 39B:
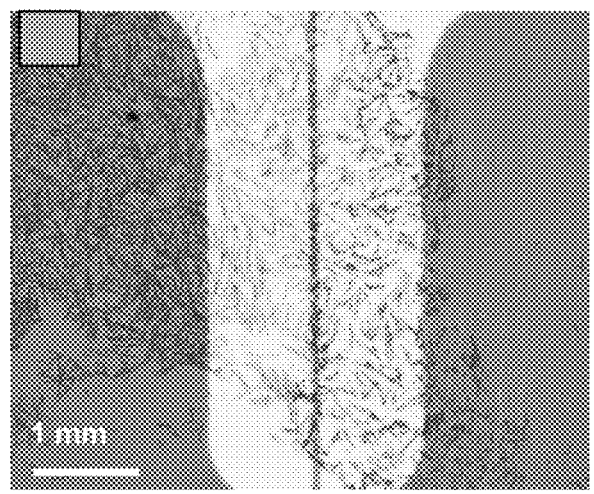
Figure 40A:
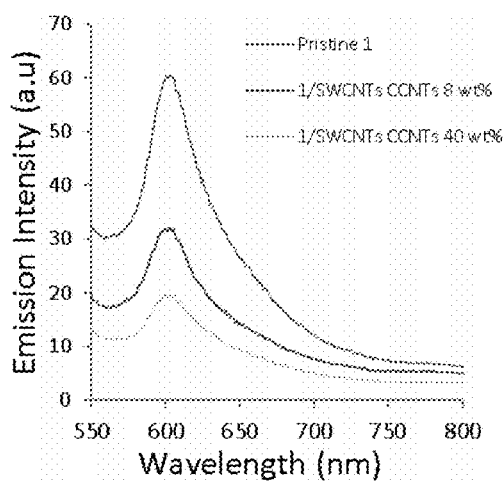
FIGS. 40A-40D present emission spectra of ONC/CNT hybrids.
Figure 40B:
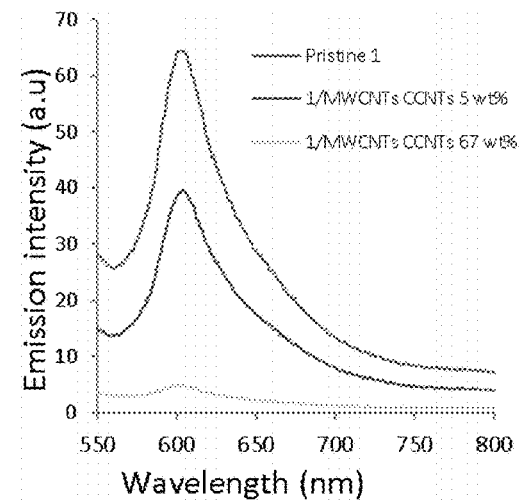
Figure 40C:
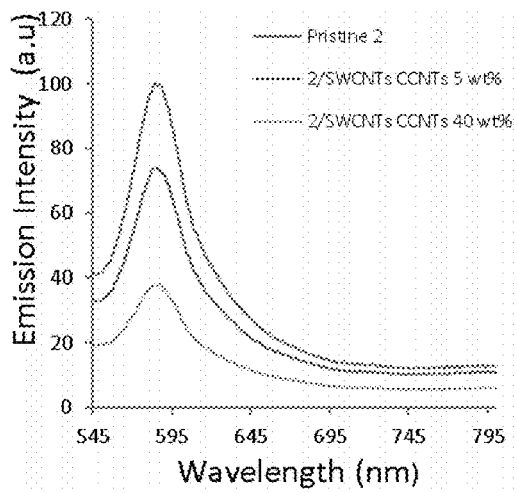
Figure 40D:
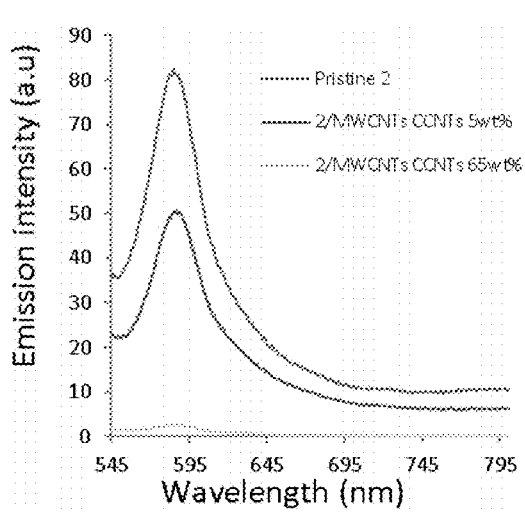

The current vs. voltage behavior of the pristine ONCs was measured using a four-point station. The ONCs were deposited onto a glass slide by dropcasting and Au electrodes were deposited on the modified glass slide using a shadow mask; the resulting construct is shown in FIGS. 39A-39B.

The interconnected 3D CNT networks in the ONC/CNT hybrid films resulted in significant conductivity even at 3% CNT concentration. Remarkably, the 4/CNT hybrids did not show any change in their conductivity after heating to 300° C., consistent with their high thermal stabilities.

The conductivities observed in the hybrid systems were higher than those of most polymer/CNT systems and were comparable to conductivities observed in composites of conductive polymers and CNTs.

Example 19

Electronic and Photonic Properties of ONC/CNT Hybrids of this Invention

In order to gain insight into the electronic interactions between the ONCs and the CNTs, the emission of ONCs in the hybrid materials by fluorescence spectroscopy and microscopy was studied. Emission measurements showed enhanced fluorescence quenching of the ONCs with increasing CNT concentration (FIGS. 40A-40D and Table 4).

TABLE 4

Fluorescence quenching of 2 and 4 with varying CNT content.

| Hybrid | Fluorescence quenching |
| --- | --- |
| 2/SWCNTs $C_{CNTs}$ 8 wt % | 45% |
| 2/SWCNTs $C_{CNTs}$ 40 wt % | 66% |
| 2/MWCNTs $C_{CNTs}$ 5 wt % | 40% |
| 2/MWCNTs $C_{CNTs}$ 67 wt % | 94% |
| 4/SWCNTs CCNTs 5 wt % | 27% |
| 4/SWCNTs $C_{CNTs}$ 40 wt % | 67% |
| 4/MWCNTs $C_{CNTs}$ 5 wt % | 38% |
| 4/MWCNTs $C_{CNTs}$ 65 wt % | >96% |

Emission measurements showed increasing fluorescence quenching of 2 and 4 in the ONC/CNT hybrids with increasing CNT content as compared to the pristine compounds with the same concentration.

Figures 41A, 41B:
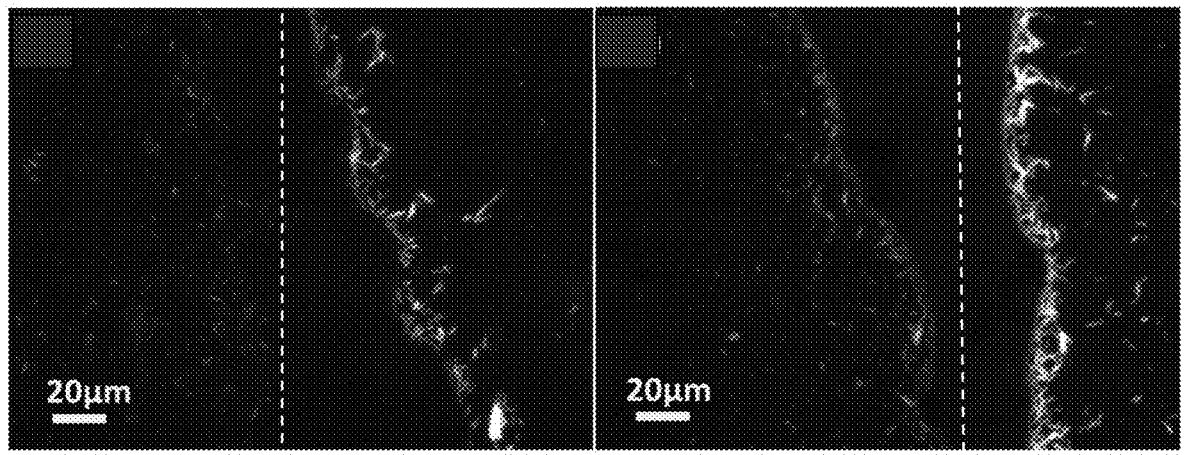
FIG. 41A-41B present florescence micrographs.

This observation was verified by fluorescence microscopy imaging, which showed that the fluorescence of ONCs hybridized with CNTs decreased compared to pristine ONCs (FIGS. 41A-41B).

Figures 42A, 42B:
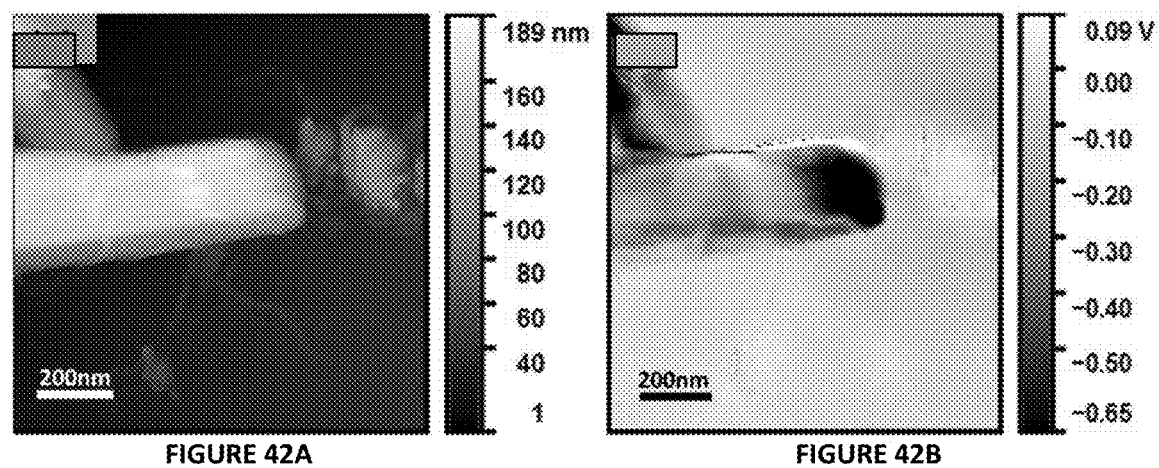
FIG. 42A-42B present AFM topography of 2/MWCNTs (FIG. 42A) and CPD-AFM image of the 2/MWCNT hybrid measured over the same region (FIG. 42B).

The electronic properties were further investigated by Kelvin probe force microscopy (KPFM). Contact potential difference (CPD-FM) images of the 2/MWCNT hybrid (FIGS. 42A-42B) showed that the potential of the ONCs is affected by the CNTs: the CPD is higher for the CNT than for the ONC, and where a CNT is attached to the ONC, the local CPD of the ONC is intermediate in value.

Figures 43A, 43B:
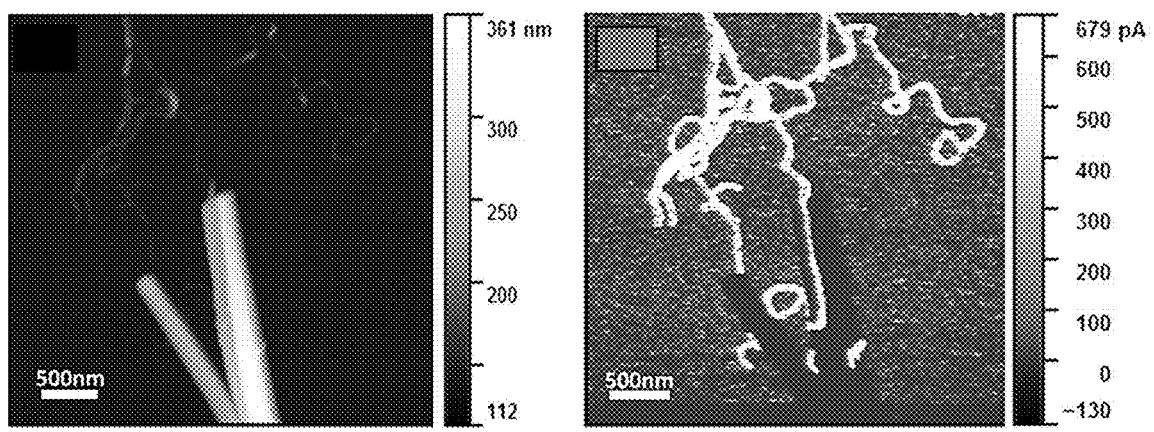
FIG. 43A-43B present CP-AFM topography of 2/MWCNT (FIG. 43A) and current image of the area in FIG. 43A at bias between probe and surface of 1.5 V (FIG. 43B).

These results, together with the fluorescence quenching of the ONCs, were indicative of substantial electronic communication between the ONCs and the CNTs. However, the current flows only along the CNTs in the hybrid materials, as observed by conducting probe force microscopy (CP-AFM, FIGS. 43A-43B). This behavior may arise from a localized charge shift at the interface between the two materials, as discussed above.

Example 20

CNT Films (Buckypapers)

Buckypaper Preparation.

The buckypapers were prepared by thoroughly washing the ONC/CNT hybrid films with chloroform, which removes most of the PDI.

Figure 44A:
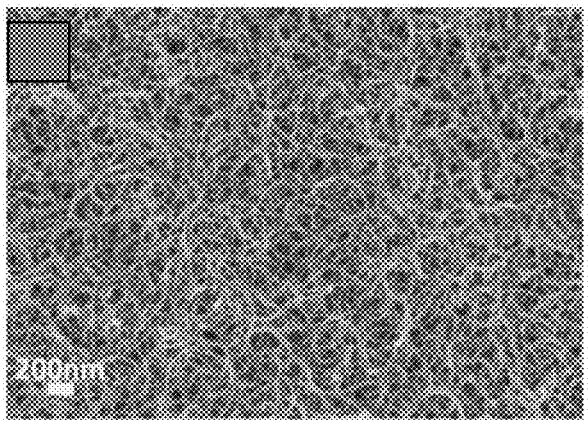
FIGS. 44A-44B present SEM images of buckypaper prepared from 2/MWCNT (FIG. 44A) and 2/SWCNT (FIG. 44B). Inset: photograph of the buckypaper imaged in FIG. 44B.
Figure 44B:
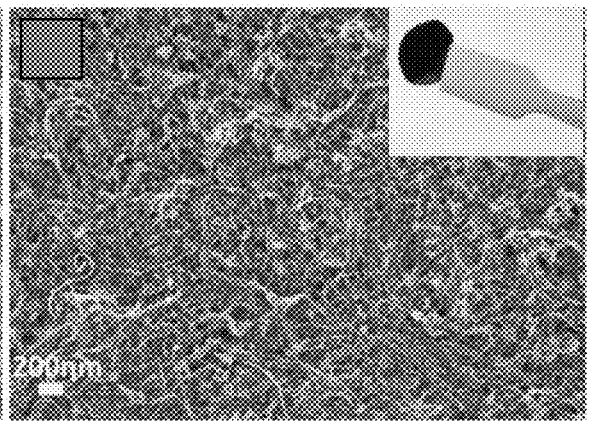
Figure 45A:
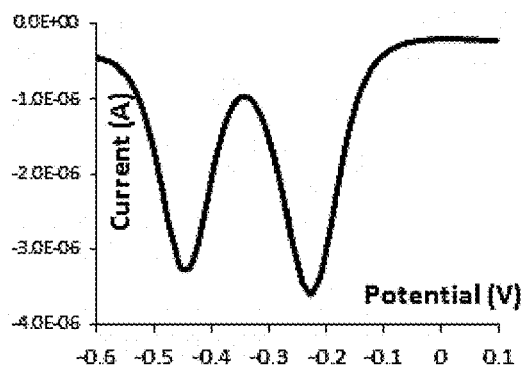
FIGS. 45A-45H present DPV voltammograms.
Figure 45B:
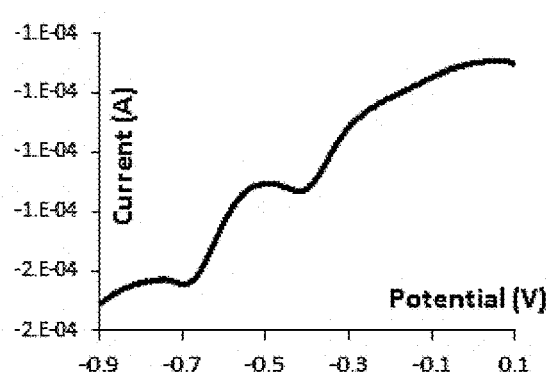
Figure 45C:
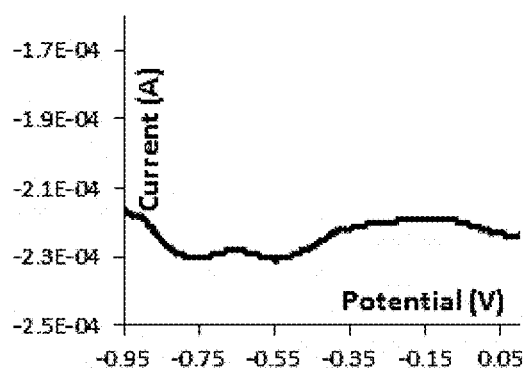
Figure 45D:
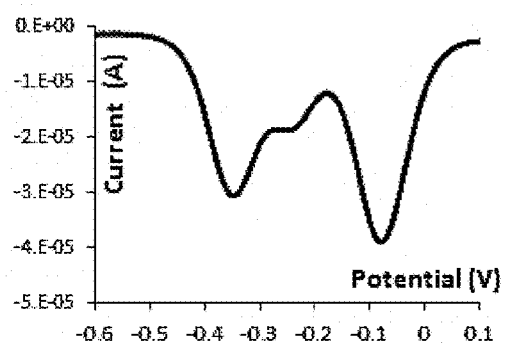
Figure 45E:
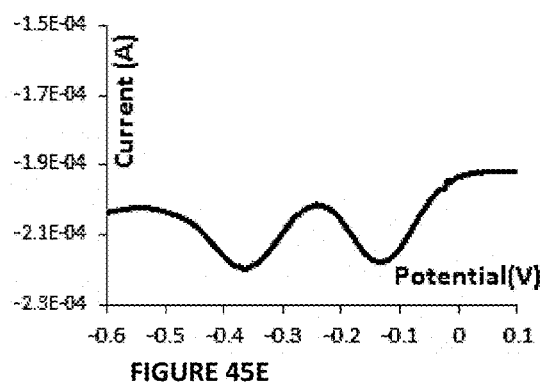
Figure 45F:
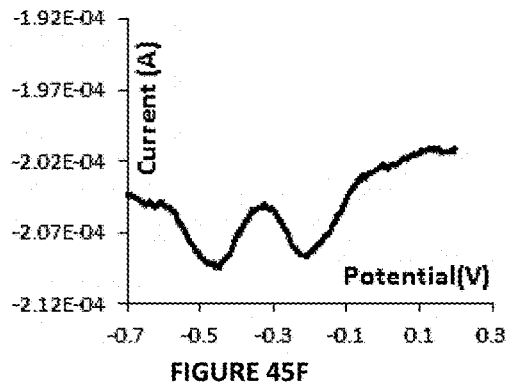
Figure 45G:
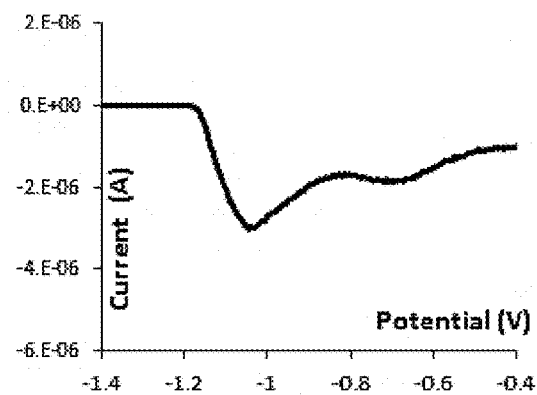
Figure 45H:
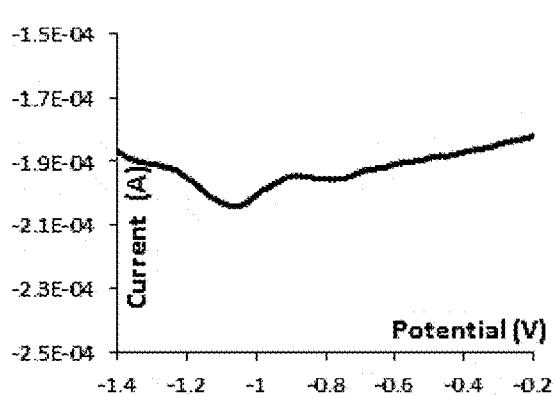

ONC/CNT hybrids were converted into CNT films ("buckypaper") by washing the hybrids with organic solvent to dissolve the ONCs. SEM images of chloroform-washed 2/CNT films show interconnected and highly exfoliated CNTs (FIGS. 44A-44B).

Electrochemistry and X-ray photoelectron spectroscopy (XPS) indicate that small amounts of PDI was still present in the film even after prolonged washing (Tables 5 and 6), attesting to the strength of the PDI/CNT interactions.

TABLE 5

The first and second reversible reduction potentials of PDI derivatives (from CV and DPV, vs Ag/AgCl under an inert atmosphere). The measurements were carried out in acetonitrile in the range of 0.1—1.5 V.

| Material | First reduction (V) vs Ag/AgCl | Second reduction (V) vs Ag/AgCl |
|---|---|---|
| 2 | −0.22 | −0.43 |
| bucky paper of 2/SWCNTs | −0.4 | −0.69 |
| bucky paper of 2/MWCNTs | −0.52 | −0.78 |
| 4 | −0.08 | −0.32 |
| bucky paper of 4/SWCNTs | −0.14 | −0.39 |
| bucky paper of 4/MWCNTs | −0.21 | −0.46 |
| 3 | −0.69 | −1 |
| bucky paper of 3/MWCNTs | −0.74 | −1.1 |

TABLE 6

Carbon and Nitrogen concentrations derived from XPS peak intensities.

| Buckypaper source | Total carbon % | CNTs carbon % | Nitro/amide nitrogen % | PDI carbon % |
|---|---|---|---|---|
| 2/SWCNTs | 93.6 | 81.9 | 1.0 | 11.7 |
| 2/MWCNTs | 93.7 | 81.1 | 1.1 | 12.6 |
| 4/SWCNTs | 93.4 | 84.0 | 1.1 | 9.4 |
| 4/MWCNTs | 97.4 | 91.4 | 0.5 | 6.0 |
| 3/MWCNTs | 98.0 | 96.0 | 0.1 | 2.0 |

Differential pulse voltammetry (DPV) of the buckypapers showed the two characteristic reduction peaks of 2-4 after washing overnight with chloroform (FIGS. 45A-45H). According to the XPS data (Tables 6 and 7), buckypaper prepared from 2/SWCNT contains 11.7 wt % of 2; the surface coverage of 2 on the SWCNTs was calculated to be 15.0% (Table 7).

TABLE 7

SWCNT surface coverage by 2

| 2 wt % | weight ratio | CNT wt % | CNT mass per 2 (g/mol) | Length of CNT per 2 (nm) | External CNT surface per 1(Å$^2$) | Percent coverage by 2 |
|---|---|---|---|---|---|---|
| 11.67 | 88.33 | 7.57 | 4355.95 | 4.27 | 1464.63 | 15.02 |

The concentration of 2 in the buckypaper prepared from 2/MWCNT was 12.6 wt % (Table 7). Furthermore, the DPV voltammograms showed that the reduction peaks of 2-4 in the buckypapers are shifted to more negative potentials than those of the pristine PDI derivatives (Table 6, FIGS. 45A-45H), confirming that electron transfer occurs from the CNTs to the PDIs, in agreement with DFT studies.

Additional support for the strong interactions between CNTs and the adsorbed PDI derivatives comes from Raman spectroscopy of the buckypapers (FIGS. 46A-46B). In the case of SWCNT buckypapers, the G-bands were upshifted relative to pristine SWCNTs, which is indicative of shifting charge density from the SWCNTs to the PDIs, with a larger shift in the case of the 2/SWCNT buckypaper. This is consistent with the observed stronger shifts in the redox potentials of 2 (Table 6). No appreciable differences were observed in the D-bands, which are sensitive to defects in the SWCNTs. In the case of MWCNT buckypapers, the same upshift in the G-bands of 2/MWCNTs and 4/MWCNTs was observed. The buckypapers are free-standing, highly porous and excellent conductors, with conductivities as high as 87 S·cm$^{-1}$ for SWCNT and 120 S·cm$^{-1}$ for MWCNT films.

Example 21

Conductive Colorant Materials

Figure 47A:
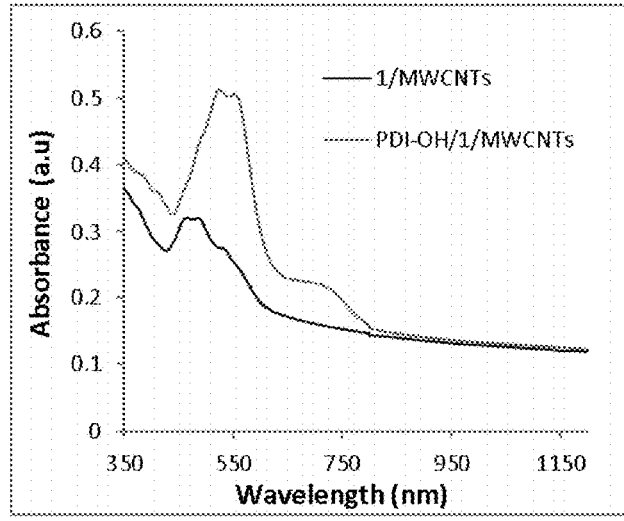
FIGS. 47A-47B present UV-vis-NIR spectrum of 2/MWCNT and spectrum after addition of PDI-OH to yield PDI-OH/2/MWCNT hybrid (FIG. 47A) and Representative IV curve of PDI-OH/2/MWCNT hybrid films. Inset: photograph of the hybrid film (FIG. 47B).
Figure 47B:
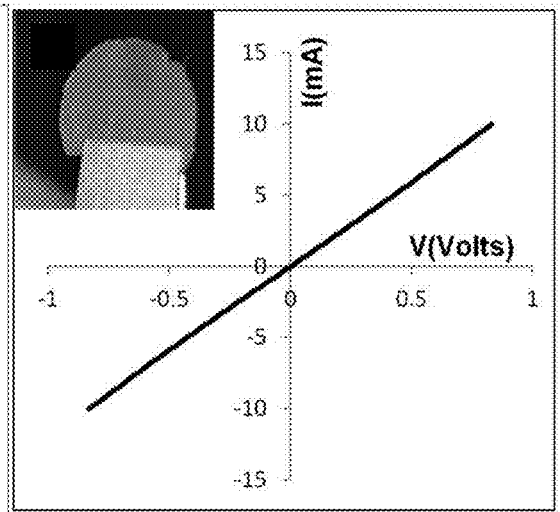

ONC/CNT films with low CNT concentrations containing simple hydrophobic organic dyes as a major component were prepared. A dispersion 2/MWCNT was used as a template to prepare an ONC/CNT hybrid with a PDI dye (PDI-OH) that otherwise would not form a stable CNT-dispersion. The resulting purple conductive film of the PDI-OH/2/MWCNT co-hybrid was obtained (FIG. 47).

Example 22

CNT Dispersion and PDI/CNT Hybrid Films

Preparation of a CNT Film on Computer Paper

A dispersion of MWCNT/2 (4 mg each—1:1 wt) in CHCl$_3$ was prepared and was dried under vacuum. 8.0 mL of acetone were added and sonicated in a bath sonicator for 8 min to form a CNT/PDI hybrid. A dark gray solution was obtained that was stable for at least 24 h.

Into a 90 mm petri dish 60 mL of PhCl were added. The above dark gray solution was added slowly 200 uL at a time. While the acetone evaporated slowly under a laminar air flow, a film was formed on the PhCl.

A piece of computer paper 34×34 mm was put flat on to the film surface of the PhCl. The paper sank and was removed from the PhCl and dried in air. The resistivity of the surface was measured. 1.2-11 MΩ for 2.0±0.1 mm distance. Preparation of CNT Films on PET (Polyethyleneterephthalate)

Effect of Redox Agent

A dispersion of MWCNT/2 (0.7 mg each—1:1 wt) in $CHCl_3$ was prepared and was dried under vacuum. 28.3 mL of acetone were added and sonicated in a bath sonicator for 8 min. A dark gray solution was obtained and it was stable for at least 24 h.

A water droplet from 4 mL $Na_2S_2O_4$ solution (60 mg in 6.0 mL) (ca. 5 cm in diameter) was positioned on a 10×10 cm PET film. The gray solution in acetone (ca. 2 mL) was deposited by drop casting on the water surface of the $Na_2S_2O_4$. This step was repeated for three times.

In seconds a film formed on the surface of the water (langmiur-blodget) the film was easily brought to saturation. The film was easily transferred to a 40×40 mm wide PET surface from the water just by touching.

The film was washed with water inside the glovebox box and then with acetone outside the glovebox. The values of resistivity: A single layer gave rise to resistivity of ca. 800 $K\Omega \cdot cm^{-1}$ and a double layer gave rise to resistivity of ca. 65 $K\Omega \cdot cm^{-1}$ and a triple layer gave rise to resistivity of ca. 30 $K\Omega \cdot cm^{-1}$ (This experiment demonstrated that there is no sensitivity to a redox cycle.

Preparation of CNT Films by Langmuir Blodgett

A homogeneous dispersion of 0.02 mg/mL MWCNT/2 (0.02 mg each—1:1 wt) in acetone was used to form a Langmuir Blodgett film over DDW. Three layers cover: first from 3.0 mL solution then 4.5 mL and the third from 8.8 mL. Each time a 110×80 mm film was formed and transferred to a PET transparency. A conductive layer was formed (including 3 layers of the dispersion) with a resistivity of 7 $K\Omega*cm^{-1}$.

Conductivity Measurement:

A solution of 0.02 mg/mL MWCNT/2 (0.02 mg each—1:1 wt) in acetone was used to form a Langmuir Blodgett film over DDW. A total volume of 13.2 mL was used to transfer 4 times a film onto 62×10.6 mm PET transparency. A conductive layer was formed with an ohmic behavior. The sample was measured under SEM and in a four-probe station. $R_s$ was found to be 17 $K\Omega \cdot sq^{-1}$. To measure the thickness of the layer a lamella was cut using FIB and imaged on the ULTRA with the IN-LENS and ESB detectors to distinguish the layer of the electron beam deposited Pt and the nanotubes layer. A total length of a 12.8 μm was measured for height of the layer. The obtained average height was found to be 98±10 nm. Therefore the volume resistivity $\rho = R_s \cdot h(cm) = 17 \ K\Omega \cdot sq^{-1} \cdot 9.8 \cdot 10 - 6 = 0.167 \pm 0.03$ W·cm; conductivity=6±0.2 S/cm Preparation of PDI/CNT Hybrid Dispersions-Solvent Effect 4.5 mg of MWCNT were dispersed in 4.5 mL of $CHCl_3$ containing 1.5 mg of 2. The suspension was sonicated in a sonication bath at 0° C. for 30 min. 1.0 mL of the black suspension (pinkish color observed) was diluted to 10 mL of $CHCl_3$ and sonicated for 5 min at 13° C. A homogeneous solution obtained with a slight pink color (no fluorescence evident by eye under UV lamp at 350 nm) the solution was homogeneous for at least two weeks.

An attempt to work with 20% wt % of 2 gave a less stable solution. Dilution of 1 mL of the 33% of 2 gave a homogeneous solution that was stable for about a week. After that time the CNTs started to precipitate and after two weeks all the CNT precipitated.

The CNT/2 dispersion was dried under reduced pressure. The solids were washed with acetone until no evident color was observed in the solvent. After the wash, 10 mL of analytical acetone were added to the solids and sonicated in a sonication bath for 30 min at 0° C. The black suspension is homogeneous for several minutes. It stays partially homogeneous for weeks and easily rehomogenized by sonication.

Preparation of Dispersion of MWCNT with 3

8 mg MWCNT dispersed in 8.0 mL of $CHCl_3$ containing 4.0 mg of 3. The suspension was sonicated in a sonication bath at 0° C. for 30 min. 1.0 mL of the black suspension (strong green-yellow fluorescent) was diluted to 10 mL of $CHCl_3$ and sonicated for 5 min at 13° C. A homogeneous solution obtained with a slight orange color and green yellow fluorescence. It was stable for at least 6 h. A control of the same MWCNT, without PDI under the same conditions was performed. The suspension of the control lost some of its homogeneity almost immediately after its sonication.

Preparation of Langmuir Blodget from Dispersion of MWCNT with 3

1 mL of 1 mg/mL MWCNT in chloroform from 3 (1:0.5 wt %) was added to 9 mL of acetone for 30 sec. Sonication gave a dark gray-orange homogeneous solution. The LB film was prepared on water in the same way as in CNT/2. 9 mL of the solution was transferred to the water. The obtained film was densified to an area of 10×6 cm and was transferred onto a transparency by settling (the 4×4 cm transparency was set in the water ca. 2 mm below the surface) prior the CNT solution addition. After the densification the gray orange aqueous solution was removed via a needle fitted syringe. The obtained film settles on all the surfaces involved, in this case glass (support) film and the polypropylene of the bath.

The transparency was gently transferred onto a petri dish and put in an oven at 120° C. for 30 min. The obtained film had a resistance of 50±8 KΩ between 2 points 50 mm apart and 40±9 KW 38 mm apart. After washing gently with chloroform until all color was removed the resistance increase roughly by 3 folds. However, after drying in an oven for 10 min at 120° C. the resistance was reduced to about the initial values.

Preparation of Co-Hybrid PDI+MWCNT+Effect of Temperature

Figure 48:
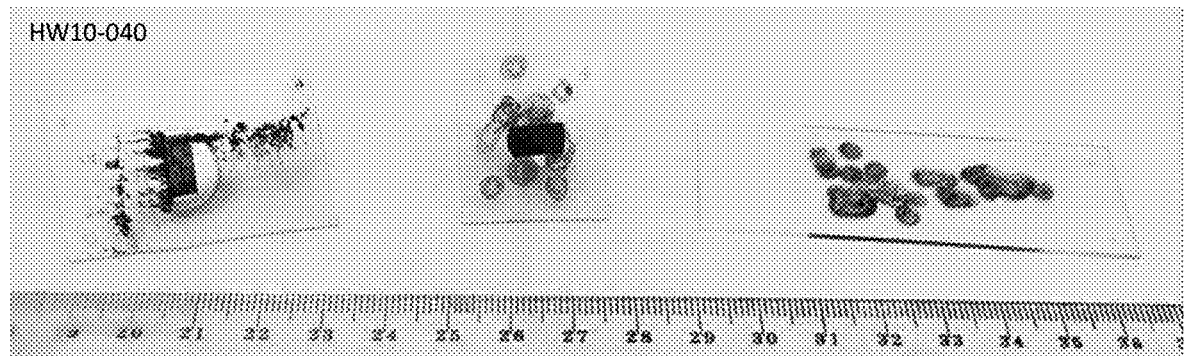
FIG. 48 presents conductive MWCNT/3/PS 2:1:10 wt hybrids (15% wt MWCNT) drop casted from $CHCl_3$ on glass slide at different temperatures (from left to right respectively 200, 150 and 120° C.). [MWCNT purchased in cheaptubes]

From a solution of 0.2 mg/mL of MWCNT+0.1 mg/mL 3+1 mg/mL polystyrene (PS), three different drop cast were made on microscope glass slides on a hot plate at 120° C., 150° C. and 200° C. In the highest temperature the black material formed became a viscous liquid that could be scraped and pressed between two slides a homogeneous mixture of exfoliated MWCNTs in a solid matrices was obtained. (FIG. 48)

Preparation of CNT/3 Dispersion—Solvent Effect 1 mL of from MWCNT/3 dispersion (as described above) was added to 1 mL of $CHCl_3$ and 3 mL of DCM. Only after 40 min sonication the solution became homogenous vs. the only 30 sec in pure $CHCl_3$. The suspension is stable for several days and can be rehomogenized easily with sonication.

Preparation of Dispersion MWCNT/5-Concentration Effect at High Concentration, of CNT: 1:0.25

10.2 mg of MWCNT with 5.1 mg of 5 in 10 mL of $CHCl_3$ [=first mixture] were sonicated for 30 min. Surprisingly, no heavy precipitate was observed as with 3. Only after 48-72 hrs solids settled down. The solution had an orange hue and greenish fluorescence.

When concentration of the CNT was doubled keeping the same concentration of 5, no homogeneous suspension was observed.

5 mL of the first mixture were added to 5.1 mg of MWCNT and sonicated for 40 min. The suspension did homogenize. However, upon the addition of additional 5 mL of CHCl₃ and 30 min sonication a similarly stable suspension was obtained with a ratio of 4:1 by weight of CNT: 5 respectively.

Example 23

Perovskite Solar Cells

Figure 49:
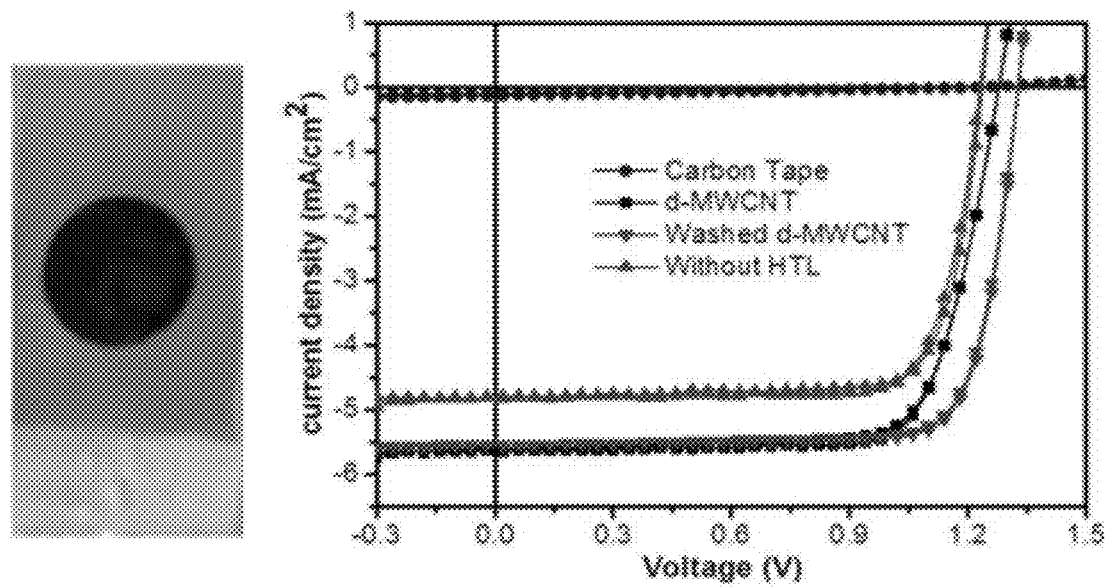
FIG. 49 presents $CsPbBr_3$ perovskite solar cell performance, comparing between carbon tape, d-MWCNT, washed d-MWCNT, without HTL. FR refers to forward scans. RS refers to reversed scans.

Various sizes of CNT films and ONC/CNT hybrid films of this invention were prepared and utilized to study the power conversion efficiency (PCE) and stability of perovskite solar cell. The perovskite solar cell using the CNT films prepared by the process of this invention showed efficiency of 5.8% compared to its counter gold electrodes 5.0% (FIG. 49). The CNT films and ONC/CNT hybrid films based on unsubstituted PDIs (Compound 3) and mono-nitro PDI derivatives (Compound 2) showed similar performance. The stabilities of the cells were monitored by measuring the photocurrent densities at an applied bias close to the initial maximum power point as a function of time. The devices with CNT films and ONC/CNT hybrid films gave almost no degradation for the continuous illumination of AM 1.5 for 7 h, whereas the standard gold electrode undergoes around 15% degradation. Further aging studies were carried out in ambient air under relative humidity (RH) of 60-70%, for 2 months. Between measurements, the devices were kept in a dry air atmosphere (in the dark) with a RH of ~15-20%. Gold electrode devices showed the significant decay of all parameters during prolonged exposures to sunlight, whereas CNT films and ONC/CNT hybrid films based devices showed stability over 2 months. These results indicate that the CNT films and ONC/CNT hybrid films based devices are superior in term of stability. They are also cost effective and simple to fabricate as large area electrodes as compared to gold electrodes.

Example 24

Hybrid Nanoclay Bentonite/2 Composition: Metal Ions Removal

A solution of $Ni^{2+}$, $Cd^{2+}$ or $Co^{2+}$ (3 ml, 10 ppm ions) was filtrated through a 1 cm diameter and 30 µm thickness membrane of 2/Bentonite (see Example 12) on a PVDF support at 2 bars pressure and 2 ml/h flow rate. The same was done with $Pb^{2+}$ ions but with 50 ppm instead of 10 ppm. The filtrate was divided into 2 fractions and the metal ion content of the filtrate was examined by ICP-MS. Results of the metal ions removal is presented in Table 8.

TABLE 8

Metal ions removal using a nanoclay bentonite/2 membrane of this invention.

| Ion | Initial concentration | Concentration after filtration | % removed |
|---|---|---|---|
| $Ni^{2+}$ | 10 ppm | 0.0659 ppm | 99.93 |
| $Co^{2+}$ | 10 ppm | 0.0195 ppm | 99.98 |
| $Cd^{2+}$ | 10 ppm | 0.124 ppm | 98.75 |
| $Pb^{2+}$ | 50 ppm | 0.295 ppm | 99.4 |

In all of the experiments, about 99% removal has been found. With $Pb^{2+}$, higher efficiency was found (50 ppm removal compared to 10 ppm in other metal ions).

Example 25

Hybrid Hydroxyethyl Cellulose/2 Composition

Preparation and Film Fabrication 14 ml of DDW were quickly added to 6 ml THF solution of 2 (0.16 mg/ml), the resulting dispersion was sonicated for 10 minutes to form dispersion A. Then 3 eq. of compound 2 in 1 ml of THF was added, the resulting solution was rapidly injected into the aqueous dispersion A. The final dispersion was divided into two fraction, each fraction was deposited on PVDF membrane by controlled pressure setup, the transmembrane pressure during filtration was set 2 bars. Hydroxyethyl cellulose (250000 Da), 20 mg, was suspended in 10 ml of DDW. The mixture was heated to 80° C. until the polymer was fully dissolved, and then cooled to R.T and 400 µL of the polymer solution was deposited on top of the ONCs film by filtration deposition at a pressure of 2 bars. The resulting film was allowed to dry in air, and the film was manually detached from the PVDF support.

Morphology

Figure 50A:
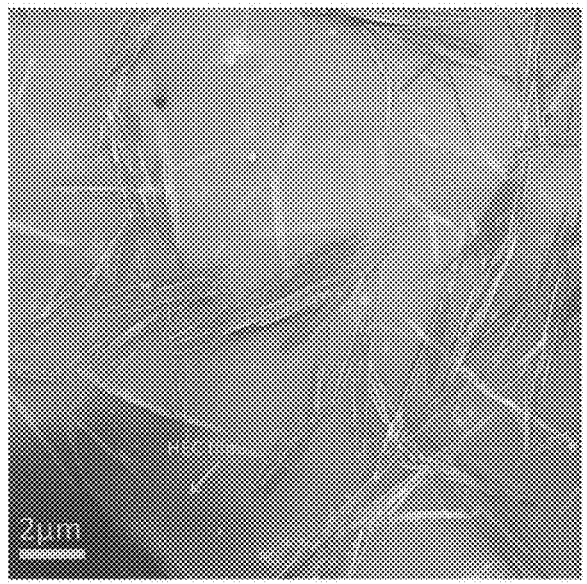
FIGS. 50A-50B present SEM images of 2/hydroxyethyl cellulose (HEC) composite films.
Figure 50B:
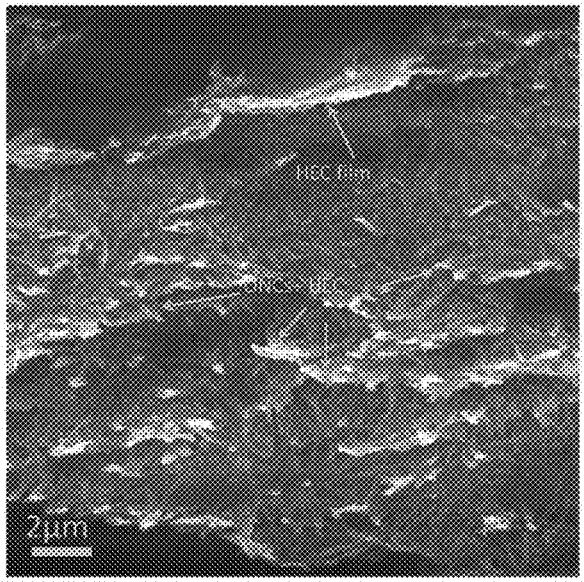

The morphology of the 2/hydroxyethyl cellulose composite film was investigated by scanning electron microscopy (SEM). The SEM images show that the ONCs are covered with homogeneous film (FIG. 50).

Example 26

Hybrid Hydroxyethyl Cellulose/2 Composition: Au NPs Filtration

Figure 51A:
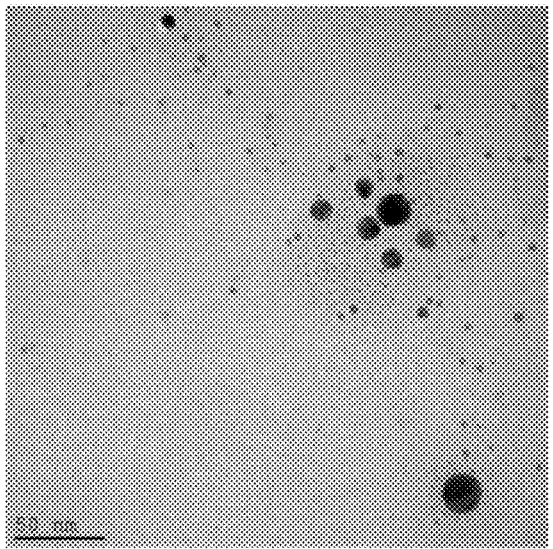
FIGS. 51A-51B present TEM images of Au particles (1-10 nm) stock solution (FIG. 51A) and filtrate (FIG. 51B), filtrated through 2/hydroxyethyl cellulose composite on a PVDF support.
Figure 51B:
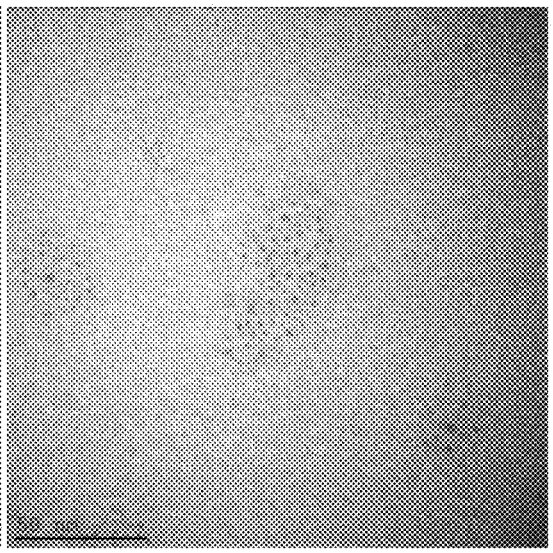

The hybrid porous films of Example 25 were tested for filtration of Au nanoparticles (1-10 nm). It was found that the cutoff of the hybrid membrane is 2 nm as shown in FIG. 51 and the filtration is efficient at 2 bars pressure. As in previous cases, both components of the hybrid membrane are recyclable.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A hybrid composition comprising a carbon nanotube (CNT) and organic nanocrystals (ONC), wherein the organic nanocrystal comprises a perylene diimide derivative, represented by the structure of formula IA, B3, II or III:

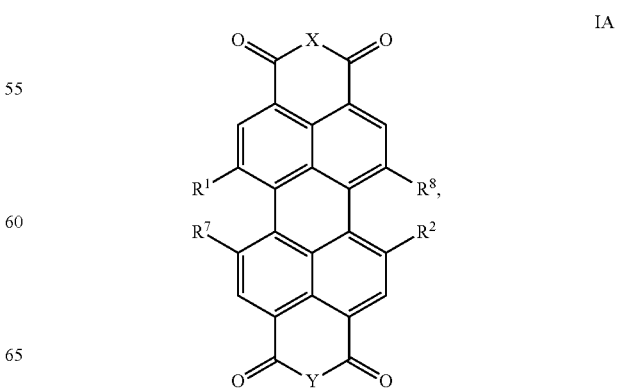

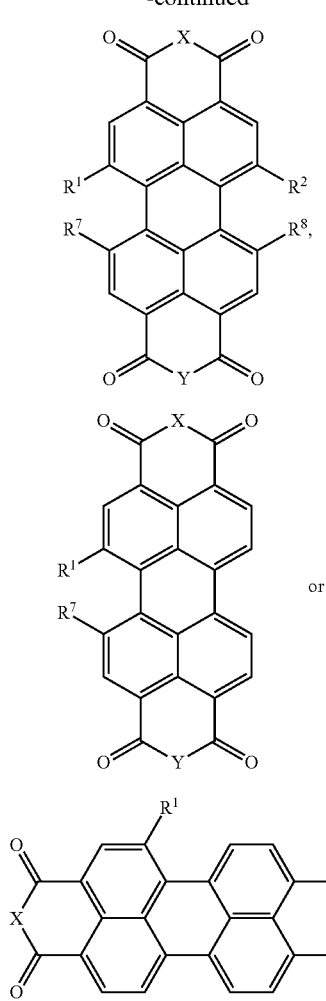

wherein,

X is —NR³;
Y is —NR⁴;
R¹ is H, R⁵, (C₁-C₁₀)alkyl, (C₁-C₁₀)haloalkyl, (C₃-C₈)cycloalkyl, aryl or heteroaryl, wherein said alkyl, haloalkyl, cycloalkyl, aryl or heteroaryl groups are optionally substituted; or R¹ is joined together with R⁷ to form a substituted or unsubstituted five or six membered ring, or a substituted or unsubstituted five or six membered fused ring;
R² is H, R⁵, (C₁-C₁₀)alkyl, (C₁-C₁₀)haloalkyl, (C₃-C₈)cycloalkyl, aryl or heteroaryl, wherein said alkyl, haloalkyl, cycloalkyl, aryl or heteroaryl groups are optionally substituted; or R² is joined together with R⁸ to form a substituted or unsubstituted five or six membered ring, or a substituted or unsubstituted five or six membered fused ring;
R³ and R⁴ are each independently H, (C₁-C₁₀)alkyl, (C₁-C₁₀)haloalkyl, (C₃-C₈)cycloalkyl, aryl or heteroaryl, wherein said alkyl, haloalkyl, cycloalkyl, aryl or heteroaryl groups are optionally substituted;
R⁵ is OR⁶, OCH₃, CF₃, halide, COR⁶, COCl, COOCOR⁶, COOR⁶, OCOR⁶, OCONHR⁶, NHCOOR⁶, NHCONHR⁶, OCOOR⁶, CON(R⁶)₂, SR⁶, SO₂R⁶, SO₂M, SOR⁶, SO₃H, SO₃M, SO₂NH₂, SO₂NH(R⁶), SO₂N(R⁶)2, NH₂, NH(R⁶), N(R⁶)2, CONH₂, CONH(R⁶), CON(R⁶)2, CO(N-heterocycle) NO₂, OH, CN, cyanate, isocyanate, thiocyanate, isothiocyanate, mesylate, tosylate, triflate, PO(OH)₂ or OPO(OH)₂; wherein M is a monovalent cation;
R⁶ is H, (C₁-C₁₀)haloalkyl, (C₃-C₈)cycloalkyl, aryl or heteroaryl, wherein said alkyl, haloalkyl, cycloalkyl, aryl or heteroaryl groups are optionally substituted;
R⁷ is H or is joined together with R¹ to form a substituted or unsubstituted five or six membered ring, or a substituted or unsubstituted five or six membered fused ring; and
R⁸ is H or is joined together with R² to form a substituted or unsubstituted five or six membered ring, or a substituted or unsubstituted five or six membered fused ring.

2. The hybrid composition of claim 1, further comprising an organic polymer.

3. The hybrid composition of claim 2, wherein said organic polymer is selected from the group consisting of: polyvinyl alcohol, polyethylene glycol (PEG), polyethylene, polypropylene, polystyrene, polyacrylonitrile, polyamide, polyimide, polyester and any combination thereof.

4. The hybrid composition of claim 3, wherein said organic polymer is polystyrene.

5. The hybrid composition according to claim 1, wherein the carbon nanotubes are single walled carbon nanotubes (SWCNTs) or a multi walled carbon nanotubes (MWCNTs).

6. The hybrid composition of claim 1, wherein the composition comprises one or more different perylene diimides derivatives.

7. The hybrid composition of claim 1, wherein the perylene diimide derivative is represented by the structure of formula 1-3, 4a, 4b or 5:

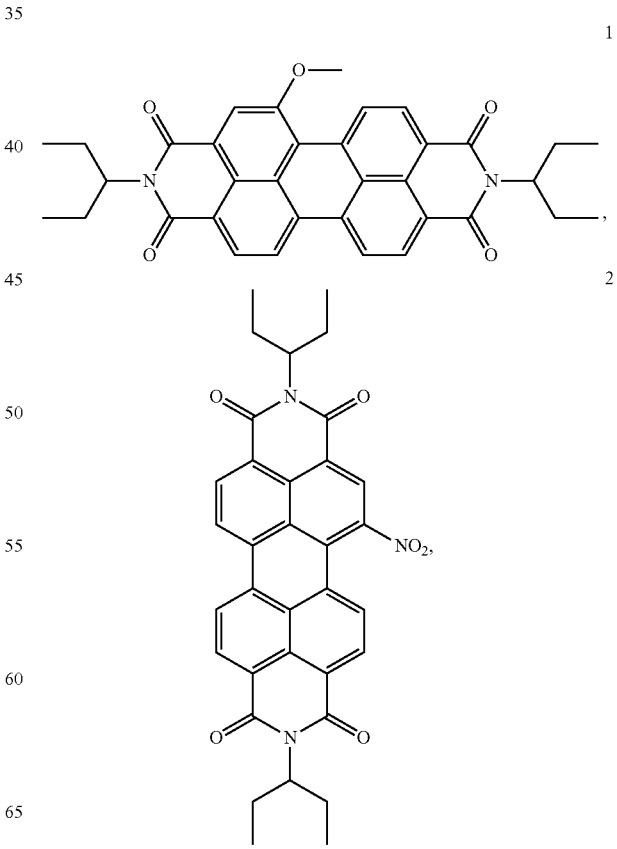

3

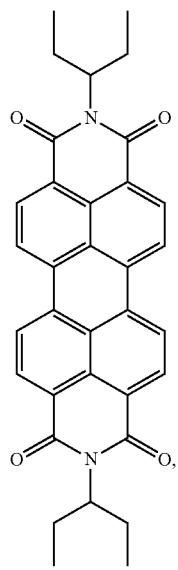

4a

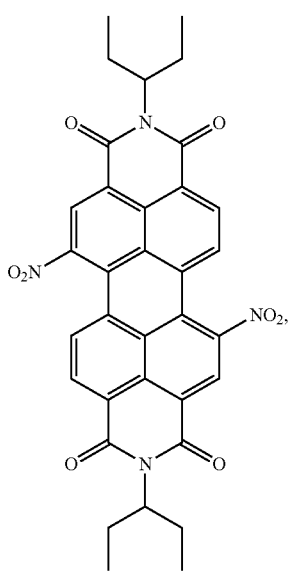

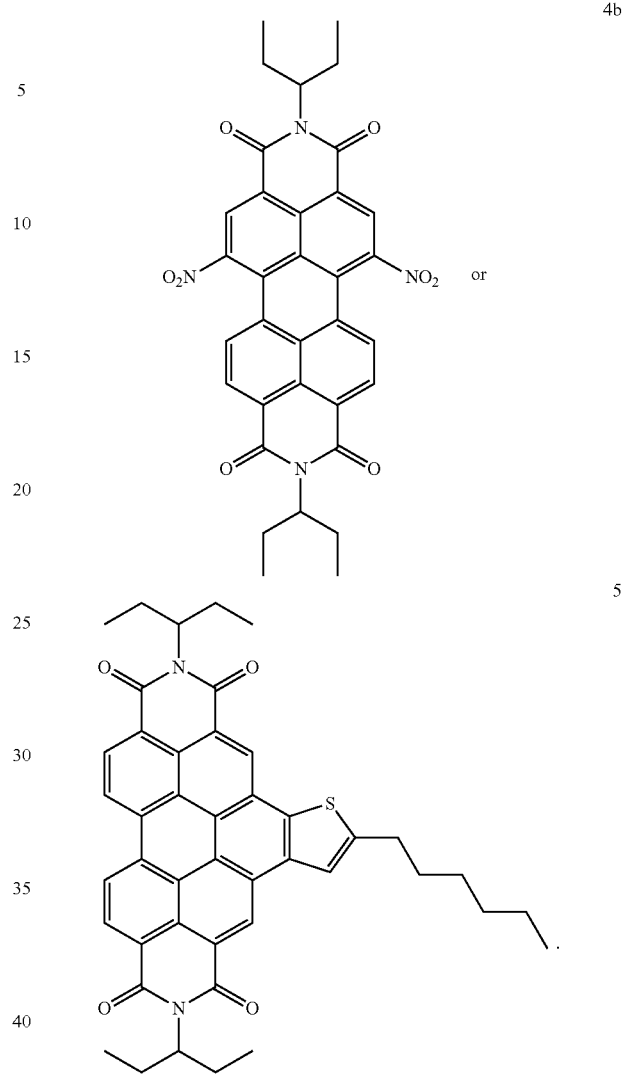

8. The hybrid composition of claim 7 wherein the perylenediimide derivative is a mixture of 4a and 4b.

9. The hybrid composition according to claim 1, wherein the composition comprises between 3 wt % to 85 wt % of CNT.

10. An electrode comprising a hybrid composition according to claim 1.

11. The electrode of claim 10, wherein said electrode is a cathode or an anode.

12. The electrode of claim 10, further comprising a binder, an additive, a current collector or any combination thereof.

13. The electrode of claim 10, wherein said hybrid composition is used as a binder, an additive, a current collector or any combination thereof.

14. A process for the preparation of the hybrid composition of claim 1, the process comprises:
   mixing a hydrophobic organic compound and a carbon nanotube (CNT) in a first organic solvent;
   optionally drying the mixture;
   adding to the mixture a second organic solvent and water to obtain an aqueous medium and mixing for a period of time to obtain the hybrid; wherein if the first organic solvent and the second organic solvent are the same, only water is added to the mixture.

15. A process for the preparation of the hybrid composition of claim 1, the process comprises:
mixing a hydrophobic organic compound and a carbon nanotube (CNT) in a first organic solvent;
optionally drying the mixture;
optionally, adding to the mixture a second organic solvent to obtain an organic medium and mixing for a period of time to obtain the hybrid.

16. The process of claim 14, wherein the hybrid is further purified by centrifugation, or precipitation to yield a homogenous dispersion of ONC/CNT hybrid composition.

17. The process of claim 15, wherein the hybrid is further purified by centrifugation, or precipitation to yield a homogenous dispersion of ONC/CNT hybrid composition.

18. The process according to claim 14, wherein the CNT is (6,5)-SWCNT, (7,6)-SWCNT, MWCNT or combination thereof.

19. The process according to claim 15, wherein the CNT is (6,5)-SWCNT, (7,6)-SWCNT, MWCNT or combination thereof.

20. The process according to claim 14, wherein the hydrophobic organic compound is perylenediimide (PDI) derivative, represented by the structure of formula IA, IB II or III:

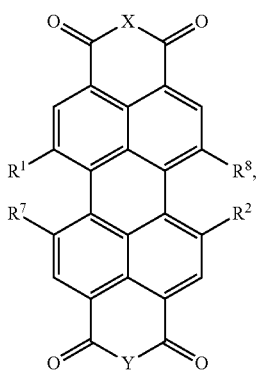

IA

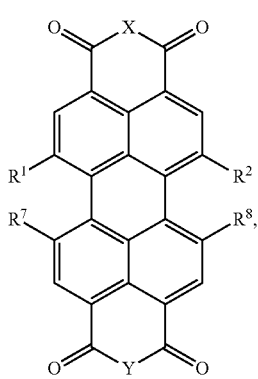

IB

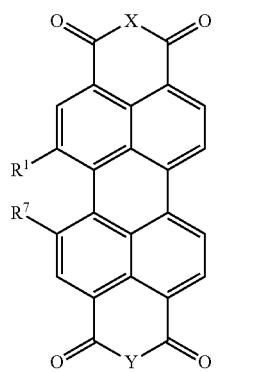

II or

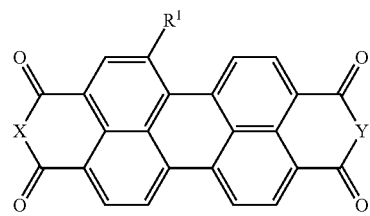

III wherein,
X is —NR³;
Y is —NR⁴;
R¹ is H, R⁵, (C₁-C₁₀)alkyl, (C₁-C₁₀)haloalkyl, (C₃-C₈) cycloalkyl, aryl or heteroaryl, wherein said alkyl, haloalkyl, cycloalkyl, aryl or heteroaryl groups are optionally substituted; or R¹ is joined together with R⁷ to form a substituted or unsubstituted five or six membered ring, or a substituted or unsubstituted five or six membered fused ring;
R² is H, R⁵, (C₁-C₁₀)alkyl, (C₁-C₁₀)haloalkyl, (C₃-C₈) cycloalkyl, aryl or heteroaryl, wherein said alkyl, haloalkyl, cycloalkyl, aryl or heteroaryl groups are optionally substituted; or R² is joined together with R⁸ to form a substituted or unsubstituted five or six membered ring, or a substituted or unsubstituted five or six membered fused ring;
R³ and R⁴ are each independently H, (C₁-C₁₀)alkyl, (C₁-C₁₀)haloalkyl, (C₃-C₈)cycloalkyl, aryl or heteroaryl, wherein said alkyl, haloalkyl, cycloalkyl, aryl or heteroaryl groups are optionally substituted;
R⁵ is OR⁶, OCH₃, CF₃, halide, CORE, COCl, COOCOR⁶, COOR⁶, OCOR⁶, OCONHR⁶, NHCOOR⁶, NHCONHR⁶, OCOOR⁶, CON(R⁶)2, SR⁶, SO₂R⁶, SO₂M, SOR⁶, SO₃H, SO₃M, SO₂NH₂, SO₂NH(R⁶), SO₂N(R⁶)₂, NH₂, NH(R⁶), N(R⁶)₂, CONH₂, CONH(R⁶), CON(R⁶)₂, CO(N-heterocycle), NO₂, OH, CN, cyanate, isocyanate, thiocyanate, isothiocyanate, mesylate, tosylate, triflate, PO(OH)₂ or OPO(OH)₂; wherein M is a monovalent cation;
R⁶ is H, (C₁-C₁₀)haloalkyl, (C₃-C₈)cycloalkyl, aryl or heteroaryl, wherein said alkyl, haloalkyl, cycloalkyl, aryl or heteroaryl groups are optionally substituted;
R⁷ is H or is joined together with R¹ to form a substituted or unsubstituted five or six membered ring, or a substituted or unsubstituted five or six membered fused ring; and
R⁸ is H or is joined together with R² to form a substituted or unsubstituted five or six membered ring, or a substituted or unsubstituted five or six membered fused ring.

21. The process according to claim 15, wherein the hydrophobic organic compound is perylenediimide (PDI) derivative, represented by the structure of formula IA, IB II or III:

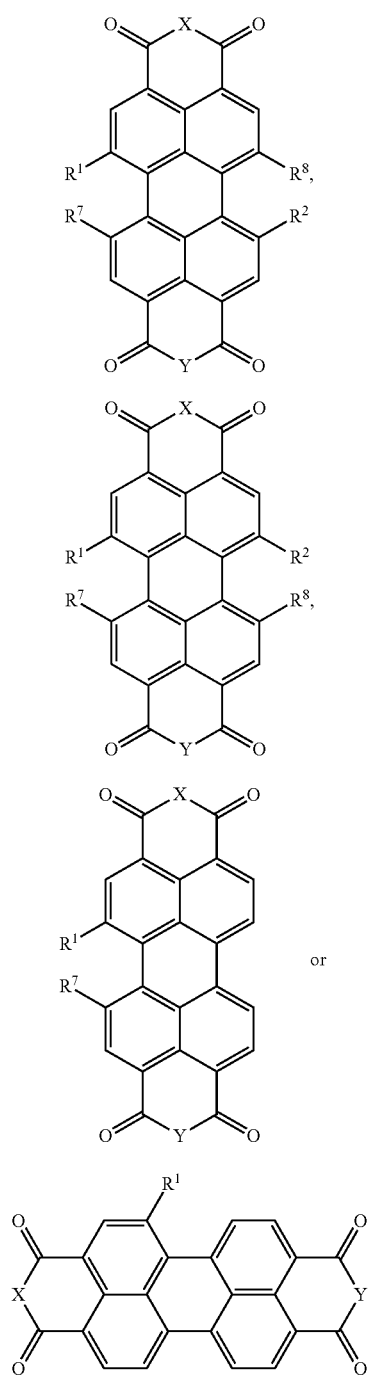

wherein,

X is —NR³;

Y is —NR⁴;

R¹ is H, R⁵, $(C_1-C_{10})$alkyl, $(C_1-C_{10})$haloalkyl, $(C_3-C_8)$cycloalkyl, aryl or heteroaryl, wherein said alkyl, haloalkyl, cycloalkyl, aryl or heteroaryl groups are optionally substituted; or R¹ is joined together with R⁷ to form a substituted or unsubstituted five or six membered ring, or a substituted or unsubstituted five or six membered fused ring;

R² is H, R⁵, $(C_1-C_{10})$alkyl, $(C_1-C_{10})$haloalkyl, $(C_3-C_8)$cycloalkyl, aryl or heteroaryl, wherein said alkyl, haloalkyl, cycloalkyl, aryl or heteroaryl groups are optionally substituted; or R² is joined together with R⁸ to form a substituted or unsubstituted five or six membered ring, or a substituted or unsubstituted five or six membered fused ring;

R³ and R⁴ are each independently H, $(C_1-C_{10})$alkyl, $(C_1-C_{10})$haloalkyl, $(C_3-C_8)$cycloalkyl, aryl or heteroaryl, wherein said alkyl, haloalkyl, cycloalkyl, aryl or heteroaryl groups are optionally substituted;

R⁵ is OR⁶, OCH₃, CF₃, halide, CORE, COCl, COOCOR⁶, COOR⁶, OCOR⁶, OCONHR⁶, NHCOOR⁶, NHCONHR⁶, OCOOR⁶, CON(R⁶)2, SR⁶, SO₂R⁶, SO₂M, SOR⁶, SO₃H, SO₃M, SO₂NH₂, SO₂NH(R⁶), SO₂N(R⁶)₂, NH₂, NH(R⁶), N(R⁶)2, CONH₂, CONH(R⁶), CON(R⁶)₂, CO(N-heterocycle), NO₂, OH, CN, cyanate, isocyanate, thiocyanate, isothiocyanate, mesylate, tosylate, triflate, PO(OH)₂ or OPO(OH)₂; wherein M is a monovalent cation;

R⁶ is H, $(C_1-C_{10})$haloalkyl, $(C_3-C_8)$cycloalkyl, aryl or heteroaryl, wherein said alkyl, haloalkyl, cycloalkyl, aryl or heteroaryl groups are optionally substituted;

R⁷ is H or is joined together with R¹ to form a substituted or unsubstituted five or six membered ring, or a substituted or unsubstituted five or six membered fused ring; and R⁸ is H or is joined together with R² to form a substituted or unsubstituted five or six membered ring, or a substituted or unsubstituted five or six membered fused ring.

22. The process according to claim 14, wherein the aqueous medium is a mixture of THF, DMSO, NMP, DMF, acetonitrile acetone or combination thereof with water.

23. A film comprising the hybrid composition according to claim 1.

24. The film according to claim 23, wherein the film is a free-standing film.

25. A conductive colorant comprising the film according to claim 23.

26. A membrane for the separation of nanoparticles, biomolecules, comprising the film according to claim 23.

* * * * *